(12) United States Patent
Li et al.

(10) Patent No.: US 11,905,294 B2
(45) Date of Patent: *Feb. 20, 2024

(54) IMIDAZO[1,5-A]PYRAZINE DERIVATIVES AS PI3Kδ INHIBITORS

(71) Applicant: BEIGENE, LTD., Grand Cayman (KY)

(72) Inventors: Jing Li, Beijing (CN); Haibo Zhao, Beijing (CN); Zhiwei Wang, Beijing (CN)

(73) Assignee: BeiGene, Ltd., Grand Cayman (KY)

( * ) Notice: Subject to any disclaimer, the term of this patent is extended or adjusted under 35 U.S.C. 154(b) by 149 days.

This patent is subject to a terminal disclaimer.

(21) Appl. No.: 17/533,442

(22) Filed: Nov. 23, 2021

(65) Prior Publication Data

US 2022/0081447 A1  Mar. 17, 2022

Related U.S. Application Data

(63) Continuation of application No. 16/643,040, filed as application No. PCT/CN2018/104559 on Sep. 7, 2018, now Pat. No. 11,220,506.

(30) Foreign Application Priority Data

Sep. 8, 2017 (WO) ................ PCT/CN2017/101058
Dec. 28, 2017 (WO) ................ PCT/CN2017/119373
May 11, 2018 (WO) ................ PCT/CN2018/086555

(51) Int. Cl.
| | | |
|---|---|---|
| *A61K 31/4985* | (2006.01) | |
| *A61P 35/00* | (2006.01) | |
| *A61P 37/00* | (2006.01) | |
| *C07D 487/04* | (2006.01) | |
| *C07D 519/00* | (2006.01) | |

(52) U.S. Cl.
CPC ......... *C07D 487/04* (2013.01); *C07D 519/00* (2013.01)

(58) Field of Classification Search
CPC ....... A61K 31/4985; A61P 35/00; A61P 37/00
See application file for complete search history.

(56) References Cited

U.S. PATENT DOCUMENTS

| | | |
|---|---|---|
| 2007/0254883 A1 | 11/2007 | Crew |
| 2019/0367523 A1 | 12/2019 | Li et al. |
| 2020/0207774 A1 | 7/2020 | Li et al. |

FOREIGN PATENT DOCUMENTS

| | | |
|---|---|---|
| AR | 102220 | 2/2017 |
| CA | 2922058 | 4/2015 |
| CN | 1898240 | 1/2007 |
| JP | 2005089352 | 4/2005 |
| JP | 2007509060 | 4/2007 |
| JP | 2012524063 | 10/2012 |
| JP | 2014508145 | 4/2014 |
| JP | 2015503601 | 2/2015 |
| JP | 2015536948 | 12/2015 |
| JP | 2020500909 | 1/2020 |
| WO | WO-2005037836 A2 | 4/2005 |
| WO | 2010120237 | 10/2010 |
| WO | WO-2010119264 A1 | 10/2010 |
| WO | WO-2012107465 A1 | 8/2012 |
| WO | WO-2013104610 A1 | 7/2013 |
| WO | WO-2014071109 A1 | 5/2014 |
| WO | WO-2014194254 A1 | 12/2014 |
| WO | WO-2015058084 A1 | 4/2015 |
| WO | WO-2016024230 A1 | 2/2016 |
| WO | 2017216292 | 12/2017 |
| WO | WO-2018103688 A1 | 6/2018 |
| WO | WO-2019047915 A1 | 3/2019 |

OTHER PUBLICATIONS

ChemSpider (ChemZoo, Inc.) Registry Compound RN 1025939-56-3, 1 page (2008).
Extended European Search Report for European Application No. 18853233.7, dated Dec. 10, 2020, 6 pages.
Fry, M. J., "Review: Phosphoinositide 3-kinase signaling in breast cancer: how big a role might it play?," Breast Cancer Res 2001, 3:304-312.
Gonzalez, S. M. et al., "Imidazo[1,2-a]pyrazines as novel PI3K inhibitors," Bioorganic & Medicinal Chemistry Letters, vol. 22, No. 5, Mar. 2012, pp. 1874-1878.
Gura, T., Cancer Models: "Systems for identifying new drugs are often faulty," Science, vol. 278, No. 5340, pp. 1041-1042 (Nov. 1997).
International Search Report and Written Opinion for International Application No. PCT/CN2017/114970, dated Mar. 6, 2018, 13 pages.
International Search Report and Written Opinion for International Application No. PCT/CN2018/104559, dated Nov. 30, 2018, 11 pages.
Johnson et al. "Relationships Between Drug Activity in NCI Preclinical in vitro and in vivo Models and Early Clinical Trials" Brit. J. Cancer. 84.10(2001):1424-1431.

(Continued)

*Primary Examiner* — Bruck Kifle
(74) *Attorney, Agent, or Firm* — FOLEY & LARDNER LLP

(57) ABSTRACT

Disclosed is a compound of Formula (I), or a stereoisomer thereof, or a pharmaceutically acceptable salt thereof, and pharmaceutical compositions comprising thereof. Also disclosed is a method of treating PI3Kδ related disorders or diseases by using the compound disclosed herein.

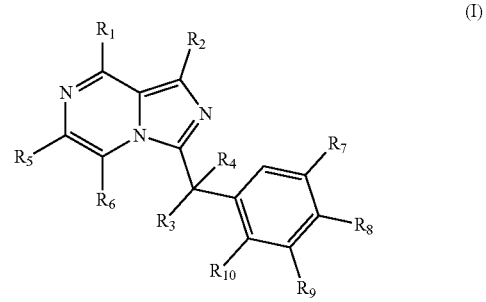

(I)

23 Claims, No Drawings

(56) References Cited

OTHER PUBLICATIONS

Pearce, H. L. et al., "Failure modes in anticancer drug discovery and development," Cancer Drug Design and Discovery, Neidle, S. (ed.), Chapter 18 in Cancer Drug Design and Discovery, Elsevier Inc., pp. 424-435 (2008).
Simone, J. V., Part XIV Oncology, 154 Introduction, In: Cecil Textbook of Medicine, 20th Edition, vol. 1, Bennett, J. C. (ed.) (1996) pp. 1004-1010.
The Merck Manual, "Acute Leukemia," (Online Edition), 6 pages (2013).
Extended European Search Report dated Jun. 21, 2023 in corresponding European Patent Application No. 23152036.2.
Xin Minxing et al., "Research Progress on Selective PI3Kδ Inhibitors", "Journal of China Pharmaceutical University" pp. 503-510.

IMIDAZO[1,5-A]PYRAZINE DERIVATIVES AS PI3Kδ INHIBITORS

CROSS REFERENCE TO RELATED APPLICATIONS

This application is a continuation of U.S. patent application Ser. No. 16/643,040 filed on Feb. 28, 2020, which is a U.S. National Stage Application under 35 U.S.C. § 371 of International Application No. PCT/CN2018/104559, filed on Sep. 7, 2018, which claims priority to, and the benefit of International Application Nos. PCT/CN2017/101058 filed on Sep. 8, 2017, PCT/CN2017/119373 filed on Dec. 28, 2017, and PCT/CN2018/086555 filed on May 11, 2018, the disclosures of which are hereby incorporated by reference in their entireties for all purposes.

FIELD OF THE INVENTION

Disclose herein is an imidazo[1,5-a]pyrazine derivative, or a stereoisomer thereof, or a pharmaceutically acceptable salt thereof, and a pharmaceutical composition comprising thereof. Also disclosed herein is a method of treating PI3K-related disorders (in particular PI3Kδ-related disorders) using the imidazo[1,5-a]pyrazine derivative disclosed herein, or a stereoisomer thereof, or a pharmaceutically acceptable salt thereof. Also disclosed herein is the imidazo[1,5-a]pyrazine derivative, or a stereoisomer thereof, or a pharmaceutically acceptable salt thereof for use in the treatment of PI3K-related disorders (in particular PI3Kδ-related disorders).

BACKGROUND OF THE INVENTION

Phosphatidylinositol-4,5-bisphosphate 3-kinases (PI3Ks) are a family of enzymes involved in various of primary cellular functions, including cell growth, proliferation, differentiation, motility, survival, metabolism and intracellular trafficking [Vanhaesebroeck, B., L. Stephens, and P. Hawkins, *PI3K signalling: the path to discovery and understanding*. Nat Rev Mol Cell Biol, 2012, 13(3): p. 195-203.]. They are kinases capable of phosphorylating phosphatidylinositol [Whitman, M., et al., *Type I phosphatidylinositol kinase makes a novel inositol phospholipid, phosphatidylinositol-3-phosphate*. Nature, 1988. 332(6165): p. 644-6.; Auger, K. R., et al., *PDGF-dependent tyrosine phosphorylation stimulates production of novel polyphosphoinositides in intact cells*. Cell, 1989. 57(1): p. 167-75.]. Phosphorylated phosphatidylinositols, which are called phosphoinositides, play important roles in signaling transduction and membrane trafficking [Martin, T. F., *Phosphoinositide lipids as signaling molecules: common themes for signal transduction, cytoskeletal regulation, and membrane trafficking*. Annu Rev Cell Dev Biol. 1998. 14: p. 231-64.].

PI3K family is divided into three classes (I, II, and III) based on structure, regulation and substrate specificity [Vanhaesebroeck, B., et al., *The emerging mechanism of isoform-specific PI3K signalling*. Nat Rev Mol Cell Biol, 2010. 11(5): p. 329-41.]. Class I PI3Ks are further divided based on sequence similarity into class IA and class IB. The class IA PI3Ks comprise three closely related kinases, PI3Kα, PI3Kβ, and PI3Kδ, which exist as heterodimers composed of a catalytic subunit (p110α, p110β, or p110δ) and a regulatory subunit (p85) [Yu, J., et al., *Regulation of the p85/p110 phosphatidylinositol 3'-kinase: stabilization and inhibition of the p110alpha catalytic subunit by the p85 regulatory subunit*. Mol Cell Biol, 1998. 18(3): p. 1379-87; Carpenter, C. L., et al., *Phosphoinositide 3-kinase is activated by phosphopeptides that bind to the SH2 domains of the 85-kDa subunit*. J Biol Chem, 1993. 268(13): p, 9478-83.; Zhang, X., et al., *Structure of lipid kinase p110beta/p85beta elucidates an unusual SH2-domain-mediated inhibitory mechanism*. Mol Cell, 2011. 41(5); p. 567-78.; Burke, J. E., et al., *Dynamics of the phosphoinositide 3-kinase p110delta interaction with p85alpha and membranes reveals aspects of regulation distinct from p110alpha*. Structure, 2011. 19(8): p. 1127-37.]. The class IB PI3K includes only PI3Kγ, which is composed of a p110γ [Stoyanov, B., et al., *Cloning and characterization of a G protein-activated human phosphoinositide-3 kinase*. Science, 1995. 269(5224): p. 690-3.] catalytic subunit that can associate with a p101 [Stephens, L. R., et al.,*The G beta gamma sensitivity of a PI3K is dependent upon a tightly associated adaptor, p101*. Cell, 1997. 89(1): p. 105-14.; Brock, C., et al., *Roles of G beta gamma in membrane recruitment and activation of p110 gamma/p101 phosphoinositide 3-kinase gamma*. J Cell Biol, 2003. 160(1): p. 89-99.] or p84 [Suire, S., et al., *p84, a new Gbetagamma-activated regulatory subunit of the type IB phosphoinositide 3-kinase p110gamma*. Curr Biol, 2005, 15(6): p. 566-70.] regulatory subunit. PI3Kα and PI3Kδ respond to signaling generally through receptor tyrosine kinases (RTKs) [Inukai, K., et al., *Five isoforms of the phosphatidylinositol 3-kinase regulatory subunit exhibit different associations with receptor tyrosine kinases and their tyrosine phosphorylations*. FEBS Lett, 2001. 490(1-2): p. 32-8.], while PI3Kγ signals through G-protein-coupled receptors (GPCRs)[Stoyanov, B., et al., *Cloning and characterization of a G protein-activated human phosphoinositide-3 kinase. Science*, 1995. 269(5224): p. 690-3.; Maier, U., A, Babich, and B. Nurnberg, *Roles of non-catalytic subunits in gbetagamma-induced activation of class I phosphoinositide 3-kinase isoforms beta and gamma*. J Biol Chem, 1999. 274(41): p. 29311-7.] and PI3Kβ signals through both [Kurosu, Fi., et al., *Heterodimeric phosphoinositide 3-kinase consisting of p85 and p110beta is synergistically activated by the betagamma subunits of G proteins and phosphotyrosyl peptide*. J Biol Chem, 1997. 272(39): p, 24252-6,]. Expression of the PI3Kα and PI3Kβ isoforms is ubiquitous, while the expression pattern of PI3Kδ and PI3Kγ seems more restricted, with both isoforms found primarily in leukocytes [Kok, K., B, Deering, and B. Vanhaesebroeck, *Regulation of phosphoinositide 3-kinase expression in health and disease. Trends Biochem Sci,* 2009. 34(3): p. 115-27.].

The relatively restricted expression pattern of PI3Kδ, in addition to data accumulated from studies in mice, where PI3Kδ was either genetically inactivated or hyper-activated or pharmacologically inactivated, suggests that this isoform plays a major role in the adaptive immune systems [Lucas, C. L. et al., *PI3Kdelta and primary immunodeficiencies*. Nat Rev Immunol, 2016]. In mice, the loss of function of PI3Kδ in B cells impairs the T cell-independent antibody response but has no effect on class-switch recombination (CSR) and somatic hypermutation (SHM) [Rolf, J., et al., *Phosphoinositide 3-kinase activity in T cells regulates the magnitude of the germinal center reaction*. J Immunol, 2010. 185(7): p. 4042-52.], both of which are essential for antibody maturation and diversity [Stavnezer, J., J. E. Guikema, and C. E. Schrader, *Mechanism and regulation of class switch recombination*. Annu Rev Immunol, 2008. 26: p. 261-92.; Li, Z., et al., *The generation of antibody diversity through somatic hypermutation and class switch recombination*. Genes Dev, 2004. 18(1): p. 1-11.]; while the hyperactivation of PI3Kδ in mature B cells interferes with CSR and SHM and inhibits the proliferation of antigen-specific B cell populations [Janas, M. L., et al., *The effect of deleting p110delta on the phenotype and function of PTEN-deficient B cells*. J Immunol, 2008. 180(2): p. 739-46; Omori, S. A., et al., *Regulation of class-switch recombination and plasma cell differentiation by phosphatidylinositol 3-kinase signaling*. Immunity, 2006. 25(4): p. 545-57.; Sander, S., et al., *PI3 Kinase and FOXO1 Transcription Factor Activity Differentially Control B Cells in the Germinal Center Light and Dark Zones*. Immunity, 2015, 43(6): p. 1075-861. Besides, PI3Kδ is also a key signaling transduction component for malignant B cells, which makes it an attractive drug target for B cell malignancies [Wei, M., et al., *Targeting PI3Kdelta: emerging therapy for chronic lymphocytic leukemia and beyond*. Med Res Rev, 2015. 35(4): p. 720-52.].

Meanwhile, PI3Kδ is required for the differentiation of naïve T cell towards T helper cells, including $T_{FH}$ (follicular helper) [Rolf, J., et al., *Phosphoinositide 3-kinase activity in T cells regulates the magnitude of the germinal center reaction*. J Immunol, 2010. 185(7): p. 4042-52.], $T_H1$, $T_H2$ and $T_H17$ [Okkenhaug, K., et al., *The p110delta isoform of phosphoinositide 3-kinase controls clonal expansion and differentiation of Th cells*. J Immunol, 2006. 177(8): p. 5122-8.; Soond, D. R., el al., *PI3K p110delta regulates T-cell cytokine production during primary and secondary immune responses in mice and humans*. Blood, 2010. 115(11): p. 2203-13.; Kurebayashi, Y., et al., *PI3K-Akt-mTORC1-S6K1/2 axis controls Th17 differentiation by regulating Gfi1 expression and nuclear translocation of RORgamma*, Cell Rep, 2012. 1(4): p. 360-73.]. The interference on $T_{FH}$ development leads to severe attenuation of T cell-dependent CSR and SHM in B cells [Rolf, J., et al., *Phosphoinositide 3-kinase activity in T cells regulates the magnitude of the germinal center reaction*. J Immunol, 2010. 185(7): p. 4042-52.], whereas the reduction on $T_H2$ and $T_H17$ cells induced by PI3Kδ deficiency could provide protections on mice with asthma [Nashed, B. F., et al., *Role of the phosphoinositide 3-kinase p110delta in generation of type 2 cytokine responses and allergic airway inflammation*. Eur J Immunol, 2007. 37(2): p. 416-24.] or multiple sclerosis [Haylock-Jacobs, S., et al., *PI3Kdelta drives the pathogenesis of experimental autoimmune encephalomyelitis by inhibiting effector T cell apoptosis and promoting Th17 differentiation*. J Autoimmun, 2011. 36(3-4): p. 278-87.] respectively. PI3Kδ is also essential for the homeostasis and function of Foxp$^{3+}$ T regulatory cells ($T_{reg}$) [Patton, D. T., et al., *Cutting edge: the phosphoinositide 3-kinase p110 delta is critical for the function of CD4+CD25+Foxp3+ regulatory T cells*. J Immunol, 2006. 177(10): p. 6598-602.]. PI3Kδ deficient mice develop colitis [Patton, D. T., et al., *Cutting edge: the phosphoinositide 3-kinase p110 delta is critical for the function of CD4+CD25+Foxp3+ regulatory T cells*. J Immunol, 2006. 177(10): p. 6598-602.] due to the reduced $T_{reg}$ functions but have increased immune response against tumors [Ali, K., et al., *Inactivation of PI(3)K p110delta breaks regulatory T-cell-mediated immune tolerance to cancer*. Nature, 2014. 510(7505): p. 407-11.]. PI3Kδ also contributes to, but is not necessary for the reprogramming of CD8+ T cells to fully activated effector cells [Pearce, V. Q., et al., *PI3Kdelta Regulates the Magnitude of CD8+ T Cell Responses after Challenge with Listeria monocytogenes*. J Immunol, 2015. 195(7): p. 3206-17.; Gracias, D. T., et al., *Phosphatidylinositol 3-Kinase p110delta Isoform Regulates CD8+ T Cell Responses during Acute Viral and Intracellular Bacterial Infections*. J Immunol, 2016. 196(3): p. 1186-98]. In contrast, the generation of memory CD8+ T cells requires the suppression of PI3Kδ signaling [Pearce, V. Q., et al., *PI3Kdelta Regulates the Magnitude of CD8+ T Cell Responses after Challenge with Listeria monocytogenes*. J Immunol, 2015. 195(7): p. 3206-17.].

PI3Kδ mutations, both gain of function (GOF) and loss of function (LOF), can induce primary immunodeficiency in human [Lucas, C. L. et al., *PI3Kdelta and primary immunodeficiencies*. Nat Rev Immunol, 2016.]. Patients lacking of PI3Kδ function presented with recurrent infections and severe B cell lymphopenia [Conley, M. E., et al., *Agammaglobulinemia and absent B lineage cells in a patient lacking the p85alpha subunit of PI3K*. J Exp Med, 2012. 209(3): p. 463-70.; Conley, M. E., et al., *Agammaglobulinemia and absent B lineage cells in a patient lacking the p85alpha subunit of PI3K*. J Exp Med, 2012, 209(3): p. 463-70.], while GOF mutations in PI3Kδ genes can cause a syndrome of combined immune-deficiency, which is referred to as activated PI3Kδ syndrome (APDS) [Angulo, I., et al., *Phosphoinositide 3-kinase delta gene mutation predisposes to respiratory infection and airway damage*. Science, 2013. 342(6160): p. 866-71.; Lucas, C. L., et al., *Dominant-activating germline mutations in the gene encoding the PI(3)K catalytic subunit p110delta result in T cell senescence and human immunodeficiency*. Nat Immunol, 2014. 15(1): p. 88-97; Deau, M. C., et al., *A human immunodeficiency caused by mutations in the PIK3R1 gene*. J Clin Invest, 2015. 125(4): p. 1764-5.; Lucas, C. L., et al., *Heterozygous splice mutation in $PIK3R_1$ causes human immunodeficiency with lymphoproliferation due to dominant activation of PI3K*. J Exp Med, 2014. 211(13): p. 2537-47.]. Patients with APDS were characterized with senescent T cells, lymphadenopathy and frequent infections [Elgizouli, M., et al., *Activating PI3Kdelta mutations in a cohort of 669 patients with primary immunodeficiency*. Clin Exp Immunol, 2016. 183(2): p. 221-9; Elkaim, E., et al., *Clinical and immunologic phenotype associated with activated phosphoinositide 3-kinase delta syndrome 2: A cohort study*. J Allergy Clin Immunol, 2016. 138(1): p. 210-218 e9.; Coulter, T. I., et al., *Clinical spectrum and features of activated phosphoinositide 3-kinase delta syndrome: A large patient cohort study*. J Allergy Clin Immunol, 2016.].

Because of the specific and critical functions of PI3Kδ in adaptive immune responses, the inhibitors of PI3Kδ are being developed for the treatment of autoimmune (such as multiple sclerosis, systemic lupus erythematosus, rheumatoid arthritis and psoriasis) and inflammatory disorders (such as asthma and chronic obstructive pulmonary disease), hematological and solid tumors as well as APDS [Lucas, C. L., et al., *PI3Kdelta and primary immunodeficiencies*. Nat Rev Immunol, 2016.; Stark, A. K., et al., *PI3K inhibitors in inflammation, autoimmunity and cancer*. Curr Opin Pharmacol, 2015. 23: p, 82-91]. Idelalisib is the first PI3Kδ inhibitor approved in 2014 for the treatment of B cell malignancies [Yang, Q., et al., *Idelalisib: First-in-Class PI3K Delta Inhibitor for the Treatment of Chronic Lymphocytic Leukemia, Small Lymphocytic Leukemia, and Follicular Lymphoma*. Clin Cancer Res, 2015. 21(7): p. 1537-42.]. In addition to idelalisib, at least 9 δ-specific and 5 δβ or δα-dual inhibitors are under clinical development [Wei, M., et al., *Targeting PI3Kdelta: emerging therapy for chronic lymphocytic leukemia and beyond*. Med Res Rev, 2015. 35(4): p. 720-52.]. Among them, a δγ-dual inhibitor duvelisib (NCT02004522) and a δ-specific inhibitor TGR-1202 (NCT02612311) are being evaluated in phase III clinical trials.

Recently, both idelalisib and duvelisib were noted with the risk of increasing infections in lung [Okkenhaug, K., M.

Graupera, and B. Vanhaesebroeck, *Targeting PI3K in Cancer: Impact on Tumor Cells, Their Protective Stroma, Angiogenesis, and Immunotherapy*. Cancer Discov, 2016. 6(10): p. 1090-1105.], which was inferred to be associated with their relatively low selectivity to PI3Kδ [Ruckle, T., M. K. Schwarz, and C. Rommel, *PI3Kgamma inhibition: towards an 'aspirin of the 21st century'*? Nat Rev Drug Discov, 2006. 5(11): p. 903-18.]. PI3Kγ is important for immune cell chemotaxis [Hawkins, P. T. and L. R. Stephens, *PI3K signalling in inflammation*. Biochim Biophys Acta, 2015. 1851(6): p. 882-97.] and plays major roles in innate immune system [Ruckle, T., M. K. Schwarz, and C. Rommel, *PI3Kgamma inhibition: towards an 'aspirin of the 21st century'*? Nat Rev Drug Discov, 2006. 5(11): p. 903-18.]. PI3Kγ knock-out mice displayed increased susceptibility to pneumococcal infection [Maus, U. A., et al., *Importance of phosphoinositide 3-kinase gamma in the host defense against pneumococcal infection*. Am J Respir Crit Care Med, 2007. 175(9): p. 958-66.], It also works in concert with PI3Kδ in multiple immune surveillance processes, including neutrophil recruitment [Liu, L. et al., *Leukocyte PI3Kgamma and PI3Kdelta have temporally distinct roles for leukocyte recruitment in vivo*. Blood, 2007. 110(4): p. 1191-8.] and T cell development [Webb, L. M., et al., *Cutting edge: T cell development requires the combined activities of the p110gamma and p110delta catalytic isoforms of phosphatidylinositol 3-kinase*. J Immunol, 2005. 175(5): p. 2783-7.]. The simultaneous genetic inactivation of PI3Kδ and PI3Kδ in mice leads to more severe impairment of thymocyte development, and multiple organ inflammation [Ji, H., et al., *Inactivation of PI3Kgamma and PI3Kdelta distorts T-cell development and causes multiple organ inflammation*. Blood, 2007. 110(8): p. 2940-7.] than in the mice with the deficiency of each isoform alone [Swat, W., et al., *Essential role of PI3Kdelta and PI3Kgamma in thymocyte survival*. Blood, 2006. 107(6): p. 2415-22.].

Therefore, there is a need of PI3Kδ inhibitors with higher selectivity against PI3Kα, β and γ as the selective PI3Kδ inhibitors are expected to have improved safety profile and would provide new therapeutic options for APDS, autoimmune and inflammatory disorders as well as cancer, e.g., glioblastoma.

SUMMARY OF THE INVENTION

The above need is met by the compounds, compositions and methods disclosed herein.

Disclosed herein is a compound of Formula (I),

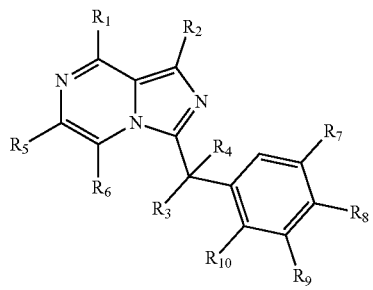

(I)

or a stereoisomer thereof, or a phamaceutically acceptable salt thereof, wherein:

$R_1$ is —$NR_aR_b$, wherein $R_a$ and $R_b$ are each independently hydrogen or $C_{1-6}$alkyl;

$R_2$ is hydrogen, F, Cl, Br, —$C_{1-6}$alkyl, —$C_{2-6}$alkenyl, —$C_{2-6}$alkynyl, cycloalkyl, heterocyclyl, aryl, heteroaryl, —CN, —$NO_2$, —$OR_{12}$, —$SO_2R_{12}$, —$COR_{12}$, —$CO_2R_{12}$, —$CONR_{12}R_{13}$, —$C(=NR_{12})NR_{13}R_{14}$, —$NR_{12}R_{13}$, —$NR_{12}COR_{13}$, —$NR_{12}CONR_{13}R_{14}$, —$NR_{12}CO_2R_{13}$, —$NR_{12}SONR_{13}R_{14}$, —$NR_{12}SO_2NR_{13}R_{14}$, or —$NR_{12}SO_2R_{13}$; wherein said —$C_{1-6}$alkyl, —$C_{2-6}$alkenyl, —$C_{2-6}$alkynyl, cycloalkyl, heterocyclyl, aryl or heteroaryl are each independently optionally substituted with at least one substituent $R_{11a}$;

$R_3$ and $R_4$, which may be the same or different, are each independently hydrogen, —$C_{1-6}$alkyl, cycloalkyl, heterocyclyl, aryl, or heteroaryl;

$R_5$ and $R_6$, which may be the same or different, are each independently hydrogen, halogen, —$C_{1-6}$alkyl, —$C_{2-6}$alkenyl, —$C_{2-6}$alkynyl, cycloalkyl, heterocyclyl, aryl, heteroaryl, —CN, —$NO_2$, —$OR_{12}$, —$SO_2R_{12}$, —$COR_{12}$, —$CO_2R_{12}$, —$CONR_{12}R_{13}$, —$C(=NR_{12})NR_{13}R_{14}$, —$NR_{12}R_{13}$, —$NR_{12}COR_{13}$, —$NR_{12}CONR_{13}R_{14}$, —$NR_{12}CO_2R_{13}$, —$NR_{12}SONR_{13}R_{14}$, —$NR_{12}SO_2NR_{13}R_{14}$, or —$NR_{12}SO_2R_{13}$; wherein said —$C_{1-6}$alkyl, —$C_{2-6}$alkenyl, —$C_{2-6}$alkynyl, cycloalkyl, heterocyclyl, aryl or heteroaryl are each independently optionally substituted with at least one substituent $R_{11a}$;

$R_7$, $R_8$ and $R_{10}$, which may be the same or different, are each independently hydrogen, halogen, —$C_{1-6}$alkyl, —$C_{2-6}$alkenyl, —$C_{2-6}$alkynyl, cycloalkyl, heterocyclyl, aryl, heteroaryl, —CN, —$NO_2$, —$OR_{12}$, —$SO_2R_{12}$, —$COR_{12}$, —$CO_2R_{12}$, —$CONR_{12}R_{13}$, —$C(=NR_{12})NR_{13}R_{14}$, —$NR_{12}R_{13}$, —$NR_{12}COR_{13}$, —$NR_{12}CONR_{13}R_{14}$, —$NR_{12}CO_2R_{13}$, —$NR_{12}SONR_{13}R_{14}$, —$NR_{12}SO_2NR_{13}R_{14}$, or —$NR_{12}SO_2R_{13}$; wherein said —$C_{1-6}$alkyl, —$C_{2-6}$alkenyl, —$C_{2-6}$alkynyl, cycloalkyl, heterocyclyl, aryl or heteroaryl are each independently optionally substituted with at least one substituent $R_{11c}$;

$R_9$ is —CN, —$NO_2$, —$OR_{12}$, —$SO_2R_{12}$, —$SO_2NR_{12}R_{13}$, —$COR_{12}$, —$CO_2R_{12}$, —$CONR_{12}R_{13}$, —$C(=NR_{12})NR_{13}R_{14}$, —$NR_{12}COR_{13}$, —$NR_{12}CONR_{13}R_{14}$, —$NR_{12}CO_2R_{13}$, —$NR_{12}SONR_{13}R_{14}$, —$NR_{12}SO_2NR_{13}R_{14}$, or —$NR_{12}SO_2R_{13}$;

$R_{11a}$, $R_{11b}$, and $R_{11c}$, which may be the same or different, are each independently hydrogen, halogen, —$C_{1-6}$alkyl, —$C_{2-6}$alkenyl, —$C_{2-6}$alkynyl, halo$C_{1-6}$alkyl haloC$_{2-6}$alkenyl, haloC$_{2-6}$alkynyl, cycloalkyl, heterocyclyl, aryl, heteroaryl, —CN, —$NO_2$, oxo, —$OR_{12}$, —$SO_2R_{12}$; —$COR_{12}$, —$CO_2R_{12}$, —$CONR_{12}R_{13}$, —$C(=NR_{12})NR_{13}R_{14}$, —$NR_{12}R_{13}$, —$NR_{12}CONR_{13}$, —$NR_{12}CONR_{13}R_{14}$, —$NR_{12}CO_2R_{13}$, —$NR_{12}SONR_{13}R_{14}$, —$NR_{12}SO_2NR_{13}R_{14}$, or —$NR_{12}SO_2R_{13}$; and $R_{12}$, $R_{13}$, and $R_{14}$, which may be the same or different, are each independently hydrogen, —$C_{1-6}$alkyl, —$C_{2-6}$alkenyl, —$C_{2-6}$alkynyl, cycloalkyl, heterocyclyl, aryl, or heteroaryl, wherein said $C_{1-6}$alkyl, —$C_{2-6}$alkenyl, —$C_{2-6}$alkynyl, cycloalkyl, heterocyclyl, aryl, or heteroaryl are each independently optionally substituted with at least one substituent $R_{15}$;

Alternatively, ($R_{12}$ and $R_{13}$), or ($R_{13}$ and $R_{14}$), or ($R_{12}$ and $R_{14}$), together with the atom(s) to which they are attached, form a 3- to 12-membered saturated, partially or fully unsaturated ring comprising 0, 1 or 2 additional heteroatoms independently selected from —NH, —O—, —S—, —SO— or —SO$_2$—, and said ring is optionally substituted with at least one substituent R$_{15}$;

R$_{15}$, at each of its occurrences, is independently hydrogen, halogen, —C$_{1-6}$alkyl, —C$_{2-6}$alkenyl, —C$_{2-6}$alkynyl, cycloalkyl, heterocyclyl, aryl, heteroaryl, —CN, —NO$_2$, oxo, —OR$_{16}$, —SO$_2$R$_{16}$, —COR$_{16}$, —CO$_2$R$_{16}$, —CONR$_{16}$R$_{12}$, —C(=NR$_{16}$)NR$_{17}$R$_{18}$, —NR$_{16}$R$_{17}$, —C$_{1-6}$alkyl-NR$_{16}$R$_{17}$, —NR$_{16}$COR$_{17}$, —NR$_{16}$CONR$_{17}$R$_{18}$, —NR$_{16}$CO$_2$R$_{17}$, —NR$_{16}$SONR$_{17}$R$_{18}$, —NR$_{16}$SO$_2$NR$_{17}$R$_{17}$R$_{18}$, or —NR$_{16}$SO$_2$R$_{17}$, wherein said C$_{1-6}$alkyl, —C$_{2-6}$alkenyl, —C$_{2-6}$alkynyl, cycloalkyl, heterocyclyl, aryl, or heteroaryl are each independently optionally substituted with halogen, R$_{19}$, —OR$_{19}$, —COR$_{19}$, —SO$_2$R$_{19}$, or —CO$_2$R$_{19}$;

wherein each of R$_{16}$, R$_{12}$, or R$_{18}$ is independently hydrogen, —C$_{1-6}$alkyl, —C$_{2-6}$alkenyl, —C$_{2-6}$alkynyl, haloC$_{1-6}$alkyl, haloC$_{2-6}$alkenyl, haloC$_{2-6}$alkynyl, cycloalkyl, heterocyclyl, aryl, or heteroaryl; or (R$_{16}$ and R$_{17}$), or (R$_{16}$ and R$_{18}$), or (R$_{17}$ and R$_{18}$), together with the atoms) to which they are attached, form a 3- to 12-membered saturated, partially or fully unsaturated ring comprising 0, 1 or 2 additional heteroatoms independently selected from —NH, —O—, —S—, —SO— or —SO$_2$—, and said ring is optionally substituted with at least one substituent R$_{19}$; and wherein R$_{19}$ is independently hydrogen, —C$_{1-6}$alkyl, —C$_{2-6}$alkenyl, —C$_{2-6}$alkynyl, haloC$_{1-6}$alkyl, haloC$_{2-6}$alkenyl, cycloalkyl, heterocyclyl, aryl, or heteroaryl, wherein said cycloalkyl, heterocyclyl, aryl, or heteroaryl are each optionally substituted with halogen, —C$_{1-6}$alkyl, —C$_{2-6}$alkenyl, haloC$_{1-6}$alkyl, haloC$_{2-6}$alkenyl, or haloC$_{2-6}$alkynyl; and wherein said —C$_{1-6}$alkyl, —C$_{2-6}$alkenyl, —C$_{2-6}$alkynyl, haloC$_{1-6}$alkyl, haloC$_{2-6}$alkenyl, or haloC$_{2-6}$alkynyl are each optionally substituted with cycloalkyl, heterocyclyl, aryl, or heteroaryl.

Disclosed herein also is a pharmaceutical composition, comprising a therapeutically effective amount of a compound of Formula (I), or a stereoisomer thereof or a pharmaceutically acceptable salt thereof disclosed herein, and a pharmaceutically acceptable excipient.

The compound of Formula (I) disclosed herein is useful as a PI3K inhibitor, in particular, a PI3Kδ inhibitor. The compound of Formula (I) disclosed herein is thus useful in treating or preventing idiopathic thrombocytopenic purpura (ITP), autoimmune hemolytic anemia, vasculitis, systemic lupus erythematosus, lupus nephritis, pemphigus, membranous nephropathy, chronic lymphocytic leukemia (CLL), Non-Hodgkin lymphoma (NHL), hairy cell leukemia, Mantle cell lymphoma, small lymphocytic lymphoma, follicular lymphoma, lymphoplasmacytic lymphoma, extranodal marginal zone lymphoma, activated B-cell like (ABC) diffuse large B cell lymphoma, or germinal center B cell (GCB) diffuse large B cell lymphoma in a subject. Thus, compositions and methods for treating various disorders or diseases mentioned above using the compound of Formula (I) are disclosed herein, and use of the compound of Formula (I) in manufacturing medicine for treating various disorders or diseases mentioned above, are also disclosed herein.

DETAILED DESCRIPTION OF THE INVENTION

In the first aspect, disclosed herein is a compound of Formula (I),

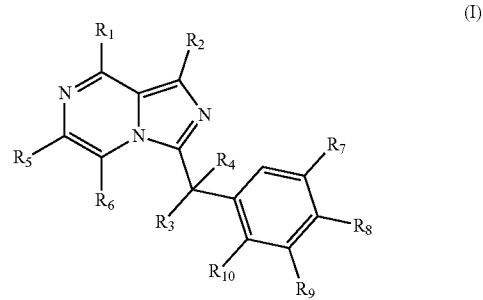

or a stereoisomer thereof, or a pharmaceutically acceptable salt thereof, wherein:

R$_1$ is —NR$_a$R$_b$, wherein R$_a$ and R$_b$ are each independently hydrogen or C$_{1-6}$alkyl;

R$_2$ is hydrogen, F, Cl, Br, —C$_{1-6}$alkyl, —C$_{2-6}$alkenyl, —C$_{2-6}$alkynyl, cycloalkyl, heterocyclyl, aryl, heteroaryl, —CN, —NO$_2$, —OR$_{12}$, —SO$_2$R$_{12}$, —COR$_{12}$, —CO$_2$R$_{12}$, —CONR$_{12}$R$_{13}$, —C(=NR$_{12}$)NR$_{13}$R$_{14}$, —NR$_{12}$R$_{13}$, —NR$_{12}$COR$_{13}$, —NR$_{12}$CONR$_{13}$R$_{14}$, —NR$_{12}$CO$_2$R$_{13}$, —NR$_{12}$SONR$_{13}$R$_{14}$, —NR$_{12}$SO$_2$NR$_{13}$R$_{14}$, or —NR$_{12}$SO$_2$R$_{13}$; wherein said —C$_{1-6}$alkyl, —C$_{2-6}$alkenyl, —C$_{2-6}$alkynyl, cycloalkyl, heterocyclyl, aryl or heteroaryl are each independently optionally substituted with at least one substituent R$_{11a}$;

R$_3$ and R$_4$, which may be the same or different, are each independently hydrogen, —C$_{1-6}$alkyl, cycloalkyl, heterocyclyl, aryl, or heteroaryl;

R$_5$ and R$_6$, which may be the same or different, are each independently hydrogen, halogen, —C$_{2-6}$alkenyl, —C$_{2-6}$alkynyl, —C$_{2-6}$alkynyl, cycloalkyl, heterocyclyl, aryl, heteroaryl, —CN, —NO$_2$, —OR$_{12}$, —SO$_2$R$_{12}$, —COR$_{12}$, —CO$_2$R$_{12}$, —CONR$_{12}$R$_{13}$, —C(=NR$_{12}$)NR$_{13}$R$_{14}$, —NR$_{12}$R$_{13}$, —NR$_{12}$COR$_{13}$, —NR$_{12}$CONR$_{13}$R$_{14}$, —NR$_{12}$CO$_2$R$_{13}$, —NR$_{12}$SONR$_{13}$R$_{14}$, —NR$_{12}$SO$_2$NR$_{13}$R$_{14}$, or —NR$_{12}$SO$_2$R$_{13}$; wherein said —C$_{1-6}$alkyl, —C$_{2-6}$alkenyl, —C$_{2-6}$alkynyl, cycloalkyl, heterocyclyl, aryl or heteroaryl are each independently optionally substituted with at least one substituent R$_{11b}$;

R$_7$, R$_8$ and R$_{10}$, which may be the same or different, are each independently hydrogen, halogen, —C$_{1-6}$alkyl, —C$_{2-6}$alkenyl, —C$_{2-6}$alkynyl, cycloalkyl, heterocyclyl, aryl, heteroaryl, —CN, —NO$_2$, —OR$_{12}$, —SO$_2$R$_{12}$, —COR$_{12}$, —CO$_2$R$_{12}$, —CONR$_{12}$R$_{13}$, —C(=NR$_{12}$)NR$_{13}$R$_{14}$, —NR$_{12}$R$_{13}$, —NR$_{12}$COR$_{13}$, —NR$_{12}$CONR$_{13}$R$_{14}$, —NR$_{12}$CO$_2$R$_{13}$, —NR$_{12}$SONR$_{13}$R$_{14}$, —NR$_{12}$SO$_2$NR$_{13}$R$_{14}$, or —NR$_{12}$SO$_2$R$_{13}$; wherein said —C$_{1-6}$alkyl, —C$_{2-6}$alkenyl, —C$_{2-6}$alkynyl, cycloalkyl, heterocyclyl, aryl or heteroaryl are each independently optionally substituted with at least one substituent R$_{11c}$;

R$_9$ is —CN, —NO$_2$, —OR$_{12}$, —SO$_2$R$_{12}$, —SO$_2$NR$_{12}$R$_{13}$, —COR$_{12}$, —CO$_2$R$_{12}$, —CONR$_{12}$R$_{13}$, —C(=NR$_{12}$)NR$_{13}$R$_{14}$, —NR$_{12}$COR$_{13}$, —NR$_{12}$CONR$_{13}$R$_{14}$, —NR$_{12}$CO$_2$R$_{13}$, —NR$_{12}$SONR$_{13}$R$_{14}$, —NR$_{12}$CO$_2$R$_{13}$, —NR$_{12}$SONR$_{13}$R$_{14}$, —NR$_{12}$SO$_2$NR$_{13}$R$_{14}$, or —NR$_{12}$SO$_2$R$_{13}$; and R$_{11a}$, R$_{11b}$, and R$_{11c}$, which may be the same or different, are each independently hydrogen hydrogen, halogen, —C$_{1-6}$alkyl, —C$_{2-6}$alkenyl, —C$_{2-6}$alkynyl, haloC$_{1-6}$alkenyl, haloC$_{2-6}$alkenyl, haloC$_{2-6}$alkynyl, cycloalkyl, heterocyclyl, aryl, heteroaryl, —CN, —NO$_2$, oxo, —OR$_{12}$, —SO$_2$R$_{12}$, —COR$_{12}$, —CO$_2$R$_{12}$, —CONR$_{12}$R$_{13}$, —C(=NR$_{12}$)NR$_{13}$R$_{14}$, —NR$_{12}$R$_{13}$, —NR$_{12}$COR$_{13}$, —NR$_{12}$CONR$_{13}$R$_{14}$, —NR$_{12}$CO$_2$R$_{13}$, —NR$_{12}$SONR$_{13}$R$_{14}$, —NR$_{12}$SO$_2$NR$_{13}$R$_{14}$, or —NR$_{12}$SO$_2$R$_{13}$; and R$_{12}$, R$_{13}$, and R$_{14}$, which may be the same or different, are each independently hydrogen, —C$_{1-6}$alkyl, —C$_{2-6}$alkynyl, —C$_{2-6}$alkynyl, cycloalkyl, heterocyclyl, acyl, or heteroaryl, wherein said C$_{1-6}$alkyl, —C$_{2-6}$alkenyl, —C$_{2-6}$alkynyl, cycloalkyl, heterocyclyl, aryl, or heteroaryl are each independently optionally substituted with at least one substituent R$_{15}$;

Alternatively, (R$_{12}$ and R$_{13}$), or (R$_{13}$ and R$_{14}$), or (R$_{12}$ and R$_{14}$), together with the atom(s) to which they are attached, form a 3- to 12-membered saturated, partially or fully unsaturated ring comprising 0, 1 or 2 additional heteroatoms independently selected from —NH, —O—, —S—, —SO— or —SO$_2$—, and said ring is optionally substituted with at least one substituent R$_{15}$;

R$_{15}$, at each of its occurrences, is independently hydrogen, halogen, —C$_{1-6}$alkyl, —C$_{2-6}$alkenyl, —C$_{2-6}$alkynyl, cycloalkyl, heterocyclyl, aryl, heteroaryl, —CN, —NO$_2$, oxo, —OR$_{16}$, —SO$_2$R$_{16}$, —COR$_{16}$, —CO$_2$R$_{16}$, —CONR$_{16}$R$_{17}$, —C(=NR$_{16}$)NR$_{17}$R$_{18}$, —NR$_{16}$R$_{17}$, —C$_{1-6}$alkyl-NR$_{16}$R$_{17}$, —NR$_{16}$COR$_{17}$, —NR$_{16}$CONR$_{17}$R$_{18}$, —NR$_{16}$CO$_2$R$_{17}$, —NR$_{16}$SONR$_{17}$R$_{18}$, —NR$_{16}$SO$_2$NR$_{17}$R$_{18}$, or —NR$_{16}$SO$_2$R$_{17}$, wherein said C$_{1-6}$alkyl, —C$_{2-6}$alkenyl, —C$_{2-6}$alkynyl, cycloalkyl, heterocyclyl, aryl, or heteroaryl are each independently optionally substituted with halogen, R$_{19}$, —OR$_{19}$, —COR$_{19}$, —SO$_2$R$_{19}$, or —CO$_2$R$_{19}$;

wherein each of R$_{16}$, R$_{17}$, or R$_{18}$ is independently hydrogen, —C$_{1-6}$alkyl, —C$_{2-6}$alkenyl, —C$_{2-6}$alkynyl, haloC$_{1-6}$alkyl, haloC$_{2-6}$alkenyl, haloC$_{2-6}$alkynyl, cycloalkyl, heterocyclyl, aryl, or heteroaryl; or (R$_{16}$ and R$_{17}$), or (R$_{16}$ and R$_{18}$), or (R$_{17}$ and R$_{18}$), together with the atom(s) to which they are attached, form a 3- to 12-membered saturated, partially or fully unsaturated ring comprising 0, 1 or 2 additional heteroatoms independently selected from —NH, —O—, —S—, —SO— or —SO$_2$—, and said ring is optionally substituted with at least one substituent R$_{19}$; and wherein R$_{19}$ is independently hydrogen, —C$_{1-6}$alkyl, —C$_{2-6}$alkenyl, —C$_{2-6}$alkynyl, haloC$_{1-6}$alkenyl, haloC$_{2-6}$alkynyl, haloC$_{2-6}$alkynyl, cycloalkyl, heterocyclyl, aryl, or heteroaryl, wherein said cycloalkyl, heterocyclyl, aryl, or heteroaryl are each optionally substituted with halogen, —C$_{1-6}$alkyl, —C$_{2-6}$alkenyl, —C$_{2-6}$alkynyl, haloC$_{1-6}$alkly, haloC$_{2-6}$alkenyl, or haloC$_{2-6}$alkynyl; and wherein said —C$_{1-6}$alkyl, —C$_{2-6}$alkenyl, —C$_{2-6}$alkynyl, haloC$_{1-6}$alkyl, haloC$_{2-6}$alkenyl, or haloC$_{2-6}$alkynyl are each optionally substituted with cycloalkyl, heterocyclyl, aryl, or heteroaryl.

In an embodiment of the first aspect, R$_1$ is —NH$_2$.

In an embodiment of the first aspect, R$_2$ is independently hydrogen, halogen, —C$_{1-6}$alkyl, C$_{3-6}$cycloalkyl or C$_{6-10}$aryl, and wherein —C$_{1-6}$alkyl, C$_{3-6}$cycloalkyl and C$_{6-10}$aryl are each independently optionally substituted with at least one substituent R$_{11a}$; preferably, R$_2$ is C$_{1-6}$alkyl; more preferably, R$_2$ is C$_{1-3}$alkyl; even more preferably, R$_2$ is methyl.

In an embodiment of the first aspect, R$_3$ and R$_4$ are each independently hydrogen or —C$_{1-6}$alkyl. In another embodiment of the first aspect, R$_3$ is hydrogen, and R$_4$ is —C$_{1-6}$alkyl; preferably, R$_3$ is hydrogen, and R$_4$ is —C$_{1-3}$alkyl; more preferably, R$_3$ is hydrogen, and R$_4$ is methyl.

In an embodiment of the first aspect, R$_5$ and R$_6$, which may be the same or different, are each independently hydrogen, halogen, —C$_{1-6}$alkyl, —C$_{2-6}$alkenyl, cycloalkyl, heterocyclyl, aryl, or heteroaryl, wherein said —C$_{1-6}$alkyl, —C$_{2-6}$alkenyl, —C$_{2-6}$alkynyl, cycloalkyl, heterocyclyl, aryl or heteroaryl are each independently optionally substituted with at least one substituent R$_{11b}$, wherein R$_{11b}$ is halogen. In a preferred embodiment, R$_5$ and R$_6$ are each independently hydrogen, halogen, or —C$_{1-6}$alkyl; in a further preferred embodiment, R$_5$ and R$_6$ are both hydrogen.

In an embodiment of the first aspect, R$_7$, R$_8$ and R$_{10}$, which may be the same or different, are each independently hydrogen, halogen, —C$_{1-6}$alkyl, —C$_{2-6}$alkynyl, —C$_{2-6}$alkynyl, cycloalkyl, heterocyclyl, aryl, heteroaryl, or —OR$_{12}$; wherein said —C$_{1-6}$alkyl, —C$_{2-6}$alkenyl, —C$_{2-6}$alkynyl, cycloalkyl, heterocyclyl, aryl or heteroaryl are each independently optionally substituted with at least one substituent R$_{11c}$, wherein R$_{11c}$ is halogen. In a preferred embodiment, R$_7$ and R$_8$ are each independently hydrogen, halogen or —C$_{1-6}$alkyl, and R$_{10}$ is —OR$_{12}$, In a more preferred embodiment, R$_7$ and R$_8$ are each independently halogen, and R$_{10}$ is C$_{1-6}$alkoxy. In an even more preferred embodiment, R$_7$ is Cl, R$_8$ is F, and R$_{10}$ is isopropoxy.

In an embodiment of the first aspect, R$_9$ is —CONR$_{12}$R$_{13}$, wherein R$_{12}$ and R$_{13}$ are as defined in Formula (I).

In a preferred embodiment, R$_9$ is —CONR$_{12}$R$_{13}$, wherein R$_{12}$ and R$_{13}$ are each hydrogen or C$_{1-6}$alklyl optionally substituted with at least one substituent R$_{15}$. More preferably, R$_{12}$ and R$_{13}$ are each hydrogen or methyl, ethyl, n-propyl or isopropyl, each optionally substituted with at least one substituent R$_{15}$. In this embodiment, R$_{15}$ is preferably hydrogen, cycloalkyl, aryl, heterocyclyl, —OR$_{16}$, or —NR$_{16}$R$_{17}$, wherein R$_{16}$ and R$_{17}$ are as defined in Formula (I) and wherein said cycloalkyl, aryl, or heterocyclyl are each independently optionally substituted with halogen, R$_{19}$, —OR$_{19}$, —COR$_{19}$, —SO$_2$R$_{19}$, or —CO$_2$R$_{19}$, wherein R$_{19}$ is as defined in Formula (I).

In a preferred embodiment, R$_9$ is —CONR$_{12}$R$_{13}$, wherein R$_{12}$ and R$_{13}$ are each hydrogen or C$_{1-6}$alklyl optionally substituted with one substituent R$_{15}$, which is heterocyclyl optionally substituted with halogen, R$_{19}$, —OR$_{19}$, —COR$_{19}$, —SO$_2$R$_{19}$, or —CO$_2$R$_{19}$, wherein R$_{19}$ is as defined in Formula (I). More preferably, R$_{12}$ is hydrogen and R$_{13}$ is C$_{1-6}$alklyl optionally substituted with one substituent R$_{15}$, which is heterocyclyl optionally substituted with halogen, R$_{19}$, —OR$_{19}$, —COR$_{19}$, —SO$_2$R$_{19}$, or —CO$_2$R$_{19}$, wherein R$_{19}$ is as defined in Formula (I). Even more preferably, the heterocyclyl group is a 4-, 5-, 6-, 7- or 8-membered saturated monocyclic ring comprising one nitrogen heteroatom or a 5-, 6-, 7- or 8-membered saturated monocyclic ring comprising one nitrogen atom and 1 additional heteroatom selected from —NH, —O—, —S—, —SO— or —SO$_2$—, optionally substituted with halogen, R$_{19}$, —OR$_{19}$, —COR$_{19}$, —SO$_2$R$_{19}$, or —CO$_2$R$_{19}$, wherein R$_{19}$ is as defined in Formula (I), Further even more preferably, the heterocyclyl group is piperidinyl (e.g., piperidin-1-yl or piperidin-4-yl) or piperazinyl (e.g., piperazin-1-yl) group optionally substituted with halogen, R$_{19}$, —OR$_{19}$, —COR$_{19}$, —SO$_2$R$_{19}$, or CO$_2$R$_{19}$, wherein R$_{19}$ is as defined in Formula (I). Further even more preferably, the heterocyclyl group is piperidinyl or piperazinyl group optionally substituted with halogen or C$_{1-6}$alkyl (e.g., methyl). Further even more preferably, R$_{12}$ is hydrogen, R$_{13}$ is ethyl and R$_{15}$ is 4-methylpiperazin-1-yl. Specifically, R$_9$ is

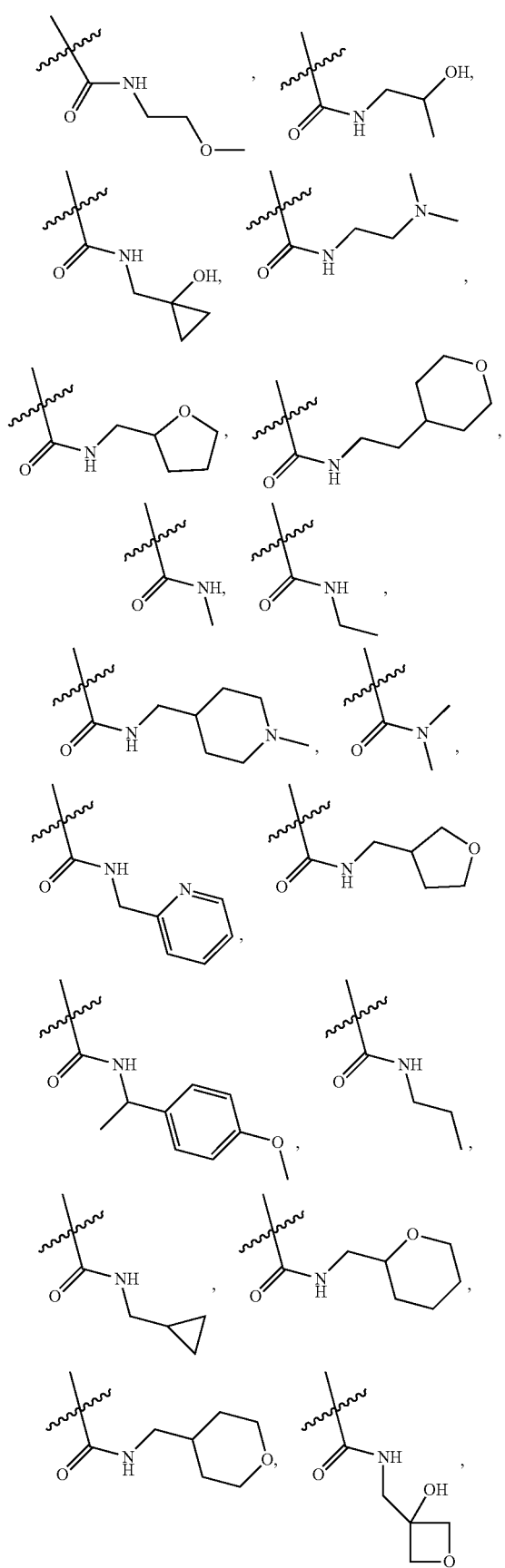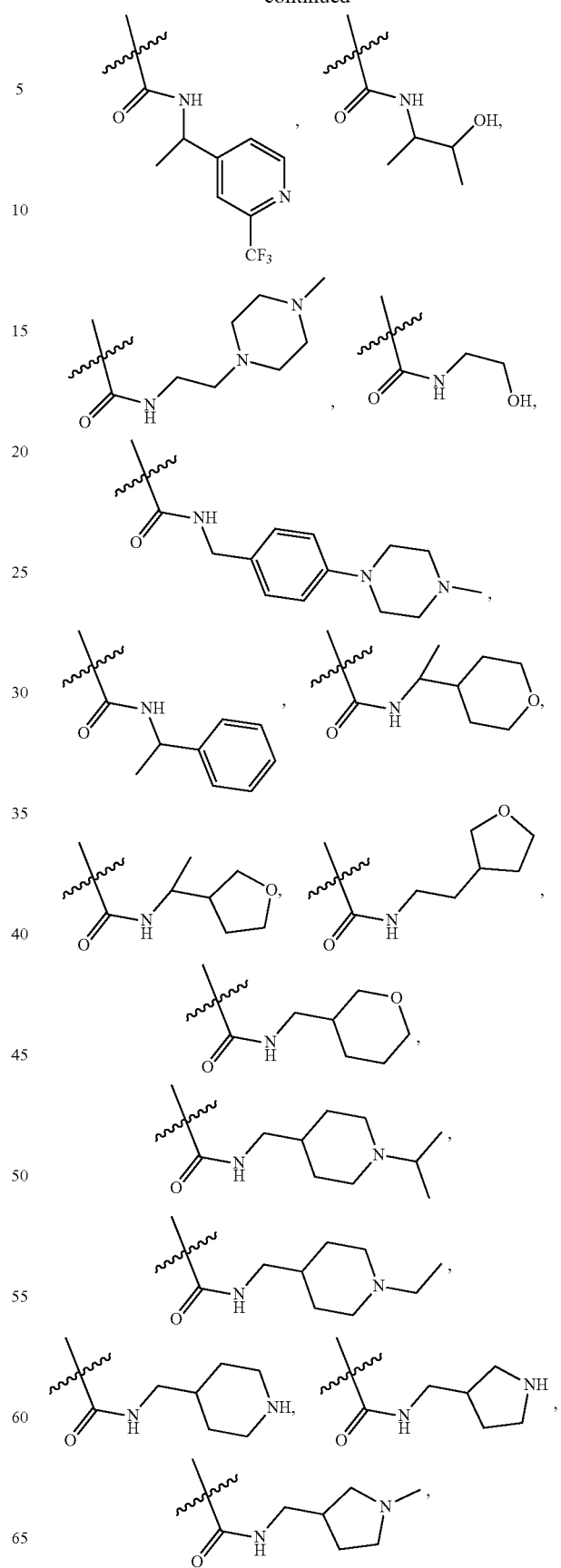

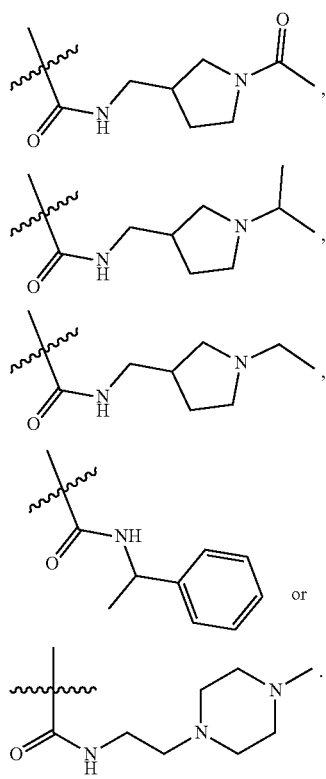

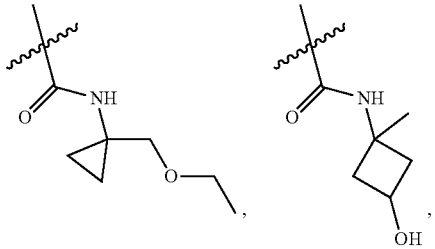

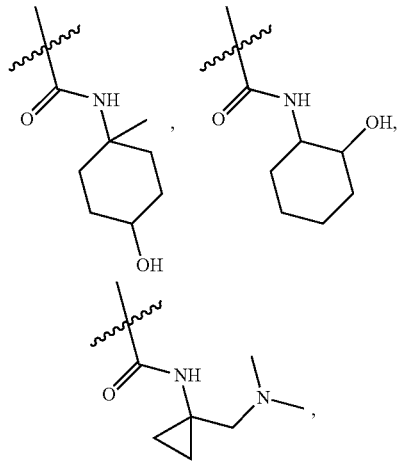

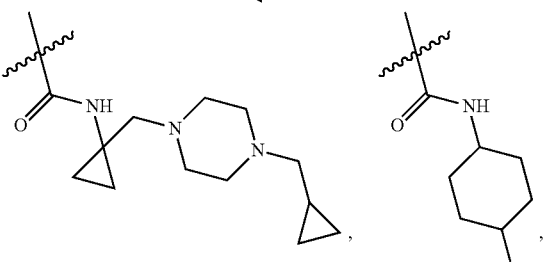

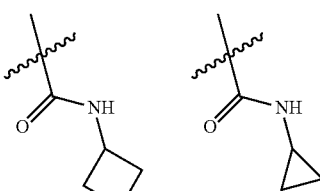

In a preferred embodiment, $R_9$ is —$CONR_{12}R_{13}$, wherein $R_{12}$ is hydrogen, and $R_{13}$ is cycloalkyl optionally substituted with at least one substituent $R_{15}$. More preferably, $R_{13}$ is a $C_3$-$C_8$ cycloalkyl optionally substituted with at least one substituent $R_{15}$. Even more preferably, $R_{13}$ is a cyclopropyl, cyclobutyl, cyclopentyl, or cyclohexyl, each optionally substituted with at least one substituent $R_{15}$. In this embodiment, $R_{15}$ is preferably —$OR_{16}$, or —$CO_2R_{16}$, or —$C_{1-6}$alkyl optionally substituted with —$OR_{19}$, wherein $R_{16}$ and $R_{19}$ are as defined in Formula (I). Specifically, $R_9$ is selected from

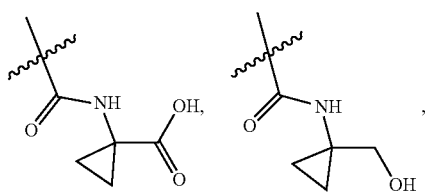

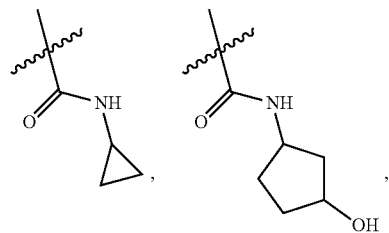

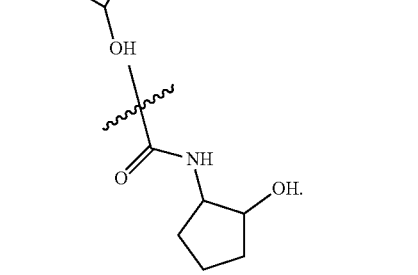

In a preferred embodiment, $R_9$ is —$CONR_{12}R_{13}$, wherein $R_{12}$ is hydrogen, and $R_{13}$ is a 5- to 8-membered heterocyclyl comprising 1 or 2 or 3 heteroatoms selected from O, NH, S, SO, or $SO_2$, optionally substituted with at least one substituent $R_{15}$. More preferably, $R_{13}$ is a 6-membered heterocyclyl comprising 1 or 2 heteroatoms selected from O or NH, optionally substituted with at least one substituent $R_{15}$. Even more preferably, $R_{13}$ is tetrahydrofuranyl or tetrahydropyranyl, each optionally substituted with at least one substituent R$_{15}$. In this embodiment, R$_{15}$ is preferably halogen or —C$_{1-6}$alkyl. Specifically, R$_9$ is

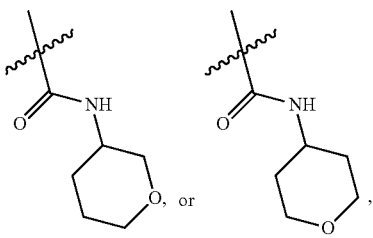 [SMILES: *C(=O)NC1CCCOC1 ; *C(=O)NC1CCOCC1]

In a preferred embodiment, R$_9$ is —CONR$_{12}$R$_{13}$, wherein R$_{12}$ is hydrogen, and R$_{13}$ is an aryl group selected from phenyl and naphthyl, optionally substituted with at least one substituent R$_{15}$. In this embodiment, R$_{15}$ is preferably halogen, —C$_{1-6}$alkyl, —OR$_{16}$, or heterocyclyl optionally substituted with halogen, R$_{19}$, or —OR$_{19}$, wherein R$_{16}$ and R$_{19}$ are as defined in Formula (I). Specifically, R$_9$ is selected from In a preferred embodiment, R$_9$ is —CONR$_{12}$R$_{13}$, wherein R$_{12}$ and R$_{13}$ together with the nitrogen atom to which they are attached, form a 3- to 12-membered saturated, partially or fully unsaturated ring comprising 0, 1 or 2 additional heteroatoms independently selected from —NH—, —O—, —S—, —SO— or —SO$_2$—, and said ring is optionally substituted with at least one substituent R$_{15}$.

More preferably, R$_9$ is —CONR$_{12}$R$_{13}$, wherein R$_{12}$ and R$_{13}$ together with the nitrogen atom to which they are attached, form a 4-, or 5- or 6- or 7- or 8-membered saturated monocyclic ring comprising 0 additional heteroatom, and said ring is optionally substituted with at least one substituent R$_{15}$. Specifically, R$_{12}$ and R$_{13}$ together with the nitrogen atom to which they are attached, form a azetidinyl, pyrrolidinyl, piperidinyl, azepanyl, or azocanyl ring, preferably, a azetidinyl, pyrrolidinyl, or piperidinyl ring. In this embodiment, R$_{15}$ is preferably halogen, —OR$_{16}$, —CO$_2$R$_{16}$, or —C$_{1-6}$alkyl optionally substituted with —OR$_{19}$, wherein R$_{16}$ and R$_{19}$ are as defined in Formula (I).

More preferably, R$_9$ is —CONR$_{12}$R$_{13}$, wherein R$_{12}$ and R$_{13}$ together with the nitrogen atom to which they are attached, form a 5-, 6-, 7- or 8-membered saturated monocyclic ring comprising 1 additional heteroatom selected from —NH—, —O—, —S—, —SO— or —SO$_2$—, and said ring is optionally substituted with at least one substituent R$_{15}$. Even more preferably, R$_{12}$ and R$_{13}$ together with the nitrogen atom to which they are attached, form a morpholinyl or piperazinyl ring, each of which is optionally substituted with at least one substituent R$_{15}$. In this embodiment, R$_{15}$ is preferably hydrogen, halogen, —C$_{1-6}$alkyl, or cycloalkyl, wherein said C$_{1-6}$alkyl, or cycloalkyl are each independently optionally substituted with halogen, R$_{19}$, —OR$_{19}$, —COR$_{19}$, or —CO$_2$R$_{19}$, wherein R$_{19}$ is as defined in Formula (I).

More preferably, R$_9$ is —CONR$_{12}$R$_{13}$, wherein R$_{12}$ and R$_{13}$ together with the nitrogen atom to which they are attached, form a 7- to 12-membered (e.g., 7-membered, 8-membered, 9-membered, 10-membered) saturated bicyclic ring comprising 0 or 1 or 2 additional heteroatoms selected from —N, —O—, —S—, —SO— or —SO$_2$—, and said ring is optionally substituted with at least one substituent R$_{15}$. Even more preferably, R$_{12}$ and R$_{13}$ together with the nitrogen atom to which they are attached, form a bicyclic bridged or spiro-ring comprising 0 or 1 or 2 additional heteroatoms selected from —N, —O—, —S—, —SO— or —SO$_2$— and optionally substituted with at least one substituent R$_{15}$. The examples of bicyclic bridged or spiro-rings include, but not limited to

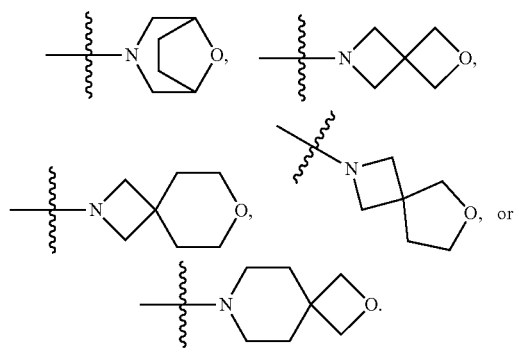

For example, R$_9$ is selected from

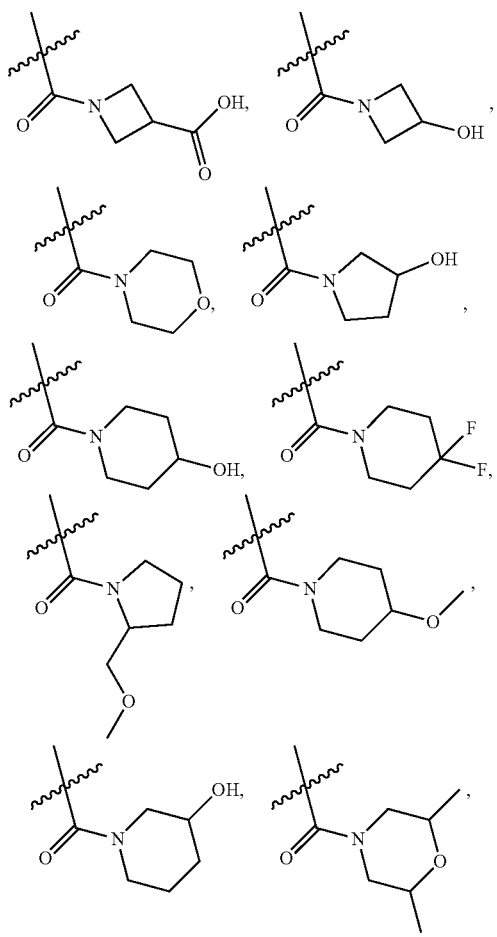

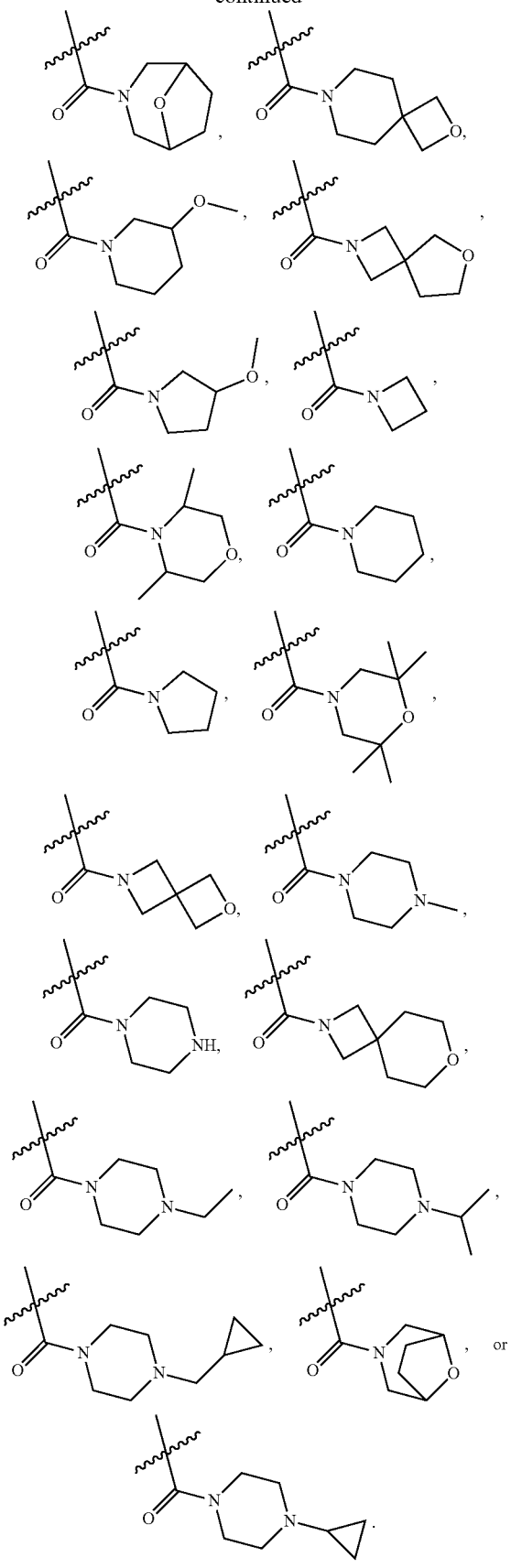

In an embodiment of the first aspect, $R_{10}$ is methoxy, ethoxy, propoxy, or isopropoxy. Preferably, $R_{10}$ is isopropoxy.
In an embodiment of the first aspect, wherein the carbon atom to which $R_3$ and $R_4$ are attached is in (S)-configuration when $R_3$ and $R_4$ are different.
In an embodiment of the first aspect, disclosed herein is a compound selected from:
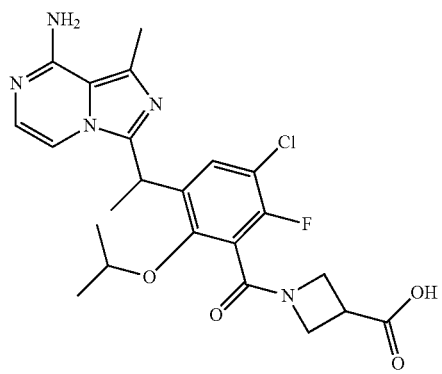
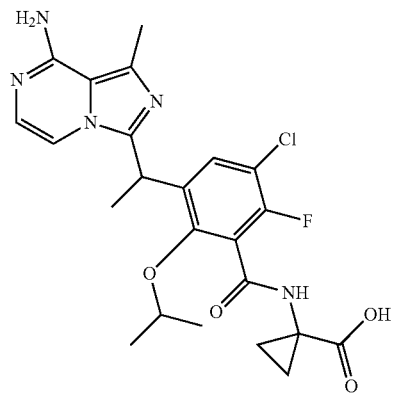
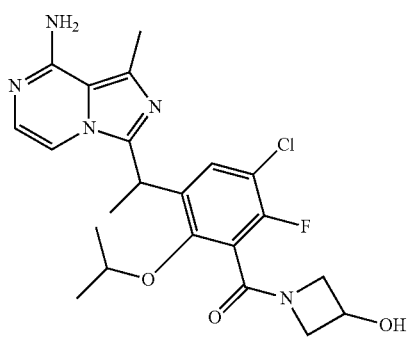
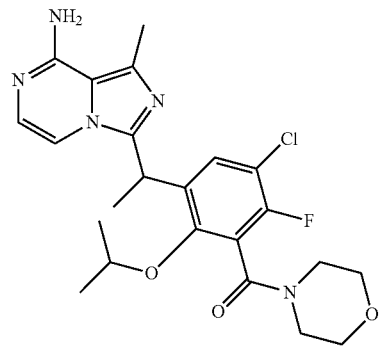
-continued
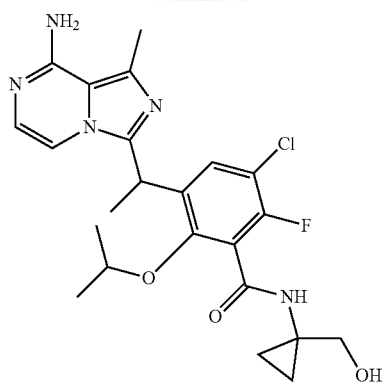
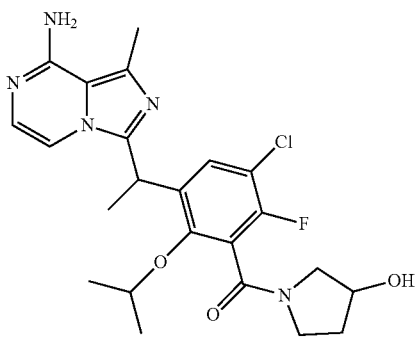
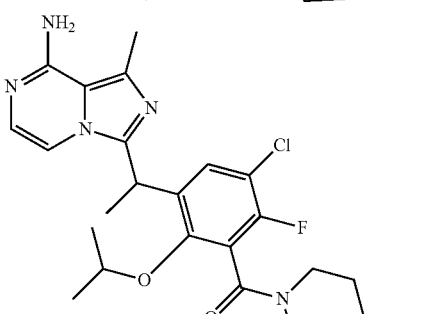
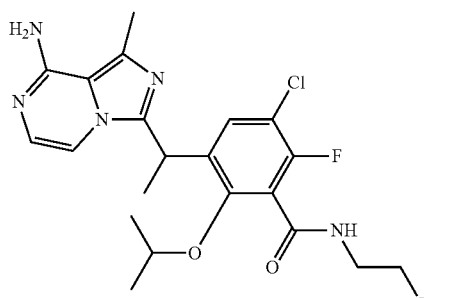
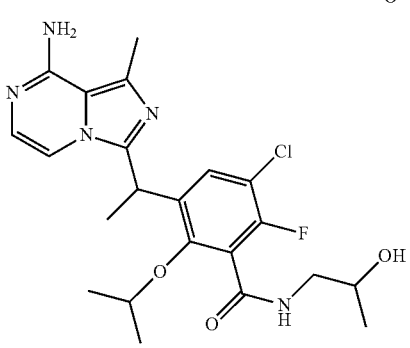

-continued
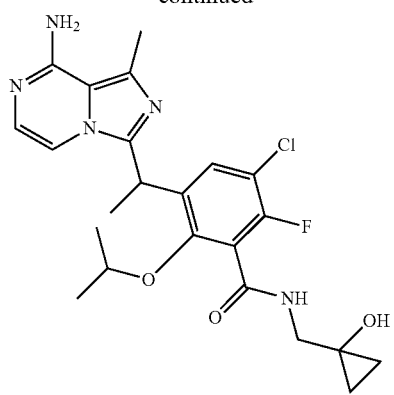
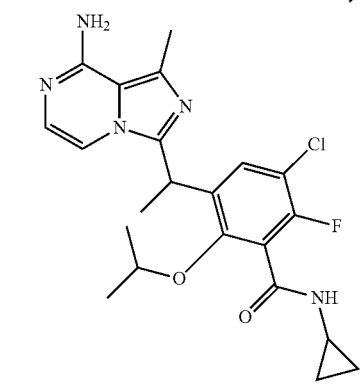
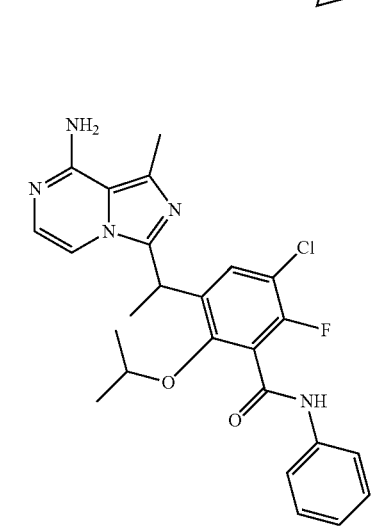
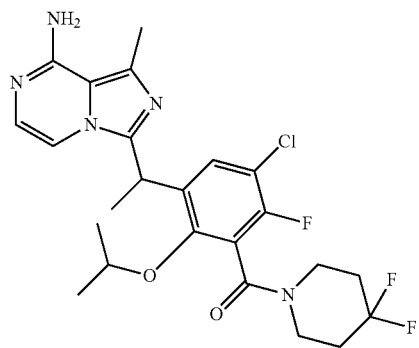
-continued
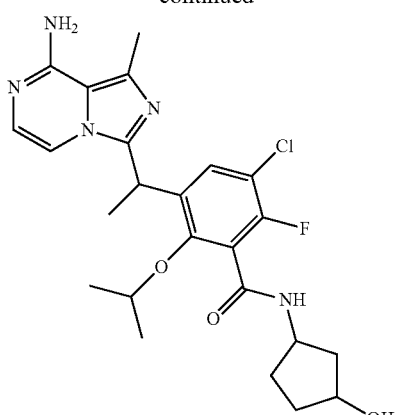
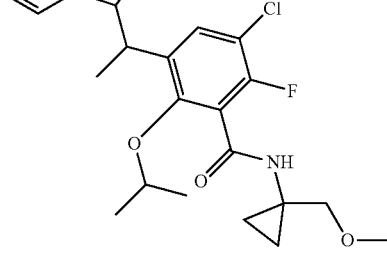
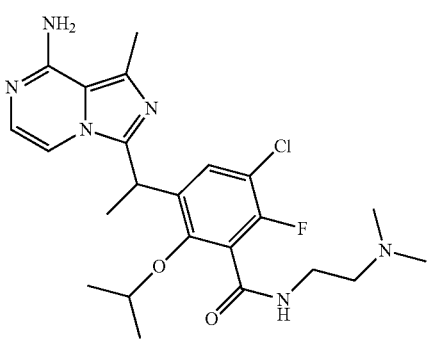
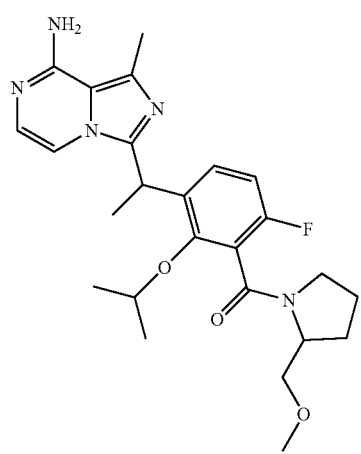

-continued
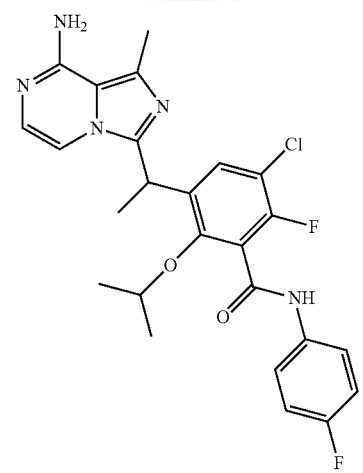
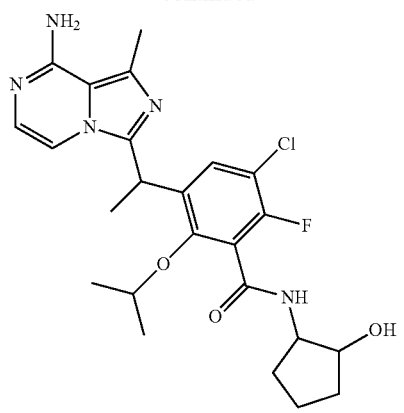
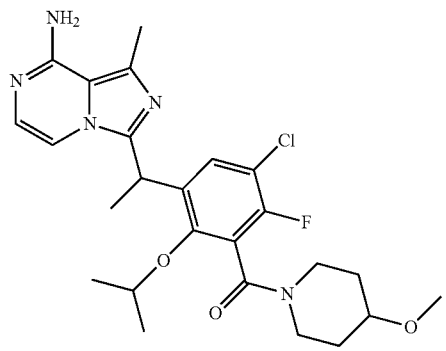
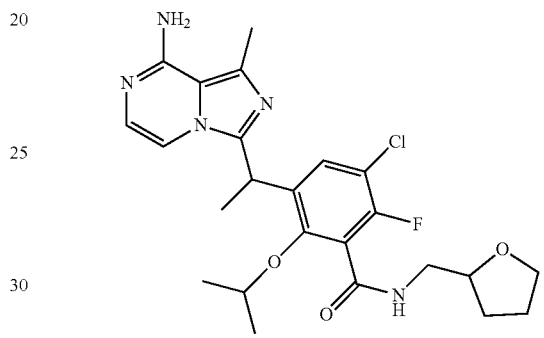
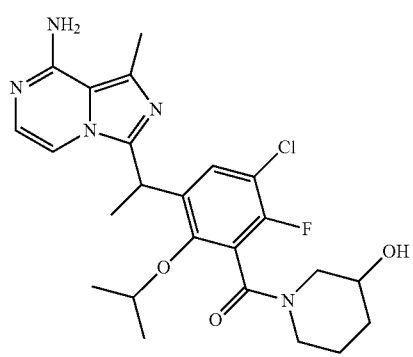
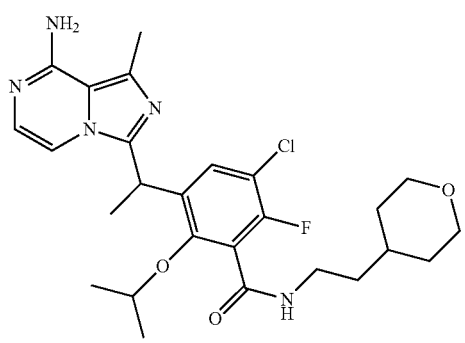
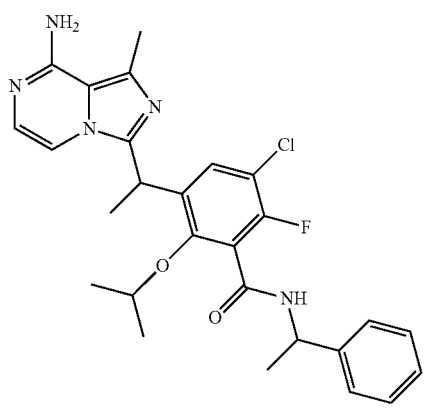
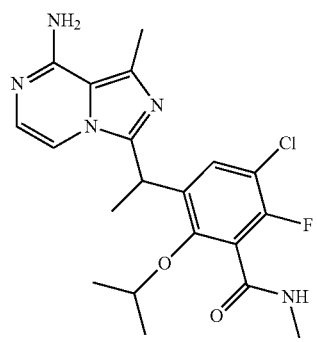

-continued
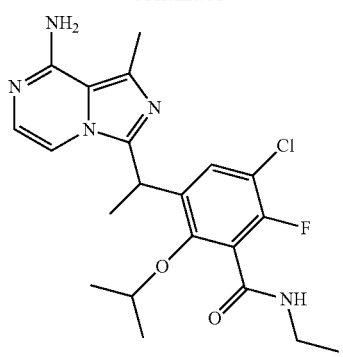
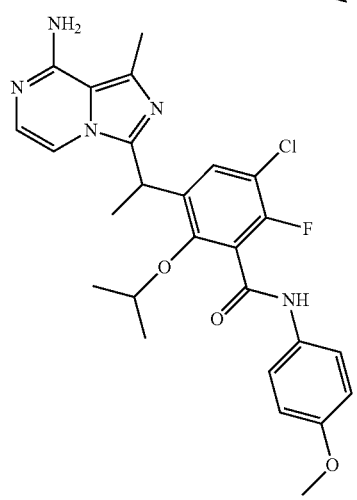
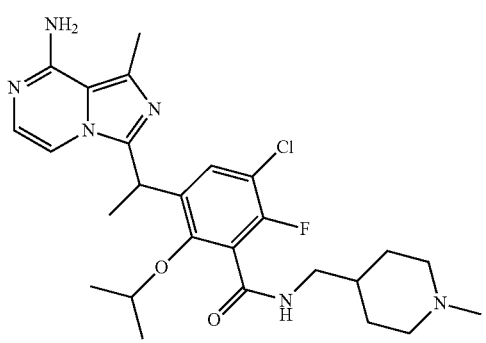
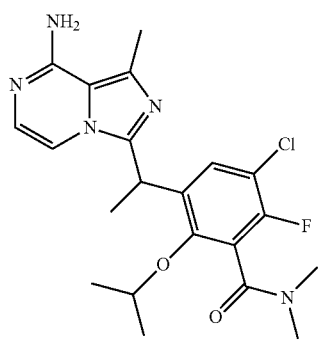
-continued
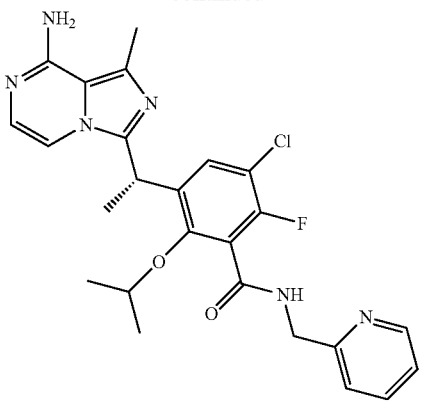
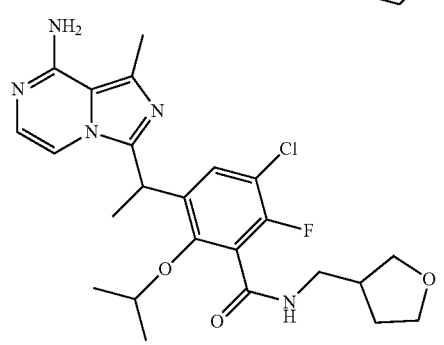
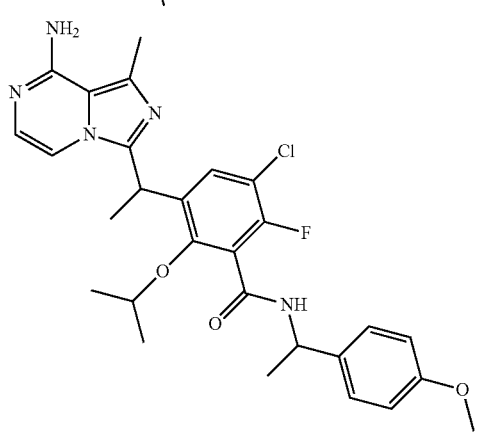
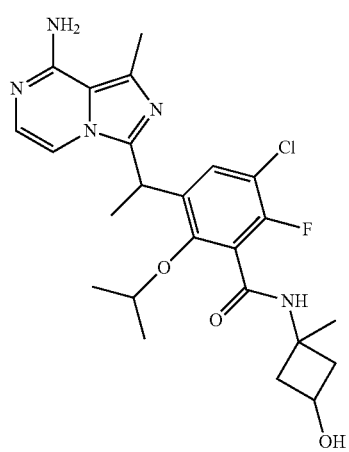

27
-continued
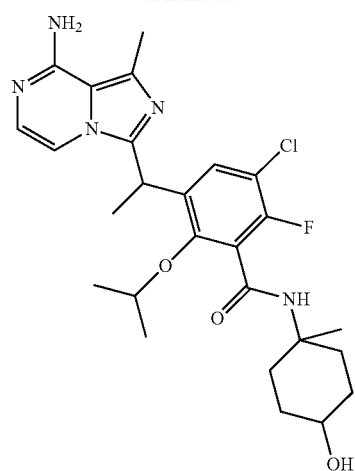
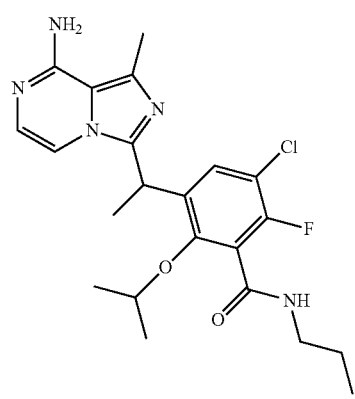
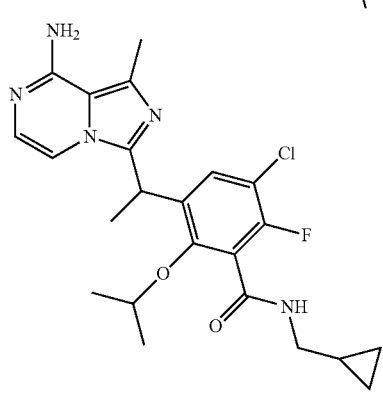
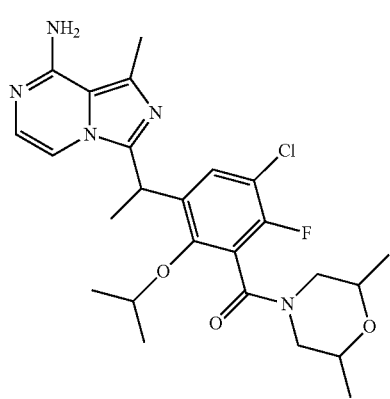
28
-continued
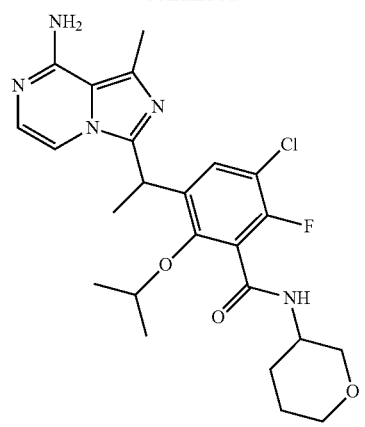
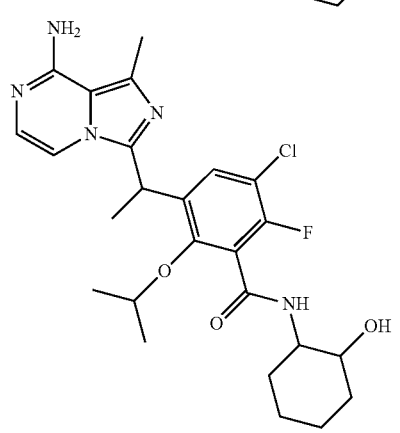
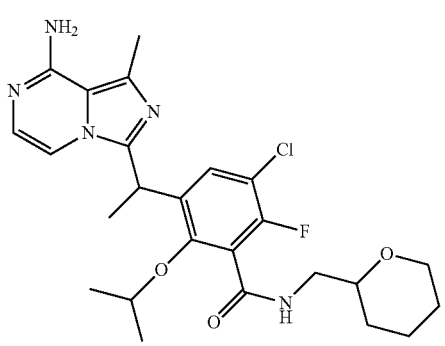
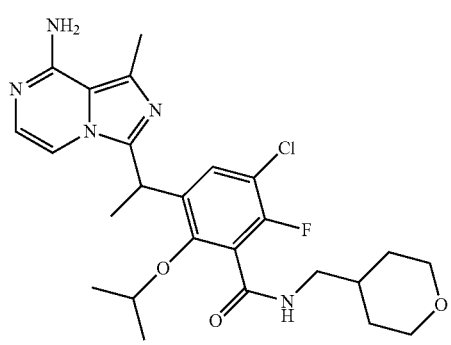

29
-continued
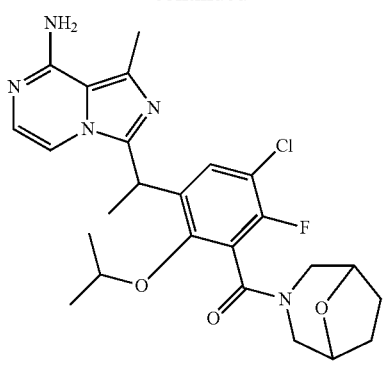
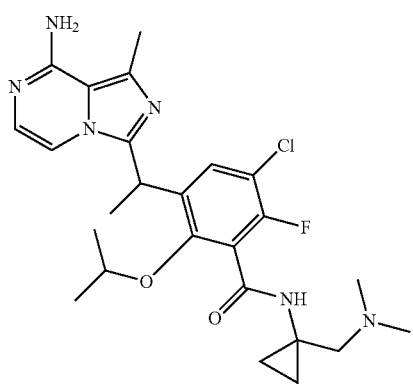
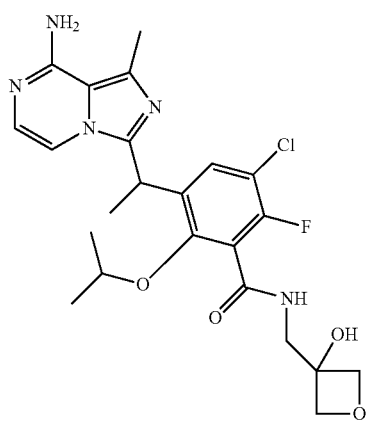
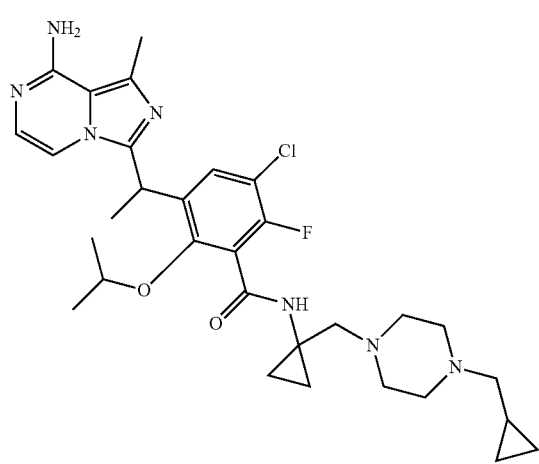
30
-continued
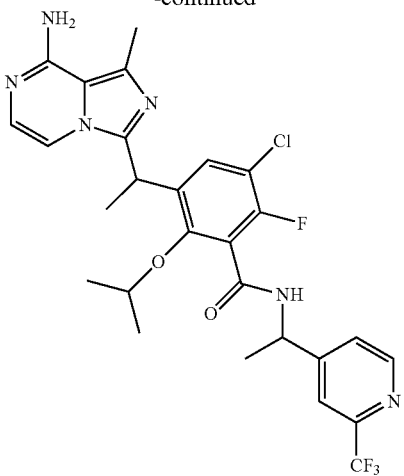
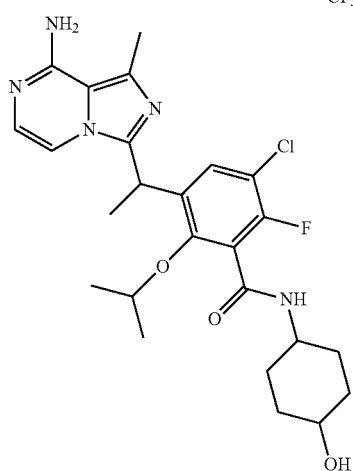
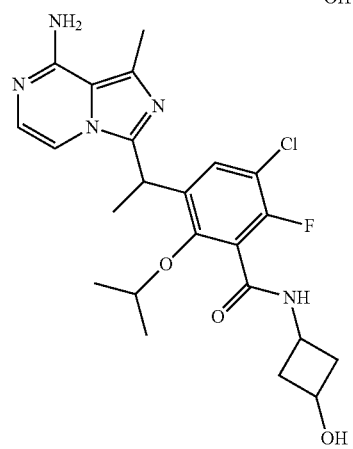
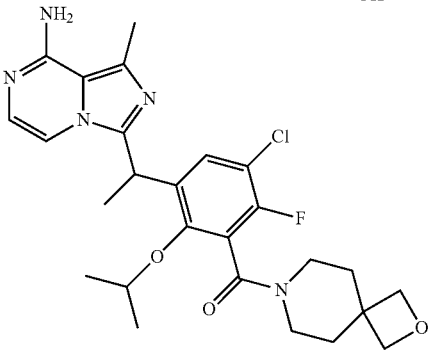

-continued
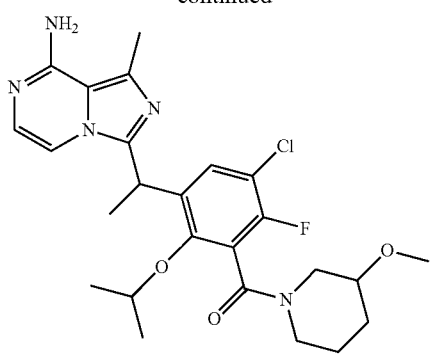
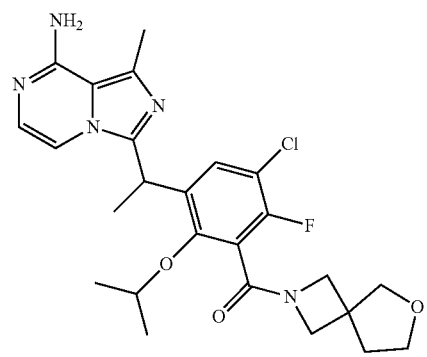
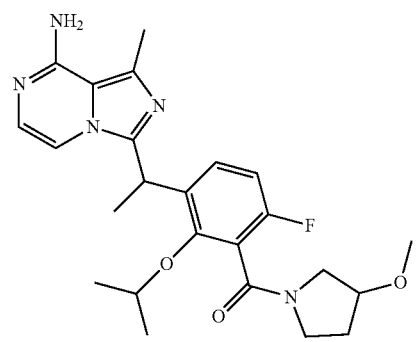
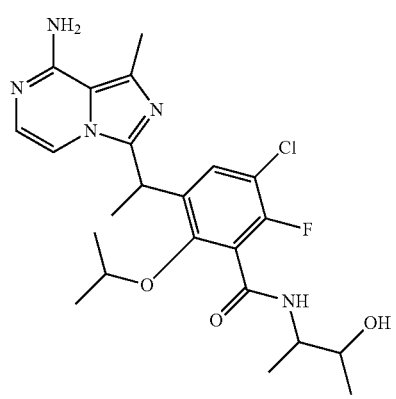
-continued
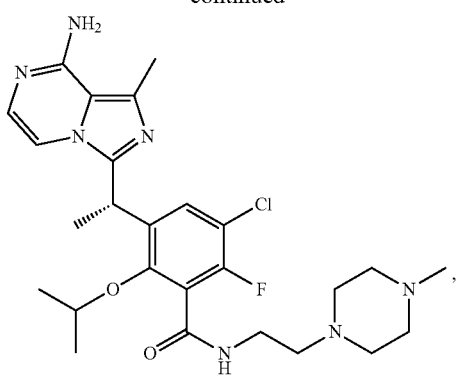
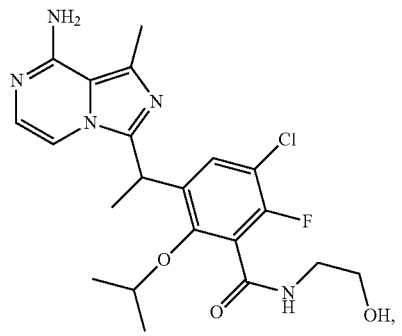
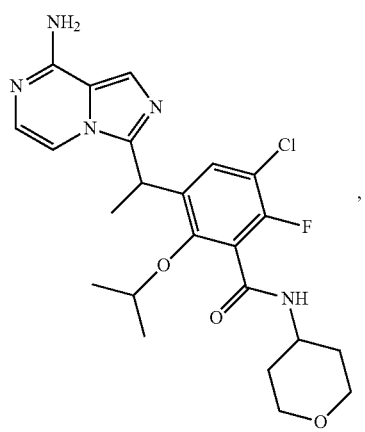
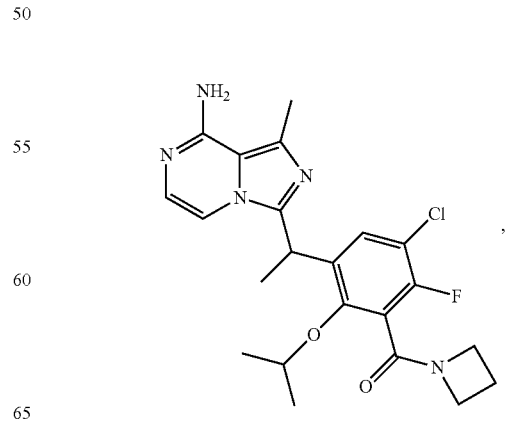

-continued
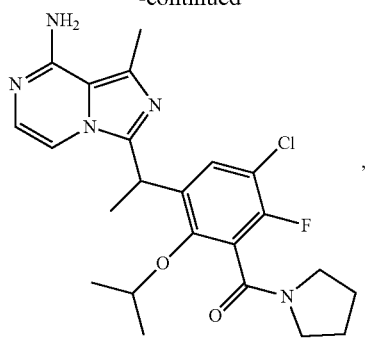
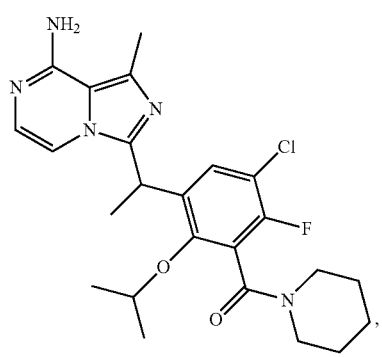
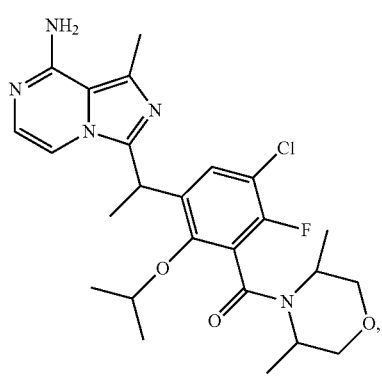
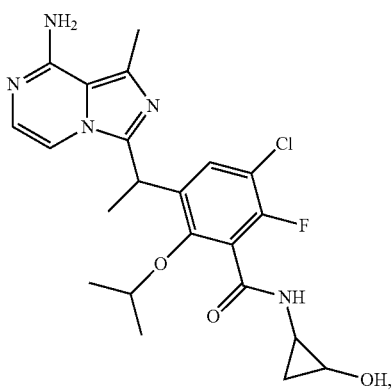
-continued
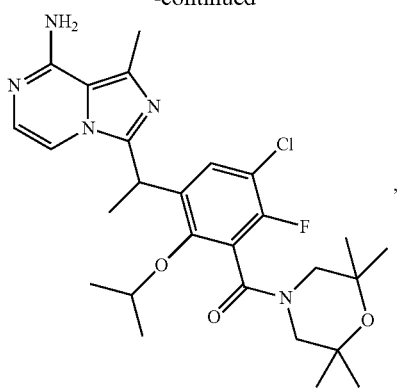
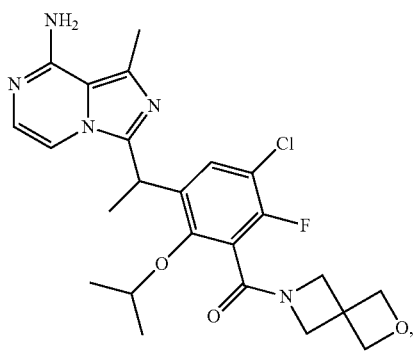
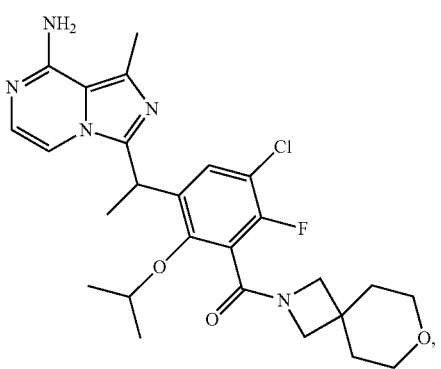
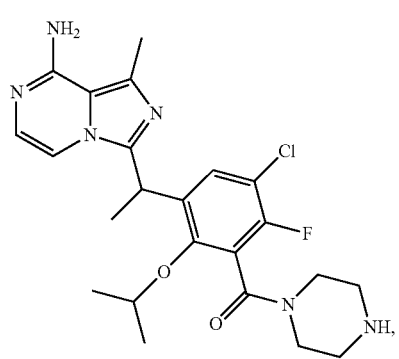

35
-continued
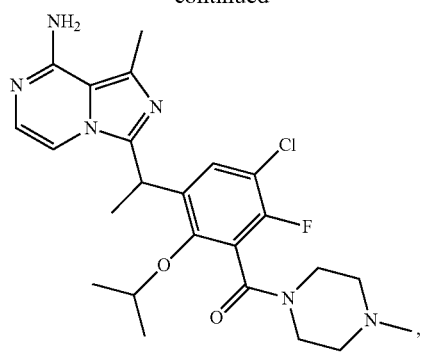
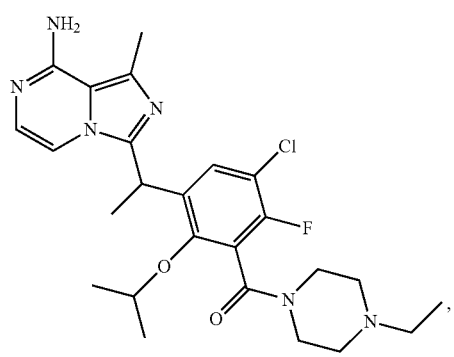
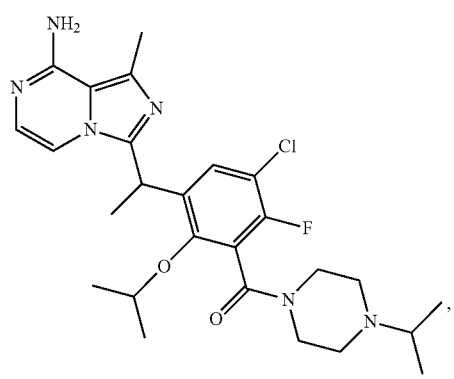
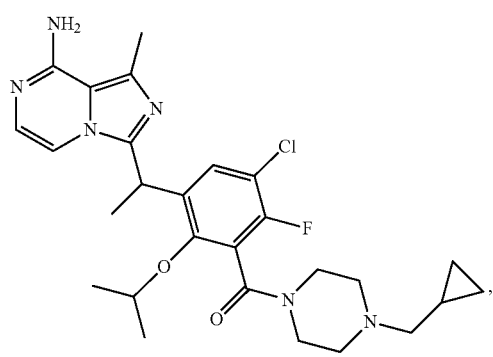
36
-continued
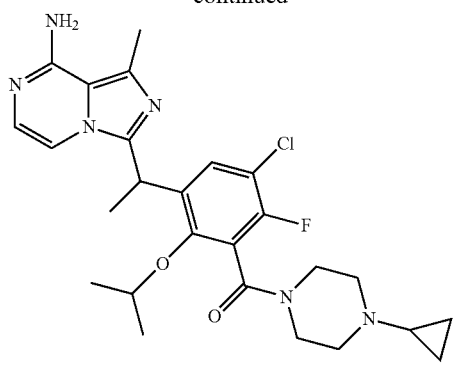
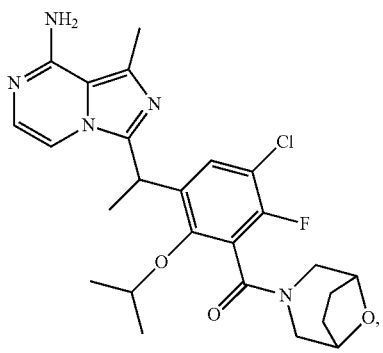
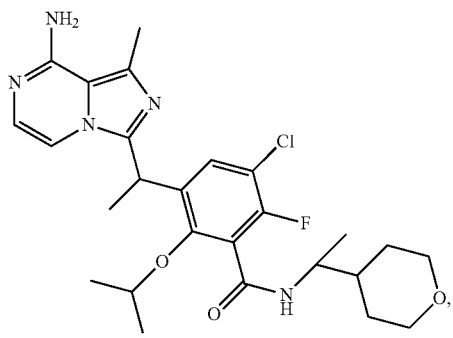
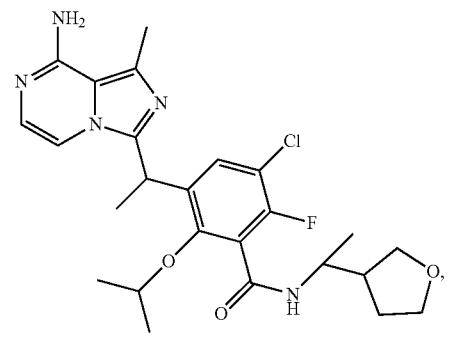
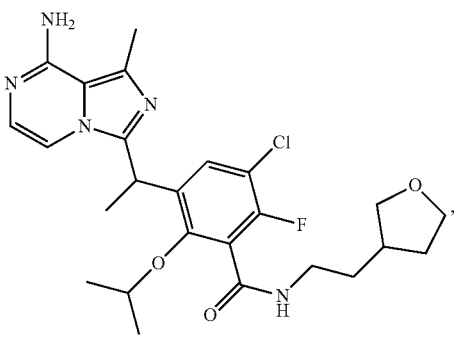

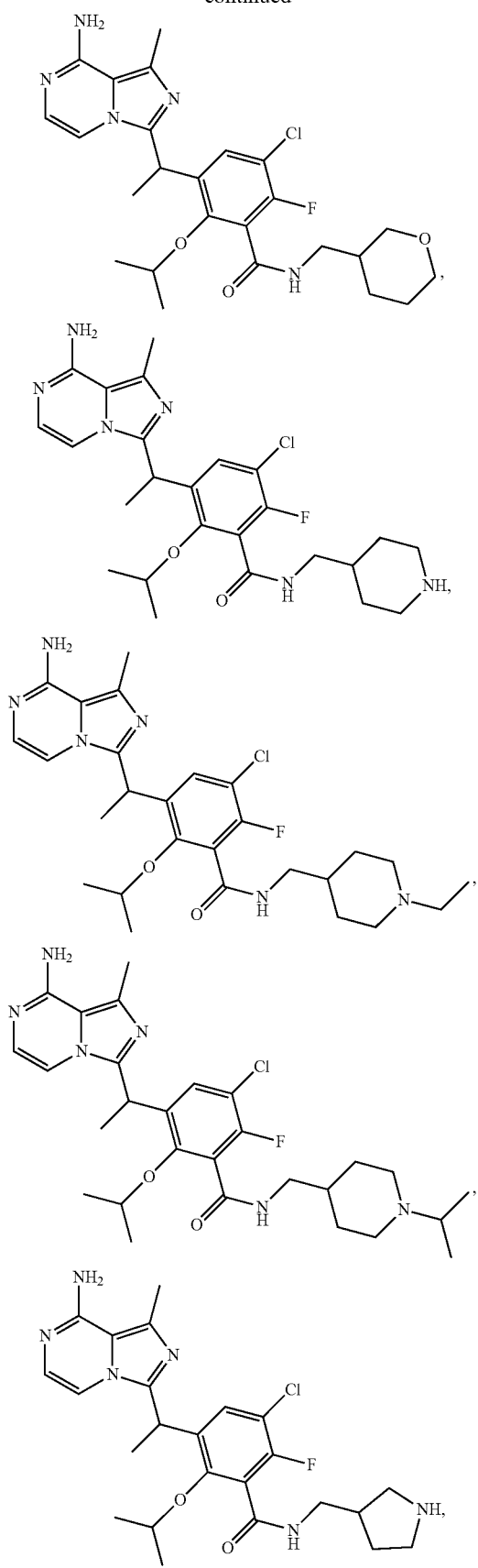
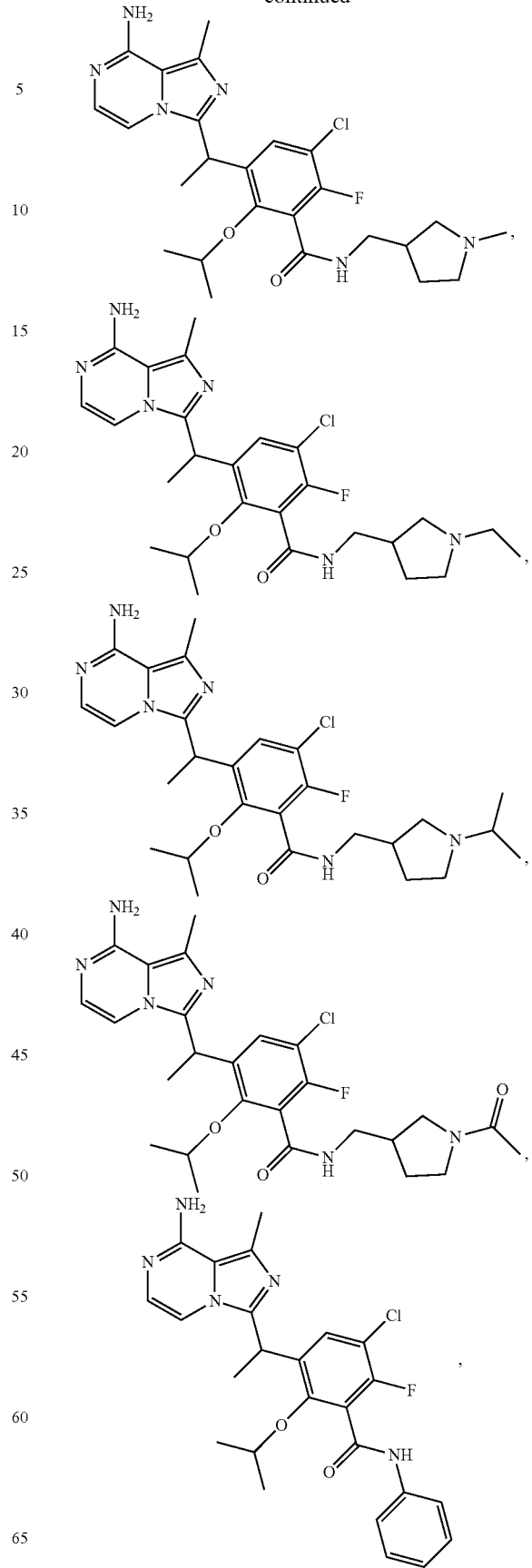

-continued
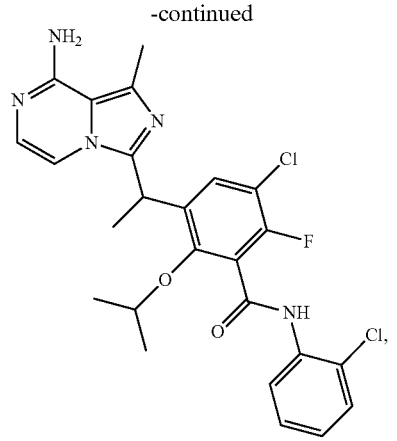
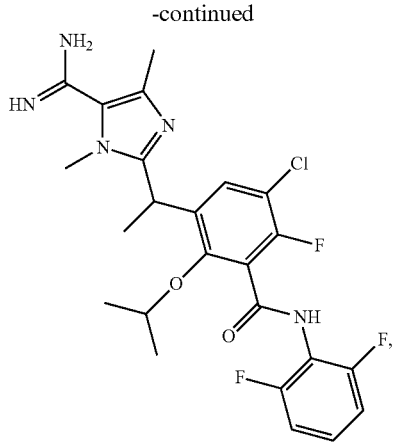
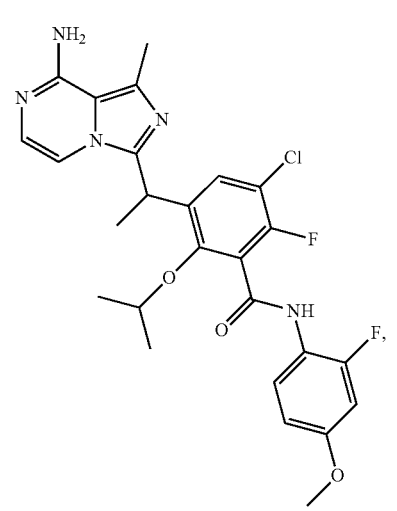
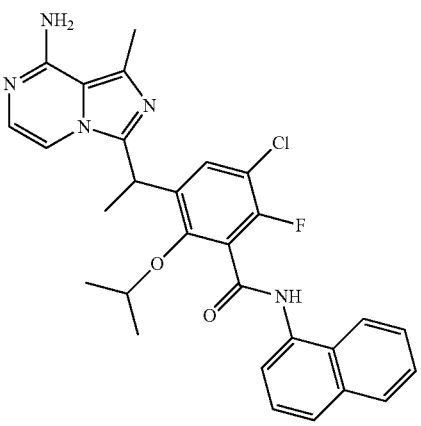

41
-continued
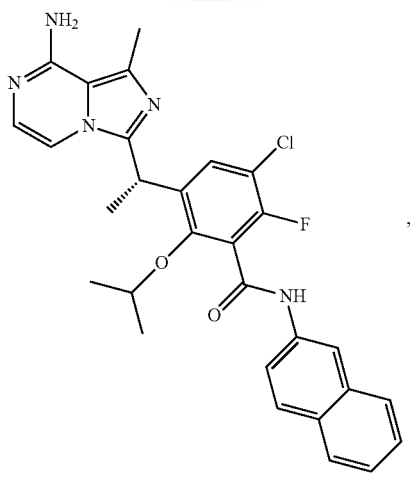
,
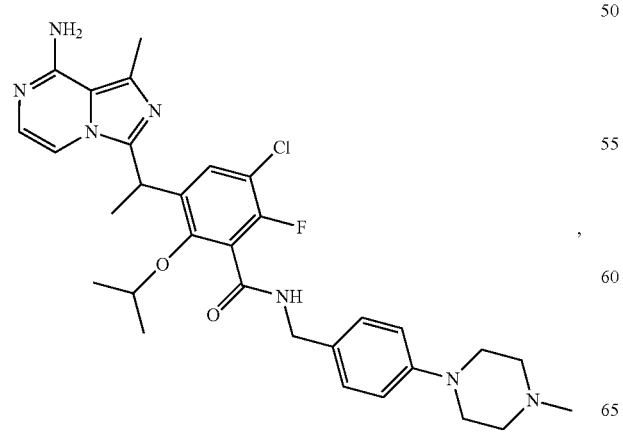
42
-continued
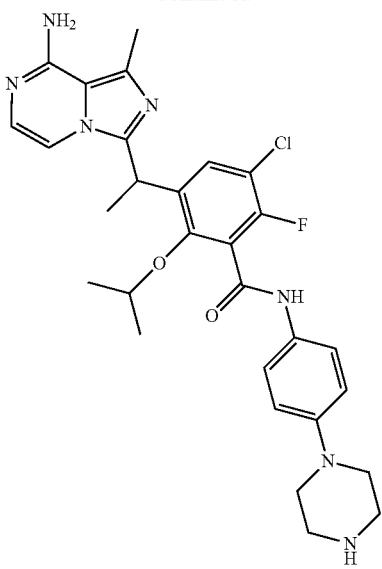
,
,

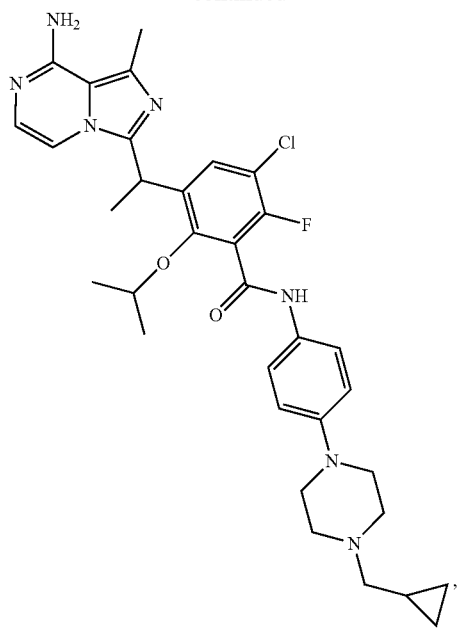
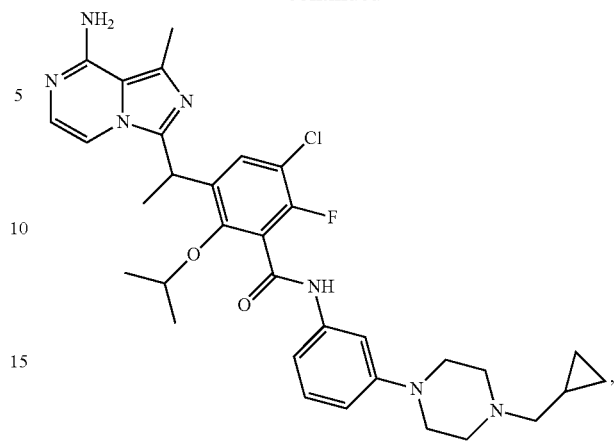
or a stereoisomer thereof, or a pharmaceutically acceptable salt thereof.
In an embodiment of the first aspect, disclosed herein is a compound selected from:
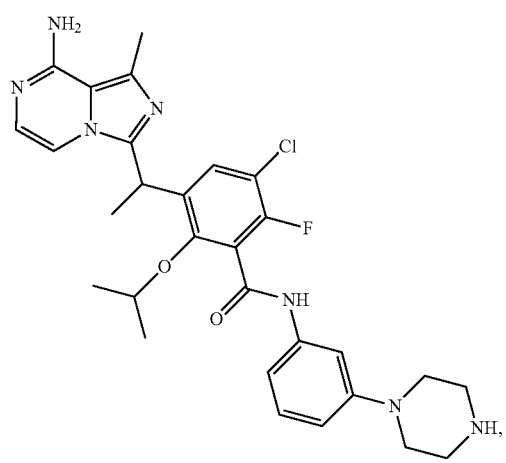
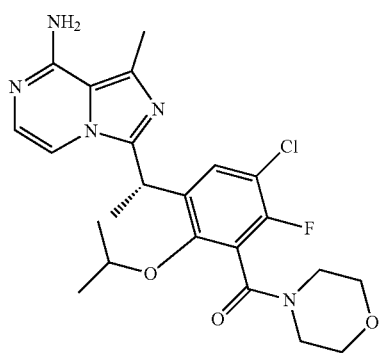
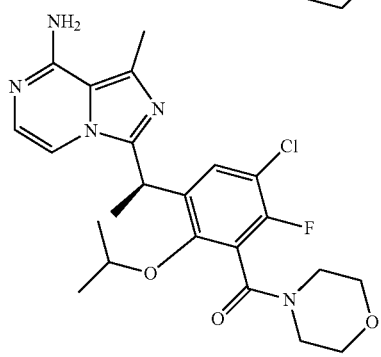
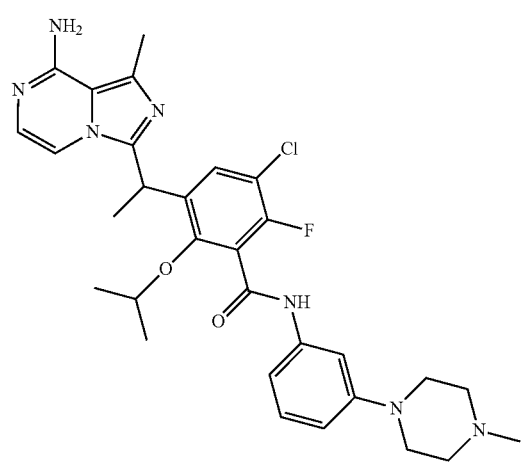
or
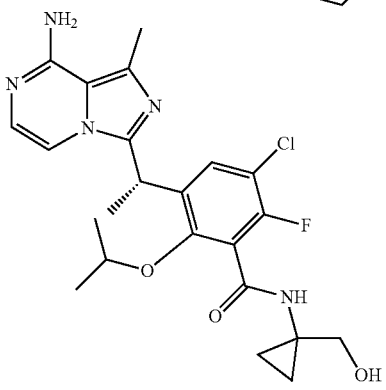

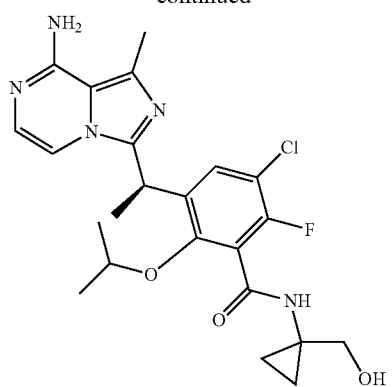
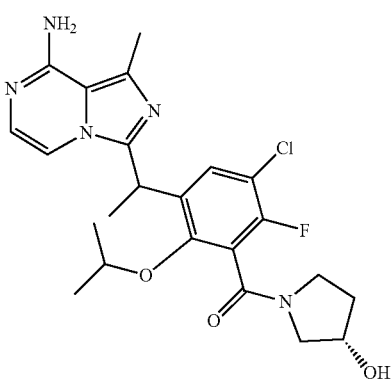
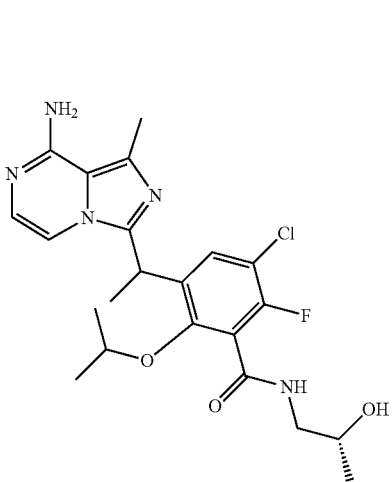
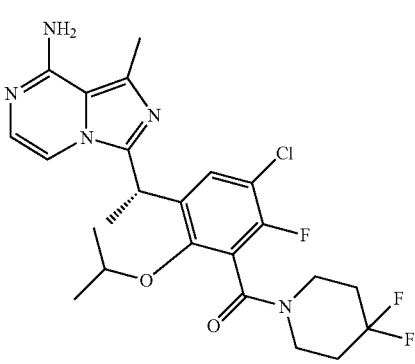
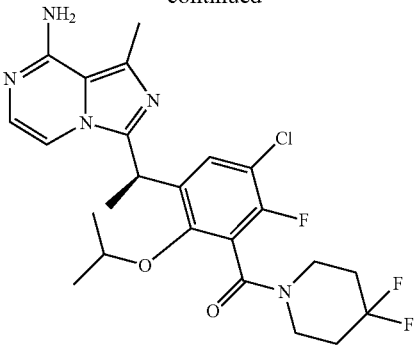
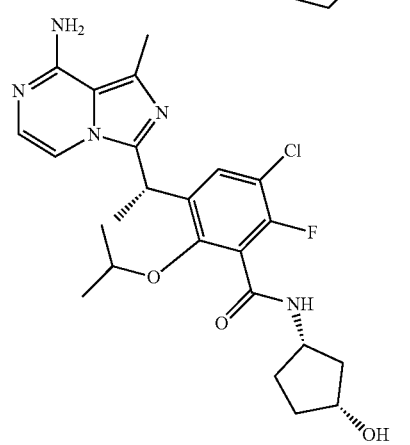
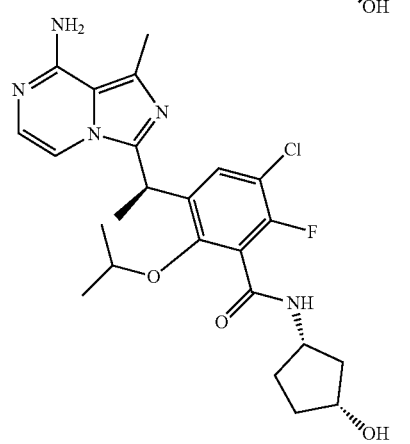
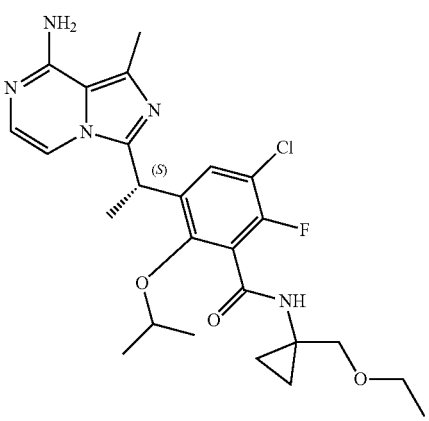

-continued
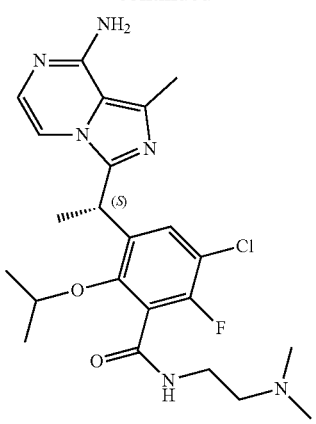
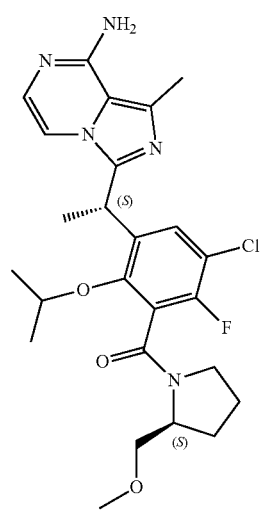
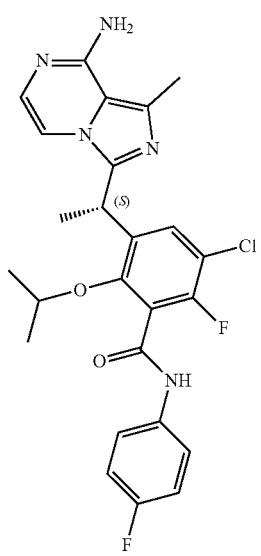
-continued
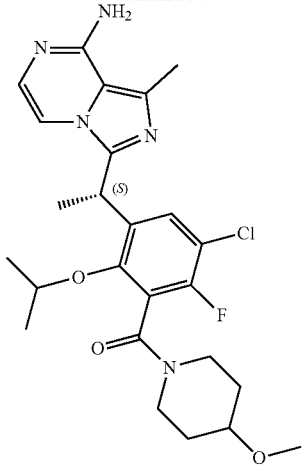
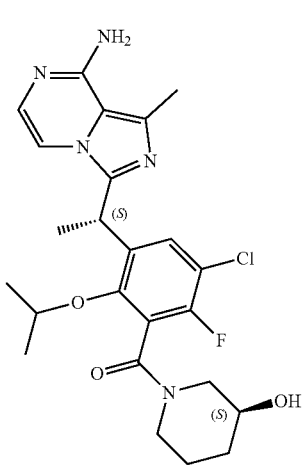
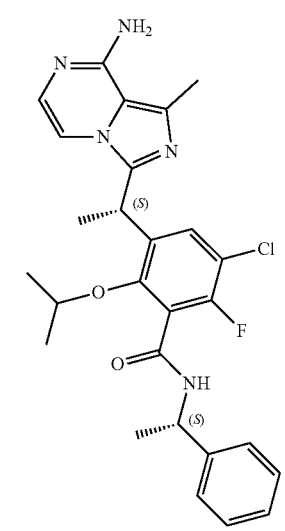

49
-continued
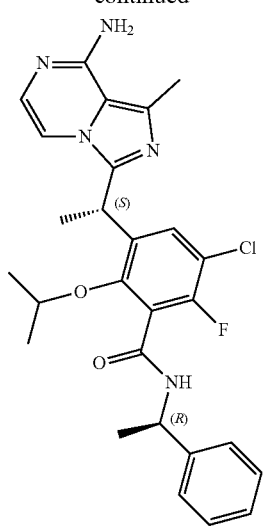
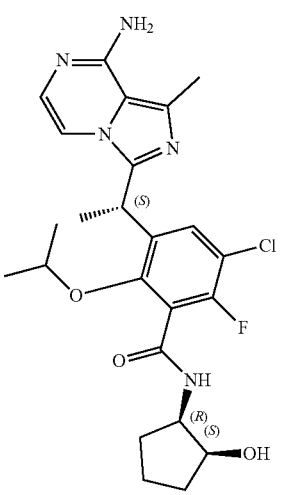
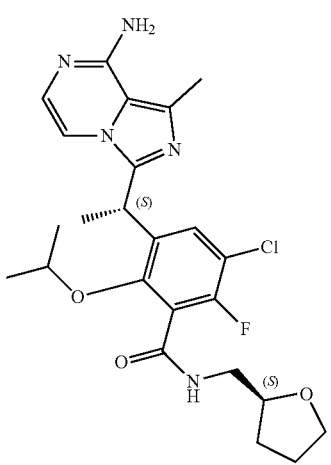
50
-continued
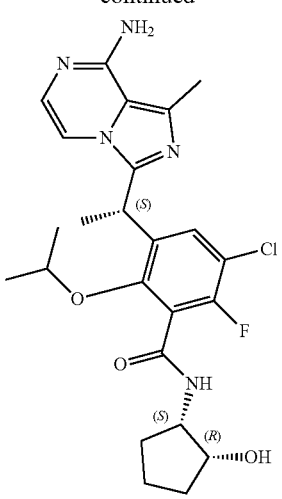
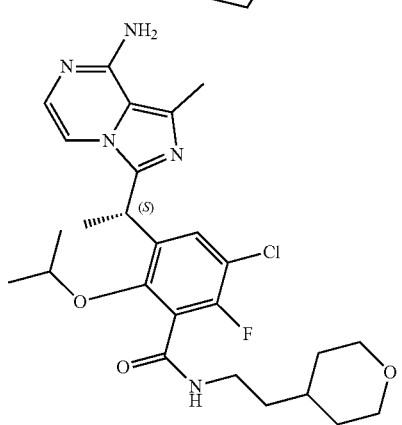
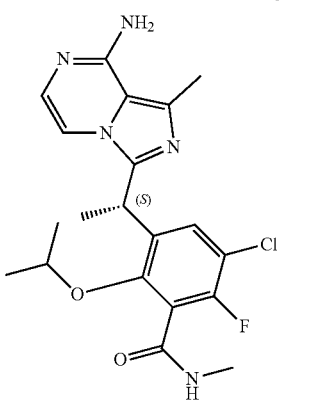
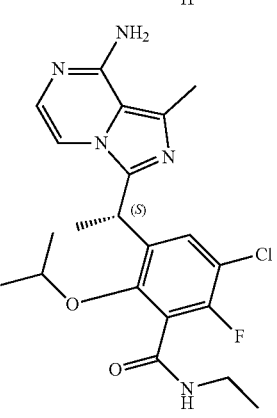

51
-continued
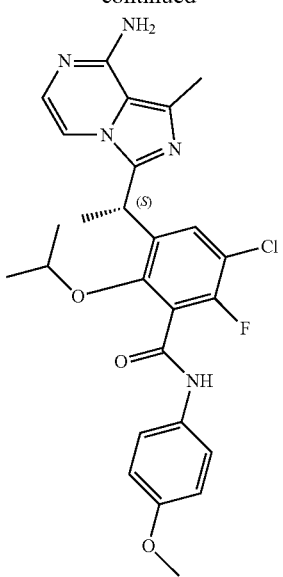
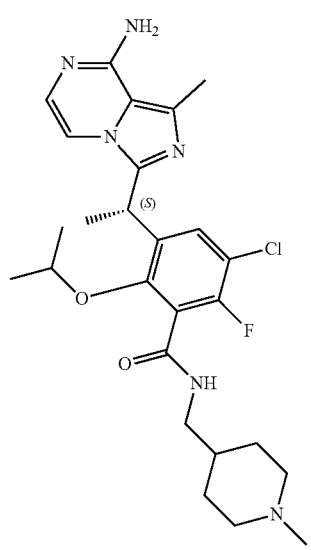
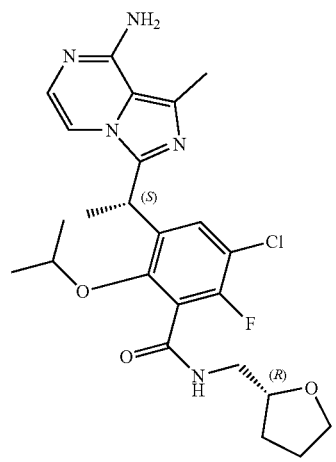
52
-continued
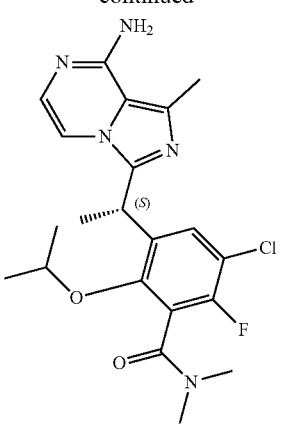
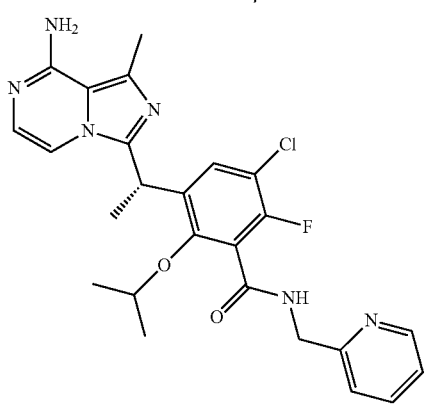
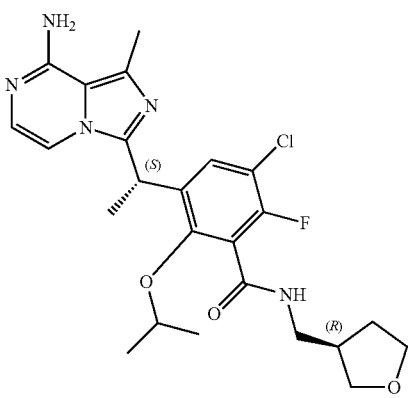
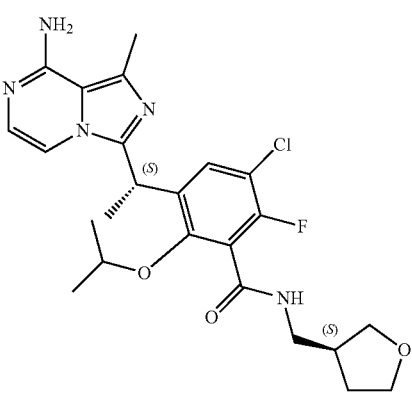

53
-continued
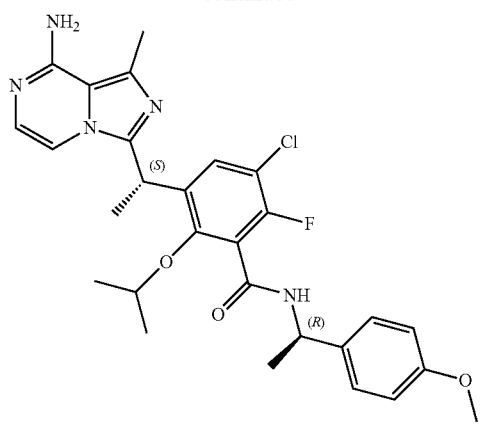
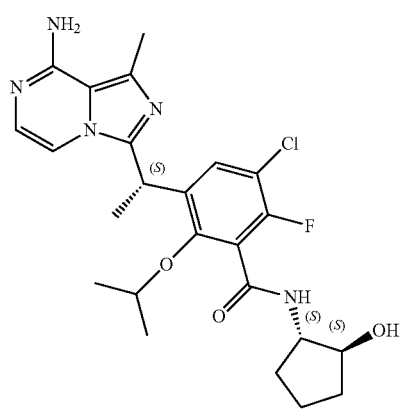
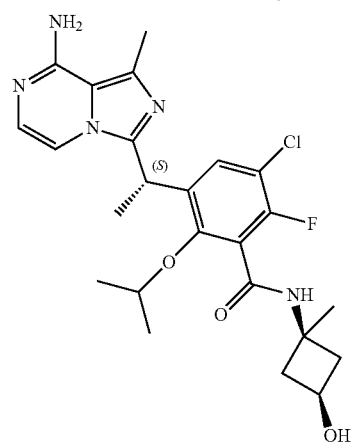
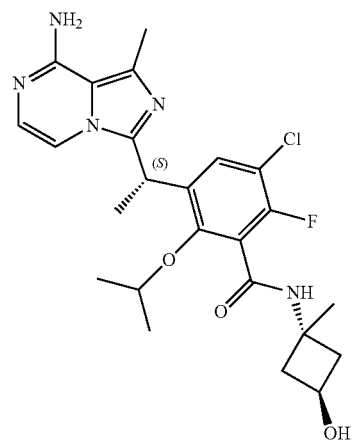
54
-continued
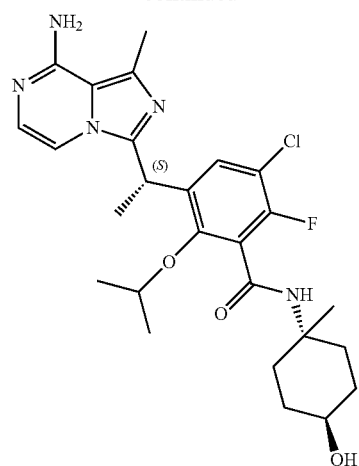
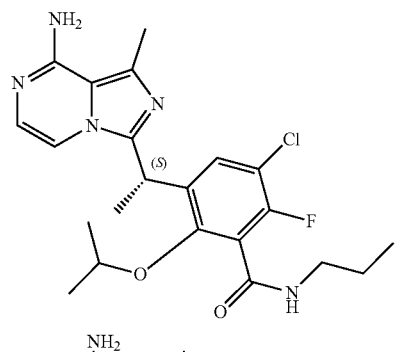
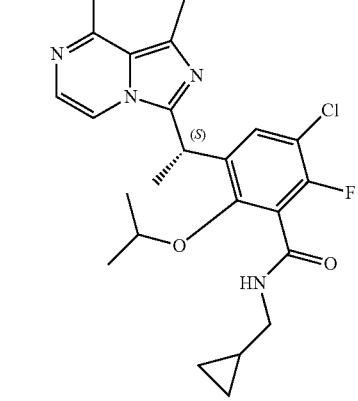
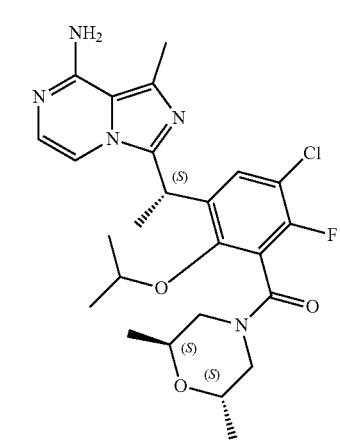

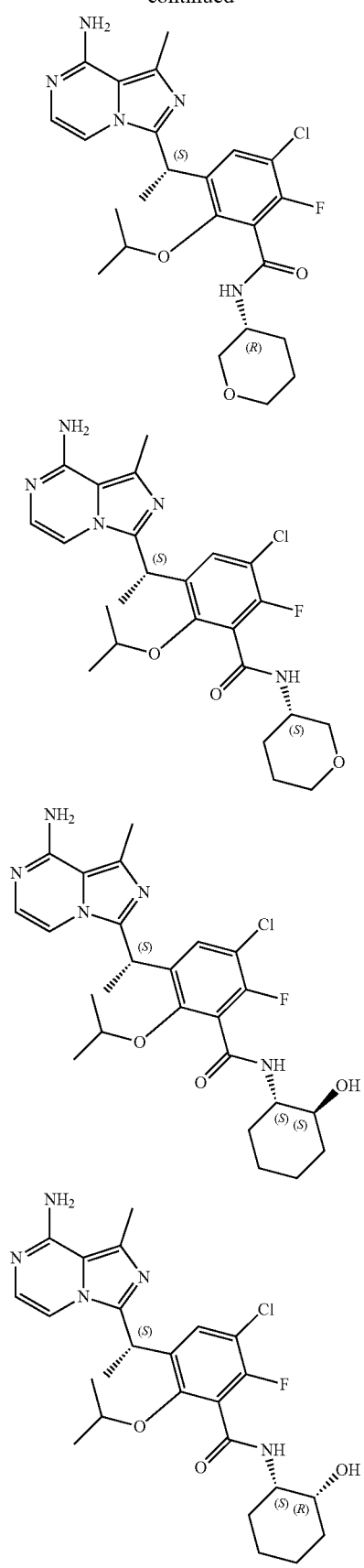
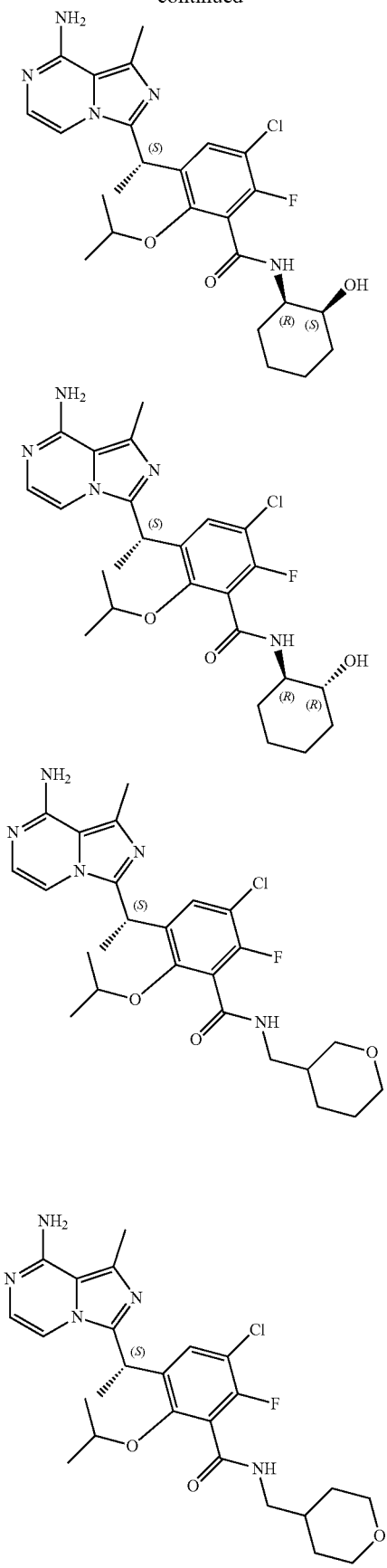

57
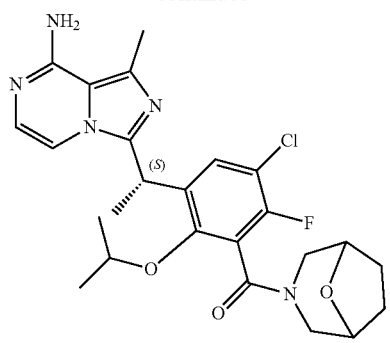
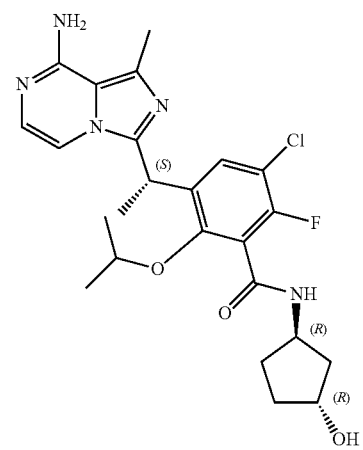
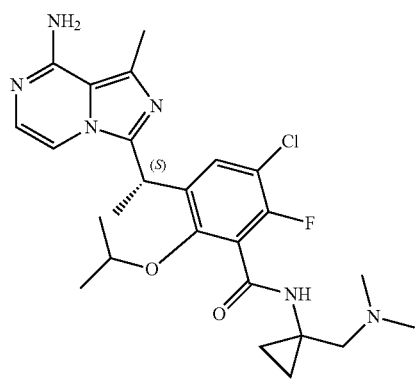
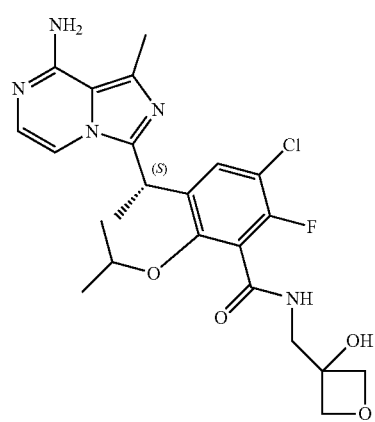
58
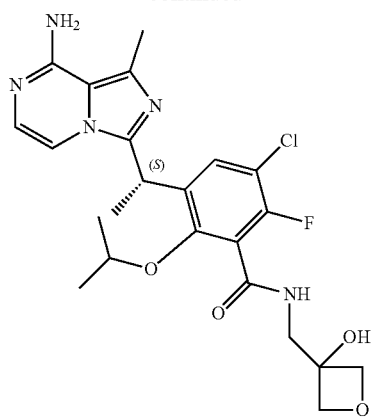
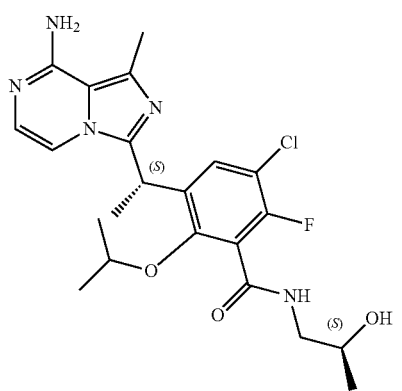
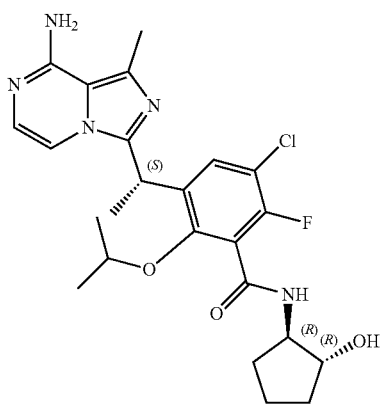
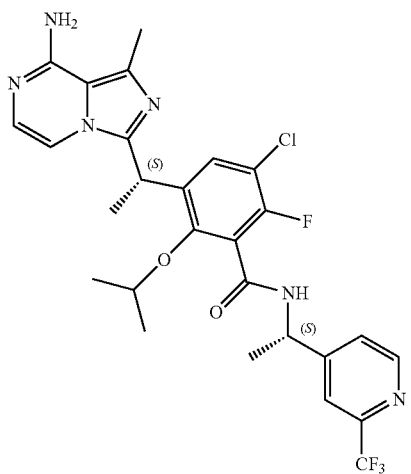

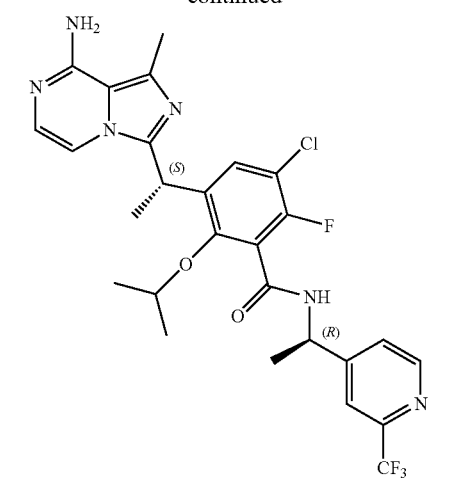
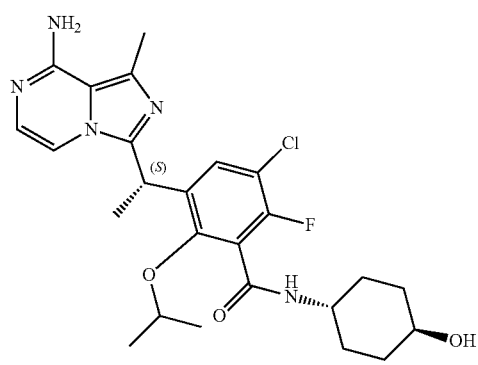
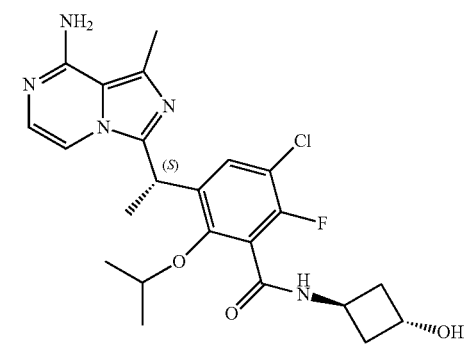
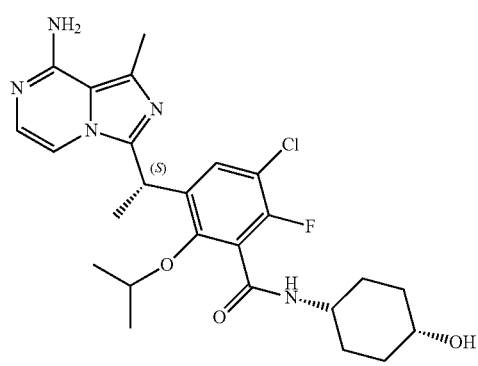
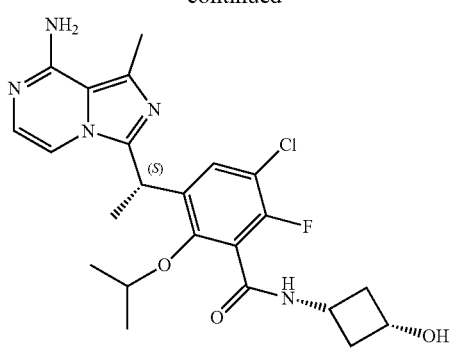
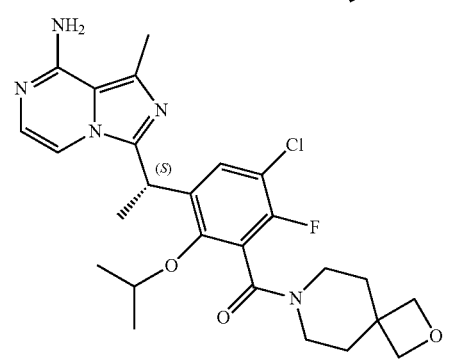
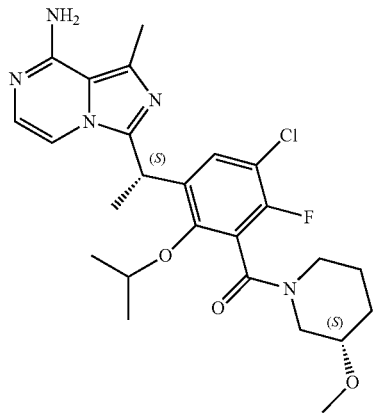
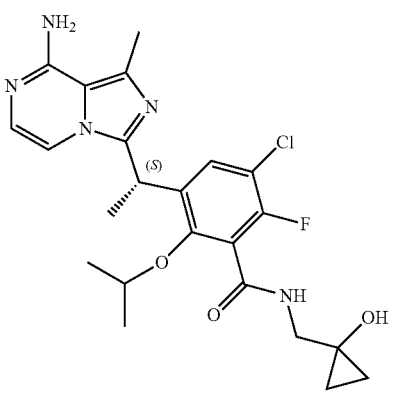

-continued

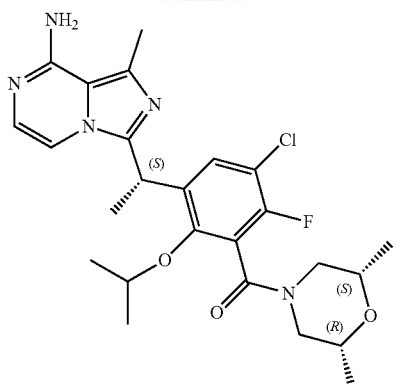
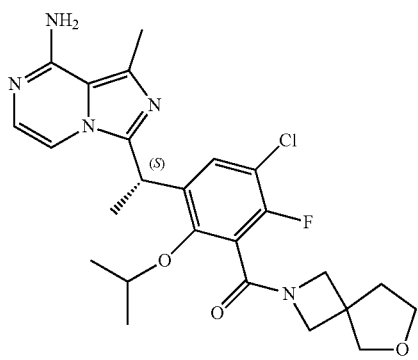
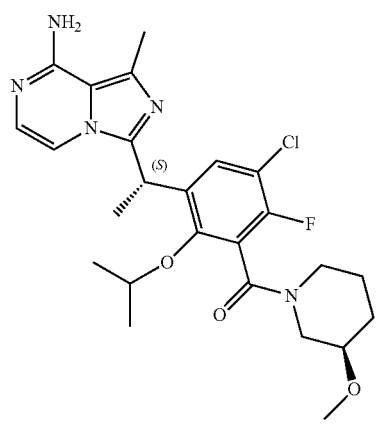
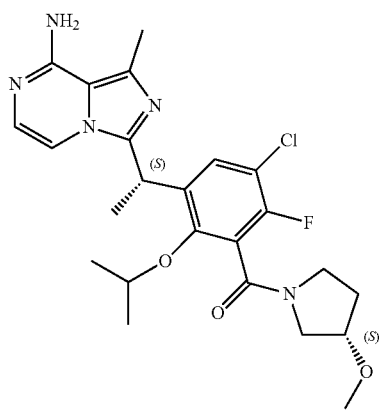

-continued

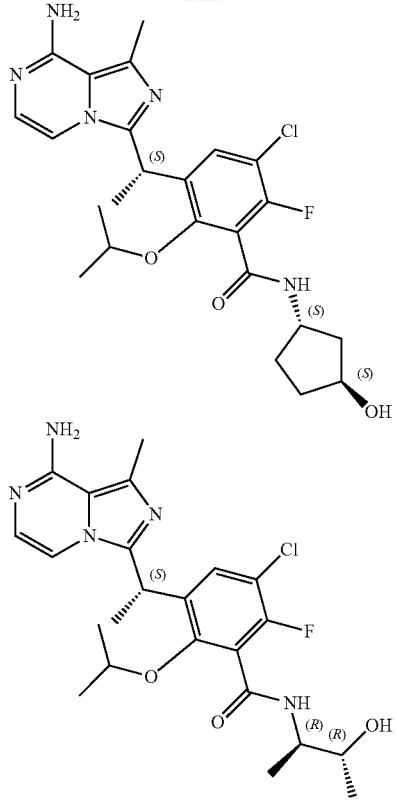
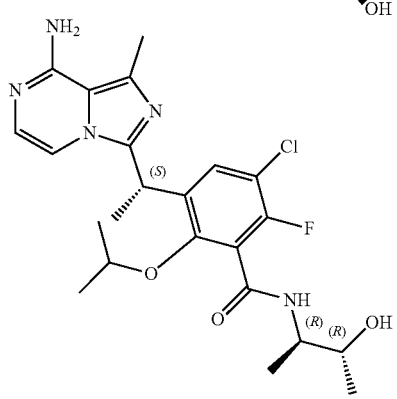
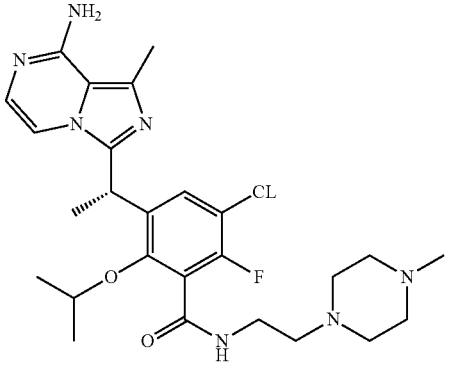

or a pharmaceutically acceptable salt thereof.

The compounds disclosed herein are effective inhibitors against PI3Kδ. Particularly, the compounds disclosed herein have been found to be selective inhibitors against PI3Kδ over PI3Kα, β and/or γ. More particularly, the compounds disclosed herein show better selectivity for PI3Kδ over each of PI3Kα, β and γ. In addition to the above selectivity, the compounds disclosed herein exhibit good pharmacokinetic profile. For example, compound 73 disclosed herein exhibits an unexpected long half-life.

In the second aspect, disclosed herein is a pharmaceutical composition comprising a therapeutically effective amount of the compound disclosed herein, or a stereoisomer thereof or a pharmaceutically acceptable salt thereof, and a pharmaceutically acceptable excipient.

In the third aspect, disclosed herein is a method for treating or preventing the following a disorders or a disease responsive to the inhibition of PI3Kδ activity by using the compound disclosed herein or a stereoisomer thereof or a pharmaceutically acceptable salt thereof; the use of the compound disclosed herein in the manufacture of a medicament for treating or preventing a disorders or a disease responsive to the inhibition of PI3Kδ activity; and the compound disclosed herein or a stereoisomer thereof or a pharmaceutically acceptable salt thereof for use in treating or preventing a disorders or a disease responsive to the inhibition of PI3Kδ activity, wherein the disorder or disease is an inflammatory disorder, an autoimmune disease or a cancer. In some embodiments, the disorder or disease is selected from the group consisting of idiopathic thrombocytopenic purpura (ITP), autoimmune hemolytic anemia, vasculitis, systemic lupus erythematosus, lupus nephritis, pemphigus, membranous nephropathy, acute lymphocytic hemolytic (ALL), acute myeloid leukemia (AML), chronic lymphocytic leukemia (CLL), Non-Hodgkin lymphoma (NHL), chronic myeloid leukemia (CML), multiple myeloma (MM), hairy cell leukemia, Mantle cell lymphoma (MCL), small lymphocytic lymphoma (SLL), follicular lymphoma, lymphoplasmacytic lymphoma, extranodal marginal zone lymphoma, activated B-cell like (ABC) diffuse large B cell lymphoma (DLBCL), or germinal center B cell (GCB) diffuse large B cell lymphoma (DLBCL), T-cell lymphoma, B-cell lymphoma, myelodysplasia syndrome (MDS), myeloproliferative disease (MPD) follicular lymphoma, Waldestrom's macroglobulinemia (WM), pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, CNS cancer, brain cancer, bone cancer, soft tissue sarcoma, non-small cell lung cancer, small-cell lung cancer, colon cancer, systemic lupus erythematosus (SLE), myestenia gravis, rheumatoid arthritis (RA), acute disseminated encephalomyelitis, idiopathic thrombocytopenic purpura, multiple sclerosis (MS), Sjoegren's syndrome, autoimmune hemolytic anemia, asthma, multiple sclerosis, psoriasis, chronic obstructive pulmonary disease or lupus.

Definitions

The following terms have the indicated meanings throughout the specification:

As used herein, including the appended claims, the singular forms of words such as "a", "an", and "the", include their corresponding plural references unless the context clearly dictates otherwise.

The term "or" is used to mean, and is used interchangeably with, the term "and/or" unless the context clearly dictates otherwise.

The term "alkyl" herein refers to a hydrocarbon group selected from linear and branched saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., $C_{1-6}$ alkyl) include, but not limited to, methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Ru"), 1,1-dimethylethyl or t-butyl ("t-Bu"), 1-pentyl, 2-pentyl, 3-pentyl, 2-methyl-2-butyl, 3-methyl-2-butyl, 3-methyl-1-butyl, 2-methylolbutyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

The term "halogen" herein refers to fluoro (F), chloro (Cl), bromo (Br) and iodo (I).

The term "haloalkyl" herein refers to an alkyl group in which one or more hydrogen is/are replaced by one or more halogen atoms such as fluoro (F), chloro (Cl), bromo (Br), and iodo (I). Examples of the haloalkyl include haloC$_{1-8}$alkyl, haloC$_{1-6}$alkyl or halo C$_{1-4}$ alkyl, but not limited to —CF$_3$, —CH$_2$Cl, —CH$_2$CF$_3$, —CCl$_2$, CF$_3$, and the like.

The term "alkenyl" herein refers to a hydrocarbon group selected from linear and branched hydrocarbon groups comprising at least one C=C double bond and from 2 to 18, such as from 2 to 8, further such as from 2 to 6, carbon atoms. Examples of the alkenyl group, e.g., $C_{2-6}$ alkenyl, include, but not limited to ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, and hexa-1,3-dienyl groups.

The term "alkynyl" herein refers to a hydrocarbon group selected from linear and branched hydrocarbon group, comprising at least one C=C triple bond and from 2 to 18, such as 2 to 8, further such as from 2 to 6, carbon atoms. Examples of the alkynyl group, e.g., $C_{2-6}$ alkynyl, include, but not limited to ethynyl, 1-propynyl, 2-propynyl (propargyl), 1-butynyl, 2-butynyl, and 3-butynyl groups.

The term "alkyloxy" herein refers to an alkyl group as defined above bonded to oxygen, represented by —Oalkyl. Examples of an alkyloxy, e.g., $C_{1-6}$alkyloxy or $C_{1-4}$ alkyloxy includes, but not limited to, methoxy, ethoxy, isopropoxy, propoxy, n-butoxy, tert-butoxy, pentoxy and hexoxy and the like.

The term "cycloalkyl" herein refers to a hydrocarbon group selected from saturated and partially unsaturated cyclic hydrocarbon groups, comprising monocyclic and polycyclic (e.g., bicyclic and tricyclic) groups. For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. In particular, Examples of the saturated monocyclic cycloalkyl group, e.g., $C_{3-8}$ cycloalkyl, include, but not limited to, cyclopropyl, cyclobutyl, cyclopentyl, cyclohexyl, cycloheptyl, and cyclooctyl groups. In a preferred embodiment, the cycloalkyl is a monocyclic ring comprising 3 to 6 carbon atoms (abbreviated as $C_{3-6}$ cycloalkyl), including but not limited to, cyclopropyl, cyclobutyl, cyclopentyl, and cyclohexyl. Examples of the bicyclic cycloalkyl groups include those having from 7 to 12 ring atoms arranged as a bicyclic ring selected from [4,4], [4,5], [5,5], [5,6] and [6,6] ring systems, or as a bridged bicyclic ring selected from bicyclo[2,2,1]heptane, bicyclo[2.2.2]octane, and bicyclo[3.2.2]nonane. Further Examples of the bicyclic cycloalkyl groups include those arranged as a bicyclic ring selected from [5,6] and [6,6] ring systems, such as

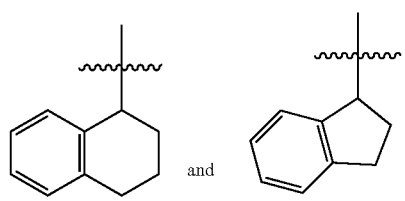 [SMILES: *C1CCCc2ccccc21 ; *C1CCc2ccccc21]
and wherein the wavy lines indicate the points of attachment. The ring may be saturated or have at, least, one double bond (i.e. partially unsaturated), but is not fully conjugated, and is not, aromatic, as aromatic is defined herein.

The term "aryl" used alone or in combination with other terms refers to a group selected from;
a. 5- and 6-membered carbocyclic aromatic rings, e.g., phenyl;
b. bicyclic ring systems such as 7 to 12 membered bicyclic ring systems, wherein at least one ring is carbocyclic and aromatic, e.g., naphthyl and indanyl; and,
c. tricyclic ring systems such as 10 to 15 membered tricyclic ring systems wherein at least one ring is carbocyclic and aromatic, e.g., fluorenyl.

The terms "aromatic hydrocarbon ring" and "aryl" are used interchangeable throughout the disclosure herein. In some embodiments, a monocyclic or bicyclic aromatic hydrocarbon ring has 5 to 10 ring-forming carbon atoms (i.e., $C_{5-10}$ aryl). Examples of a monocyclic or bicyclic aromatic hydrocarbon ring include, but not limited to, phenyl, naphth-1-yl, naphth-2-yl, anthracenyl, phenanthrenyl, and the like. In some embodiments, the aromatic hydrocarbon ring is a naphthalene ring (naphthol-1-yl or naphth-2-yl) or phenyl ring. In some embodiments, the aromatic hydrocarbon ring is a phenyl ring.

The term "heteroaryl" herein refers to a group selected from:
a. 5-, 6- or 7-membered aromatic, monocyclic rings comprising at least one heteroatom, for example, from 1 to 4, or, in some embodiments, from 1 to 3, in some embodiments, from 1 to 2, heteroatoms, selected from nitrogen (N), sulfur (S) and oxygen (O) as ring atom(s), with the remaining ring atoms being carbon;
b. 8- to 12-membered bicyclic rings comprising at least one heteroatom, for example, from 1 to 4, or, in some embodiments, from 1 to 3, or, in other embodiments, 1 or 2, heteroatoms, selected from N, O, and S as ring atom(s), with the remaining ring atoms being carbon and wherein at least one ring is aromatic and at least one heteroatom is present in the aromatic ring; and
c. 11- to 14-membered tricyclic rings comprising at least one heteroatom, for example, from 1 to 4, or in some embodiments, from 1 to 3, or, in other embodiments, 1 or 2, heteroatoms, selected from N, O, and S as ring atom(s), with the remaining ring atoms being carbon and wherein at least one ring is aromatic and at least one heteroatom is present in an aromatic ring.

In a preferred embodiment, heteroaryl is 5- to 6-membered heteroaryl comprising one nitrogen atom and 0 or 1 additional heteroatom selected from N, O and S, including but not limited to pyridinyl, isoxazolyl, and oxazolyl.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring(s) of the heteroaryl group can be oxidized to form N-oxides.

The terms "aromatic heterocyclic ring" and "heteroaryl" are used interchangeable throughout the disclosure herein. In some embodiments, a monocyclic or bicyclic aromatic heterocyclic ring has 5-, 6-, 7-, 8-, 9- or 10-ring forming members with 1, 2, 3, or 4 heteroatom ring members independently selected from nitrogen (N), sulfur (S) and oxygen (O) and the remaining ring members being carbon. In some embodiments, the monocyclic or bicyclic aromatic heterocyclic ring is a monocyclic or bicyclic ring comprising 1 or 2 heteroatom ring members independently selected from nitrogen (N), sulfur (5) and oxygen (O). In some embodiments, the monocyclic or bicyclic aromatic heterocyclic ring is a 5- to 6-membered heteroaryl ring, which is monocyclic and which has 1 or 2 heteroatom ring members independently selected from nitrogen (N), sulfur (S) and oxygen (O). In some embodiments, the monocyclic or bicyclic aromatic heterocyclic ring is a 8- to 10-membered heteroaryl ring, which is bicyclic and which has 1 or 2 heteroatom ring members independently selected from nitrogen, sulfur and oxygen.

Examples of the heteroaryl group or the monocyclic or bicyclic aromatic heterocyclic ring include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl (such as 1,2,3-thiadiazolyl, 1,2,4-thiadiazolyl, or 1,3,4-thiadiazolyl), tetrazolyl, thienyl (such as thien-2-yl, thien-3-yl), triazinyl, benzothienyl, furyl or furanyl, benzofuryl, benzoimidazolyl, indolyl, isoindolyl, indolinyl, oxadiazolyl (such as 1,2,3-oxadiazolyl, 1,2,4-oxadiazolyl, or 1,3,4-oxadiazolyl), phthalazinyl, pyrazinyl, pyridazinyl, pyrrolyl, triazolyl (such as 1,2,3-triazolyl, 1,2,4-triazolyl, or 1,3,4-triazolyl), quinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-3,4-diazolyl, 1-thia-2,3-diazolyl, 1-thia-2,5-diazolyl, 1-thia-2,5-diazolyl, 1-thia-3,4-diazolyl, furazanyl (such as furazan-2-yl, furazan-3-yl), benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" herein refers to a ring selected from 3-, 4-, 5-, 6-, 7-, 8-, 9-, 10-, 11- or 12-membered monocyclic, bicyclic and tricyclic, saturated and partially unsaturated rings comprising at least, one carbon atoms in addition to at least one heteroatom, such as from 1-4 heteroatoms, further such as from 1-3, or further such as 1 or 2 heteroatoms, selected from nitrogen (N), sulfur (S), oxygen (O), —SO— or —SO$_2$— as ring atom(s).

In some embodiments, a heterocyclyl group is 4-, 5-, 6-, 7- or 8-membered monocyclic ring with at least one heteroatom selected from N, O and S. In some preferred embodiment, a heterocyclyl group is a 4-, 5-, 6-, 7- or 8-membered saturated monocyclic ring comprising one nitrogen heteroatom. The exemplary heterocyclyl group is azetidinyl, pyrrolidinyl, piperidinyl, azepanyl, and azocanyl. In other embodiment, a heterocyclyl group is a 5-, 6-, 7- or 8-membered saturated monocyclic ring comprising one nitrogen atom and 1 additional heteroatom selected from —NH, —O—, —S—, —SO— or —SO$_2$—. The exemplary heterocyclyl group is a morpholino, morpholinyl or piperazinyl ring. In some embodiment, a heterocyclyl group is a 7- to 12-membered saturated bicyclic ring comprising one nitrogen atom and 0 or 1 or 2 additional heteroatoms selected from —NH, —O—, —S—, —SO— or —SO$_2$—. In some preferred embodiment, the heterocyclyl group is a bicyclic bridged or Spiro-ring.

"Heterocycle" herein also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl, "Heterocycle" herein also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocycle is not a heteroaryl as defined herein. In a preferred embodiment, heterocyclyl is 5- to 6-membered heterocyclyl comprising one nitrogen atom and 0 or 1 additional heteroatom selected from N, O and S, including but not limited to pyrrolyl, dihydropyridine, morpholino, morpholinyl and tetrahydropyranyl.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, morpholinyl, morpholino, 2-morpholinyl, 3-morpholinyl, oxiranyl, thiiranyl, azetidinyl, oxetanyl, thiepanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepanyl, 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. A substituted heterocycle also includes a ring system substituted with one or more oxo moieties, such as piperidinyl N-oxide, morpholinyl-N-oxide, 1-oxo-1-thiomorpholinyl and 1,1-dioxo-1-thiomorpholinyl.

Compounds disclosed herein may contain an asymmetric center and may thus exist as enantiomers. "Enantiomers" refer to two stereoisomers of a compound which are non-superimposable mirror images of one another. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" as used herein means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds disclosed herein contain olefinic double bonds, unless specified otherwise, such double bonds are meant to include both E and Z geometric isomers.

Some of the compounds disclosed herein may exist with different points of attachment of hydrogen, referred to as tautomers. For example, compounds including carbonyl —CH$_2$C(O)— groups (keto forms) may undergo tautomerism to form hydroxyl —CH=C(OH)— groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

"Diastereomers" refers to stereoisomers of a compound with two or more chiral centers but which are not mirror images of one another. Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents [Eliel, E. and Wilen, S. *Stereochemistry of Organic Compounds*. New York: John Wiley & Sons, Inc., 1994; Lochmuller, C. H., et al. "*Chromatographic resolution of enantiomers: Selective review*." J. Chromatogr., 113(3) (1975): pp. 283-302]. Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. *Drug Stereochemistry: Analytical Methods and Pharmacology*, New York: Marcel Dekker, Inc., 1993.

"Pharmaceutically acceptable salts" refers to those salts which are, within the scope of sound medical judgment, suitable for use in contact with the tissues of humans and lower animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "a pharmaceutically acceptable salt thereof" include salts of at least one compound of Formula (I), and salts of the stereoisomers of the compound of Formula (I), such as salts of enantiomers, and/or salts of diastereomers.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, rabbit) and most preferably a human.

The term "effective amount" or "therapeutically effective amount" refers to an amount of the active ingredient, such as compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In some embodiments, "therapeutically effective amount" is an amount of at least one compound and/or at least one stereoisomer thereof, and/or at least one pharmaceutically acceptable salt thereof disclosed herein effective to "treat" as defined above, a disease or disorder in a subject. In the case of combination therapy, the "therapeutically effective amount" refers to the total amount of the combination objects for the effective treatment of a disease, a disorder or a condition.

The term "at least one substituent" disclosed herein includes, for example, from 1 to 5, such as from 1 to 4, further as 1, 2 or 3, substituents, provided that the valence allows. For example, "at least one substituent $R_{15}$" disclosed herein includes from 1 to 4, such as from 1 to 3, further as 1 or 2, substituents selected from the list of $R_{15}$ as disclosed herein.

The pharmaceutical composition comprising the compound disclosed herein can be administrated via oral, inhalation, rectal, parenteral or topical administration to a subject in need thereof. For oral administration, the pharmaceutical composition may be a regular solid formulation such as tablets, powder, granule, capsules and the like, a liquid formulation such as water or oil suspension or other liquid formulation such as syrup, solution, suspension or the like; for parenteral administration, the pharmaceutical composition may be solution, water solution, oil suspension concentrate, lyophilized powder or the like, Preferably, the formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All formulations of the pharmaceutical composition disclosed herein can be produced by the conventional methods in the pharmaceutical field. For example, the active ingredient can be mixed with one or more excipients, then to make the desired formulation. The "pharmaceutically acceptable excipient" refers to conventional pharmaceutical carriers suitable for the desired pharmaceutical formulation, for example: a diluent, a vehicle such as water, various organic solvents, etc., a filler such as starch, sucrose, etc. a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye.

The term "disease" refers to any disease, discomfort, illness, symptoms or indications, and can be interchangeable with the term "disorder" or "condition."

Throughout this specification and the claims which follow, unless the context requires otherwise, the term "comprise", and variations such as "comprises" and "comprising" are intended to specify the presence of the features thereafter, but do not exclude the presence or addition of one or more other features. When used herein the term "comprising" can be substituted with the term "containing", "including" or sometimes "having".

Throughout this specification and the claims which follow, the term "$C_{n-m}$" indicates a range which includes the endpoints, wherein n and m are integers and indicate the number of carbons. Examples include $C_{1-8}$, $C_{1-6}$, and the like.

Unless specifically defined elsewhere in this document, all other technical and scientific terms used herein have the meaning commonly understood by one of ordinary skill in the art to which this invention belongs.

General Synthesis

Compounds disclosed herein, including salts thereof, can be prepared using known organic synthesis techniques and can be synthesized according to any of numerous possible synthetic routes.

The reaction for preparing compounds disclosed herein can be carried out in suitable solvents which can be readily selected by one of skill in the art of organic synthesis.

Suitable solvents can be substantially non-reactive with the starting materials, the intermediates, or products at the temperatures at which the reactions are carried out, e.g., temperatures which can range from the solvent's boiling temperature. A given reaction can be carried out in one solvent or mixture of solvents.

The selection of appropriate protecting group, can be readily determined by one skilled in the art.

Reactions can be monitored according to any suitable method known in the art, such as NMR, UV, HPLC, LC-MS and TLC. Compounds can be purified by a variety of methods, including HPLC and normal phase silica chromatography.

Chiral analytic HPLC was used for the retention time analysis of different chiral examples, the conditions were divided into the methods as below according to the column, mobile phase, solvent ration used.

Method A

| Method A | |
|---|---|
| Column | CHIRAL CEL OD-H |
| Column size | 4.6 cm × 150 cm, 5 um |
| Injection | 0.3 ml |
| Mobile phase | Hex:EtOH (0.1% DEA) = 90:10 |
| Flow rate | 1 ml/min |
| Wave length | UV 214 nm |
| Temperature | 35° C. |

Method B

| Method B | |
|---|---|
| Column | CHIRAL CEL OD-H |
| Column size | 4.6 cm × 150 cm, 5 um |
| Injection | 0.3 ml |
| Mobile phase | Hex:EtOH (0.1% DEA) = 85:15 |
| Flow rate | 1 ml/min |
| Wave length | UV 214 nm |
| Temperature | 35° C. |

Method C

| Method C | |
|---|---|
| Column | CHIRAL PKA IA |
| Column size | 4.6 cm × 150 cm, 5 um |
| Injection | 0.3 ml |
| Mobile phase | Hex:EtOH (0.1% DEA) = 85:15 |
| Flow rate | 1 ml/min |
| Wave length | UV 214 nm |
| Temperature | 35° C. |

Method D

| Method D | |
|---|---|
| Column | CHIRAL PKA IA |
| Column size | 4.6 cm × 150 cm, 5 um |
| Injection | 0.3 ml |
| Mobile phase | Hex:EtOH (0.1% DEA) = 90:10 |
| Flow rate | 1 ml/min |
| Wave length | UV 214 nm |
| Temperature | 35° C. |

Method E

| Method E | |
|---|---|
| Column | CHIRAL PKA AS-H |
| Column size | 4.6 cm × 150 cm, 5 um |
| Injection | 0.3 ml |
| Mobile phase | Hex:EtOH (0.1% DEA) = 85:15 |
| Flow rate | 1 ml/min |
| Wave length | UV 214 nm |
| Temperature | 35° C. |

Method F

| Method F | |
|---|---|
| Column | CHIRAL PKA AS-H |
| Column size | 4.6 cm × 150 cm, 5 um |
| Injection | 0.3 ml |
| Mobile phase | Hex:EtOH (0.1% DEA) = 90:10 |
| Flow rate | 1 ml/min |
| Wave length | UV 214 nm |
| Temperature | 35° C. |

Method G

| Method G | |
|---|---|
| Column | CHIRAL PKA AS-H |
| Column size | 4.6 cm × 150 cm, 5 um |
| Injection | 0.3 ml |
| Mobile phase | Hex:EtOH (0.1% DEA) = 95:05 |
| Flow rate | 1 ml/min |
| Wave length | UV 214 nm |
| Temperature | 35° C. |

Method H

| Method H | |
|---|---|
| Column | CHIRAL CEL OD-H |
| Column size | 4.6 cm × 150 cm, 5 um |
| Injection | 0.3 ml |
| Mobile phase | Hex:EtOH (0.1% DEA) = 95:5 |
| Flow rate | 1 ml/min |
| Wave length | UV 214 nm |
| Temperature | 35° C. |

Method I

| Method I | |
|---|---|
| Column | CHIRAL PKA AD-H |
| Column size | 4.6 cm × 150 cm, 5 um |
| Injection | 0.3 ml |
| Mobile phase | Hex:EtOH (0.1% DEA) = 90:10 |
| Flow rate | 1 ml/min |
| Wave length | UV 214 nm |
| Temperature | 35° C. |

Method J

| Method J | |
|---|---|
| Column | CHIRAL PKA IA |
| Column size | 4.6 cm × 150 cm, 5 um |
| Injection | 0.3 ml |
| Mobile phase | Hex:EtOH (0.1% DEA) = 80:20 |

-continued

Method J

| | |
|---|---|
| Flow rate | 1 ml/min |
| Wave length | UV 214 nm |
| Temperature | 35° C. |

Method K

Method K

| | |
|---|---|
| Column | CHIRAL CEL OD-H |
| Column size | 4.6 cm × 150 cm, 5 um |
| Injection | 0.3 ml |
| Mobile phase | Hex:EtOH (0.1% DEA) = 80:20 |
| Flow rate | 1 ml/min |
| Wave length | UV 214 nm |
| Temperature | 35° C. |

Method L

Method L

| | |
|---|---|
| Column | CHIRAL PKA AS-H |
| Column size | 4.6 cm × 150 cm, 5 um |
| Injection | 0.3 ml |
| Mobile phase | Hex:EtOH (0.1% DEA) = 92:08 |
| Flow rate | 1 ml/min |
| Wave length | UV 214 nm |
| Temperature | 35° C. |

Scheme I

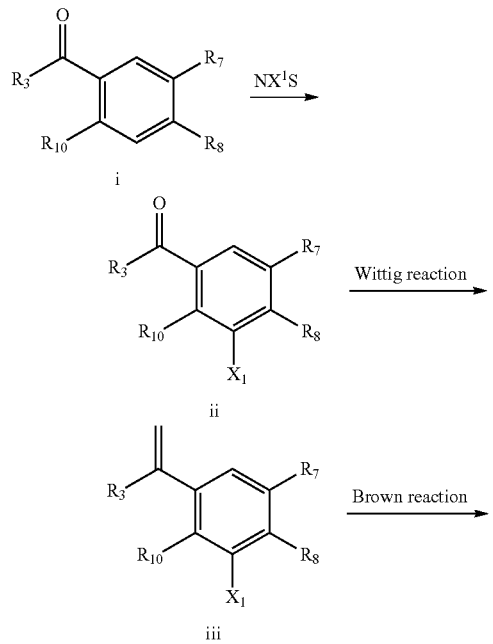

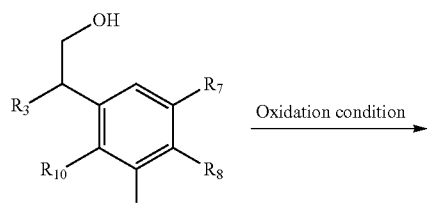

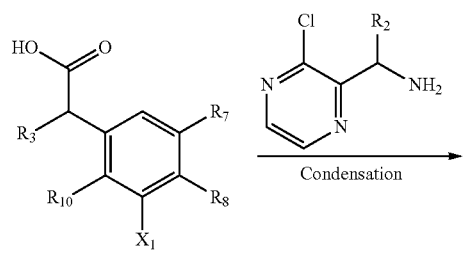

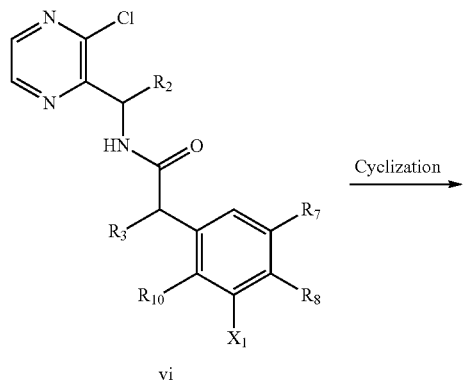

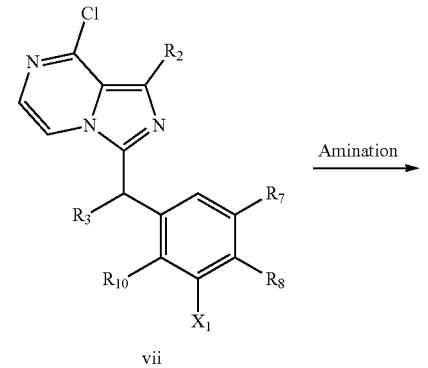

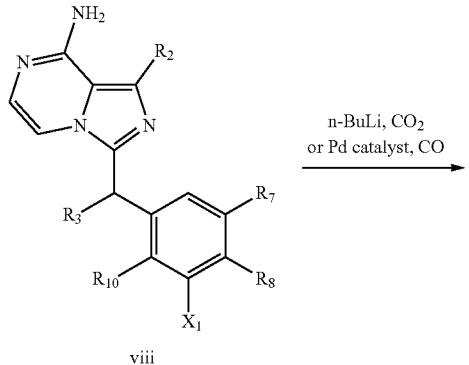

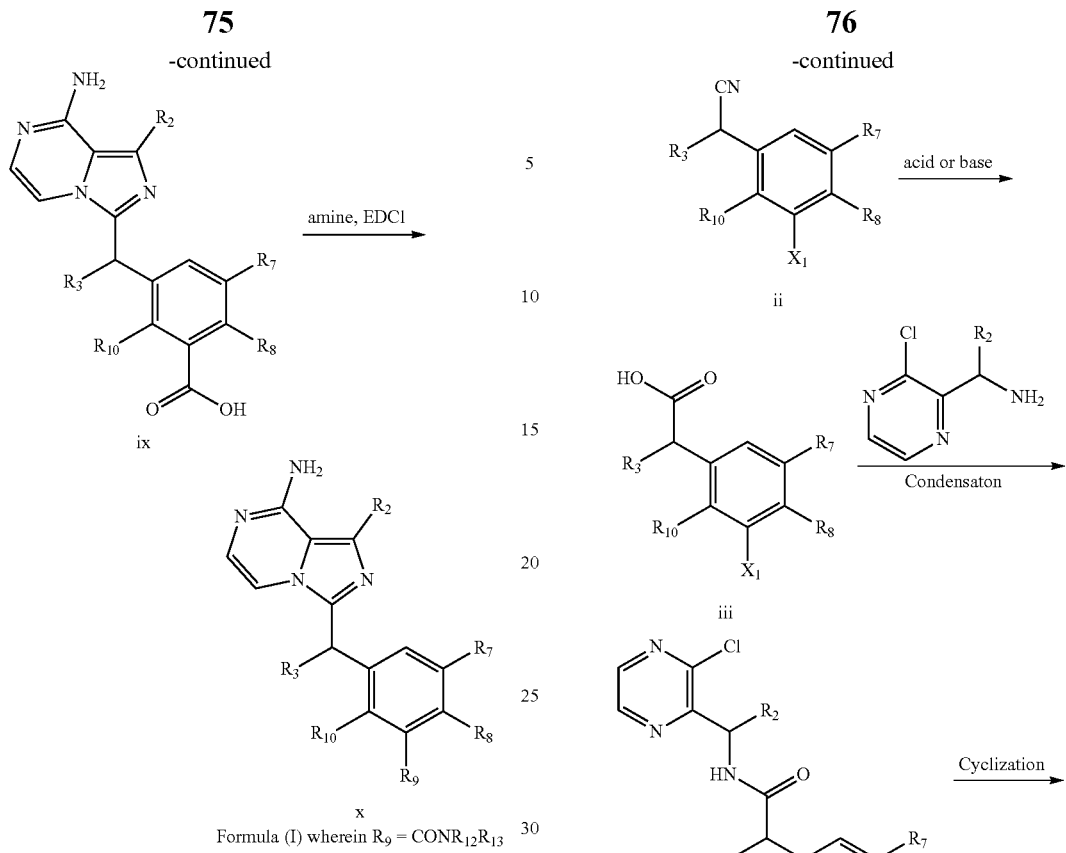

For example, compounds of Formula (I) wherein $R_9$ is —$CONR_{12}R_{13}$ can be formed as shown in scheme I. The compound (i) can be halogenated with N-chlorosuccinamide, N-bromosuccinamide or N-iodosuccinamide to give compound (ii) wherein $X^1$=Cl, Br, or I, respectively. A Wittig reaction is then carried out from compound (ii) under standard condition (e.g., $Ph_3PCH_3Br/nBuLi$ or other bases such as NaH) to give compound (iii) which is carried out under standard Brown reaction condition using $BH_3/H_2O_2$ to give compound (iv) which was oxidized directly by NaClO/$NaClO_2$ or Jones reagent to afford the acid compound (v), the compound (v) was used for condensation under HOBt or EDCI with suitable amine in Scheme I to give compound (vi) that was cyclized directly by $Tf_2O$ or $POCl_3$ to afford compound (vii). Amination of compound (vii) to give compound (viii) which is used for $CO_2$ or CO insertion under nBuLi or palladium catalysts gives compound (ix). Compound (ix) is then reacted with different amines in the presence of HOBt/EDCI to give compound (x) (i.e., Formula (I) wherein $R_9$ is —$CONR_{12}R_{13}$).

Scheme II

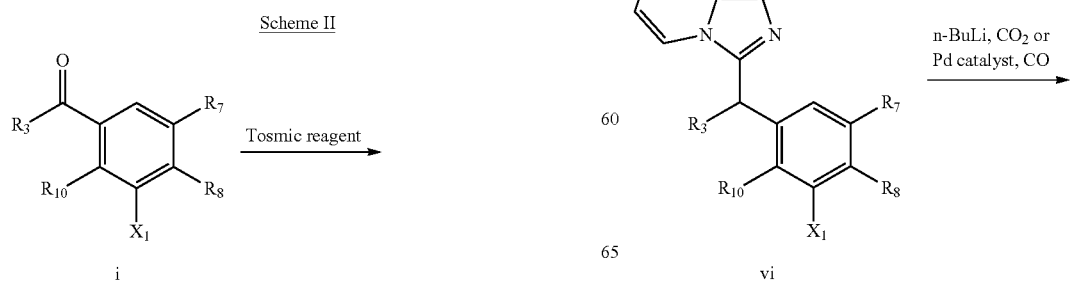

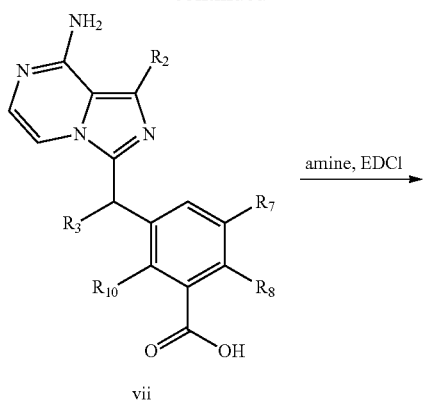

vii

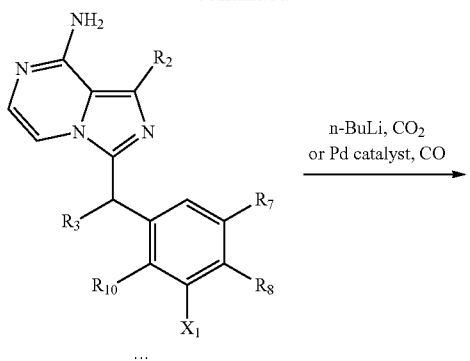

iii

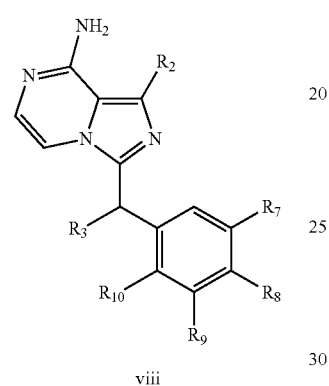

viii
Formula (I) wherein $R_9$ = $CONR_{12}R_{13}$

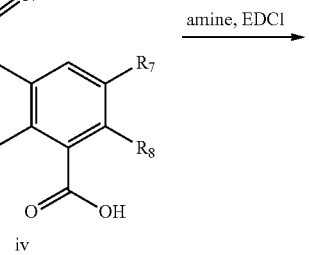

iv

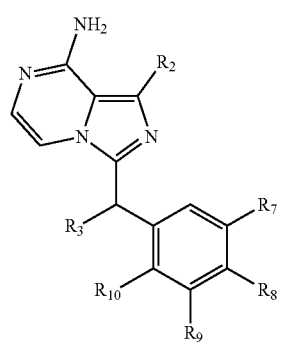

v
Formula (I) wherein $R_9$ = $CONR_{12}R_{13}$

The compounds of Formula (I) wherein $R_9$ is —$CONR_{12}R_{13}$ can also be synthesized as the route in Scheme II. Compound (I) can be converted to compound (ii) by using tosmic reagent, followed by hydrolysis under acidic or basic condition to give compound (iii) which is used for condensation under HOBt or EDCI to give compound (iv). Compound (iv) is then subject to cyclization under $Tf_2O$ or $POCl_3$ to give compound (v). Amination of compound (v) gives compound (vi) which is conducted with $CO_2$ and lithium reagent or CO and palladium catalysts to give compound (vii) that is used for condensation with different amines to give compound (viii) (i.e., Formula (I) wherein $R_9$ is —$CONR_{12}R_{13}$).

Scheme III

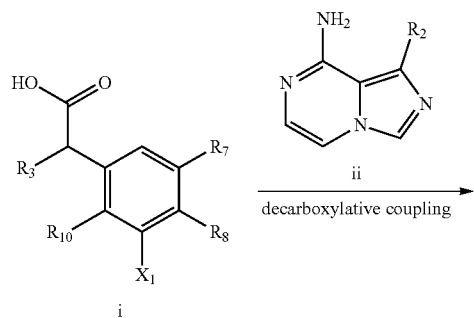

i

The compounds of Formula (I) wherein $R_9$ is —$CONR_{12}R_{13}$ can also be synthesized as the route in scheme III. The acid (i.e., compound (i)) is subject to decarboxylative coupling under metal catalysts or other radical reagents with compound (ii) to give compound (iii) which is conducted with $CO_2$ and lithium reagent or CO and palladium catalysts to give compound (iv) that is used for condensation with different amines to give compound (v) (i.e., Formula (I) wherein $R_9$ is —$CONR_{12}R_{13}$).

Scheme IV

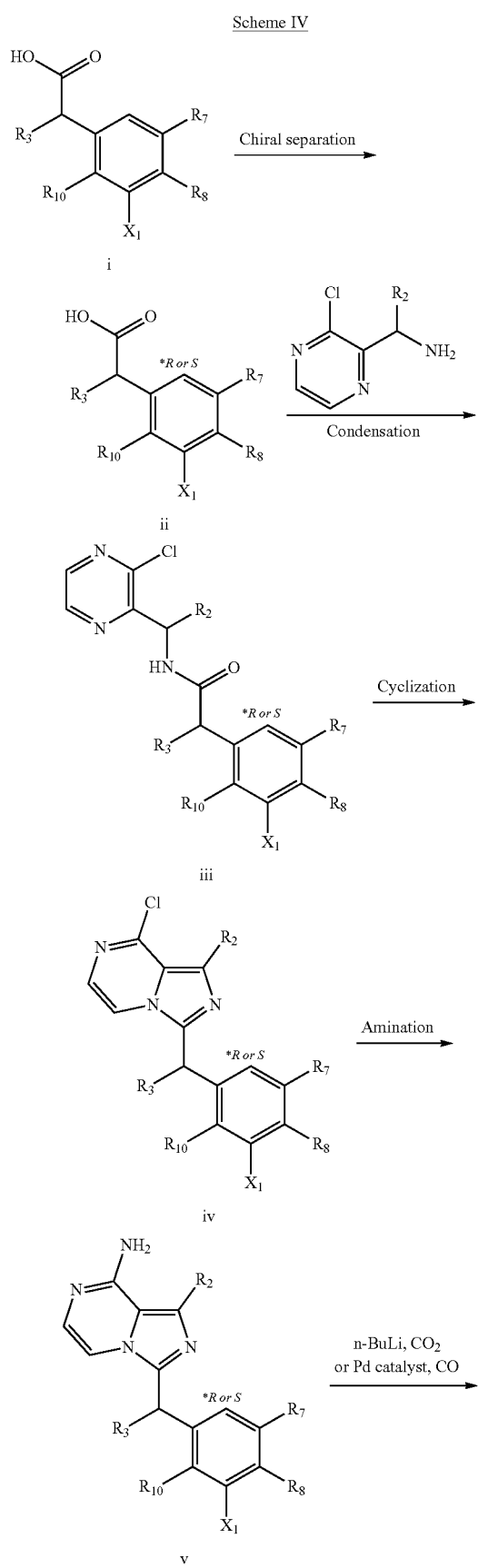

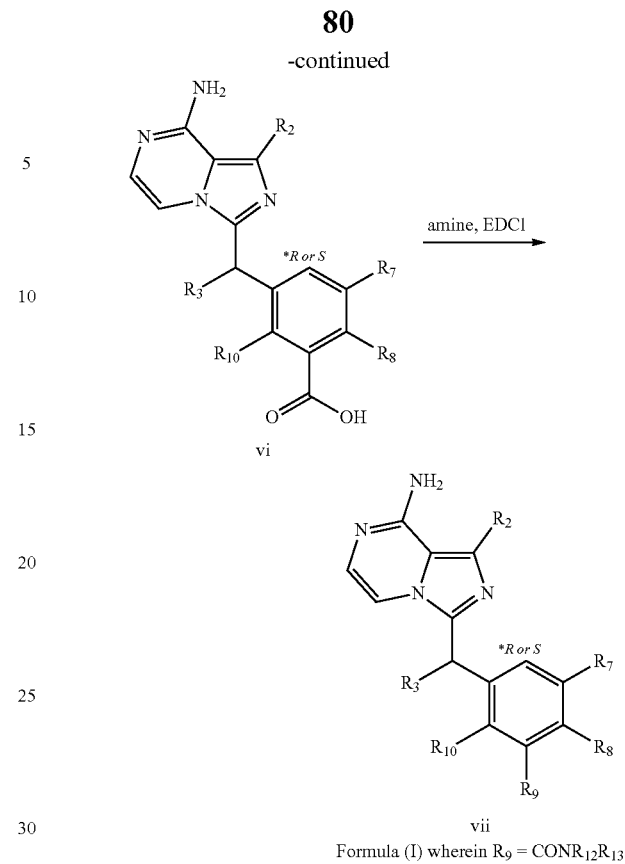

The compounds of Formula (I) wherein $R_9$ is —$CONR_{12}R_{13}$ can also be synthesized as the route in Scheme IV. Compound (i) can be chirally separated to give chiral acid ii with R or S configuration. Chiral compound (ii) is used for condensation under HOBt or EDCI to give chiral compound (iii) which is then subject to cyclization under $Tf_2O$ or $POCl_3$ to give chiral compound (iv). Amination of chiral compound iv gives chiral compound v which is conducted with $CO_2$ and lithium reagent or CO and palladium catalysts to give chiral compound (vi) that is used for condensation with different amines to give chiral compound (vii) (i.e., Formula (I) wherein $R_9$ is —$CONR_{12}R_{13}$).

Scheme V

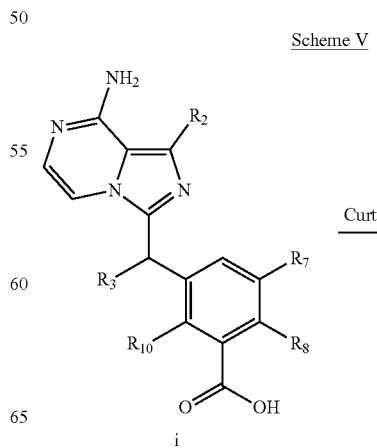

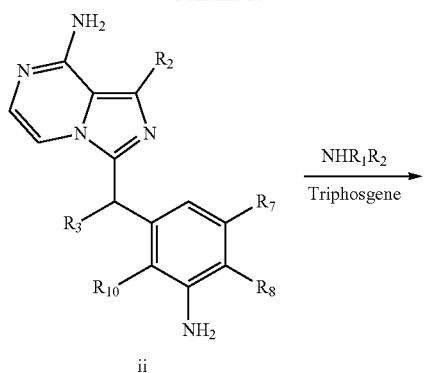

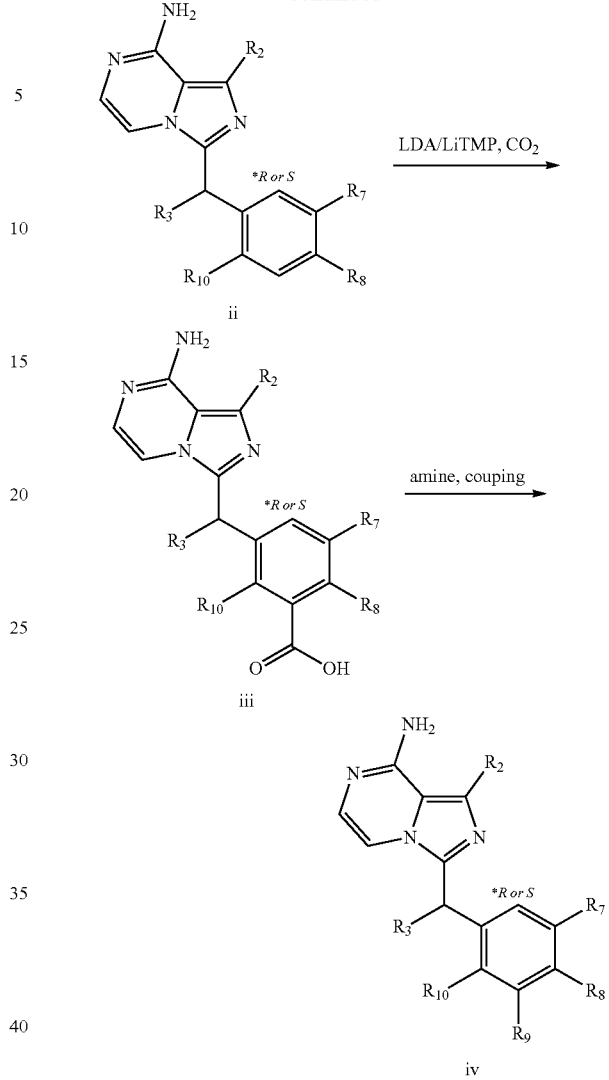

For example, compounds of Formula (I) wherein $R_9$ is —$NR_{12}CONR_{13}R_{14}$ can also be formed as shown in Scheme V. The compound (i) may be subject to Curtius rearrangement to give compound (ii) which is then reacted with triphosgene and versatile amines to give compound (iii) (i.e., Formula (I) wherein $R_9$ is —$NR_{12}CONR_{13}R_{14}$).

Scheme VI

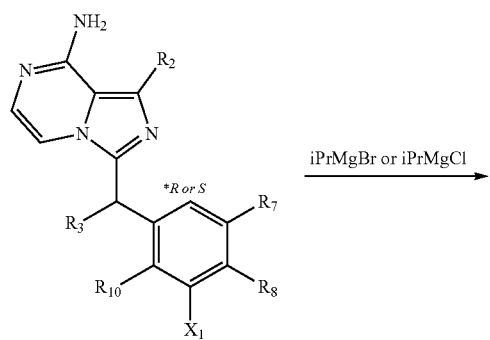

i. $X_1$ = Br, I and Cl

For example, compounds of Formula (I) wherein $R_9$ is —$CONR_{12}R_{13}$ can also be formed as shown in Scheme VI. The halogen of the compound (i) (i.e., $X_1$) can be removed by iPrMgBr or iPrMgCl to give compound (ii) which is then reacted with LDA or LiTMP in the presence of $CO_2$ to give compound (iii) which is used for the coupling with different amines under HATU, HOBt, EDCI, PyBOP and etc. to give compound (iv) (i.e., Formula (I) wherein $R_9$ is —$CONR_{12}R_{13}$).

Abbreviations
HOBt Hydroxybenzotriazole
EDCI 1-Ethyl-3-(3-dimethylaminopropyl)carbodiimide hydrochloride
$Tf_2O$ Trifluoromethanesulfonic anhydride
HATU N-[(dimethylamino)-1H-1,2,3-triazolo-[4,5-b]pyridin-1-ylmethylene]-N-methylmethanaminium hexafluorophosphate N-oxide
PyBOP Benzotriazole-1-yl-oxytripyrrolidinophosphonium hexafluorophosphate
LDA lithium diisopropyl amide
LiTMP lithium tetramethylpiperidine
NBS N-Bromosuccinimide DMF N,N-Dimethylformamide
THF Tetrahydrofuran
PE Petroleum ether
EA Ethyl acetate
aq. aqueous
TLC thin layer chromatography
DCM Dichloromethane
i-PrOH isopropanol
EtOAc ethyl acetate

EXAMPLE

Example 1

1-(3-(1-(8-amino-1-methylimidazo[1,5-a]pyrazin-3-yl)ethyl)-5-chloro-6-fluoro-2-isopropoxybenzoyl)azetidine-3-carboxylic acid (Compound 1)

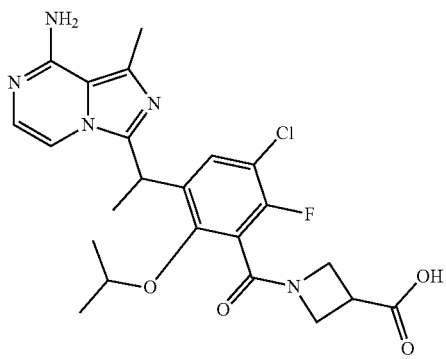 [SMILES: Cc1nc(C(C)c2cc(Cl)c(F)c(C(=O)N3CC(C(=O)O)C3)c2OC(C)C)n2ccnc(N)c12]

Step 1: 1-(5-chloro-4-fluoro-2-hydroxyphenyl)ethan-1-one (1-1)

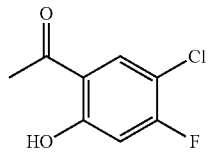

To a 2 L three-necked flask, equipped with a magnetic stirrer was added 4-chloro-3-fluorophenol (160 g, 1.1 mol) and acetyl chloride (129 g, 0.69 mol). The mixture was stirred for 1 h. Then aluminum chloride (219 g, 1.6 mol) was added into the mixture in portions. The mixture was heated to 160° C. and kept at 150° C. for 2 hrs. The mixture was cooled and diluted with HCl (2 M, 500 mL) The resulting hot liquid was cooled and extracted with ethyl acetate (3×500 mL). The combined organic phase was washed with water (500 mL) and brine (500 mL), dried over anhydrous sodium sulfate, filtered and concentrated to afford 200 g (crude) of 1-(5-chloro-4-fluoro-2-hydroxyphenyl)ethan-1-one as a yellow solid. $^1$H NMR (400 MHz, CDCl$_3$) δ 12.48-12.41 (m, 1H), 7.78 (d, J=8.1 Hz, 1H), 6.77 (d, J=10.3 Hz, 1H), 2.61 (s, 3H).

Step 2: 1-(3-bromo-5-chloro-4-fluoro-2-hydroxyphenyl)ethan-1-one (1-2)

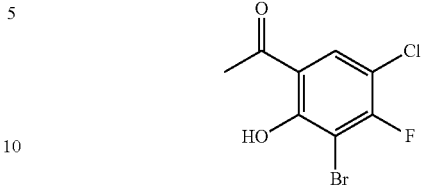

To a solution of 1-(5-chloro-4-fluoro-2-hydroxyphenyl)ethan-1-one (110 g, 412 mmol) in DMF (1 L) was added NBS (114 g, 640 mmol) in portions. The mixture was stirred at room temperature for 1 h. The mixture was diluted with water (3 L), extracted with ethyl acetate (3×1 L). The combined organic phase was washed with brine (3×1 L), dried over anhydrous sodium sulfate, filtered and concentrated to afford 150 g (crude) of 1-(5-chloro-4-fluoro-2-hydroxyphenyl)ethan-1-one as a yellow solid, $^1$H NMR (400 MHz, CDCl$_3$) δ 13.21 (d, J=1.8 Hz, 1H), 7.80 (d, J=7.8 Hz, 1H), 2.66 (s, 3H).

Step 3: 1-(3-bromo-5-chloro-4-fluoro-2-isopropoxyphenyl)ethan-1-one (1-3)

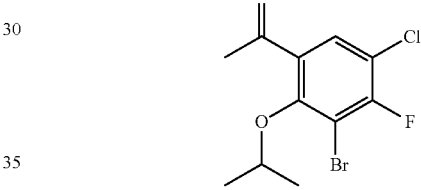

To a solution of 1-(3-bromo-5-chloro-4-fluoro-2-hydroxyphenyl)ethan-1-one (150 g, 560 mmol) and 2-iodopropane (143 g, 841 mmol) in DMF (1 L) was added NaHCO$_3$ (71 g, 845 mmol). The mixture was stirred at 60° C. overnight. The mixture was cooled and diluted with water (3 L), extracted with ethyl acetate (3×1 L). The combined organic phase was washed with brine (3×1 L), dried over anhydrous sodium sulfate, filtered and concentrated. The residue was purified by silica gel column chromatography (elution with hexane/ethyl acetate=50/1) to afford 140 g (80%) of 1-(3-bromo-5-chloro-4-fluoro-2-isopropoxyphenyl)ethan-1-one as a yellow oil. $^1$H NMR (400 MHz, CDCl$_3$) δ 7.57 (d, J=8.2 Hz, 1H), 4.45-4.39 (m, 1H), 2.61 (s, 3H), 1.31 (t, J=6.7 Hz, 6H).

Step 4: 3-bromo-1-chloro-2-fluoro-4-isopropoxy-5-(prop-1-en-2-yl)benzene (1-4)

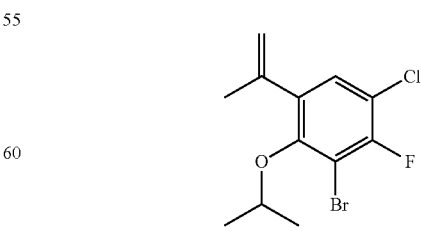

To a mixture of bromo(methyl)triphenylphosphane (41 g, 115 mmol) in THF (400 mL) was added n-BuLi (1.6 M, 72 mL, 115 mmol) dropwise at 0° C. The mixture was stirred at 0° C. for 30 mins. A solution of 1-(3-bromo-5-chloro-4-fluoro-2-isopropoxy phenyl)ethan-1-one (30 g, 97 mmol) in THF (100 mL) was added to the mixture by dropwise at 0° C. The mixture was stirred at 0° C. for 4 hrs. The mixture was quenched with water (500 mL), extracted with ethyl acetate (3×200 mL). The combined organic phase was washed with brine, dried over anhydrous sodium sulfate, filtered and concentrated. The residue was purified by silica gel column chromatography (elution with hexane/ethyl acetate=100/1) to afford 5.0 g (17%) of 3-bromo-1-chloro-2-fluoro-4-isopropoxy-5-(prop-1-en-2-yl)benzene as a yellow oil. $^1$H NMR (400 MHz, CDCl$_3$) δ 7.21-7.17 (m, 1H), 5.20-5.16 (m, 1H), 5.13-5.10 (m, 1H), 4.54-4.44 (m, 1H), 2.10-2.08 (m, 3H), 1.29-1.25 (m, 6H).

Step 5: 2-(3-bromo-5-chloro-4-fluoro-2-isopropoxyphenyl)propan-1-ol (1-5)

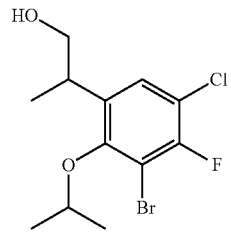 [SMILES: CC(C)Oc1c(C(C)CO)cc(Cl)c(F)c1Br]

To a 3 L flask equipped with a magnetic stirrer was added 3-bromo-1-chloro-2-fluoro-4-isopropoxy-5-(prop-1-en-2-yl)benzene (170 g, 553 mmol) and BH$_3$.THF (1 M, 1660 mL). The mixture was stirred overnight at room temperature. The mixture was quenched with water (100 mL) carefully. A solution of NaOH (22 g, 550 mmol) in water (400 mL) was added to the mixture by dropwise at 0° C., then H$_2$O$_2$ (30%, 188 mL) was added to the mixture by dropwise at 0° C. The mixture was stirred at room temperature for 4 hrs. The mixture was quenched with NaHSO$_3$ solution (1 L) carefully in ice-water bath. Then the mixture was extracted with ethyl acetate (3×1000 mL). The combined organic phase was washed with brine, dried over anhydrous sodium sulfate, filtered and concentrated to afford 200 g (crude) of 2-(3-bromo-5-chloro-4-fluoro-2-isopropoxyphenyl)propan-1-ol as a yellow oil.

Step 6: 2-(3-bromo-5-chloro-4-fluoro-2-isopropoxyphenyl)propanoic acid (1-6)

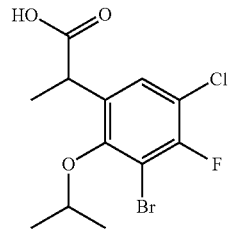 [SMILES: CC(C)Oc1c(C(C)C(=O)O)cc(Cl)c(F)c1Br]

To a solution of 2-(3-bromo-5-chloro-4-fluoro-2-isopropoxyphenyl)propan-1-ol (200 g, 614 mmol) and TEMPO (0.8 g, 5.1 mmol) in acetonitrile (1 L) was added phosphate buffer (PH=6.7, 1 L). The mixture was cooled in water bath. A mixture of NaClO (10%, 500 mL) and NaClO$_2$ (180 g in water 500 mL) was added dropwise to the mixture during 30 mins. The mixture was stirred for 2 hrs, then the mixture was extracted with ethyl acetate (2×1000 mL). The combined organic phase was treated with HCl (2 M, 500 mL), the organic phase was separated, washed with brine, dried over anhydrous sodium sulfate, filtered and concentrated. The residue was triturated with acetonitrile (150 mL), the precipitate was collected by filtration to afford 90 g (43%) of 2-(3-bromo-5-chloro-4-fluoro-2-isopropoxyphenyl)propanoic acid as a white solid. $^1$H NMR (400 MHz, DMSO-d6) δ 12.55 (s, 1H), 7.51 (d, J=8.4 Hz, 1H), 4.60-4.50 (m, 1H), 4.03 (q, J=7.2 Hz, 1H), 2.08 (s, 3H), 1.37 (d, J=7.3 Hz, 3H), 1.31-1.27 (m, 6H). MS (ESI) m/e [M—H]$^-$ 336.9, 338.9.

Step 7: 2-(3-bromo-5-chloro-4-fluoro-2-isopropoxyphenyl)-N-(1-(3-chloropyrazin-2-yl)ethyl)propanamide (1-7)

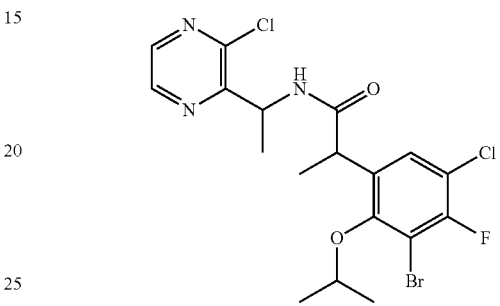

To a solution of 2-(3-bromo-5-chloro-4-fluoro-2-isopropoxyphenyl)propanoic acid (13.0 g, 38.3 mmol) and 1-(3-chloropyrazin-2-yl)ethan-1-amine (6.0 g, 38.1 mmol) in dichloromethane (150 mL) were added Et$_3$N (11.6 g, 114.6 mmol), HOBT (6.2 g, 45.9 mmol) and EDCI (8.8 g, 45.9 mmol). The mixture was stirred for 3 hrs. The mixture was diluted with water (300 mL), extracted with dichloromethane (3×100 mL). The combined organic phase was dried and concentrated. The residue was purified by silica gel column chromatography (elution with dichloromethane/ethyl acetate from 20/1 to 5/1) to afford 11.4 g (62%) of 2-(3-bromo-5-chloro-4-fluoro-2-isopropoxyphenyl)-N-(1-(3-chloropyrazin-2-yl)ethyl)propanamide as a yellow solid. $^1$H NMR (400 MHz, CDCl$_3$) δ 8.30 (d, J=2.4 Hz, 1H), 8.26 (d, J=2.4 Hz, 1H), 7.31 (d, J=8.1 Hz, 1H), 6.96 (d, J=7.6 Hz, 1H), 5.47-5.39 (m, 1H), 4.73-4.63 (m, 1H), 4.15-4.07 (m, 1H), 1.51-1.42 (m, 9H), 1.32 (d, J=6.2 Hz, 3H). MS (ESI) m/e [M+1]478.0, 480.0.

Step 8: 3-(1-(3-bromo-5-chloro-4-fluoro-2-isopropoxyphenyl)ethyl)-8-chloro-1-methylimidazo[1,5-a]pyrazine (1-8)

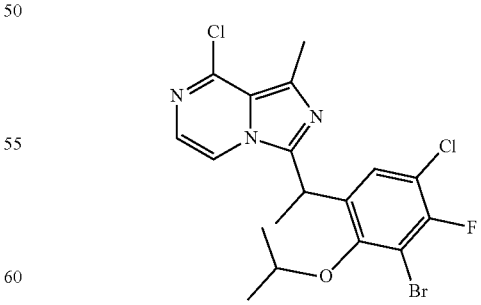

To a solution of 2-(3-bromo-5-chloro-4-fluoro-2-isopropoxyphenyl)-N-(1-(3-chloropyrazin-2-yl)ethyl)propanamide (11.4 g, 23.8 mmol) in dichloromethane (130 mL) was added a solution of Tf$_2$O in dichloromethane (30 mL) dropwise. Then a solution of pyridine (9.4 g, 119 mmol) in dichloromethane (40 mL) was added by dropwise to the mixture. The mixture was stirred at room temperature for 1 h. The mixture was quenched with water (200 mL), extracted with dichloromethane (3×100 mL). The combined organic phase was dried and concentrated. The residue was purified by silica gel column chromatography (elution with dichloromethane/ethyl acetate from 20/1 to 5/1) to afford 8.0 g (73%) of 3-(1-(3-bromo-5-chloro-4-fluoro-2-isopropoxyphenyl)ethyl)-8-chloro-1-methylimidazo[1,5-a]pyrazine as a yellow solid. $^1$H NMR (400 MHz, CDCl$_3$) δ 7.57 (d, J=4.8 Hz, 1H), 7.30 (d, J=7.8 Hz, 1H), 7.15 (d, J=4.6 Hz, 1H), 4.84-4.69 (m, 2H), 2.82 (s, 3H), 1.86 (d, J=7.0 Hz, 3H), 1.53 (d, J=6.1 Hz, 3H), 1.38 (d, J=6.1 Hz, 3H). MS (ESI) m/e [M+1]+459.9, 462.0.

Step 9: 3-(1-(3-bromo-5-chloro-4-fluoro-2-isopropoxyphenyl)ethyl)-1-methylimidazo[1,5-a]pyrazin-8-amine(1-9)

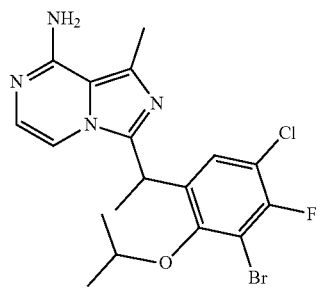 [SMILES: Cc1nc(C(C)c2cc(Cl)c(F)c(Br)c2OC(C)C)n2ccnc(N)c12]

A mixture of 3-(1-(3-bromo-5-chloro-4-fluoro-2-isopropoxyphenyl)ethyl)-8-chloro-1-methylimidazo[1,5-a]pyrazine (1.01 g, 2.2 mmol) and NH$_3$ in iPrOH (20 mL) in a steel tube was stirred at 90° C. for 48 hrs. After completion, the mixture was evaporated in vacuo. The residue was added 50 mL ethyl acetate, washed with water (30 mL×2), dried over Na$_2$SO$_4$, filtered and evaporated in vacuo to give the crude product, then the crude product was stirred in petroleum (250 mL) and filtrated to give the product (0.96 g, 98.3%) as a white solid.

Step 10: 3-(1-(8-amino-1-methylimidazol[1,5-a]pyrazin-3-yl)ethyl)-5-chloro-6-fluoro-2-isopropoxybenzoic acid (1-10)

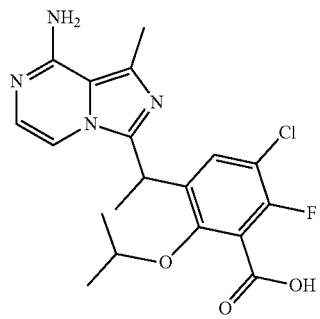 [SMILES: Cc1nc(C(C)c2cc(Cl)c(F)c(C(=O)O)c2OC(C)C)n2ccnc(N)c12]

To a solution of compound 1-9 (1.15 g, 2.6 mmol) in THF (50 mL) was added n-BuLi (2.4 M, 3.5 mL) dropwise at −78° C. The mixture was stirred for 10 min, CO$_2$ gas was bubbled into the mixture. The mixture was stirred for 30 min. The mixture was warmed to room temperature and quenched with water (50 mL), washed with ethyl acetate (30 mL). The water layer was separated, acidified with concentrated HCl to pH=1 and concentrated to afford 1.1 g (crude) of 3-(1-(8-amino-1-methylimidazo[1,5-a]pyrazin-3-yl)ethyl)-5-chloro-6-fluoro-2-isopropoxybenzoic acid as a yellow solid. MS (ESI) m/e [M+H]$^+$ 407.1.

Step 11: Methyl 1-(3-(1-(8-amino-1-methylimidazo[1,5-a]pyrazin-3-yl)ethyl)-5-chloro-6-fluoro-2-isopropoxybenzoyl)azetidine-3-carboxylate (1-11)

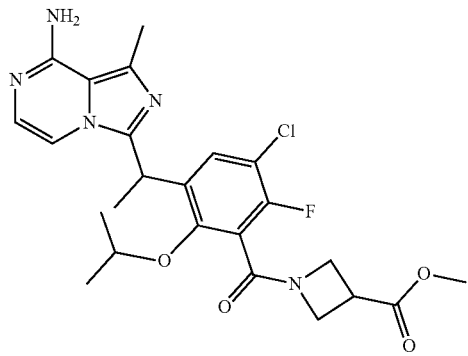 [SMILES: COC(=O)C1CN(C(=O)c2c(F)c(Cl)cc(C(C)c3nc(C)c4c(N)nccn34)c2OC(C)C)C1]

To a solution of compound 1-10 (200 mg, crude) and methyl azetidine-3-carboxylate hydrochloride (75 mg, 0.5 mmol) in DMF (20 mL) was added Et$_3$N (1.0 g, 10 mmol), and PyBOP (260 mg, 0.5 mmol). The mixture was stirred for 2 hrs. The mixture was diluted with water (50 mL), extracted with ethyl acetate (3×30 mL). The combined organic phase was washed with water (50 mL), brine (50 mL), dried over anhydrous sodium sulfate, filtered and concentrated to afford 100 mg (crude) of methyl 1-(3-(1-(8-amino-1-methylimidazo[1,5-a]pyrazin-3-yl)ethyl)-5-chloro-6-fluoro-2-isopropoxybenzoyl)azetidine-3-carboxylate as a yellow oil. MS (ESI) m/e [M+H]$^+$ 504.2.

Step 12: 1-(3-(1-(8-amino-1-methylimidazo[1,5-a]pyrazin-3-yl)ethyl)-5-chloro-6-fluoro-2-isopropoxybenzoyl)azetidine-3-carboxylic acid trifluoroacetate (1-12)

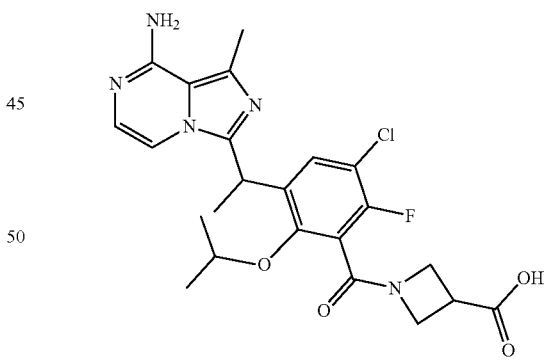

To a solution of compound 1-11 (100 mg, crude) in MeOH (10 mL) was added NaOH aqueous solution (1 M, 10 mL). The mixture was stirred for 6 hrs, and concentrated under vacuum. The residue was purified by prep-HPLC to afford 30 mg (25%) of 1-(3-(1-(8-amino-1-methylimidazo[1,5-a]pyrazin-3-yl)ethyl)-5-chloro-6-fluoro-2-isopropoxybenzoyl)azetidine-3-carboxylic acid trifluoroacetate, $^1$H NMR (400 MHz, DMSO-d6) δ 8.51 (brs, 2H), 7.53-7.43 (m, 2H), 6.93 (d, J=5.9 Hz, 0.5H), 6.86 (d, J=5.9 Hz, 0.5H), 4.88-4.80 (m, 1H), 4.44-4.36 (m, 1H), 4.23 (t, J=9.5 Hz, 1H), 4.11-4.01 (m, 2H), 3.96-3.85 (m, 1H), 3.50-3.37 (m, 1H), 2.64 (s, 3H), 1.64 (t, J=6.6 Hz, 3H), 1.26-1.11 (m, 6H). MS (ESI) m/e [m+H]+ 490.1.

Example 2

1-(3(1-(8-amino-1-methylimidazo[1,5-a]pyrazin-3-yl)ethyl)-5-chloro-6-fluoro-2-isopropoxybenzamido)cyclopropane-1-carboxylic acid (Compound 2)

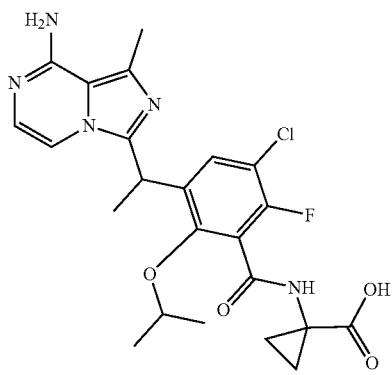 [SMILES: Cc1nc(C(C)c2cc(Cl)c(F)c(C(=O)NC3(C(=O)O)CC3)c2OC(C)C)n2ccnc(N)c12]

The desired compound was prepared from compound 1-10 and ethyl 1-aminocyclopropane-1-carboxylate in a similar manner to compound 1 in Example 1. $^1$H NMR (400 MHz, DMSO-d6) δ 9.05 (s, 1H), 8.60 (s, 2H), 7.54-7.47 (m, 2H), 6.95 (d, J=5.8 Hz, 1H), 4.85 (q, J=7.0 Hz, 1H), 4.78-4.67 (m, 1H), 2.64 (s, 3H), 1.61 (d, J=7.0 Hz, 3H), 1.46-1.38 (m, 1H), 1.15 (d, J=5.9 Hz, 3H), 1.10-1.01 (m, 5H). MS (ESI) m/e [M+H]+ 490.1.

Example 3

(3-(1-(8-amino-1-methylimidazo[1,5-a]pyrazin-3-yl)ethyl)-5-chloro-6-fluoro-2-isopropoxyphenyl)(3-hydroxyazetidin-1-yl)methanone (Compound 3)

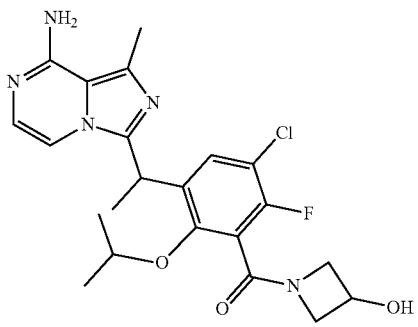 [SMILES: Cc1nc(C(C)c2cc(Cl)c(F)c(C(=O)N3CC(O)C3)c2OC(C)C)n2ccnc(N)c12]

The desired compound was prepared from compound 1-10 and azetidin-3-ol in a similar manner to compound 1-11 in Example 1. $^1$H NMR (400 MHz, DMSO-d6) δ 7.39-7.33 (m, 1H), 7.24-7.19 (m, 1H), 6.87-6.78 (m, 1H), 6.46 (s, 2H), 5.90-5.80 (m, 1H), 4.81-4.73 (m, 1H), 4.57-4.45 (m, 1H), 4.42-4.30 (m, 1H), 4.28-4.19 (m, 1H), 4.07-399 (m, 1H), 3.81-3.67 (m, 2H), 2.57 (s, 3H), 1.70-1.55 (m, 3H), 1.40-1.15 (m, 6H). MS (ESI) m/e [M+1]+ 462.1.

Example 4

(3-(1-(8-amino-1-methylimidazo[1,5-a]pyrazin-3-yl)ethyl)-5-chloro-6-fluoro-2-isopropoxyphenyl)(morpholino)methanone (Compound 4)

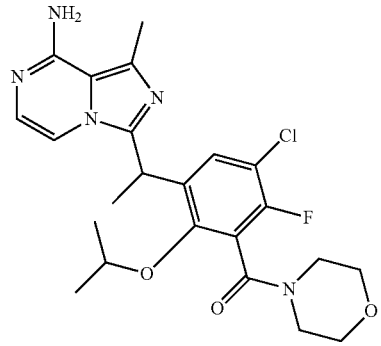

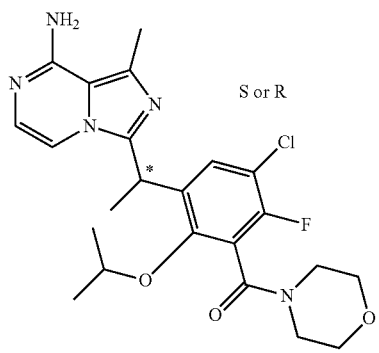

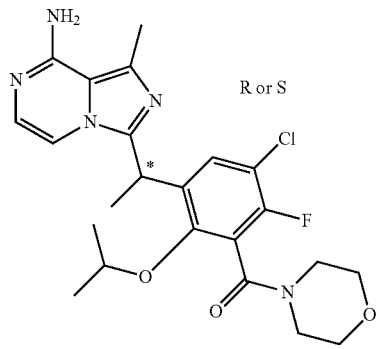

The desired compound was prepared from compound 1-10 and morpholine in a similar manner to compound 1-11 in Example 1. $^1$H NMR (400 MHz, DMSO-d6) δ 7.46 (d, J=8.7 Hz, 0.3H), 7.36 (d, J=8.5 Hz, 0.7H), 7.26 (d, J=5.0 Hz, 0.3H), 7.17 (d, J=5.0 Hz, 0.7H), 6.86 (d, J=5.0 Hz, 0.3H), 6.82 (d, J=5.0 Hz, 0.71H), 6.53-6.42 (m, 2H), 4.81-4.70 (m, 1H), 4.45-4.35 (m, 0.7H), 4.31-4.21 (m, 0.3H), 3.79-3.55 (m, 4H), 3.55-3.46 (m, 2H), 3.15-2.99 (m, 2H), 2.59-2.55 (m, 3H), 1.67 (d, J=7.1 Hz, 2H), 1.56 (d, J=7.1 Hz, 1H), 1.25 (t, J=6.5 Hz, 4H), 1.17 (d, J=6.1 Hz, 1H), 0.99 (d, J=6.0 Hz, 1H). MS (ESI) m/e [M+1]+ 476.1.

The compound 4 was separated by chiral column to give compound 4A (peak 1, S or R, retention time (RT) at 8.78 min in chiral analysis, Method A) and compound 4B (peak 2, R or S, retention time (RT) at 8.19 min in chiral analysis, Method A).

Compound 4A: ¹H NMR (400 MHz, DMSO-d6) δ 7.46 (d, J=8.7 Hz, 0.3H), 7.36 (d, J=8.5 Hz, 0.7H), 7.26 (d, J=5.0 Hz, 0.3H), 7.17 (d, J=5.0 Hz, 0.7H), 6.86 (d, J=5.0 Hz, 0.3H), 6.82 (d, J=5.0 Hz, 0.7H), 6.53-6.42 (m, 2H), 4.81-4.70 (m, 1H), 4.45-4.35 (m, 0.7H), 4.31-4.21 (m, 0.3H), 3.79-3.55 (m, 4H), 3.55-3.46 (m, 2H), 3.15-2.99 (m, 2H), 2.59-2.55 (m, 3H), 1.67 (d, J=7.1 Hz, 2H), 1.56 (d, J=7.1 Hz, 1H), 1.25 (t, J=6.5 Hz, 4H), 1.17 (d, J=6.1 Hz, 1H), 0.99 (d, J=6.0 Hz, 1H). MS (ESI) m/e [M+1]⁺ 476.1.

Compound 4B: ¹H NMR (400 MHz, DMSO-d6) δ 7.46 (d, J=8.7 Hz, 0.3H), 7.35 (d, J=8.5 Hz, 0.7H), 7.25 (d, J=5.1 Hz, 0.3H), 7.16 (d, J=5.0 Hz, 0.7H), 6.85 (d, J=5.0 Hz, 0.3H), 6.82 (d, J=5.0 Hz, 0.7H), 6.53-6.42 (m, 2H), 4.81-4.70 (m, 1H), 4.45-4.35 (m, 0.7H), 4.31-4.21 (m, 0.3H), 3.79-3.55 (m, 4H), 3.55-3.45 (m, 2H), 3.14-3.00 (m, 2H), 2.59-2.55 (m, 3H), 1.67 (d, J=7.1 Hz, 2H), 1.56 (d, J=7.1 Hz, 1H), 1.25 (t, J=6.5 Hz, 4H), 1.17 (d, J=6.1 Hz, 1H), 0.99 (d, J=6.0 Hz, 1H). MS (ESI) m/e [M+1]⁺ 476.1.

The chiral separation conditions are shown below.

| Column | CHIRALPAK IG |
|---|---|
| Column size | 2 cm × 25 cm, 5 um |
| Injection | 1 ML |
| Mobile phase | Hex(0.2% IPAmine):IPA = 70:30 |
| Flow rate | 20 mL/min |
| Wave length | UV 220 nm |
| Temperature | 25° C. |
| Sample solution | 15.3 mg/mL in DCM:EtOH = 1:2 |
| Prep-HPLC equipment | Prep-Gilson-HPLC |

Example 5

3-(1-(8-amino-1-methylimidazo[1,5-a]pyrazin-3-yl)ethyl)-5-chloro-6-fluoro-N-(1-(hydroxymethyl)cyclopropyl)-2-isopropoxybenzamide (Compound 5)

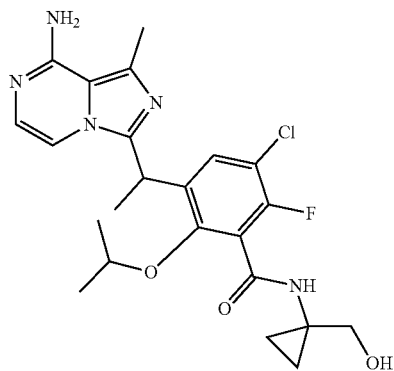

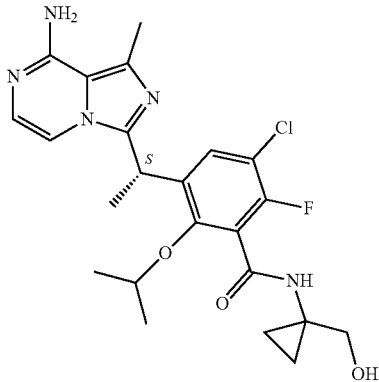

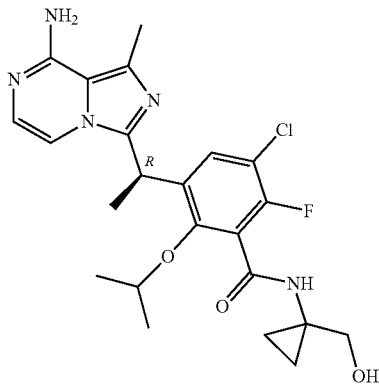

The desired compound was prepared from compound 1-10 and (1-aminocyclopropyl)methanol in a similar manner to compound 1-11 in Example 1. ¹H NMR (400 MHz, DMSO-d6) δ 8.92 (s, 1H), 7.36 (d, J=8.6 Hz, 1H), 7.23 (d, J=5.1 Hz, 1H), 6.85 (d, J=5.0 Hz, 1H), 6.44 (s, 2H), 4.75 (q, J=6.9 Hz, 1H), 4.67 (t, J=5.6 Hz, 1H), 4.49 (dt, J=12.1, 6.0 Hz, 1H), 3.55 (d, J=5.7 Hz, 2H), 2.56 (s, 3H), 1.56 (d, J=7.1 Hz, 3H), 1.18 (d, J=6.0 Hz, 3H), 1.08 (d, J=6.0 Hz, 3H), 0.78 (t, J=5.7 Hz, 2H), 0.61 (t, J=5.7 Hz, 2H). MS (ESI) m/e [M+1]⁺ 476.4.

The compound 5 was separated by chiral column to give compound 5A (peak 1, S, retention time (RT) at 4.80 min in chiral analysis, Method A) and compound 5B (peak 2, R, retention time (RT) at 6.11 min in chiral analysis, Method A).

Compound 5A: ¹H NMR (400 MHz, DMSO-d6) δ 8.92 (s, 1H), 7.36 (d, J=8.6 Hz, 1H), 7.23 (d, J=5.1 Hz, 1H), 6.85 (d, J=5.0 Hz, 1H), 6.44 (s, 2H), 4.75 (q, J=6.9 Hz, 1H), 4.67 (t, J=5.6 Hz, 1H), 4.49 (dt, J=12.1, 6.0 Hz, 1H), 3.55 (d, J=5.7 Hz, 2H), 2.56 (s, 3H), 1.56 (d, J=7.1 Hz, 3H), 1.18 (d, J=6.0 Hz, 3H), 1.08 (d, J=6.0 Hz, 3H), 0.78 (t, J=5.7 Hz, 2H), 0.61 (t, J=5.7 Hz, 2H). MS (ESI) m/e [M+1]⁺ 476.4. The absolute (S) configuration of chiral center in compound 5A was confirmed by x-ray analysis of single crystal.

Compound 5B: ¹H NMR (400 MHz, DMSO-d6) δ 8.92 (s, 1H), 7.36 (d, J=8.6 Hz, 1H), 7.23 (d, J=5.1 Hz, 1H), 6.85 (d, J=5.0 Hz, 1H), 6.44 (s, 2H), 4.75 (q, J=6.9 Hz, 1H), 4.67 (t, J=5.6 Hz, 1H), 4.49 (dt, J=12.1, 6.0 Hz, 1H), 3.55 (d, J=5.7 Hz, 2H), 2.56 (s, 3H), 1.56 (d, J=7.1 Hz, 3H), 1.18 (d, J=6.0 Hz, 3H), 1.08 (d, J=6.0 Hz, 3H), 0.78 (t, J=5.7 Hz, 2H), 0.61 (t, J=5.7 Hz, 2H). MS (ESI) m/e [M+1]⁺ 476.4.

The chiral separation conditions are shown below.

| | |
|---|---|
| Column | CHIRAL ART Cellulose-SB |
| Column size | 2 cm × 25 cm, 5 um |
| Injection | 0.4 ML |
| Mobile phase | Hex:EtOH = 80:20 |
| Flow rate | 20 mL/min |
| Wave length | UV 220 nm |
| Temperature | 25° C. |
| Sample solution | 21 mg/mL in EtOH:DCM = 3:1 |
| Prep-HPLC equipment | Prep-Gilson-HPLC |

Example 6

(3-(1-(8-amino-1-methylimidazo[1,5-a]pyrazin-3-yl)ethyl)-5-chloro-6-fluoro-2-isopropoxyphenyl)((S)-3-hydroxypyrrolidin-1-yl)methanone (Compound 6)

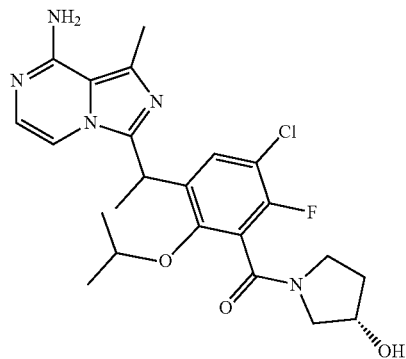 [SMILES: Cc1nc(C(C)c2cc(Cl)c(F)c(C(=O)N3CC[C@H](O)C3)c2OC(C)C)n2ccnc(N)c12]

The desired compound was prepared from compound 1-10 and (S)-pyrrolidin-3-ol in a similar manner to compound 1-11 in Example 1. $^1$H NMR (400 MHz, DMSO-d6) δ 7.42-7.27 (m, 1H), 7.26-7.13 (m, 1H), 6.87-6.75 (m, 1H), 6.49-6.42 (m, 2H), 5.08-4.99 (m, 1H), 4.82-4.71 (m, 1H), 4.48-4.30 (m, 1.5H), 4.30-4.19 (m, 0.5H), 3.68-3.38 (m, 2H), 3.23-3.04 (m, 1H), 3.03-2.92 (m, 1H), 2.60-2.55 (m, 3H), 2.04-1.72 (m, 2H), 1.66 (d, J=6.8 Hz, 2H), 1.54 (d, J=6.5 Hz, 1H), 1.29-1.13 (m, 5H), 0.92 (dd, J=12.8, 6.0 Hz, 1H). MS (ESI) m/e [M+1]$^+$ 476.1.

Example 7

(3-(1-(8-amino-1-methylimidazo[1,5-a]pyrazin-3-yl)ethyl)-5-chloro-6-fluoro-2-isopropoxyphenyl)(4-hydroxypiperidin-1-yl)methanone (Compound 7)

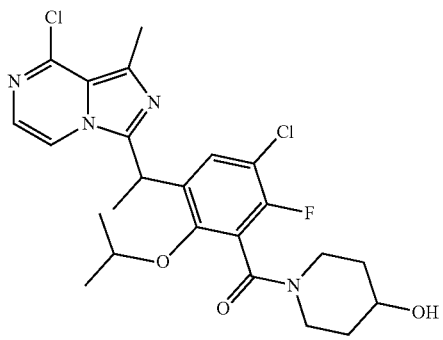 [SMILES: Cc1nc(C(C)c2cc(Cl)c(F)c(C(=O)N3CCC(O)CC3)c2OC(C)C)n2ccnc(Cl)c12]

The desired compound was prepared from compound 1-10 and piperidin-4-ol in a similar manner to compound 1-11 in Example 1. $^1$H NMR (400 MHz, DMSO-d6) δ 7.36-7.27 (m, 1H), 7.17-7.12 (m, 1H), 6.84 (dd, J=5.0, 1.9 Hz, 0.3H), 6.79-6.75 (m, 0.7H), 6.17 (s, 2H), 4.80-4.68 (m, 1H), 4.64-4.28 (m, 2H), 4.17-4.09 (m, 0.4H), 4.07-3.96 (m, 0.4H), 3.95-3.87 (m, 0.3H), 3.84-3.66 (m, 1H), 3.48-3.39 (m, 0.3H), 3.39-3.24 (m, 0.7H), 3.24-3.12 (m, 1H), 2.98-2.87 (m, 1H), 2.58 (s, 3H), 1.88-1.73 (m, 1H), 1.71-1.65 (m, 3H), 1.58 (d, J=7.0 Hz, 1H), 1.48-1.35 (m, 2H), 1.28 (d, J=6.1 Hz, 1H), 1.27-1.19 (m, 3.5H), 1.17 (d, J=6.1 Hz, 0.5H), 1.04 (dd, J=9.6, 6.1 Hz, 1H). MS (ESI) m/e [M+1]+ 490.1.

Example 8

3-(1-(8-amino-1-methylimidazo[1,5-a]pyrazin-3-yl)ethyl)-5-chloro-6-fluoro-2-isopropoxy-N-(2-methoxyethyl)benzamide (Compound 8)

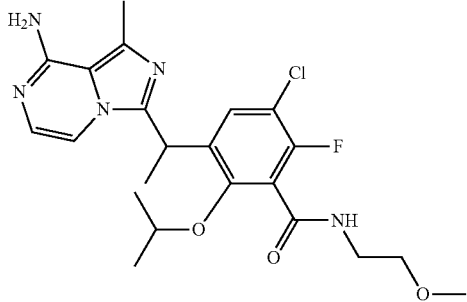 [SMILES: COCCNC(=O)c1c(F)c(Cl)cc(C(C)c2nc(C)c3c(N)nccn23)c1OC(C)C]

The desired compound was prepared from compound 1-10 and 2-methoxyethan-1-amine in a similar manner to compound 1-11 in Example 1. $^1$H NMR (400 MHz, DMSO-d6) δ 8.78 (t, J=5.4 Hz, 1H), 7.38 (d, J=8.6 Hz, 1H), 7.25 (d, J=5.0 Hz, 1H), 6.85 (d, J=5.0 Hz, 1H), 6.48 (s, 2H), 4.77 (q, J=7.1 Hz, 1H), 4.52-4.45(m, 1H), 3.45-3.37 (m, 4H), 3.25 (s, 3H), 2.57 (s, 3H), 1.58 (d, J=7.1 Hz, 3H), 1.18 (d, J=6.0 Hz, 3H), 1.08 (d, J=6.0 Hz, 3H). MS (ESI) m/e [M+1]$^+$ 464.1.

Example 9

3-(1-(8-amino-1-methylimidazo[1,5-a]pyrazin-3-yl)ethyl)-5-chloro-6-fluoro-N-((R)-2-hydroxypropyl)-2-isopropoxybenzamide (Compound 9)

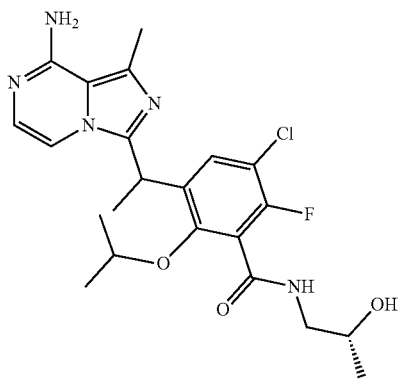 [SMILES: Cc1nc(C(C)c2cc(Cl)c(F)c(C(=O)NC[C@@H](C)O)c2OC(C)C)n2ccnc(N)c12]

The desired compound was prepared from compound 1-10 and (R)-1-aminopropan-2-ol in a similar manner to compound 1-11 in Example 1. ¹H NMR (400 MHz, DMSO-d6) δ 8.65 (t, J=5.6 Hz, 1H), 7.38 (d, J=8.5 Hz, 1H), 7.24 (d, J=5.0 Hz, 1H), 6.85 (d, J=4.4 Hz, 1H), 6.42 (s, 2H), 4.81-4.73 (m, 1H), 4.69 (d, J=2.8 Hz, 1.11), 4.53-4.42 (m, 1H), 3.78-3.68 (m, 1H), 3.27-3.18 (m, 1H), 3.15-3.05 (m, 1H), 2.56 (s, 3H), 1.58 (d, J=6.9 Hz, 3H), 1.18 (d, J=6.0 Hz, 3H), 1.11-1.05 (m, 6H). MS (ESI) m/e [M+1]⁺ 464.1.

Example 10

3-(1-(8-amino-1-methylimidazo[1,5-a]pyrazin-3-yl)ethyl)-5-chloro-6-fluoro-N-((1-hydroxycyclopropyl)methyl)-2-isopropoxybenzamide (Compound 10)

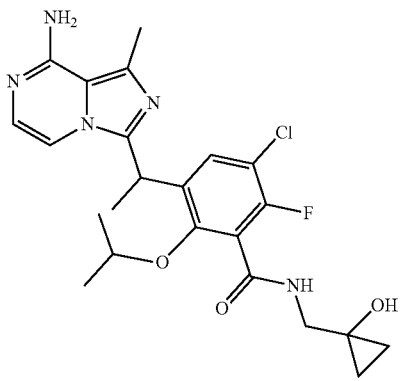 [SMILES: Cc1nc(C(C)c2cc(Cl)c(F)c(C(=O)NCC3(O)CC3)c2OC(C)C)n2ccnc(N)c12]

The desired compound was prepared from compound 1-10 and 1-(aminomethyl)cyclopropan-1-ol in a similar manner to compound 1-11 in Example 1. ¹H NMR (400 MHz, DMSO-d6) δ 8.71 (t, J=5.7 Hz, 1H), 7.37 (d, J=8.6 Hz, 1H), 7.24 (d, J=5.0 Hz, 1H), 6.85 (d, J=5.1 Hz, 1H), 6.42 (s, 2H), 5.26 (s, 1H), 4.77 (q, J=6.9 Hz, 1H), 4.59-4.52 (m, 1H), 3.40 (d, J=5.8 Hz, 2H), 2.57 (s, 3H), 1.58 (d, I=7.1 Hz, 3H), 1.19 (d, J=6.0 Hz, 3H), 1.09 (d, J=6.0 Hz, 3H), 0.54 (s, 4H). MS (ESI) m/e [M+1]⁺ 476.1.

Example 11

3-(1-(8-amino-1-methylimidazo[1,5-a]pyrazin-3-yl)ethyl)-5-chloro-N-cyclopropyl-6-fluoro-2-isopropoxybenzamide (Compound 11)

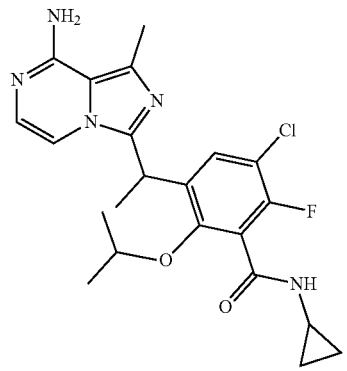 [SMILES: Cc1nc(C(C)c2cc(Cl)c(F)c(C(=O)NC3CC3)c2OC(C)C)n2ccnc(N)c12]

The desired compound was prepared from compound 1-10 and cyclopropylamine in a similar manner to compound 1-11 in Example 1. ¹H NMR (400 MHz, DMSO-d6) δ 8.73 (d, J=4.1 Hz, 1H), 7.40 (d, J=8.6 Hz, 1H), 7.25 (d, J=5.0 Hz, 1H), 6.86 (d, J=4.9 Hz, 1H), 6.43 (s, 2H), 4.76 (q, J=7.0 Hz, 1H), 4.46-4.37 (m, 1H), 2.85-2.76 (m, 1H), 2.56 (s, 3H), 1.57 (d, J=7.0 Hz, 3H), 1.19 (d, J=6.0 Hz, 3H), 1.07 (d, J=6.0 Hz, 3H), 0.70 (q, J=6.5 Hz, 2H), 0.49-0.43(m, 2H). MS (ESI) m/e [M+1]⁺ 446.1.

Example 12

3-(1-(8-amino-1-methylimidazo[1,5-a]pyrazin-3-yl)ethyl)-5-chloro-6-fluoro-2-isopropoxy-N-phenylbenzamide (Compound 12)

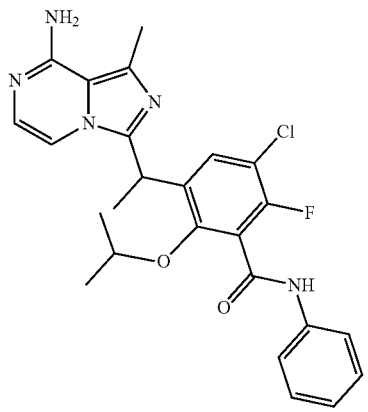 [SMILES: Cc1nc(C(C)c2cc(Cl)c(F)c(C(=O)Nc3ccccc3)c2OC(C)C)n2ccnc(N)c12]

The desired compound was prepared from compound 1-10 and aniline in a similar manner to compound 1-11 in Example 1. ¹H NMR (400 MHz, DMSO-d6) δ 10.72 (s, 1H), 7.65 (d, J=8.0 Hz, 2H), 7.52 (d, J=8.6 Hz, 1H), 7.36 (t, J=7.8 Hz, 2H), 7.30 (d, J=5.0 Hz, 1H), 7.13 (t, J=7.3 Hz, 1H), 6.87 (d, J=4.9 Hz, 1H), 6.43 (s, 2H), 4.81 (q, J=6.8 Hz, 1H), 4.49-4.39 (m, 1H), 2.57 (s, 3H), 1.61 (d, J=7.0 Hz, 3H), 1.19 (d, J=6.0 Hz, 3H), 1.05 (d, J=6.0 Hz, 3H). MS (ESI) m/e [M+1]⁺ 482.1.

Example 13

(3-(1-(8-amino-1-methylimidazo[1,5-a]pyrazin-3-yl)ethyl)-5-chloro-6-fluoro-2-isopropoxyphenyl)(4,4-difluoropiperidin-1-yl)methanone (Compound 13)

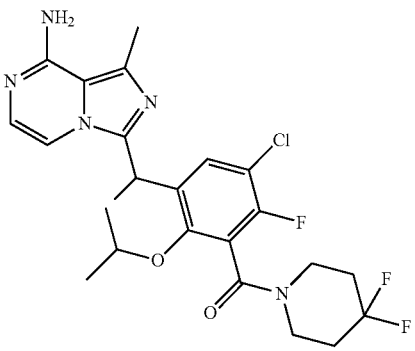

13A

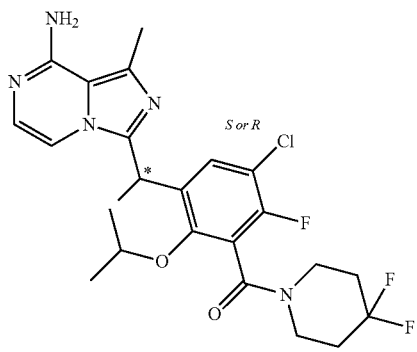

13B

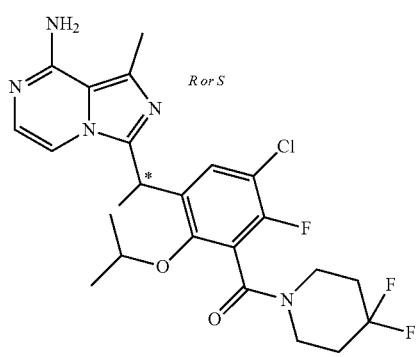

The desired compound was prepared from compound 1-10 and 4,4-difluoropiperidine in a similar manner to compound 1-11 in Example 1. $^1$H NMR (400 MHz, DMSO-d6) δ 7.51-7.46 (m, 0.3H), 7.42-7.35 (m, 0.7H), 7.28-7.23 (m, 0.3H), 7.20-7.14 (m, 0.7H), 6.88-6.81 (m, 1H), 6.45 (s, 2H), 4.81-4.70 (m, 1H), 4.34-4.34 (m, 1H), 4.04-3.94 (m, 1H), 3.84-3.72 (m, 1H), 3.65-3.55 (m, 1H), 3.22-3.15 (m, 1H), 2.57 (s, 3H), 2.18-1.87 (m, 4H), 1.71-1.65 (m, 2H), 1.60-1.54 (m, 1H), 1.27-1.20 (m, 4H), 1.17-1.12 (m, 1H), 1.00-0.95 (m, 1H). MS (ESI) m/e [M+1]$^+$ 510.1.

The compound 13 was separated by chiral column to give compound 13A (peak 1, S or R, retention time (RT) at 8.65 min in chiral analysis, Method H) and compound 13B (peak 2, R or S, retention time (RT) at 11.06 min in chiral analysis, Method H).

Compound 13A: $^1$H NMR (400 MHz, DMSO-d6) δ 7.51-7.46 (m, 0.3H), 7.42-7.35 (m, 0.7H), 7.28-7.23 (m, 0.3H), 7.20-7.14 (m, 0.7H), 6.88-6.81 (m, 1H), 6.45 (s, 2H), 4.81-4.70 (m, 1H), 4.34-4.34 (m, 1H), 4.04-3.94 (m, 1H), 3.84-3.72 (m, 1H), 3.65-3.55 (m, 1H), 3.22-3.15 (m, 1H), 2.57 (s, 3H), 2.18-1.87 (m, 4H), 1.71-1.65 (m, 2H), 1.60-1.54 (m, 1H), 1.27-1.20 (m, 4H), 1.17-1.12 (m, 1H), 1.00-0.95 (m, 1H). MS (ESI) m/e [M+1]$^+$ 510.1.

Compound 13B: $^1$H NMR (400 MHz, DMSO-d6) δ 7.48 (d, J=8.6 Hz, 0.3H), 7.38 (d, J=8.5 Hz, 0.7H), 7.25 (d, J=4.7 Hz, 0.3H), 7.16 (d, J=4.9 Hz, 0.7H), 6.87-6.81 (m, 1H), 6.44 (s, 2H), 4.80-4.70 (m, 1H), 4.44-4.34 (m, 1H), 4.03-3.93 (m, 1H), 3.84-3.72 (m, 1H), 3.65-3.55 (m, 1H), 3.22-3.15 (m, 1H), 2.57 (s, 3H), 2.18-1.86 (m, 4H), 1.67 (d, J=7.0 Hz, 2H), 1.56 (d, J=7.1 Hz, 1H), 1.23 (t, J=5.7 Hz, 4H), 1.14 (d, J=6.0 Hz, 1H), 0.97 (d, J=5.9 Hz, 1H). MS (ESI) m/e [M+1]$^+$ 510.1.

The chiral separation conditions are shown below.

| | |
|---|---|
| Column | CHIRAL ART Cellulose-SB |
| Column size | 2 cm × 25 cm, 5 um |
| Injection | 0.4 ML |
| Mobile phase | Hex:EtOH = 80:20 |
| Flow rate | 20 mL/min |
| Wave length | UV 220 nm |
| Temperature | 25° C. |
| Sample solution | 21 mg/mL in EtOH:DCM = 3:1 |
| Prep-HPLC equipment | Prep-Gilson-HPLC |

Example 14

3-(1-(8-amino-1-methylimidazo[1,5-a]pyrazin-3-yl)ethyl)-5-chloro-6-fluoro-N-((1S,3R)-3-hydroxycyclopentyl)-2-isopropoxybenzamide (Compound 14)

14

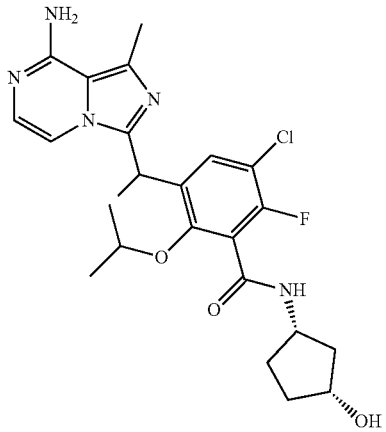

14A

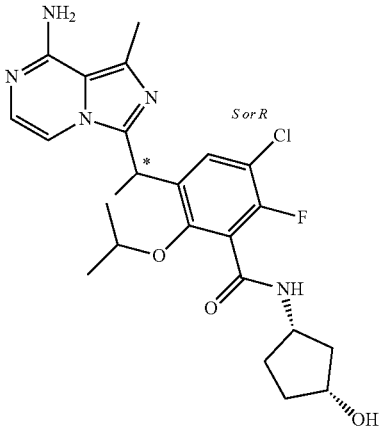

99
-continued

14B

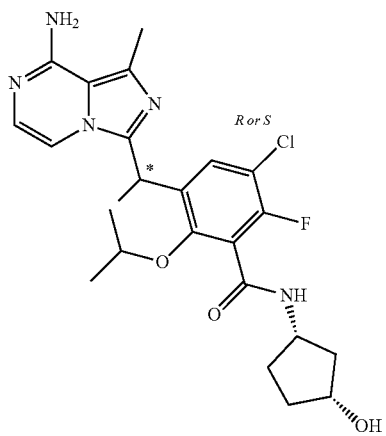

The desired compound was prepared from compound 1-10 and (1R,3S)-3-aminocyclopentan-1-ol in a similar manner to compound 1-11 in Example 1. $^1$H NMR (400 MHz, DMSO-d6) δ 8.70 (d, J=7.3 Hz, 1H), 7.41 (d, J=8.5 Hz, 1H), 7.31 (d, j=5.1 Hz, 1H), 6.91-6.74 (m, 3H), 4.79 (q, J=6.8 Hz, 1H), 4.61 (d, J=3.8 Hz, 1H), 4.51-4.41 (m, 1H), 4.17-4.03 (m, 2H), 2.58 (s, 3H), 2.23-2.14 (m, 1H), 1.90-1.80 (m, 1H), 1.76-1.64 (m, 1H), 1.64-1.49 (m, 5H), 1.42-1.32 (m, 1H), 1.19 (d, J=6.0 Hz, 3H), 1.07 (d, J=6.0 Hz, 3H). MS (ESI) m/e [M+1]$^+$ 490.1.

The compound 14 was separated by chiral column to give compound 14A (peak 1, S or R, retention time (RT) at 5.17 min in chiral analysis, Method I) and compound 14B (peak 2, R or S, retention time (RT) at 8.01 min in chiral analysis, Method I).

Compound 14A: $^1$H NMR (400 MHz, DMSO-d6) δ 8.70 (d, I=7.3 Hz, 1H), 7.41 (d, J=8.5 Hz, 1H), 7.31 (d, J=5.1 Hz, 1H), 6.91-6.74 (m, 3H), 4.79 (q, J=6.8 Hz, 1H), 4.61 (d, J=3.8 Hz, 1H), 4.51-4.41 (m, 1H), 4.17-4.03 (m, 2H), 2.58 (s, 3H), 2.23-2.14 (m, 1H), 1.90-1.80 (m, 1H), 1.76-1.64 (m, 1H), 1.64-1.49 (m, 5H), 1.42-1.32 (m, 1H), 1.19 (d, J=6.0 Hz, 3H), 1.07 (d, J=6.0 Hz, 3H). MS (ESI) m/e [M+1]$^+$ 490.1.

Compound 14B: $^1$H NMR (400 MHz, DMSO-d6) 8.69 (d, J=7.3 Hz, 1H), 7.39 (d, J=8.5 Hz, 1H), 7.28 (d, J=5.1 Hz, 1H), 6.87 (d, J=5.0 Hz, 1H), 6.68 (s, 2H), 4.78 (q, J=6.8 Hz, 1H), 4.61 (d, J=3.8 Hz, 1H), 4.51-4.41 (m, 1H), 4.17-4.03 (m, 2H), 2.57 (s, 3H), 2.23-2.14 (m, 1H), 1.90-1.80 (m, 1H), 1.76-1.64 (m, 1H), 1.64-1.49 (m, 5H), 1.42-1.32 (m, 1H), 1.19 (d, J=6.0 Hz, 3H), 1.08 (d, J=6.0 Hz, 3H). MS (ESI) m/e [M+1]$^+$ 490.1.

The chiral separation conditions are shown below.

| Column | CHIRAL ART Cellulose-SB |
|---|---|
| Column size | 2 cm × 25 cm, 5 um |
| Injection | 0.4 ML |
| Mobile phase | Hex:EtOH = 80:20 |
| Flow rate | 20 mL/min |
| Wave length | UV 220 nm |
| Temperature | 25° C. |
| Sample solution | 21 mg/mL in EtOH:DCM = 3:1 |
| Prep-HPLC equipment | Prep-Gilson-HPLC |

Example 15

(S)-3-(1-(8-amino-1-methylimidazo[1,5-a]pyrazin-3-yl)ethyl)-5-chloro-N-(1-(ethoxymethyl)cyclopropyl)-6-fluoro-2-isopropoxybenzamide (Compound 15)

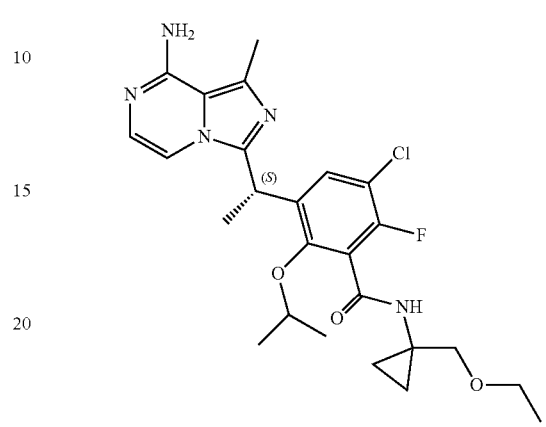

Step 1: 1-(5-chloro-4-fluoro-2-hydroxyphenyl)ethan-1-one (15-1)

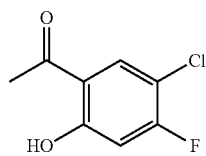

To a 2 L three-necked flask equipped with a magnetic stirrer was added 4-chloro-3-fluorophenol (160 g, 1.1 mol) and acetyl chloride (129 g, 1.6 mmol). The mixture was stirred for 1 h. Then aluminum chloride (219 g, 1.6 mmol) was added into the mixture in portions. The mixture was heated to 160° C. and kept at 160° C. for 2 hrs. The mixture was cooled and diluted with HCl (2 M, 500 mL). The resulting hot liquid was cooled and extracted with EtOAc (500 mL×3). The combined organic phase was washed with water (500 mL), and brine (500 mL), dried over anhydrous sodium sulfate, filtered and concentrated to give the product (200 g, crude) as a yellow solid. $^1$H NMR (400 MHz, CDCl$_3$) δ 12.48-12.41 (m, 1H), 7.78 (d, J=8.1 Hz, 1H), 6.77 (d, J=10.3 Hz, 1H), 2.61 (s, 3H).

Step 2: 1-(3-bromo-5-chloro-4-fluoro-2-hydroxyphenyl)ethan-1-one (15-2)

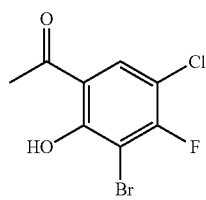

To a solution of 1-(5-chloro-4-fluoro-2-hydroxyphenyl) ethan-1-one (110 g, 583 mmol) in DMF (1 L) was added NBS (114 g, 640 mmol) in portions. The mixture was stirred at room temperature for 1 h. The mixture was diluted with water (3 L), extracted with EtOAc (1 L×3). The combined organic phase was washed with brine (1 L×3), dried over anhydrous sodium sulfate, filtered and concentrated to give the product (150 g, crude) as a yellow solid. ¹H NMR (400 MHz, CDCl₃) δ 13.21 (d, J=1.8 Hz, 1H), 7.80 (d, J=7.8 Hz, 1H), 2.66 (s, 3H).

Step 3: 1-(3-bromo-5-chloro-4-fluoro-2-isopropoxyphenyl)ethan-1-one (15-3)

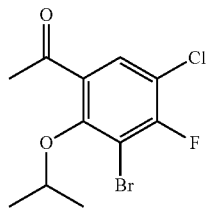 [SMILES: CC(=O)c1cc(Cl)c(F)c(Br)c1OC(C)C]

To a solution of 1-(3-bromo-5-chloro-4-fluoro-2-hydroxyphenyl)ethan-1-one (150 g, 560 mmol) and 2-iodopropane (143 g, 841 mmol) in DMF (1 L) was added NaHCO₃ (71 g, 845 mmol). The mixture was stirred at 60° C. overnight. The mixture was cooled and diluted with water (3 L), extracted with EtOAc (1 L×3). The combined organic phase was washed with brine (1 L×3), dried over anhydrous sodium sulfate, filtered and concentrated. The residue was purified by silica gel column chromatography (elution with hexane/ethyl acetate=50/1) to give the product (140 g, 80%) as a yellow oil. ¹H NMR (400 MHz, CDCl3) δ 7.57 (d, J=8.2 Hz, 1H), 4.45-4.39 (m, 1H), 2.61 (s, 3H), 1.31 (t, J=6.7 Hz, 6H).

Step 4: 2-(3-bromo-5-chloro-4-fluoro-2-isopropoxyphenyl)propanenitrile (15-4)

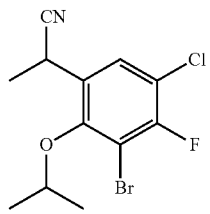 [SMILES: CC(C)Oc1c(C(C)C#N)cc(Cl)c(F)c1Br]

1-(3-bromo-5-chloro-4-fluoro-2-isopropoxyphenyl) ethan-1-one (165 g, 533 mmol) in DME (420 mL) was added TOSMIC (156 g, 799 mmol), the solution was stirred at 0° C. a solution of t-BuOK (119.6 g, 1066 mmol) in t-BuOH (840 mL) was added to the above solution by dropwise under N₂ and maintained the temperature below 10° C., the resulting solution was stirred at room temperature overnight. After completion, the reaction mixture was washed with water (1 L) and extracted with ethyl acetate (500 mL×3), dried over MgSO₄, filtered and evaporated in vacuo. The residue was purified by column chromatography (PE/EA=20:1~10:1) to give the product (118 g, 69.2%) as yellow solid. ¹H NMR (400 MHz, CDCl₃) δ 7.51 (d, J=7.8 Hz, 1H), 4.69 (dt, J=12.3, 6.2 Hz, 1H), 4.31 (q, J=7.2 Hz, 1H), 1.56 (d, J=7.2 Hz, 3H), 1.44 (d, J=6.2 Hz, 3H), 1.30 (d, J=6.2 Hz, 3H).

Step 5: 2-(3-bromo-5-chloro-4-fluoro-2-isopropoxyphenyl)propanoic acid (15-5)

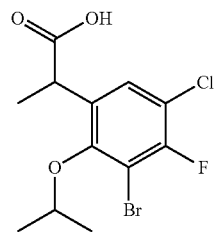 [SMILES: CC(C)Oc1c(C(C)C(=O)O)cc(Cl)c(F)c1Br]

2-(3-bromo-5-chloro-4-fluoro-2-isopropoxyphenyl)propanenitrile (118 g, 369 mmol) in EtOH (307 mL) was added a.q. NaOH (6 N, 307 mL), the resulting solution was stirred at 100° C. overnight. After completion, the reaction was cooled to room temperature, adjusted pH to 3~4 by addition of 1N HCl, extracted with ethyl acetate (500 mL×3), the combined ethyl acetate phrase was dried over MgSO₄, filtered and evaporated to give the crude product (122 g, 97.4%) as yellow oil which was used in the next step without further purification, LC-MS (M–H)⁺=336.9.

Step 6: (S)-2-(3-bromo-5-chloro-4-fluoro-2-isopropoxyphenyl)propanoic acid (15-6)

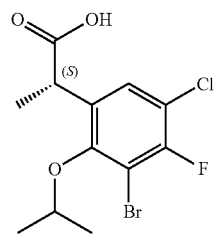

2-(3-bromo-5-chloro-4-fluoro-2-isopropoxyphenyl)propanoic acid (122 g, 359 mmol) and (1R,2S)-1-amino-2,3-dihydro-1H-inden-2-ol (54 g, 359 mmol) in i-PrOH (500 mL) was stirred at 100° C., for 1 h, cooled to r.t, concentrated to afford crude salt, which was slurried in PE/EA=10:1 (500 mL) for 1~2 h, undissolved solid was collected and refluxed in PE/EA/i-PrOH=20:2:1 (230 mL) for another 1 h, the solid was collected by filtration and dried in vacuo to give the chiral salt which was neutralized by addition of aq. HCl (1N) to pH to 2~3, extracted with ethyl acetate (200 mL×3), dried over MgSO₄, concentrated to afford the product as yellow oil (44.2 g, 36.2%). ¹H NMR (400 MHz, DMSO-d6), δ 12.59 (s, 1H), 7.52 (d, J=8.4 Hz, 1H), 4.55 (dt, J=12.3, 6.1 Hz, 1H), 4.04 (q, J=7.0, 1H), 1.3$ (d, J=7.3 Hz, 3H), 1.34-1.26 (m, 6H). LC-MS (M–H)⁺=336.9. RetTime in chiral-HPLC: 2.61 min. The absolute (S) configuration of chiral center in compound 15-6 was confirmed by x-ray analysis of single crystal.

Step 7: (2S)-2-(3-bromo-5-chloro-4-fluoro-2-isopropoxyphenyl)-N-(1-(3-chloropyrazin-2-yl)ethyl)propanamide (15-7)

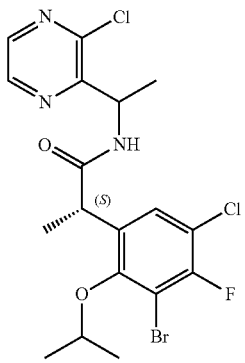

(S)-2-(3-bromo-5-chloro-4-fluoro-2-isopropoxyphenyl)propanoic acid (52 g, 153 mmol), 1-(3-chloropyrazin-2-yl)ethan-1-amine hydrochloride (29.7 g, 153 mmol), EDCI (43.9 g, 229.7 mmol), HOBT (31 g, 229.7 mmol) and Et$_3$N (49.5 g, 489.6 mmol) in DCM (500 mL) was stirred at room temperature overnight under N$_2$. After completion, the reaction solution was washed with H$_2$O (500 mL), extracted with DCM (500 mL×3), combined DCM phase was dried over MgSO$_4$, concentrated and purified by column chromatography (PE/EA=10:1~5:1) to give the product (69 g, 94%) as yellow oil. LC-MS (M+11)$^+$=479.6.

Step 8: (S)-3-(1-(3-bromo-5-chloro-4-fluoro-2-isopropoxyphenyl)ethyl)-8-chloro-1-methylimidazo[1,5-a]pyrazine (15-8)

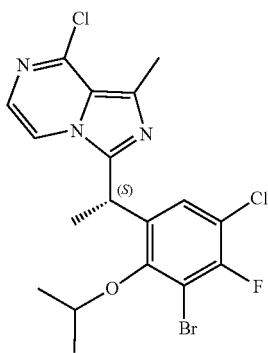

(2S)-2-(3-bromo-5-chloro-4-fluoro-2-isopropoxyphenyl)-N-(1-(3-chloropyrazin-2-yl)ethyl)propanamide (69 g, 144 mmol) in DCM (1 L) was added Tf$_2$O (89.4 g, 317 mmol) by dropwise at 0° C., then pyridine (28.5 g, 360 mmol) was added by dropwise at 0° C., TLC showed the reaction was completed, H$_2$O (500 mL) was added, extracted with DCM (500 mL×3), combined DCM phase was dried over MgSO$_4$, concentrated to afford crude product which was slurried in i-PrOH (60 mL) for 1~2 h, filtrated to give pure product as white solid (55 g, 83.4%). LC-MS (M+H)$^{30}$=461.9.

Step 9: (S)-3-(1-(3-bromo-5-chloro-4-fluoro-2-isopropoxyphenyl)ethyl)-1-methylimidazo[1,5-a]pyrazin-8-amine (15-9)

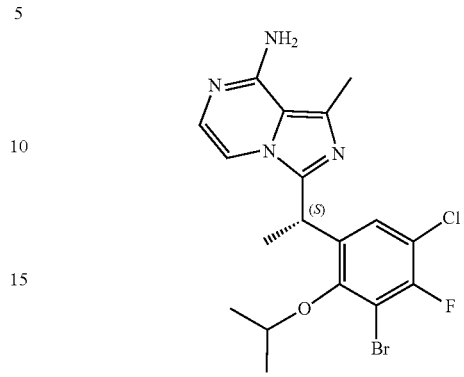

To a pressure tank equipped with a magnetic stirrer were added (S)-3-(1-(3-bromo-5-chloro-4-fluoro-2-isopropoxyphenyl)ethyl)-8-chloro-1-methylimidazo[1,5-a]pyrazine (45 g, 97.6 mmol) and NH$_3$ in i-PrOH (w/w 30%, 300 mL, excess). Then the mixture was stirred at 90° C. for two days. The mixture was cooled and diluted with DCM (500 mL), washed with water (100 mL×3), brine (100 mL), dried over Na$_2$SO$_4$, filtered and concentrated to give the product (41 g, 95%) as a yellow solid which was used in the next step without further purification. $^1$H NMR (400 MHz, CDCl$_3$) δ 7.27 (d, J=7.6 Hz, 1H), 7.15 (d, J=5.1 Hz, 1H), 6.88 (d, J=5.0 Hz, 1H), 4.78-4.69 (m, 2H), 2.72 (s, 3H), 1.80 (d, J=7.2 Hz, 3H), 1.49 (d, J=6.2 Hz, 3B), 1.39 (d, J=6.2 Hz, 3H). LC-MS (M+H)$^+$=441.0, 443.0.

Step 10: (S)-6-(1-(8-amino-1-methylimidazo[1,5-a]pyrazin-3-yl)ethyl)-2-bromo-4-chloro-3-fluorophenol (15-10)

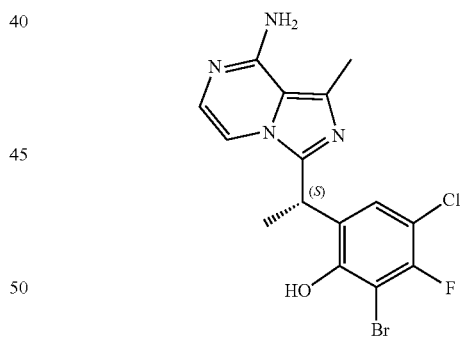

To a mixture of (S)-3-(1-(3-bromo-5-chloro-4-fluoro-2-isopropoxyphenyl)ethyl)-1-methylimidazo[1,5-a]pyrazin-8-amine (41 g, 92.8 mmol) in DCM (500 mL) was added BBr$_3$ (70 g, 279 mmol) by dropwise at 0° C. Then the mixture was stirred at room temperature overnight. The mixture was cooled to 0° C., and then quenched with MEOH (400 mL) carefully. The mixture was concentrated, the residue was diluted with a mixture of DCM (500 mL) and i-PrOH (100 mL). Then the mixture was washed with saturated NaHCO$_3$ solution (100 mL×2). The organic layers were separated, washed with brine, dried over Na$_2$SO$_4$, filtered and concentrated to give the product (38 g, 100%) as a yellow solid which was used for the next step without further purification. $^1$H NMR (400 MHz, CDCl$_3$) δ 7.18 (d, J=5.2 Hz, 1H), 7.12

(d, J=7.9 Hz, 1H), 7.02 (d, J=5.1 Hz, 1H), 4.28 (q, J=7.3 Hz, 1H), 4.08-398 (m, 1H), 2.72 (s, 3H), 1.70 (d, J=7.3 Hz, 3H), 1.21 (d, J=6.1 Hz, 6H). LC-MS (M+H)$^+$=399.0, 401.0.

Step 11: ethyl-(S)-3-(8-amino-1-methylimidazo[1,5-a]pyrazin-3-yl)ethyl)-5-chloro-6-fluoro-2-hydroxybenzoate (15-11)

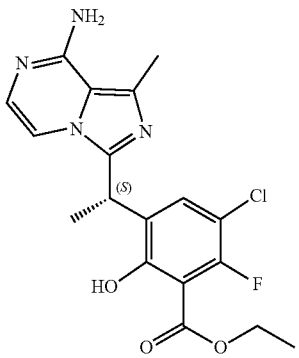

To a mixture of (S)-6-(1-(8-amino-1-methylimidazo[1,5-a]pyrazin-3-yl)ethyl)-2-bromo-4-chloro-3-fluorophenol (38 g, 32.5 mmol) in EtOH (1000 mL) were added Pd(dppf)Cl$_2$ (3.5 g, 4.8 mmol) and NaOAc (11.7 g, 143 mmol). The mixture was degassed and refilled with CO (1 atm). The mixture was stirred at 70° C. overnight. The mixture was cooled down and concentrated in vacuo. The residue was diluted with water (200 mL), extracted with EtOAc (200 mL×3). The combined organic phase was washed with brine, dried over Na$_2$SO$_4$, filtered and concentrated. The residue was purified by column chromatography (DCM/MeOH from DCM 100% to 20/1) to give the product (32 g, 82%) as a yellow solid. $^1$H NMR (400 MHz, CDCl$_3$) δ 7.28-7.24 (m, 1H), 7.07 (d, J=5.1 Hz, 1H), 6.85 (d, J=5.1 Hz, 1H), 5.30 (s, 1H), 4.81 (q, J=7.1 Hz, 1H), 4.48 (q, J=7.1 Hz, 2H), 2.75 (s, 3H), 1.74 (d, J=7.1 Hz, 3H), 1.43 (t, J=7.1 Hz, 3H). LC-MS (M+H)$^+$=393.1.

Step 12: ethyl (S)-3-(1-(8-amino-1-methylimidazo[1,5-a]pyrazin-3-yl)ethyl)-5-chloro-6-fluoro-2-isopropoxybenzoate (15-12)

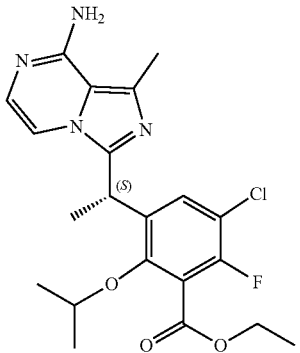

ethyl (S)-3-(1-(8-amino-1-methylimidazo[1,5-a]pyrazin-3-yl)ethyl)-5-chloro-6-fluoro-2-hydroxybenzoate (32 g, 81.5 mmol), i-PrOH (24.4 g, 406.7 mmol), PPh$_3$ (49.1 g, 187.5 mmol) in toluene (400 mL) was added di-tert-butyl (E)-diazene-1,2-dicarboxylate (43.2 g, 187.5 mmol) at room temperature. The resulting solution was stirred at 60° C. for 3 hrs under N$_2$. After completion, the reaction mixture was concentrated in vacuo, washed with H$_2$O (500 mL), extracted with EtOAc (500 mL×3), combined EtOAc phase was dried over MgSO$_4$, purified by column chromatography (PE/EA=20:1) to give the product (25.4 g, 71.8%) as yellow solid. LC-MS (M+H)$^+$=435.1.

Step 13: (S)-3-(1-(8-amino-1-methylimidazo[1,5-a]pyrazin-3-yl)ethyl)-5-chloro-6-fluoro-2-isopropoxybenzoic acid (15-13)

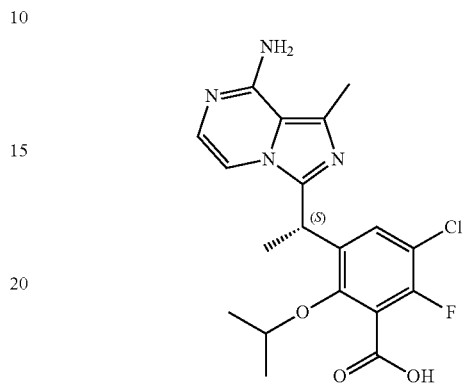

ethyl (S)-3-(1-(8-amino-1-methylimidazo[1,5-a]pyrazin-3-yl)ethyl)-5-chloro-6-fluoro-2-isopropoxybenzoate (25.4 g, 58.5 mmol) in MeOH (100 mL) and H$_2$O (100 mL) was added NaOH (18.7 g, 468 mmol), the resulting solution was stirred at room temperature overnight. After completion, the reaction solution was concentrated in vacuo to remove most of the MeOH, remaining solution was extracted with EtOAc (100 mL×2), the aqueous phase was adjusted pH to 2~3, blown solid was precipitated, collected by filtration, dried in vacuo to give the product (15.8 g), the aqueous phase was extracted with DCM (100 mL×5), combined DCM phase was dried over MgSO$_4$ and concentrated in vacuo to give another part of product (2.2 g), total yield (18 g, 75.6%). $^1$H NMR (400 MHz, DMSO-d6) δ 7.78 (brs, 2H), 7.40-7.32 (m, 2H), 6.93 (d, J=5.3 Hz, 1H), 4.80 (q, J=7.0 Hz, 1H), 4.55 (dt, J=12.1, 6.0 Hz, 1H), 2.60 (s, 3-H), 1.60 (d, 7.0 Hz, 3H), 1.20 (d, J=6.0 Hz, 3H), 1.13 (d, J=6.0 Hz, 3H), LC-MS (M+H)$^+$=407.1.

Step 14: (S)-3-(1-(8-amino-1-methylimidazo[1,5-a]pyrazin-3-yl)ethyl)-5-chloro-N-(1-(ethoxymethyl)cyclopropyl)-6-fluoro-2-isopropoxybenzamide (15-14)

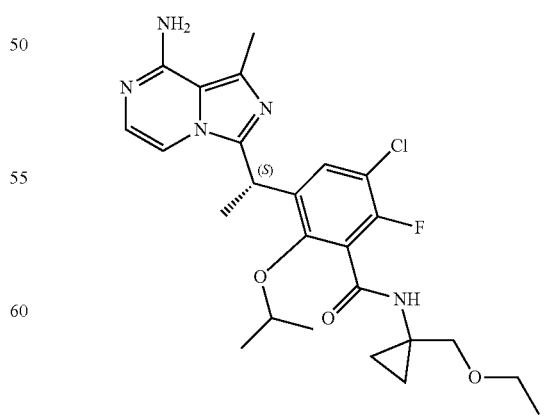

To a solution of (S)-3-(1-(8-amino-1-methylimidazo[1,5-a]pyrazin-3-yl)ethyl)-5-chloro-6-fluoro-2-isopropoxybenzoic acid (100 mg, 0.25 mmol) and 1-(ethoxymethyl)cyclopropan-1-amine hydrochloride (60 mg, 0.4 mmol) in DMF (10 mL) were added Et₃N (125 mg, 1.25 mmol) and PyBop (210 mg, 0.4 mmol). The mixture was stirred at room temperature for 1 h. The mixture was diluted with water (30 mL), extracted with EtOAc (30 mL×3). The combined organic layers were washed with water (50 mL×2) and brine (50 mL), dried over Na₂SO₄, filtered and evaporated. The residue was purified by thin layer chromatography (DCM/MeOH=15/1) to give the product (90 mg, 71%). ¹H NMR (400 MHz, DMSO-d6) δ 8.98 (brs, 1H), 7.36 (d, J=8.9 Hz, 1H), 7.24 (brs, 1H), 6.86 (brs, 1H), 6.44 (brs, 2H), 4.77 (brs, 1H), 4.51 (brs, 1H), 3.56-3.41 (m, 4H), 2.57 (s, 3H), 1.58 (brs, 3H), 1.19 (brs, 3H), 1.09 (brs, 6H), 0.77 (brs, 2H), 0.70 (brs, 2H). LC-MS (M+H)⁺=504.2. RefTime in chiral-HPLC: 2.75 min, Method J.

Example 16

(S)-3-(1-(8-amino-1-methylimidazol[1,5-a]pyrazin-3-yl)ethyl)-5-chloro-N-(2-(dimethylamino)ethyl)-6-fluoro-2-isopropoxybenzamide (Compound 16)

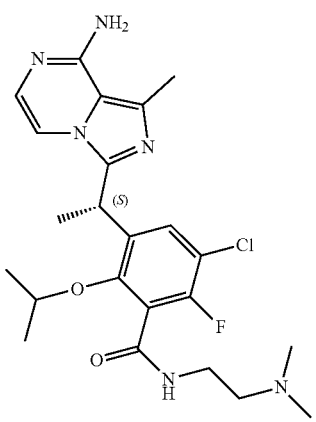

This compound (50.3 mg, 21.4%) was prepared from compound 15-13 and N¹,N¹-dimethylethane-1,2-diamine a similar manner to compound 15-14 in Example 15. ¹H NMR (400 MHz, DMSO-d6) δ 8.66 (t, J=5.5 Hz, 1H), 738 (d, J=8.6 Hz, 1H), 7.25 (d, J=5.0 Hz, 1H), 6.85 (d, J=5.0 Hz, 1H), 6.43 (s, 2H), 4.77 (q, J=7.0 Hz, 1H), 4.52 (dt, J=12.2, 6.1 Hz, 1H), 3.35-3.25 (m, 2H), 2.56 (s, 3H), 2.37 (s, 2H), 2.17 (s, 6H), 1.58 (d, J=7.1 Hz, 3H), 1.18 (d, J=6.0 Hz, 3H), 1.08 (d, J=6.0 Hz, 3H). LC-MS (M+H)⁺=477.2. RetTime in chiral-HPLC: 4.34 min, Method A.

Example 17

(3-((S)-1-(8-amino-1-methylimidazo[1,5-a]pyrazin-3-yl)ethyl)-5-chloro-6-fluoro-2-isopropoxyphenyl)((S)-2-(methoxymethyl)pyrrolidin-1-yl)methanone (Compound 17)

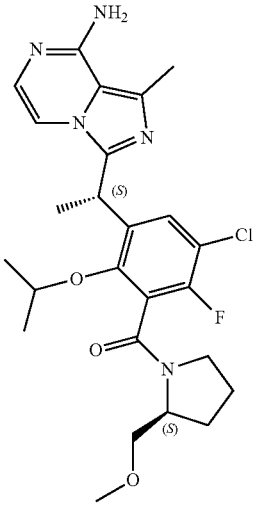

This compound (26.4 mg, 10.6%) was prepared from compound 15-13 and (S)-2-(methoxymethyl)pyrrolidine in a similar manner to compound 15-14 in Example 15. ¹H NMR (400 MHz, DMSO-d6) δ 7.43-7.29 (m, 1H), 7.27-7.16 (m, 1H), 6.90-6.75 (m, 1H), 6.56-6.34 (m, 2H), 4.76 (dd, J=13.8, 7.0 Hz, 1H), 4.39 (ddd, J=24.1, 12.2, 6.0 Hz, 1H), 3.73-3.41 (m, 3H), 3.33-3.27 (m, 3H), 3.22-3.10 (m, 1H), 3.00-2.80 (m, 1H), 2.62-2.54 (m, 3H), 2.02-1.72 (m, 4H), 1.70-1.63 (m, 3H), 1.30-1.15 (m, 6H), LC-MS (M+H)³⁰=504.2. Ret-Time in chiral-HPLC: 4.36 min and 4.82 min, Method C.

Example 18

(S)-3-(1-(8-amino-1-methylimidazo[1,5-a]pyrazin-3-yl)ethyl)-5-chloro-6-fluoro-N-(4-fluorophenyl)-2-isopropoxybenzamide (Compound 18)

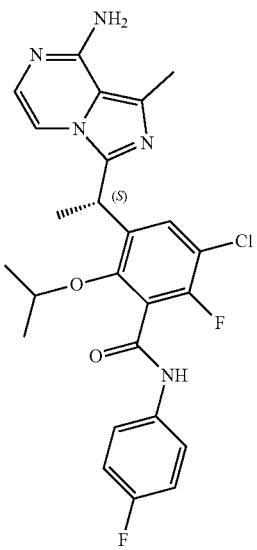

This compound (8 mg, 6.5%) was prepared from compound 15-13 and 4-fluoroaniline in a similar manner to compound 15-14 in Example 15. $^1$H NMR (400 MHz, DMSO-d6) δ 10.79 (s, 1H), 7.75-7.62 (m, 2H), 7.57-7.30 (m, 2H), 7.28-7.05 (m, 3H), 6.92-6.68 (m, 2H), 4.89-4.75 (m, 1H), 4.48-4.36 (m, 1H), 2.60-2.54 (m, 3H), 1.69-1.51 (m, 3H), 1.20-1.11 (m, 3H), 1.07-0.98 (m, 3H). LC-MS (M+H)$^+$=500.1 RetTime in chiral-HPLC: 4.10 min, Method C.

Example 19

(S)-(3-(1-(8-amino-1-methylimidazo[1,5-a]pyrazin-3-yl)ethyl)-5-chloro-6-fluoro-2-isopropoxyphenyl)(4-methoxypiperidin-1-yl)methanone (Compound 19)

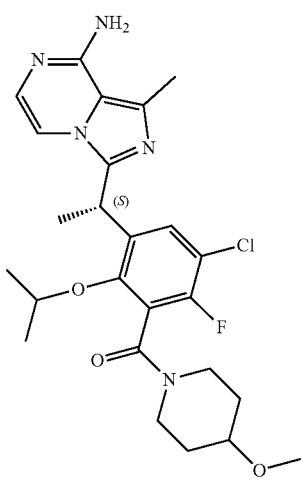

This compound (36.4 mg, 14.6%) was prepared from compound 15-13 and 4-methoxypiperidine in a similar manner to compound 15-14 in Example 15. $^1$H NMR (400 MHz, DMSO-d6) δ 7.47-7.13 (m, 2H), 6.89-6.75 (m, 1H), 6.74-6.47 (m, 2H), 4.86-4.67 (m, 1H), 4.48-4.23 (m, 1H), 4.19-3.71 (m, 1H), 3.60-3.36 (m, 2H), 3.29-3.23 (m, 3H), 3.21-2.89 (m, 2H), 2.62-2.55 (m, 3H), 2.01-1.29 (m, 7H), 1.29-0.94 (m, 6H). LC-MS (M+H)$^+$=504.2. RetTime in chiral-HPLC: 4.35 min, Method C.

Example 20

(3-((S)-1-(8-amino-1-methylimidazo[1,5-a]pyrazin-3-yl)ethyl)-5-chloro-6-fluoro-2-isopropoxyphenyl)((S)-3-hydroxypiperidin-1-yl)methanone (Compound 20)

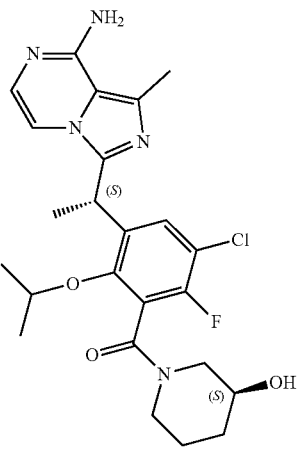

This compound (31 mg, 12.8%) was prepared from compound 15-13 and (S)-piperidin-3-ol in a similar manner to compound 15-14 in Example 15. $^1$H NMR (400 MHz, DMSO-d6) δ 7.46-7.10 (m, 2H), 6.90-6.76 (m, 1H), 6.72-6.42 (m, 2H), 5.15-4.65 (m, 2H), 4.51-4.26 (m, 1H), 3.24-2.90 (m, 2H), 2.89-2.64 (m, 2H), 2.61-2.55 (m, 3H), 2.01-1.71 (m, 1H), 1.71-1.61 (m, 3B), 1.59-1.53 (m, 1H), 1.42-1.31 (m, 2H), 1.30-1.12 (m, 6H). LC-MS (M+H)$^+$=490.2. RetTime in chiral-HPLC: 5.68 min, Method C.

Example 21

3-((S)-1-(8-amino-1-methylimidazo[1,5-a]pyrazin-3-yl)ethyl)-5-chloro-6-fluoro-2-isopropoxy-N-((S)-1-phenylethyl)benzamide (Compound 21)

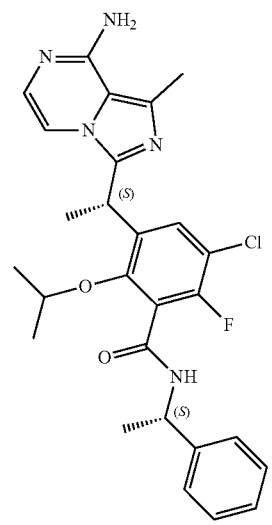

This compound (46 mg, 36.5) was prepared from compound 15-13 and (S)-1-phenylethan-1-amine in a similar manner to compound 15-14 in Example 15. ¹H NMR (400 MHz, DMSO-d6) δ 9.21 (d, J=8.1 Hz, 1H), 7.46 (d, J=8.5 Hz, 1H), 7.42-7.30 (m, 5H), 7.28-7.17 (m, 2H), 6.91 (d, J=5.2 Hz, 1H), 5.10 (p, J=7.0 Hz, 1H), 4.79 (q, J=6.8 Hz, 1H), 4.27 (dt, J=12.0, 6.0 Hz, 1H), 2.58 (s, 3H), 1.57 (d, J=7.0 Hz, 3H), 1.40 (d, J=7.0 Hz, 3H), 1.03 (d, J=6.0 Hz, 3H), 0.86 (d, J=5.9 Hz, 3H). LC-MS (M+H)⁺=509.8. RetTime in chiral-HPLC: 2.67 min, Method F.

Example 22

3-((S)-1-(8-amino-1-methylimidazo[1,5-a]pyrazin-3-yl)ethyl)-5-chloro-6-fluoro-2-isopropoxy-N-((R)-1-phenylethyl)benzamide (Compound 22)

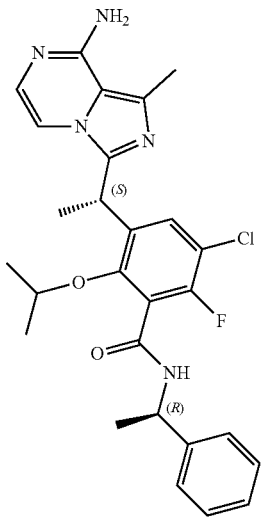

This compound (26 mg, 20.7%) was prepared from compound 15-13 and (R)-1-phenylethan-1-amine in a similar manner to compound 15-14 in Example 15. ¹H NMR (400 MHz, DMSO-d6) δ 9.21 (d, J=8.1 Hz, 1H), 7.47 (d, J=8.6 Hz, 1H), 7.41-7.31 (m, 5H), 7.30-7.09 (m, 2H), 6.90 (d, J=5.3 Hz, 1H), 5.09 (p, J=7.0 Hz, 1H), 4.79 (q, J=6.9 Hz, 1H), 4.28-4.16 (m, 1H), 2.58 (s, 3H), 1.56 (d, J=7.0 Hz, 3H), 1.40 (d, J=7.0 Hz, 3H), 1.01 (d, J=6.0 Hz, 3H), 0.87 (d, J=6.0 Hz, 3H). LC-MS (M+H)⁺=509.8. RetTime in chiral-HPLC: 5.35 min, Method A Example 23

3((S)-1-(8-amino-1-methylimidazo[1,5-a]pyrazin-3-yl)ethyl)-5-chloro-6-fluoro-N-((1R,2S)-2-hydroxycyclopentyl)-2-isopropoxybenzamide (Compound 23)

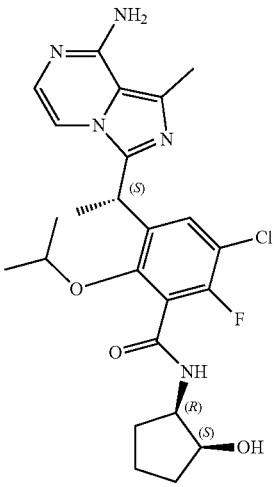

This compound (14.1 mg, 11.7%) was prepared from compound 15-13 and (1S,2R)-2-aminocyclopentan-1-ol in a similar manner to compound 15-14 in Example 15. ¹H NMR (400 MHz, DMSO-d6) δ 8.29 (d, J=7.4 Hz, 1H), 7.35 (d, J=8.6 Hz, 1H), 7.24 (d, J=5.1 Hz, 1H), 6.85 (d, J=5.0 Hz, 1H), 6.53 (s, 2H), 4.77 (q, J=7.4 Hz, 1H), 4.61-4.47 (m, 2H), 4.08-3.94 (m, 2H), 2.57 (s, 3H), 192-1.67 (m, 3H), 1.65-1.44 (m, 6H), 1.19 (d, J=6.0 Hz, 3H), 1.11 (d, J=6.0 Hz, 3H). LC-MS (M+H)⁺=489.8. RetTime in chiral-HPLC: 4.63 min, Method A.

Example 24

3-((S)-1-(8-amino-1-methylimidazo[1,5-a]pyrazin-3-yl)ethyl)-5-chloro-6-fluoro-2-isopropoxy-N-(((S)-tetrahydrofuran-2-yl)methyl)benzamide (Compound 24)

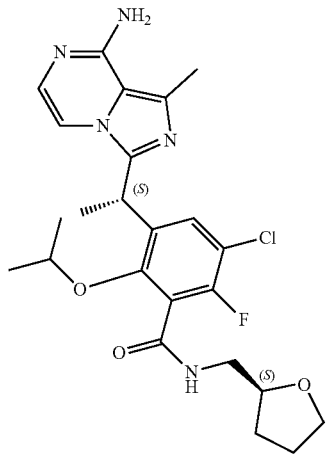

This compound (20.63 mg, 17.1%) was prepared from compound 15-13 and (S)-(tetrahydrofuran-2-yl)methanamine in a similar manner to compound 15-14 in Example 15. $^1$H NMR (400 MHz, DMSO-D6) δ 8.78 (t, J=5.8 Hz, 1H), 7.41 (d, J=8.6 Hz, 1H), 7.32 (d, J=5.3 Hz, 1H), 6.90 (s, 2H), 6.88 (d, J=5.2 Hz, 1H), 4.79 (q, J=7.0 Hz, 1H), 4.49 (dt, J=12.1, 6.0 Hz, 1H), 3.92 (p, J=6.3 Hz, 1H), 3.75 (dd, J=14.0, 7.2 Hz, 1H), 3.61 (dd, J=14.5, 7.3 Hz, 1H), 3.31-3.26 (m, 2H), 2.58 (s, 3H), 1.96-1.74 (m, 3H), 1.64-1.50 (m, 4H), 1.18 (d, J=6.0 Hz, 3H), 1.08 (d, J=6.1 Hz, 3H), LC-MS (M+H)$^+$=489.8. RetTime in chiral-HPLC: 5.52 min, Method A.

Example 25

3-((S)-1-(8-amino-1-methylimidazo[1,5-a]pyrazin-3-yl)ethyl)-5-chloro-6-fluoro-N-((1S,2R)-2-hydroxy-cyclopentyl)-2-isopropoxybenzamide (Compound 25)

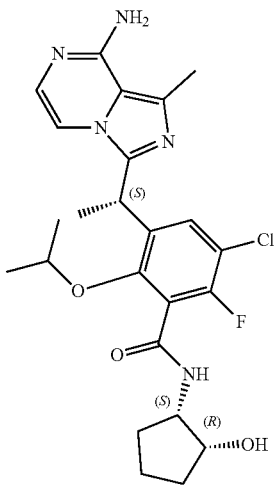

This compound (23.32 mg, 19.3%) was prepared from compound 15-13 and (1R,2S)-2-aminocyclopentan-1-ol in a similar manner to compound 15-14 in Example 15. $^1$H NMR (400 MHz, DMSO-d6) δ 8.34 (d, J=7.1 Hz, 1H), 7.57 (s, 2H), 7.46-7.38 (m, 2H), 6.93 (d, J=5.4 Hz, 1H), 4.82 (q, J=6.8 Hz, 1H), 4.60 (d, J=2.7 Hz, 1H), 4.52 (dt, J=11.9, 5.9 Hz, 1H), 4.01 (brs, 2H), 2.60 (s, 3H), 1.90-1.65 (m, 3H), 1.64-1.43 (m, 6H), 1.18 (d, J=6.1 Hz, 3H), 1.04 (d, J=5.9 Hz, 3H). LC-MS (M+H)$^+$=489.8. RetTime in chiral-HPLC: 4.68 min, Method A Example 26

(S)-3-(1-(8-amino-1-methylimidazol[1,5-a]pyrazin-3-yl)ethyl)-5-chloro-6-fluoro-2-isopropoxy-N-(2-(tetrahydro-2H-pyran-4-yl)ethyl)benzamide (Compound 26)

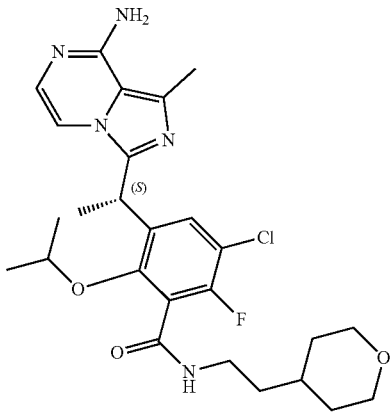

This compound (15 mg, 11.8%) was prepared from compound 15-13 and 2-(tetrahydro-2H-pyran-4-yl)ethan-1-amine in a similar manner to compound 15-14 in Example 15. $^1$H NMR (400 MHz, DMSO-d6) δ 8.66 (t, J=5.5 Hz, 1H), 7.41 (d, J=8.6 Hz, 1H), 7.29 (d, J=5.1 Hz, 1H), 6.87 (d, J=4.9 Hz, 1H), 6.65 (s, 2H), 4.78 (q, J=7.0 Hz, 1H), 4.45 (dt, J=12.1, 5.9 Hz, 1H), 3.93-3.74 (m, 2H), 3.34-3.15 (m, 3H), 2.57 (s, 3H), 1.65-1.50 (m, 6H), 1.47-1.37 (m, 2H), 1.27-1.12 (m, 5H), 1.08 (d, J=6.0 Hz, 3H). LC-MS (M+H)$^+$=517.8. RetTime in chiral-HPLC: 6.39 min, Method A Example 27

(S)-3-(1-(8-amino-1-methylimidazo[1,5-a]pyrazin-3-yl)ethyl)-5-chloro-6-fluoro-2-isopropoxy-N-methyl-benzamide (Compound 27)

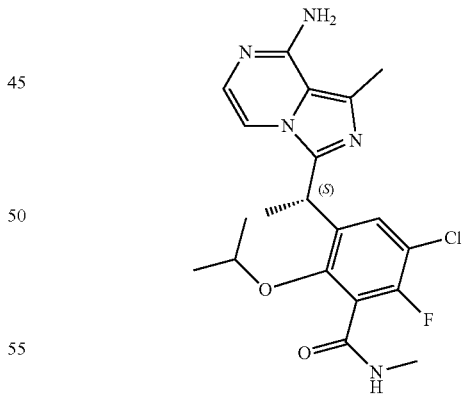

This compound (11 mg, 10.6%) was prepared from compound 15-13 and methanamine in a manner similar to similar manner to compound 15-14 in Example 15, $^1$H NMR (400 MHz, DMSO-d6) δ 8.60 (t, J=4.7 Hz, 1H), 7.40 (d, J=8.6 Hz, 1H), 7.26 (d, J=5.1 Hz, 1H), 6.87 (d, J=5.0 Hz, 1H), 6.58 (s, 2H), 4.77 (q, J=7.0 Hz, 1H), 4.39 (dt, J=12.1, 6.0 Hz, 1H), 2.75 (d, J=4.6 Hz, 3H), 2.57 (s, 3H), 1.58 (d, J=7.1 Hz, 3H), 1.19 (d, J=6.1 Hz, 3H), 1.09 (d, J=6.1 Hz, 3H), LC-MS (M+H)$^+$=419.8. RetTime in chiral-HPLC: 4.44 min, Method A

Example 28

(S)-3-(1-(8-amino-1-methylimidazo[1,5-a]pyrazin-3-yl)ethyl)-5-chloro-6-fluoro-2-isopropoxy-N-ethyl-benzamide (Compound 28)

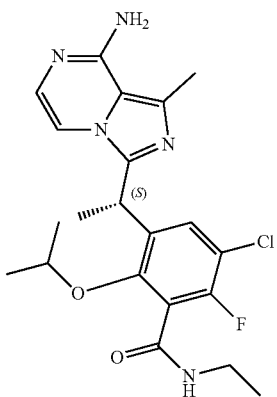

This compound (36.1 mg, 33.8%) was prepared from compound 15-13 and ethanamine in a similar manner to compound 15-14 in Example 15. $^1$H NMR (400 MHz, DMSO-d6) δ 8.68 (t, J=5.3 Hz, 1H), 7.41 (d, J=8.6 Hz, 1H) 7.28 (d, J=5.1 Hz, 1H), 6.87 (d, J=5.1 Hz, 1H), 6.60 (s, 2H), 4.78 (q, J=7.1 Hz, 1H), 4.45 (dt, J=12.1, 6.0 Hz, 1H), 3.28-3.18 (m, 2H), 2.57 (s, 3H), 1.58 (d, J=7.1 Hz, 3H), 1.19 (d, J=6.0 Hz, 3H), 1.13-1.04 (m, 6H). LC-MS (M+H)$^+$=433.8. RetTime in chiral-HPLC: 5.12 min, Method A

Example 29

(S)-3-(1-(8-amino-1-methylimidazol[1,5-a]pyrazin-3-yl)ethyl)-5-chloro-6-fluoro-2-isopropoxy-N-(4-methoxyphenyl)benzamide (Compound 29)

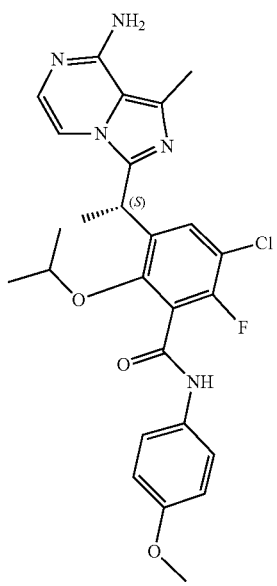

This compound (35 mg, 18.2%) was prepared from compound 15-13 and 4-methoxyaniline in a similar manner to compound 15-14 in Example 15. $^1$H NMR (400 MHz, DMSO-d6) δ 10.60 (s, 1H), 7.60-7.50 (m, J=8.7, 4.2 Hz, 3H), 7.43 (d, J=5.4 Hz, 1H), 7.39 (s, 2H), 6.98-6.87 (m, 3H), 4.85 (q, J=6.9 Hz, 1H), 4.45 (dt, J=12.1, 6.2 Hz, 1H), 3.74 (s, 3H), 2.60 (s, 3H), 1.61 (d, J=7.1 Hz, 3B), 1.18 (d, J=6.1 Hz, 3H), 1.04 (d, J=6.1 Hz, 3H). LC-MS (M±H)$^+$=511.8. RetTime in chiral-HPLC: 3.97 min, Method B

Example 30

(S)-3-(1-(8-amino-1-methylimidazo[1,5-a]pyrazin-3-yl)ethyl)-5-chloro-6-fluoro-2-isopropoxy-N-((1-methylpiperidin-4-yl)methyl)benzamide (Compound 30)

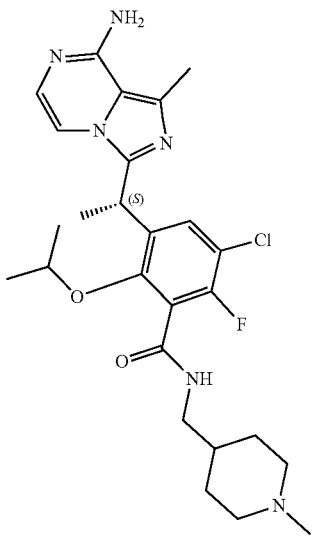

This compound (13 mg, 10.2%) was prepared from compound 15-13 and (1-methylpiperidin-4-yl)methanamine in a similar manner to compound 15-14 in Example 15. $^1$H NMR (400 MHz, DMSO-d6) δ 10.50 (brs, 1H), 8.84 (t, J=5.8 Hz, 1H), 7.63 (brs, 1H), 7.50 (d, J=8.5 Hz, 1H), 7.44 (d, J=5.5 Hz, 1H), 6.96 (d, J=5.4 Hz, 1H), 4.82 (q, J=6.9 Hz, 1H), 4.43 (dt, J=11.8, 6.0 Hz, 1H), 3.43-3.34 (m, 2H), 3.18-3.05 (m, 2H), 2.96-2.82 (m, 2H), 2.68 (s, 3H), 2.59 (s, 3H), 1.84 (d, J=13.3 Hz, 2H), 1.78-1.65 (m, 1H), 1.59 (d, J=7.0 Hz, 3H), 1.54-1.39 (m, 2H), 1.18 (d, J=6.0 Hz, 3H), 1.07 (d, J=6.0 Hz, 3H). LC-MS (M+H)$^+$=516.8. RetTime in chiral-HPLC: 2.78 min, Method B

Example 31

3-((S)-1-(8-amino-1-methylimidazo[1,5-a]pyrazin-3-yl)ethyl)-5-chloro-6-fluoro-2-isopropoxy-N-(((R)-tetrahydrofuran-2-yl)methyl)benzamide (Compound 31)

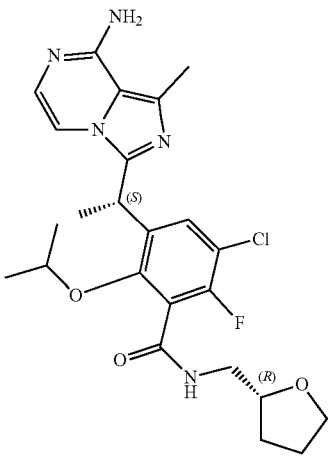

This compound (8 mg, 6.6%) was prepared from compound 15-13 and (R)-(tetrahydrofuran-2-yl)methanamine in a similar manner to compound 15-14 in Example 15. $^1$H NMR (400 MHz, DMSO-d6) δ 8.78 (t, J=5.7 Hz, 1H), 7.40 (d, J=8.6 Hz, 1H), 7.28 (d, J=5.1 Hz, 1H), 6.87 (d, J=5.1 Hz, 1H), 6.65 (s, 2H), 4.78 (q, J=6.9 Hz, 1H), 4.48 (dt, J=12.2, 6.1 Hz, 1H), 3.92 (dt, J=12.0, 6.4 Hz, 1H), 3.75 (dd, J=14.2, 7.0 Hz, 1H), 3.61 (dd, J=14.4, 7.3 Hz, 1H), 3.35-3.22 (m, 2H), 2.57 (s, 3H), 1.97-1.73 (m, 3H), 1.63-1.51 (m, 4H), 1.18 (d, J=6.1 Hz, 3H), 1.08 (d, J=6.0 Hz, 3H). LC-MS (M+H)$^+$=489.8. RetTime in chiral-HPLC: 3.49 min, Method B

Example 32

(S)-3-(1-(8-amino-1-methylimidazo[1,5-a]pyrazin-3-yl)ethyl)-5-chloro-6-fluoro-2-isopropoxy-N,N-dimethylbenzamide (Compound 32)

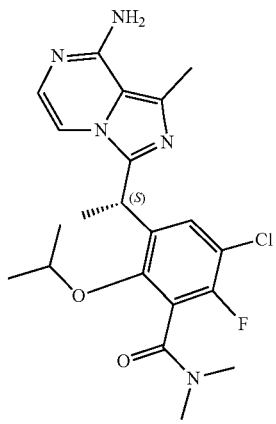

This compound (26 mg, 24.4%) was prepared from compound 15-13 and dimethylamine in a similar manner to compound 15-14 in Example 15. $^1$H NMR (400 MHz, DMSO-d6) δ 7.53-6.97 (m, 4H), 6.94-6.79 (m, 1H), 4.86-4.73 (m, 1H), 4.42-4.15 (m, 1H), 3.08-2.97 (m, 3H), 2.91-2.71 (m, 3H), 2.59 (s, 3H), 1.75-1.51 (m, 3H), 1.30-0.92 (m, 6H), LC-MS (M+H)$^+$=433.8. RetTime in chiral-HPLC: 4.05 min and 4.01 min, Method B

Example 33

(S)-3-(1-(8-amino-1-methylimidazo[1,5-a]pyrazin-3-yl)ethyl)-5-chloro-6-fluoro-2-isopropoxy-N-(pyridin-2-ylmethyl)benzamide (Compound 33)

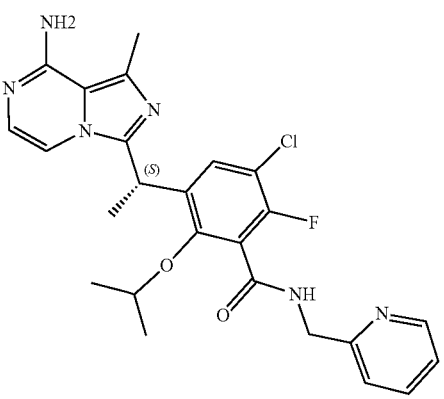

This compound (103 mg 83.1%) was prepared from compound 15-13 and pyridin-2-ylmethanamine in a similar manner to compound 15-14 in Example 15. $^1$H NMR (400 MHz, DMSO-d6) δ 9.33 (brs, 1H), 8.51 (brs, 1H), 7.83-7.79 (m, 1H), 7.48-7.45 (m, 1H), 7.40-7.34 (m, 2H), 7.30-7.28 (m, 1H), 7.18 (brs, 2H), 6.91-6.90 (m, 1H), 4.81-4.79 (m, 1H), 4.52 (brs, 2H), 4.42-4.40 (m, 1H) 2.59-2.58 (m, 3H), 1.60-1.58 (m, 3H), 1.12-1.10 (m, 3H), 0.99-0.98 (m, 3H). LC-MS (M+H)+=497.2. RetTime in chiral-HPLC: 2.83 min, Method E

Example 34

3-((S)-1-(8-amino-1-methylimidazo[1,5-a]pyrazin-3-yl)ethyl)-5-chloro-6-fluoro-2-isopropoxy-N-(((R)-tetrahydrofuran-3-yl)methyl)benzamide (Compound 34)

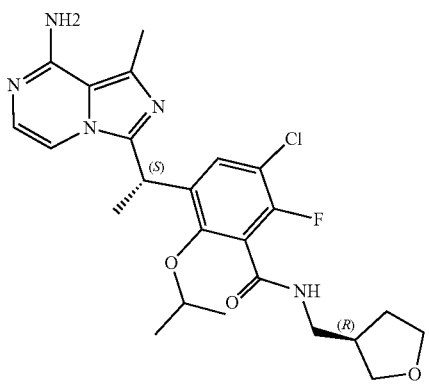

This compound (93.8 mg, 81.7%) was prepared from compound 15-13 and (R)-(tetrahydrofuran-3-yl)methanamine in a similar manner to compound 15-14 in Example 15. $^1$H NMR (400 MHz, DMSO-d6) δ 8.83 (brs, 1H), 7.47-7.45 (m, 1H), 7.38-7.37 (m, 1H), 7.18-7.07 (brs, 2H), 6.91-6.90 (m, 1H), 4.81-4.77 (m, 1H), 4.44-4.41 (m, 1H), 3.75-3.59 (m, 3H), 3.43-3.40 (m, 1H), 3.21-3.17 (m, 2H), 2.58 (brs, 3H), 2.44-2.40 (m, 2H), 1.95-1.91 (m, 1H), 1.59-1.58 (m, 3H), 1.07-1.06 (m, 3H). LC-MS (M+H)+=490.2. RetTime in chiral-HPLC: 2.59 min, Method E Example 35

3-((S)-1-(8-amino-1-methylimidazo[1,5-a]pyrazin-3-yl)ethyl)-5-chloro-6-fluoro-2-isopropoxy-N-4(((S)-tetrahydrofuran-3-yl)methyl)benzamide (Compound 35)

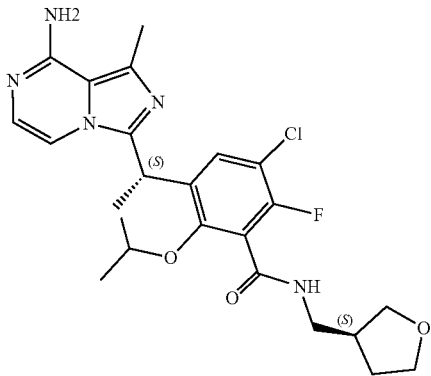

This compound (93.0 mg, 78.2%) was prepared from compound 15-13 and (S)-(tetrahydrofuran-3-yl)methanamine in a similar manner to compound 15-14 in Example 15. $^1$H NMR (400 MHz, DMSO-d6) δ 8.83-8.80 (t, 1H), 7.45-7.43 (d, J=8.4 Hz, 1H), 7.33-7.32 (d, J=5.2 Hz, 1H), 6.89-6.87 (d, J=5.2z, 1H), 6.83(brs, 2H), 4.82-4.76 (m, 1H), 4.47-4.41 (m, 1H), 3.75-3.59 (m, 3H), 3.45-3.40 (m, 1H), 3.27-3.14 (m, 2H), 2.57 (s, 3H), 2.47-2.37 (m, 2H), 1.98-1.89 (m, 1H), 1.62-1.53 (m, 4H), 1.19-1.17 (d, J=6.4 Hz, 3H), 1.08-1.07 (d, J=6.0 Hz, 3H). LC-MS (M+H)+=490.1. RetTime in chiral-HPLC: 3.56 min, Method F Example 36

3-((S)-1-(8-amino-1-methylimidazo[1,5-a]pyrazin-3-yl)ethyl)-5-chloro-6-fluoro-2-isopropoxy-N-((R)-1-(4-methoxyphenyl)ethyl)benzamide (Compound 36)

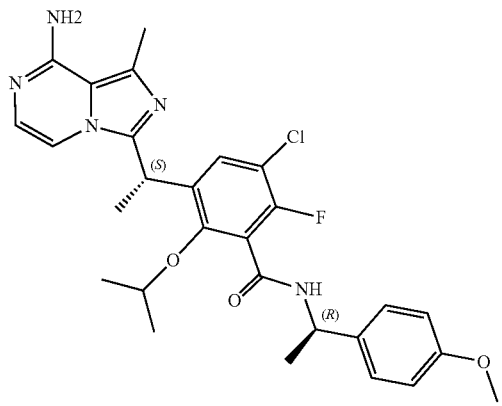

This compound (98.3 mg, 82.1%) was prepared from compound 15-13 and (R)-1-(4-methoxyphenyl)ethan-1-amine in a similar manner to compound 15-14 in Example 15.

$^1$H NMR (400 MHz, DMSO-d6) δ 9.14-9.12 (d, J=8.0 Hz, 1H), 7.45-7.43 (d, J=8.4 Hz, 1H), 7.35-7.34 (d, J=5.2 Hz, 1H), 7.39-7.26 (d, J=8.4 Hz, 2H), 7.05 (brs, 2H), 6.91-6.89 (m, 3H), 5.07-5.03 (m, 1H), 4.80-4.75 (m, 1H), 4.25-4.21 (m, 1H), 3.73 (s, 3H), 2.57 (s, 3H), 1.57-1.55 (d, J=7.2 Hz, 3H), 1.39-1.37 (d, J=6.8 Hz, 3H), 1.01-1.03 (d, J=6.0 Hz, 3H), 0.89-0.90 (d, J=6.0 Hz, 3H). LC-MS (M+H)+=539.8. RetTime in chiral-HPLC: 8.996 min, Method G.

Example 37

3-((S)-1-(8-amino-1-methylimidazo[1,5-a]pyrazin-3-yl)ethyl)-5-chloro-6-fluoro-2-isopropoxy-N-((1S,2S)-2-hydroxycyclopentyl)benzamide (Compound 37)

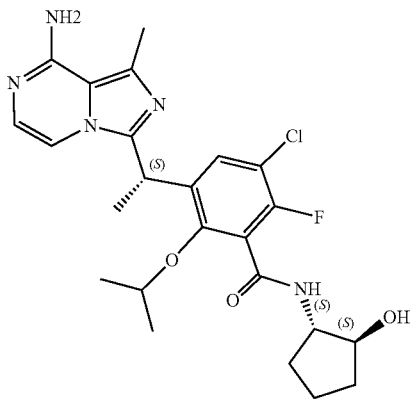

This compound (78.0 mg, 74.7%) was prepared from compound 15-13 and (1S,2S)-2-aminocyclopentan-1-ol in a similar manner to compound 15-14 in Example 15, $^1$H NMR (400 MHz, DMSO-d6) δ 8.60-8.58 (d, J=8.0 Hz, 1H), 7.43-7.41 (d, J=8.8 Hz, 1H), 7.33-7.32 (d, J=5.2 Hz, 1H), 6.89-6.88 (m, 3H), 4.80-4.75 (m, 2H), 4.52-4.48 (m, 1H), 3.95-3.90 (m, 2H), 2.57 (s, 3H), 1.99-1.96 (m, 1H), 1.78-1.74 (m, 1H), 1.66-1.61 (m, 2H), 1.58-1.56 (d, J=7.2 Hz, 3H), 1.48-1.36 (m, 3H), 1.18-1.16 (d, J=6.4 Hz, 3H), 1.06-1.05 (d, J=5.6 Hz, 3H). LC-MS (M+H)+=489.8. RetTime in chiral-HPLC: 3.012 min, Method F Example 38

3-((S)-1-(8-amino-1-methylimidazo[1,5-a]pyrazin-3-yl)ethyl)-5-chloro-6-fluoro-2-isopropoxy-N-((1S,3R)-3-hydroxy-1-methylcyclobutyl)benzamide (Compound 38)

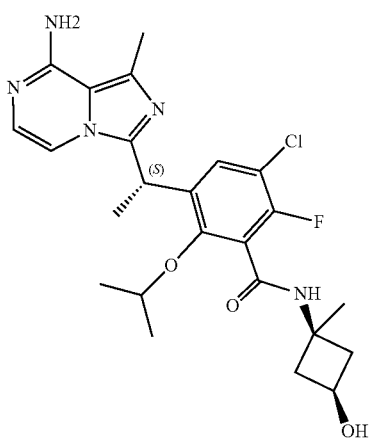

This compound (58.3 mg, 52.9%) was prepared from compound 15-13 and (1S,3S)-3-amino-3-methylcyclobutan-1-ol in a similar manner to compound 15-14 in Example 15, ¹H NMR (400 MHz, DMSO-d6) δ 8.84 (s, 1H), 7.43-7.41 (d, J=8.8 Hz, 1H), 7.36-7.34 (d, J=5.6 Hz, 1H), 7.06 (brs, 1H), 6.91-6.90 (d, J=5.2 Hz, 1H), 5.08-5.06 (d, J=6.4 Hz, 1H), 4.82-4.77 (m, 1H), 4.58-4.52 (m, 1H), 4.03-3.97 (m, 1H), 2.58 (s, 3H), 2.39-2.34 (m, 2H), 2.05-2.00 (m, 2H), 1.59-1.57 (d, J=6.8 Hz, 3H), 1.36 (s, 3H),1.21-1.19 (d, J=6.0 Hz, 3H),1.10-1.09 (d, J=6.0 Hz, 3H), LC-MS (M+H)+=489.8. RetTime in chiral-HPLC: 5.309 min, Method A Example 39

3-((S)-1-(8-amino-1-methylimidazo[1,5-a]pyrazin-3-yl)ethyl)-5-chloro-6-fluoro-N-((1r,3S)-3-hydroxy-1-methylcyclobutyl)-2-isopropoxybenzamide (Compound 39)

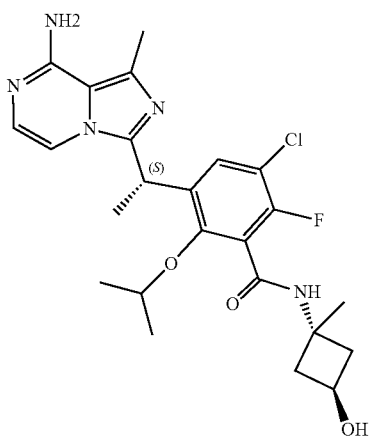

This compound (61.2 mg, 56.3%) was prepared from compound 15-13 and (1R,3R)-3-amino-3-methylcyclobutan-1-ol in a similar manner to compound 15-14 in Example 15. ¹H NMR (400 MHz, DMSO-d6) δ 8.70 (s, 1H), 7.43-7.41 (d, J=8.8 Hz, 1H), 7.36-7.34 (d, J=5.2 Hz, 1H), 7.02 (brs, 1H), 6.91-6.90 (d, J=5.2 Hz, 1H), 5.06-5.05 (d, J=5.6 Hz, 1H), 4.82-4.77 (m, 1H), 4.56-4.49 (m, 1H), 4.12-4.07 (m, 1H), 2.63-2.60 (m, 2H), 2.58 (s, 3H), 1.82-1.77 (m, 2H), 1.58-1.57 (d, J=6.8 Hz, 3H), 1.43 (s, 3H), 1.20-1.18 (d, J=6.4 Hz, 3H), 1.08-1.07 (d, J=6.0 Hz, 3H). LC-MS (M+H)+=489.8. RetTime in chiral-HPLC: 5,500 min, Method A Example 40

3-((S)-1-(8-amino-1-methylimidazo[1,5-a]pyrazin-3-yl)ethyl)-5-chloro-6-fluoro-N-((1R,4S)-4-hydroxy-1-methylcyclohexyl)-2-isopropoxybenzamide (Compound 40)

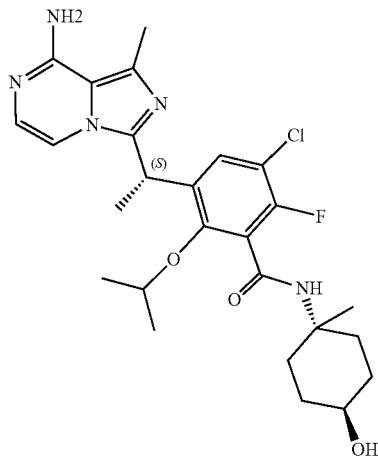

This compound (61.2 mg, 54.1%) was prepared from compound 15-13 and (1R,4R)-4-amino-4-methylcyclohexan-1-ol in a similar manner to compound 15-14 in Example 15. ¹H NMR (400 MHz, DMSO-d6) δ 8.11 (s, 1H), 7.42-7.37 (m, 2H), 7.13 (brs, 1H), 6.92-6.91 (d, J=5.2 Hz, 1H), 4.83-4.78 (m, 1H), 4.63-4.56 (m, 1H), 4.53-4.52 (m, 1H), 3.45-3.42 (m, 2H), 2.58 (s, 3H), 2.24-2.16 (m, 2H), 1.59-1.54 (m, 5H), 1.42-1.38 (m, 2H), 1.30 (s, 3H), 1.27-1.23 (m, 2H), 1.20-1.18 (d, J=5.6 Hz, 3H), 1.09-1.07 (d, J=6.0 Hz, 31H). LC-MS (M+H)⁺=417.8. RetTime in chiral-HPLC: 5.609 min, Method A.

Example 41

(S)-3-(1-(8-amino-1-methylimidazo[1,5-a]pyrazin-3-yl)ethyl)-5-chloro-6-fluoro-2-isopropoxy-N-propyl-benzamide (Compound 41)

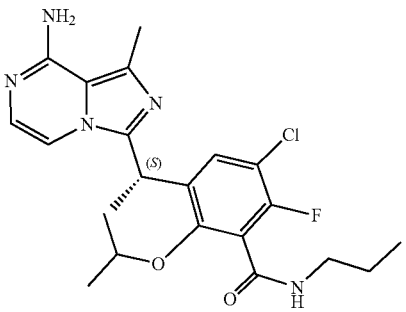

This compound (63 mg, 57.3%) was prepared from compound 15-13 and propan-1-amine in a similar manner to compound 15-14 in Example 15, ¹H NMR (400 MHz, DMSO-d6) δ 8.66 (s, 1H), 7.41 (d, J=4.8 Hz, 1H), 7.31 (brs, 1H), 6.86 (brs, 3H), 4.77 (brs, 1H), 4.44 (brs, 1H), 3.21-3.10 (m, 2H), 2.56 (s, 3H), 1.57 (brs, 3H), 1.48 (brs, 2H), 1.17 (brs, 3H), 1.06 (brs, 3H), 0.87 (brs, 3H). LC-MS (M+H)⁺=448.2. RetTime in chiral-HPLC: 3.43 min, Method C

Example 42

(S)-3-(1-(8-amino-1-methylimidazo[1,5-a]pyrazin-3-yl)ethyl)-5-chloro-N-(cyclopropylmethyl)-6-fluoro-2-isopropoxybenzamide (Compound 42)

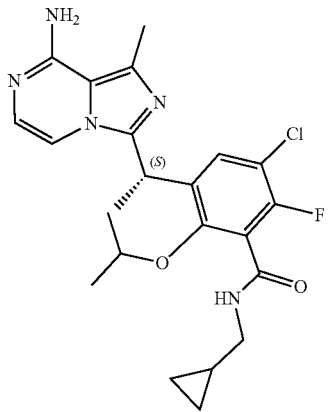

This compound (73 mg, 64.3%) was prepared from compound 15-13 and cyclopropylmethanamine in a similar manner to compound 15-14 in Example 15, ¹H NMR (400 MHz, DMSO-d6) δ 8.81 (s, 1H), 7.41 (brs, 1H), 7.28 (brs, 1H), 6.88 (brs, 1H), 6.52 (s, 2H), 4.79 (brs, H), 4.53 (brs, 1H), 3.11 (brs, 2H), 2.57 (s, 3H), 1.59 (brs, 3H), 1.20 (brs, 3H), 1.10 (brs, 3H), 0.99-0.91 (m, 1H), 0.45 (brs, 2H), 0.22 (brs, 2H). LC-MS (M+H)³⁰=460.2. RetTime in chiral-HPLC: 3.7 min, Method C

Example 43

(3-((S)-1-(8-amino-1-methylimidazo[1,5-a]pyrazin-3-yl)ethyl)-5-chloro-6-fluoro-2-isopropoxyphenyl)((2S,6S)-2,6-dimethylmorpholino)methanone (Compound 43)

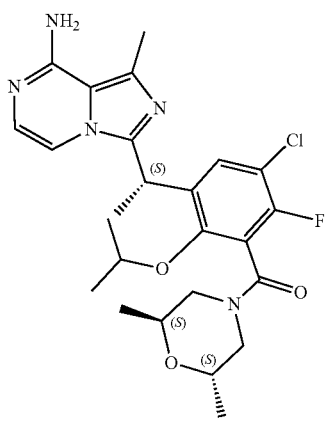

This compound (59 mg, 47.6%) was prepared from compound 15-13 and (2S,6S)-2,6-dimethylmorpholine in a similar manner to compound 15-14 in Example 15. ¹H NMR (400 MHz, DMSO-d6) δ 7.47 (d, J=8.8 Hz, 0.3H), 7.37-7.30 (m, 1H), 7.22 (d, J=4.4 Hz, 0.7H), 7.03-6.69 (m, 3H), 4.86-4.66 (m, 1H), 4.43-4.15 (m, 1H), 4.10-3.89 (m, 1H), 3.87-3.58 (m, 2H), 3.40-3.33 (m, 1H), 3.09-2.94 (m, 1H), 2.92-2.72 (m, 1H), 2.60-2.51 (m, 3H), 1.65 (d, J=6.9 Hz, 2H), 1.52 (d, J=6.7 Hz, 1H), 1.33-1.17 (m, 4H), 1.15-1.05 (m, 4H), 0.99 (d, J=6.3 Hz, 1H), 0.90 (d, J=6.2 Hz, 1H), 0.86 (d, J=5.6 Hz, 2H). LC-MS (M+H)⁺=504.2. RetTime in chiral-HPLC: 2.77 min and 3.98 min, Method F.

Example 44

3-((S)-1-(8-amino-1-methylimidazo[1,5-a]pyrazin-3-yl)ethyl)-5-chloro-6-fluoro-2-isopropoxy-N-((R)-tetrahydro-2H-pyran-3-yl)benzamide (Compound 44)

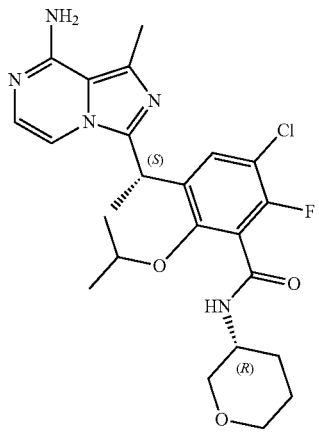

This compound (82 mg, 68%) was prepared from compound 15-13 and (R)-tetrahydro-2H-pyran-3-amine in a similar manner to compound 15-14 in Example 15. ¹H NMR (400 MHz, DMSO-d6) δ 8.67 (d, J=7.7 Hz, 1H), 7.36 (d, J=8.6 Hz, 1H), 7.22 (d, J=5.0 Hz, 1H), 6.82 (d, J=5.0 Hz, 1H), 6.40 (s, 2H), 4.76-4.71 (m, 1H), 4.48-4337 (m, 1H), 3.85-3.77 (m, 1H), 3.76-3.70 (m, 1H), 3.69-3.62 (m, 1H), 3.29-3.25 (m, 1H), 3.15-3.09 (m, 1H), 2.53 (s, 3H), 1.89-1.81 (m, 1H), 1.69-1.62 (m, 1H), 1.54 (d, J=7.1 Hz, 3H), 1.50-1.40 (m, 2H), 1.15 (d, J=6.1 Hz, 3H), 1.03 (d, J=6.5, 3H). LC-MS (M+H)⁺=490.1. RetTime in chiral-HPLC: 3.47 min, Method F

Example 45

3-((S)-1-(8-amino-1-methylimidazol[1,5-a]pyrazin-3-yl)ethyl)-5-chloro-6-fluoro-2-isopropoxy-N-((S)-tetrahydro-2H-pyran-3-yl)benzamide (Compound 45)

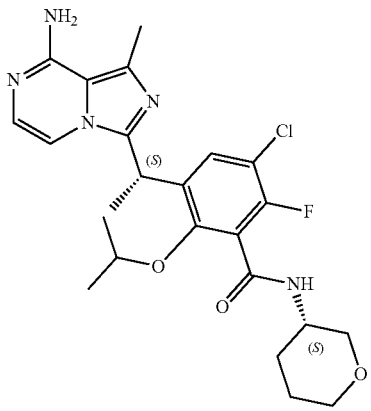

This compound (31 mg, 25.7%) was prepared from compound 15-13 and (S)-tetrahydro-2H-pyran-3-amine in a similar manner to compound 15-14 in Example 15. $^1$H NMR (400 MHz, DMSO-d6) δ 8.71 (d, J=7.5 Hz, 1H), 7.42 (d, J=8.6 Hz, 1H), 7.30 (d, J=5.2 Hz, 1H), 6.88 (d, J=5.1 Hz, 1H), 6.73 (s, 2H), 4.76-4.71 (m, 1H), 4.51-4.41 (m, 1H), 3.85-3.76 (m, 1H), 3.76-3.71 (m, 1H), 3.69-3.63 (m, 1H), 3.31-3.27 (m, 1H), 3.20 3.11 (m, 1H), 2.57 (s, 3H), 1.90-1.87 (m, 1H), 1.69-1.65 (m, 1H), 1.57 (d, J=7.0 Hz, 3H), 1.54-1.41 (m, 2H), 1.18 (d, J=6.0 Hz, 3H), 1.06 (d, J=6.0 Hz, 3H). LC-MS (M+H)$^+$=489.8. RetTime in chiral-HPLC: 9.75 min, Method D

Example 46

3((S)-1-(8-amino-1-methylimidazo[1,5-a]pyrazin-3-yl)ethyl)-5-chloro-6-fluoro-N-((1S,2S)-2-hydroxycyclohexyl)-2-isopropoxybenzamide (Compound 46)

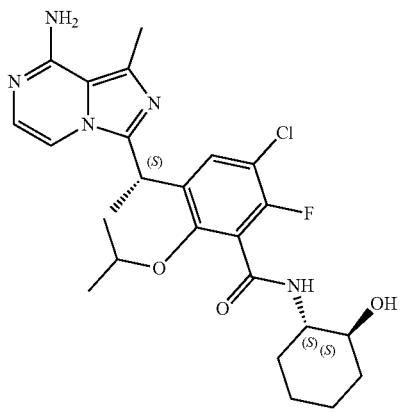

This compound (32 mg, 26%) was prepared from compound 15-13 and (1S,2S)-2-aminocyclohexan-1-ol in a similar manner to compound 15-14 in Example 15. $^1$H NMR (400 MHz, DMSO-d6) δ 8.53 (d, J=7.9 Hz, 1H), 7.36 (d, J=8.5 Hz, 1H), 7.27 (d, J=5.1 Hz, 1H), 6.87 (d, J=5.1 Hz, 1H), 6.64 (s, 2H), 4.81-4.74 (m, 1H), 4.69-4.58 (m, 1H), 4.48 (d, J=5.6 Hz, 1H), 3.65-3.55 (m, 1H), 3.29-3.22 (m, 1H), 2.57 (s, 3H), 1.96-1.78 (m, 2H), 1.65-1.59 (m, 2H), 1.56 (d, J=7.1 Hz, 3H), 1.37-1.17 (m, 4H), 1.15 (d, J=6.0 Hz, 3H), 1.02 (d, J=6.0 Hz, 3H). LC-MS (M+H)$^+$=503.8, RetTime in chiral-HPLC: 3.12 min, Method F

Example 47

3-((S)-1-(8-amino-1-methylimidazo[1,5-a]pyrazin-3-yl)ethyl)-5-chloro-6-fluoro-N-((1S,2R)-2-hydroxycyclohexyl)-2-isopropoxybenzamide (Compound 47)

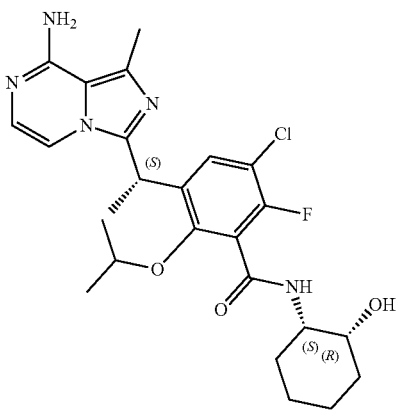

This compound (26 mg, 21%) was prepared from compound 15-13 and (1R,2S)-2-aminocyclohexan-1-ol in a similar manner to compound 15-14 in Example 15. $^1$H NMR (400 MHz, DMSO-d6) δ 8.36 (d, J=8.1 Hz, 1H), 7.37 (d, J=8.5 Hz, 1H), 7.31 (d, J=5.2 Hz, 1H), 6.88 (d, J=5.1 Hz, 1H), 6.79 (s, 2H), 4.80-4.75 (m, 1H), 4.55-4.50 (m, 1H), 4.48 (d, J=3.6 Hz, 1H), 3.90-3.82 (m, 1H), 3.80-3.75 (m, 1H), 2.57 (s, 3H), 1.72-1.63 (m, 2H), 1.61-1.51 (m, 5H), 1.50-1.42 (m, 2H), 1.35-1.22 (m, 2H), 1.17 (d, J=5.9 Hz, 3H), 1.04 (d, J=6.0 Hz, 3H), LC-MS (M+H)$^+$=503.8. RetTime in chiral-HPLC: 6.17 min, Method D

Example 48

3-((S)-1-(8-amino-1-methylimidazo[1,5-a]pyrazin-3-yl)ethyl)-5-chloro-6-fluoro-N-((1R,2S)-2-hydroxycyclohexyl)-2-isopropoxybenzamide (Compound 48)

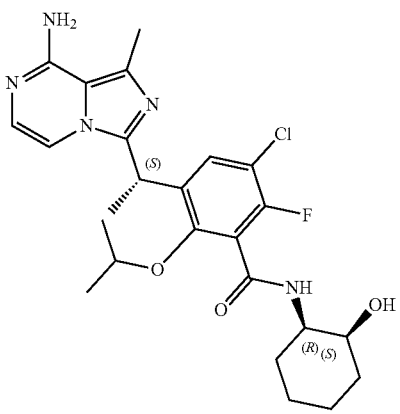

This compound (43 mg, 34.7%) was prepared from compound 15-13 and (1S,2R)-2-aminocyclohexan-1-ol in a similar manner to compound 15-14 in Example 15. ¹H NMR (400 MHz, DMSO-d6) δ 8.33 (d, J=8.1 Hz, 1H), 7.36 (d, J=8.5 Hz, 1H), 7.27 (d, J=5.2 Hz, 1H), 6.86 (d, J=5.1 Hz, 1H), 6.69 (s, 2H), 4.81-4.73 (m, 1H), 4.58-4.49 (m, 1H), 4.46 (d, J=3.6 Hz, 1H), 3.90-3.83 (m, 1H), 3.81-3.75 (m, 1H), 2.57 (s, 3H), 1.73-1.64 (m, 2H), 1.62-1.51 (m, 5H), 1.50-1.43 (m, 2H), 1.34-1.25 (m, 2H), 1.18 (d, J=6.0 Hz, 3H), 1.10 (d, J=6.0 Hz, 3H). LC-MS (M+H)⁺503.8. RetTime in chiral-HPLC: 6.14 min, Method D Example 49

3-((S)-1-(8-amino-1-methylimidazol[1,5-a]pyrazin-3-yl)ethyl)-5-chloro-6-fluoro-N-((1R,2R)-2-hydroxycyclohexyl)-2-isopropoxybenzamide (Compound 49)

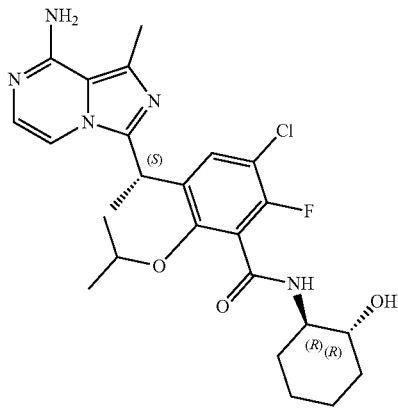

This compound (53 mg, 42.7%) was prepared from compound 15-13 and (1R,2R)-2-aminocyclohexan-1-ol in a similar manner to compound 15-14 in Example 15. ¹H NMR (400 MHz, DMSO-d6) δ 8.50 (d, 7.9 Hz, 1H), 7.37 (d, J=8.5 Hz, 1H), 7.26 (d, J=5.1 Hz, 1H), 6.86 (d, J=5.1 Hz, 1H), 6.60 (s, 2H), 4.81-4.73 (m, 1H), 4.69-4.59 (m, 1H), 4.48 (d, J=5.6 Hz, 1H), 3.64-3.54 (m, 1H), 3.30-3.24 (m, 1H), 2.57 (s, 3H), 1.96-1.79 (m, 2H), 1.65-1.60 (s, 2H), 1.57 (d, J=7.1 Hz, 3H), 1.33-1.17 (m, 4H), 1.16 (d, J=6.0 Hz, 3H), 1.08 (d, J=5.9 Hz, 3H). LC-MS (M+H)⁺=503.8. RetTime in chiral-HPLC: 6.63 min, Method D Example 50

3-((S)-1-(8-amino-1-methylimidazo[1,5-a]pyrazin-3-yl)ethyl)-5-chloro-6-fluoro-2-isopropoxy-N-((tetrahydro-2H-pyran-3-yl)methyl)benzamide (Compound 50)

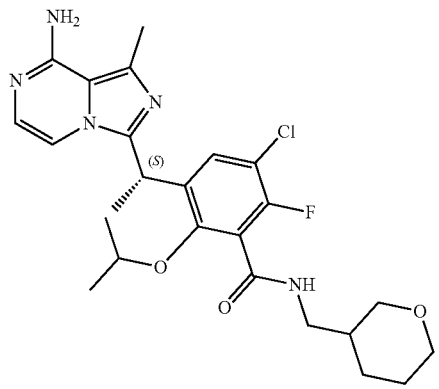

This compound (66 mg, 53%) was prepared from compound 15-13 and (tetrahydro-2H-pyran-3-yl)methanamine in a similar manner to compound 15-14 in Example 15. ¹H NMR (400 MHz, DMSO-d6) δ 8.66 (t, J=5.8 Hz, 1H), 7.39 (d, J=8.6 Hz, 1H), 7.28 (d, J=5.2 Hz, 1H), 6.83 (d, Hz, 1H), 6.73 (s, 2H), 4.78-4.70 (m, 1H), 4.45-4.35 (m, 1H), 3.76-3.70 (m, 1H), 3.69-3.63 (m, 1H), 3.26-3.22 (m, 1H), 3.09-3.02 (m, 3H), 2.53 (s, 3H), 1.78-1.65 (m, 2H), 1.54 (d, J=7.1 Hz, 3H), 1.51-1.48 (m, 1H), 1.45-1.33 (m, 1H), 1.22-1.17 (m, 1H), 1.14 (d, J=6.1 Hz, 3H), 1.04 (d, J=6.0 Hz, 3H). LC-MS (M+H)⁺=504.2. RetTime in chiral-HPLC: 3.31 min, Method F Example 51

(S)-3-(1-(8-amino-1-methylimidazo[1,5-a]pyrazin-3-yl)ethyl)-5-chloro-6-fluoro-2-isopropoxy-N-((tetrahydro-2H-pyran-4-yl)methyl)benzamide (Compound 51)

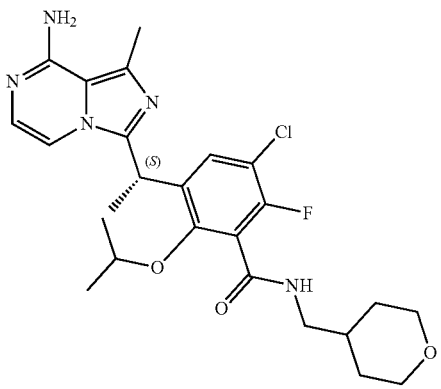

This compound (61 mg, 49%) was prepared from compound 15-13 and (tetrahydro-2H-pyran-4-yl)methanamine in a similar manner to compound 15-14 in Example 15. ¹H NMR (400 MHz, DMSO-d6) δ 8.69 (t, J=5.7 Hz, 1H), 7.40

(d, J=8.6 Hz, 1H), 7.29 (d, J=5.2 Hz, 1H), 6.84 (d, J=5.2 Hz, 1H), 6.79 (s, 2H), 4.80-4.71 (m, 1H), 4.47-4.36 (m, 1H), 3.84-3.78 (m, 2H), 3.24-3.17 (m, 2H), 3.08 (t, J=6.3 Hz, 2H), 2.54 (s, 3H), 1.74-1.64 (m, 1H), 1.59-1.50 (m, 5H), 1.21-1.11 (m, 5H), 1.04 (d, J=6.1 Hz, 3H). LC-MS (M+H)⁺=504.2. RetTime in chiral-HPLC: 4.68 min, Method L.

Example 52

(3-((S)-1-(8-amino-1-methylimidazo[1,5-a]pyrazin-3-yl)ethyl)-5-chloro-6-fluoro-2-isopropoxyphenyl)(8-oxa-3-azabicyclo[3.2.1]octan-3-yl)methanone (Compound 52)

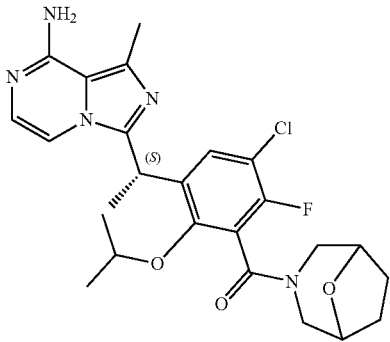

This compound (32 mg, 26%) was prepared from compound 15-13 and 8-oxa-3-azabicyclo[3.2.1]octane in a similar manner to compound 15-14 in Example 15. ¹H NMR (400 MHz, DMSO-d6) δ 7.50-7.33 (m, 1H), 7.31-7.11 (m, 1H), 6.91-6.81 (m, 0.6H), 6.80-6.70 (m, 0.4H), 6.55-6.31 (m, 2H), 4.85-4.66 (m, 1H), 4.64-4.51 (m, 0.4H), 4.42 (brs, 1H), 4.33-3.99 (m, 2.6H), 3.29-3.23 (m, 1H), 3.16-3.03 (m, 1H), 3.03-2.78 (m, 2H), 2.57 (s, 3H), 1.87 (brs, 2H), 1.77-1.63 (m, 3H), 1.58-1.49 (m, 1H), 1.37-1.10 (m, 6H), 0.96-0.77 (m, 1H). LC-MS (M+H)⁺=501.8., RetTime in chiral-HPLC: 5.17 min, Method B.

Example 53

3-((S)-1-(8-amino-1-methylimidazo[1,5-a]pyrazin-3-yl)ethyl)-5-chloro-6-fluoro-N-((1R,3R)-3-hydroxycyclopentyl)-2-isopropoxybenzamide (Compound 53)

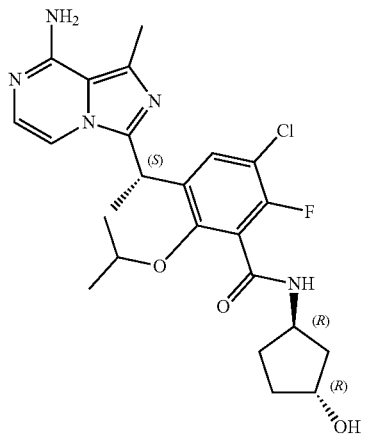

This compound (45 mg, 37.5%) was prepared from compound 15-13 and (1R,3R)-3-aminocyclopentan-1-ol in a similar manner to compound 15-14 in Example 15. ¹H NMR (400 MHz, DMSO-d6) δ 8.67 (d, J=7.5 Hz, 1H), 7.45 (d, J=8.6 Hz, 1H), 7.40 (d, J=5.4 Hz, 1H), 7.38-7.25 (m, 2H), 6.92 (d, J=5.3 Hz, 1H), 4.84-4.76 (m, 1H), 4.54 (d, J=3.6 Hz, 1H), 4.50-4.41 (m, 1H), 4.39-4.30 (m, 1H), 4.19-4.13 (m, 1H), 2.58 (s, 3H), 2.07-1.97 (m, 1H), 1.84 (d, J=3.9 Hz, 2H), 1.61-1.54 (m, 4H), 1.50-1.35 (m, 2H), 1.17 (d, J=6.1 Hz, 3H), 1.05 (d, J=6.1 Hz, 3H). LC-MS (M+H)⁺=489.8, RetTime in chiral-HPLC: 3.45 min, Method B Example 54

(S)-3-(1-(8-amino-1-methylimidazo[1,5-a]pyrazin-3-yl)ethyl)-5-chloro-N-(1-((dimethylamino)methyl)cyclopropyl)-6-fluoro-2-isopropoxybenzamide (Compound 54)

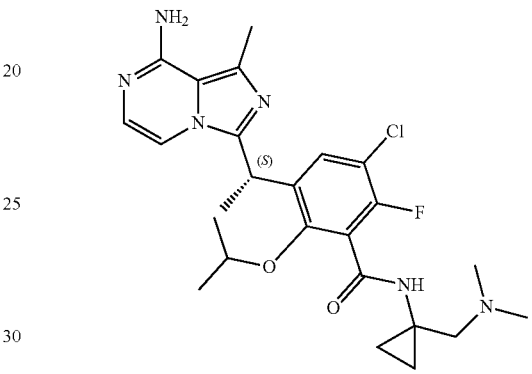

This compound (33 mg, 26.6%) was prepared from compound 15-13 and 1-((dimethylamino)methyl)cyclopropan-1-amine in a similar manner to compound 15-14 in Example 15. ¹H NMR (400 MHz, DMSO-d6) δ 9.21 (s, 1H), 7.52 (d, J=8.6 Hz, 1H), 7.38 (d, J=5.2 Hz, 1H), 7.03 (s, 2H), 6.91 (d, J=5.2 Hz, 1H), 4.83 4.74 (m, 1H), 4.38-4.24 (s, 1H), 3.30-3.17 (m, 2H), 2.77 (s, 6H), 2.57 (s, 3H), 1.58 (d, J=7.0 Hz, 3H), 1.20-1.11 (m, 5H), 1.05 (d, J=6.0 Hz, 3H), 0.93-0.78 (m, 2H), LC-MS (M+H)⁺=502.8. RetTime in chiral-HPLC: 3.57 min, Method A Example 55

(S)-3-(1-(8-amino-1-methylimidazo[1,5-a]pyrazin-3-yl)ethyl)-5-chloro-6-fluoro-N-((3-hydroxyoxetan-3-yl)methyl)-2-isopropoxybenzamide (Compound 55)

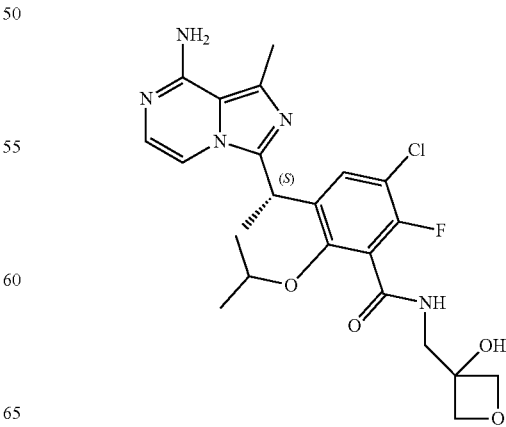

This compound (51 mg, 42%) was prepared from compound 15-13 and 3-(aminomethyl)oxetan-3-ol in a similar manner to compound 15-14 in Example 15. ¹H NMR (400 MHz, DMSO-d6) δ 8.87 (t, J=5.7 Hz, 1H), 7.41 (d, J=8.5 Hz, 1H), 7.30 (d, J=5.2 Hz, 1H), 6.88 (d, J=5.1 Hz, 1H), 6.80 (s, 2H), 5.87 (s, 1H), 4.83-4.73 (m, 1H), 4.54-4.74 (m, 1H), 4.47-4.42 (m, 2H), 4.41-4.36 (m, 2H), 3.64-3.48 (m, 2H), 2.58 (s, 3H), 1.58 (d, J=7.0 Hz, 3H), 1.18 (d, J=6.0 Hz, 3H), 1.08 (d, J=6.0 Hz, 3H). LC-MS (M+H)⁺=491.8. RetTime in chiral-HPLC: 5.8 min, Method B.

Example 56

(S)-3-(1-(8-amino-1-methylimidazo[1,5-a]pyrazin-3-yl)ethyl)-5-chloro-N-(1-((4-(cyclopropylmethyl)piperazin-1-yl)methyl)cyclopropyl)-6-fluoro-2-isopropoxybenzamide (Compound 56)

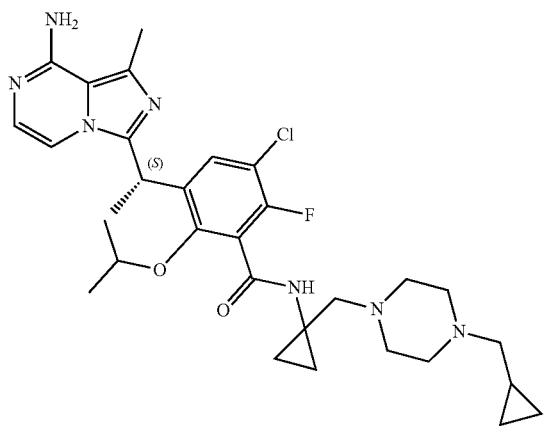

This compound (55 mg, 37.4%) was prepared from compound 15-13 and 1-((4-(cyclopropylmethyl)piperazin-1-yl)methyl)cyclopropan-1-amine in a similar manner to compound 15-14 in Example 15. ¹H NMR (400 MHz, DMSO-d6) δ 8.83 (s, 1H), 7.34 (d, J=8.5 Hz, 1H), 7.24 (d, J=5.0 Hz, 1H), 6.85 (d, J=5.0 Hz, 1H), 6.43 (s, 2H), 4.81-4.72 (m, 1H), 4.71-4.61 (m, 1H), 3.33-3.24 (m, 2H), 2.56 (s, 3H), 2.47-2.23 (m, 7H), 2.13 (d, J=6.4 Hz, 2H), 1.56 (d, J=7.0 Hz, 3H), 1.18 (d, J=5.9 Hz, 3H), 1.07 (d, 5.9 Hz, 3H), 0.82-0.74 (m, 1H), 0.73-0.69 (m, 2H), 0.68-0.60 (m, 2H), 0.47-0.37 (m, 2H), 0.08-0.01 (m, 2H). LC-MS (M+H)⁺=597.8 RetTime in chiral-HPLC: 2.6 min, Method B.

Example 57

3-((S)-1-(8-amino-1-methylimidazo[1,5-a]pyrazin-3-yl)ethyl)-5-chloro-6-fluoro-N-((S)-2-hydroxypropyl)-2-isopropoxybenzamide (Compound 57)

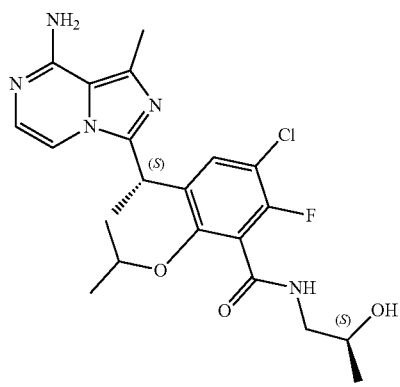

This compound (19 mg, 16.7%) was prepared from compound 15-13 and (S)-1-aminopropan-2-ol in a similar manner to compound 15-14 in Example 15. ¹H NMR (400 MHz, DMSO-d6) δ 8.67 (t, J=5.6 Hz, 1H), 7.41 (d, J=8.5 Hz, 1H), 7.32 (d, J=5.0 Hz, 1H), 7.00-6.70 (m, 3H), 4.88-4.74 (m, 1H), 4.70 (d, J=4.6 Hz, 1H), 4.54-4.42 (m, 1H), 3.78-3.66 (m, 1H), 3.24-3.16 (m, 1H), 3.15-3.07 (m, 1H), 2.58 (s, 3H), 1.58 (d, J=7.0 Hz, 3H), 1.18 (d, J=6.0 Hz, 3H), 1.07 (t, J=5.6 Hz, 6H). LC-MS (M+H)⁺=463.8. RetTime in chiral-HPLC: 3.02 min, Method B.

Example 58

3-((S)-1-(8-amino-1-methylimidazo[1,5-a]pyrazin-3-yl)ethyl)-5-chloro-6-fluoro-N-((1R,2R)-2-hydroxycyclopentyl)-2-isopropoxybenzamide (Compound 58)

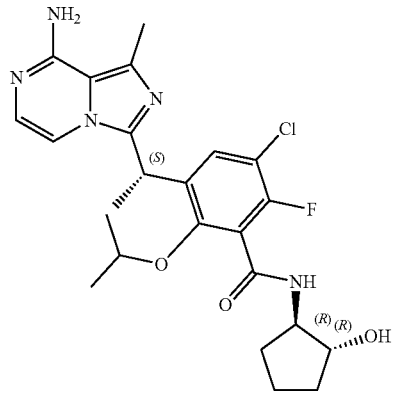

This compound (81 mg, 67%) was prepared from compound 15-13 and (1R,2R)-2-aminocyclopentan-1-ol in a similar manner to compound 15-14 in Example 15. ¹H NMR (400 MHz, DMSO-d6) δ 8.57 (d, J=7.2 Hz, 1H), 7.39 (d, J=8.6 Hz, 1H), 7.28 (d, J=5.2 Hz, 1H), 6.85 (d, J=5.1 Hz, 1H), 6.69 (s, 2H) 4.81-4.71 (m, 2H), 4.53-4.43 (m, 1H), 3.98-3.85 (m, 2H), 2.55 (s, 3H), 2.01-1.91 (m, 1H), 1.80-

1.70 (m, 1H), 1.68-1.59 (m, 2H), 1.55 (d, J=7.1 Hz, 3H), 1.48-1.33 (m, 2H), 1.16 (d, J=6.1 Hz, 3H), 1.04 (d, J=6.0 Hz, 3H), LC-MS (M+H)⁺=489.8. RetTime in chiral-HPLC: 2.99 min, Method B.

Example 59

3-((S)-1-(8-amino-1-methylimidazo[1,5-a]pyrazin-3-yl)ethyl)-5-chloro-6-fluoro-2-isopropoxy-N-((S)-1-(2-(trifluoromethyl)pyridin-4-yl)ethyl)benzamide (Compound 59A) and 3((S)-1-(8-amino-1-methyl-imidazo[1,5-a]pyrazin-3-yl)ethyl)-5-chloro-6-fluoro-2-isopropoxy-N-((R)-1-(2-(trifluoromethyl)pyridin-4-yl)ethyl)benzamide (Compound 59B)

Compound 59A

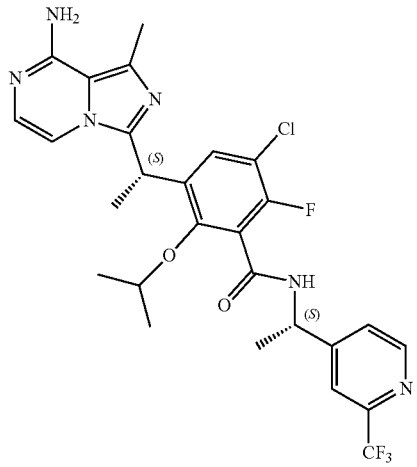

Compound 59B

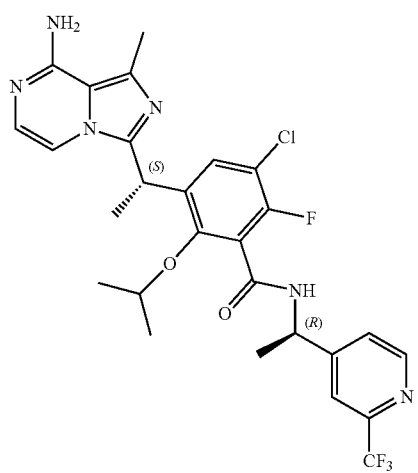

These compounds were prepared from compound 15-13 and 1-(2-(trifluoromethyl)pyridin-4-yl)ethan-1-amine in a similar manner to compound 15-14 in Example 15. The isomers were obtained by chiral separation.

Compound 59A: 136 mg, 31.9%. ¹H NMR (400 MHz, DMSO-d6) δ 9.42 (d, J=7.6 Hz, 1H), 8.77 (d, J=5.0 Hz, 1H), 7.89 (s, 1H), 7.71 (d, J=4.9 Hz, 1H), 7.49 (d, J=8.7 Hz, 1H), 7.29 (d, J=5.1 Hz, 1H), 6.86 (d, J=5.0 Hz, 1H), 6.46 (s, 2H), 5.26-5.16 (m, 1H), 4.81-4.73 (m, 1H), 4.27-4.16 (m, 1H), 2.56 (s, 3H), 1.57 (d, J=7.1 Hz, 3H), 1.43 (d, J=7.1 Hz, 3H), 1.07 (d, J=6.1 Hz, 3H), 0.93 (d, J=6.1 Hz, 3H). LC-MS (M+H)⁺=578.7. RetTime in chiral-HPLC: 3.68 min, Method C.

Compound 59B: 103 mg, 24%, ¹H NMR (400 MHz, DMSO-d6) δ 9.42 (d, J=7.5 Hz, 1H), 8.77 (d, J=4.6 Hz, 1H), 7.89 (s, 1H), 7.72 (d, J=4.1 Hz, 1H), 7.46 (d, J=8.5 Hz, 1H), 7.28 (d, J=4.7 Hz, 1H), 6.85 (d, J=4.7 Hz, 1H), 6.47 (s, 2H), 5.29-5.17 (m, 1H), 4.82-4.69 (m, 1H), 4.32-4.18 (m, 1H), 2.56 (s, 3H), 1.59 (d, J=6.8 Hz, 3H), 1.43 (d, J=6.8 Hz, 3H), 1.06 (d, J=5.7 Hz, 3H), 0.89 (d, J=5.7 Hz, 3H), LC-MS (M=H)⁺=578.7. RetTime in chiral-HPLC: 4.18 min, Method C.

| Column | CHIRALPAK ID |
|---|---|
| Column size | 2 cm × 25 cm, 5 um |
| Injection | 0.3 ml |
| Mobile phase | Hex(10 mMNH₃—MeOH):EtOH = 80:20 |
| Flow rate | 20 ml/min |
| Wave length | UV 220 nm |
| Temperature | 25° C. |
| Sample solution | 58 mg/ml in EtOH:DCM = 3:1 |
| Prep-HPLC equipment | Prep-HPLC-Gilson |

Example 60

3((S)-1-(8-amino-1-methylimidazo[1,5-a]pyrazin-3-yl)ethyl)-5-chloro-6-fluoro-N-((trans)-4-hydroxycyclohexyl)-2-isopropoxybenzamide (Compound 60)

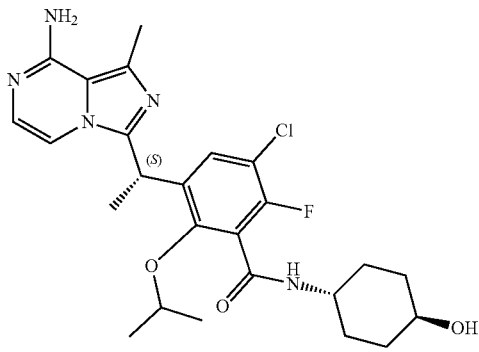

This compound (50 mg, 39%) was prepared from compound 15-13 and trans-4-aminocyclohexan-1-ol in a similar manner to compound 15-14 in Example 1.5, ¹H NMR (400 MHz, DMSO-d6) δ 8.57 (d, J=7.8 Hz, 1H), 7.38 (d, J=8.6 Hz, 1H), 7.25 (d, J=5.1 Hz, 1H), 6.85 (d, J=5.0 Hz, 1H), 6.42 (brs, 2H), 4.76 (q, J=7.2 Hz, 1H), 4.55 (d, J=4.3 Hz, 1H), 4.51-4.43 (m, 1H), 3.65 (brs, 1H), 3.34 (brs, 1H), 2.56 (s, 3H), 1.87-1.76 (m, 4H), 1.56 (d, J=7.1 Hz, 3H), 1.28-1.20 (m, 4H), 1.17 (d, J=6.0 Hz, 3H), 1.06 (d, J=6.0 Hz, 3H). LC-MS (M+H)⁺=504.2. RetTime in chiral-HPLC: 4.372 min, Method C.

Example 61

3-((S)-1-(8-amino-1-methylimidazo[1,5-a]pyrazin-3-yl)ethyl)-5-chloro-6-fluoro-N-((trans)-3-hydroxycyclobutyl)-2-isopropoxybenzamide (Compound 61)

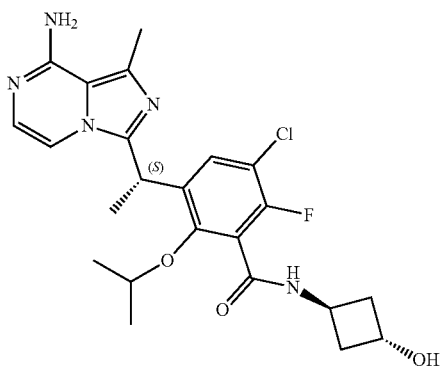

This compound (80 mg, 75%) was prepared from compound 15-13 and trans-3-aminocyclobutan-1-ol in a similar manner to compound 15-14 in Example 15. $^1$H NMR (400 MHz, DMSO-d6) δ 8.96 (brs, 1H), 7.45 (d, J=8.7 Hz, 1H), 7.32 (brs, 1H), 6.89 (brs, 1H), 6.72 (brs, 2H), 5.09 (brs, 1H), 4.79 (brs, 1H), 4.44 (brs, 1H), 4.28 (brs, 2H), 2.58 (s, 3H), 2.16 (brs, 4H), 1.58 (brs, 3H), 1.19 (brs, 3H), 1.07 (brs, 3H). LC-MS (M+H)$^+$=476.2. RetTime in chiral-HPLC: 2.669 min, Method K.

Example 62

3((S)-1-(8-amino-1-methylimidazo[1,5-a]pyrazin-3-yl)ethyl)-5-chloro-6-fluoro-N-((cis)-4-hydroxycyclohexyl)-2-isopropoxybenzamide (Compound 62)

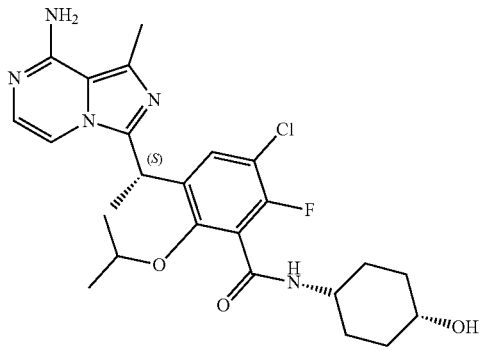

This compound (70 mg, 55%) was prepared from compound 15-13 and cis-4-aminocyclohexan-1-ol in a similar manner to compound 15-14 in Example 15. $^1$H NMR (400 MHz, DMSO-d6) δ 8.61 (brs, 1H), 7.35 (d, J=8.4 Hz, 1H), 7.25 (brs, 1H), 6.85 (brs, 1H), 6.50 (brs, 2H), 4.76 (brs, 1H), 4.48 (brs, 1H), 4.38 (brs, 1H), 3.75 (brs, 1H), 3.66 (brs, 1H), 2.55 (brs, 3H), 1.69-1.41 (m, 8H), 1.17 (brs, 3H), 1.05 (brs, 31H). LC-MS (M+H)$^+$=504.2. RetTime in chiral-HPLC: 2.045 min, Method L.

Example 63

3-((S)-1-(8-amino-1-methylimidazo[1,5-a]pyrazin-3-yl)ethyl)-5-chloro-6-fluoro-N-((cis)-3-hydroxycyclobutyl)-2-isopropoxybenzamide (Compound 63)

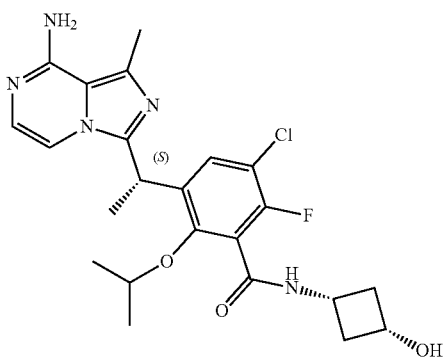

This compound (70 mg, 59%) was prepared from compound 15-13 and cis-3-aminocyclobutan-1-ol in a similar manner to compound 15-14 in Example 15. $^1$H NMR (400 MHz, DMSO-d6) δ 8.89 (brs, 1H), 7.44 (d, J=8.3 Hz, 1H), 7.32 (brs, 1H), 6.89 (brs, 1H), 6.81 (brs, 2H), 5.13 (brs, 1H), 4.79 (brs, 1H), 4.42 (brs, 1H), 3.82 (brs, 2H), 2.59-2.51 (m, 5H), 1.77 (brs, 2H), 1.58 (brs, 3H), 1.19 (brs, 3H), 1.07 (brs, 3H). LC-MS (M+H)$^+$=476.2. HPLC: 214 nm, 98%; 254 nm, 98%. RetTime in chiral-HPLC: 3.358 min. RetTime in chiral-HPLC: 3.36 min, Method F.

Example 64

(S)-(3-(1-(8-amino-1-methylimidazo[1,5-a]pyrazin-3-yl)ethyl)-5-chloro-6-fluoro-2-isopropoxyphenyl)(2-oxa-7-azaspiro[3.5]nonan-7-yl)methanone (Compound 64)

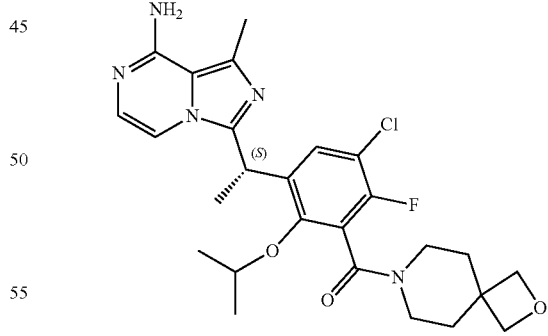

This compound (70 mg, 54%) was prepared from compound 15-13 and 2-oxa-7-azaspiro[3.5]nonane oxalate in a similar manner to compound 15-14 in Example 15. $^1$H NMR (400 MHz, DMSO-d6) δ 7.41 (d, J=6.5 Hz, 0.3H), 7.31 (d, J=6.5 Hz, 0.7H), 7.25 (brs, 0.3H), 7.16 (brs, 0.7H), 6.85 (brs, 1H), 6.56 (brs, 2H), 4.74 (brs, 1H), 4.43-4.17 (m, 4.7H), 3.76 (brs, 0.6H), 3.57 (brs, 0.6H), 3.34 (brs, 0.8H), 3.14 (brs, 0.8H), 2.95 (brs, 1.5H), 2.59-2.53 (m, 3H), 1.87 (brs, 1H), 1.82-1.60 (m, 5H), 1.57-1.52 (brs, 1H), 1.20 (brs, 4H), 1.13

(brs, 1H), 0.95 (brs, 1H). LC-MS (M+H)⁺=516.2. RetTime in chiral-HPLC: 6.206 min, Method F Example 65

(3-((S)-1-(8-amino-1-methylimidazo[1,5-a]pyrazin-3-yl)ethyl)-5-chloro-6-fluoro-2-isopropoxyphenyl)((S)-3-methoxypiperidin-1-yl)methanone (Compound 65)

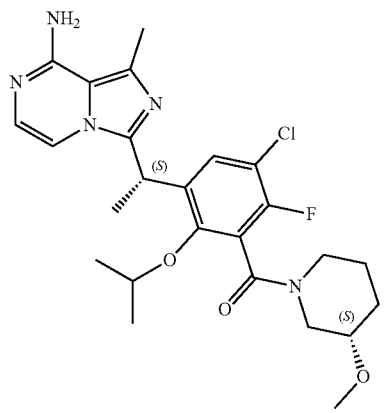

This compound (70 mg, 55%) was prepared from compound 15-13 and (S)-3-methoxypiperidine in a similar manner to compound 15-14 in Example 15. ¹H NMR (400 MHz, DMSO-d6) δ 7.51-7.22 (m, 2H), 7.00 (brs, 2H), 6.92-6.79 (m, 1H), 4.87-4.72 (m, 1H), 4.57-4.46 (m, 0.3H), 4.46-4.34 (m, 0.6H), 4.30-4.21 (m, 0.2H), 4.14 (d, J=13.2 Hz, 0.3H), 4.06-3.94 (m, 0.5H), 3.60 (brs, 0.3H), 3.52-3.40 (m, 0.7 H), 3.31 (s, 1.5H), 3.27 (s, 1H), 3.24-3.10 (m, 1H), 3.08-2.88 (m, 2.5H), 2.58 (brs, 3H), 2.02-1.78 (m, 1H), 1.77-1.60 (m, 3H), 1.60-1.52 (m, 1.5H), 1.51-1.29 (m, 1.5H), 1.29-1.12 (m, 4.8H), 0.97 (d, J=5.9 Hz, 0.8H), 0.88 (d, J=5.8 Hz, 0.4H), LC-MS (M+H)⁺=516.2. RetTime in chiral-HPLC: 6.817 min, Method G.

Example 66

(S)-3(1-(8-amino-1-methylimidazo[1,5-a]pyrazin-3-yl)ethyl)-5-chloro-6-fluoro-N-((1-hydroxycyclopropyl)methyl)-2-isopropoxybenzamide (Compound 66)

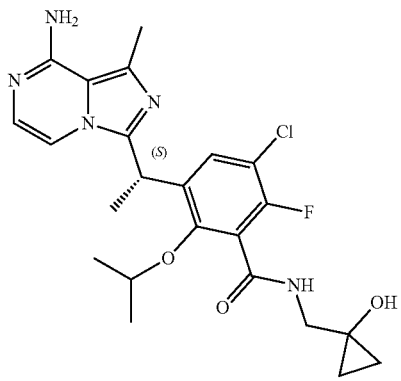

This compound (50 mg, 42%) was prepared from compound 15-13 and 1-(aminomethyl)cyclopropan-1-ol in a similar manner to compound 15-14 in Example 15. ¹H NMR (400 MHz, DMSO-d6) δ 8.74 (t, J=5.7 Hz, 1H), 7.42 (d, J=8.5 Hz, 1H), 7.35 (d, J=5.3 Hz, 1H), 7.08 (brs 2H), 6.89 (d, J=5.2 Hz, 1H), 5.28 (s, 1H), 4.80 (q, J=7.0 Hz, 1H), 4.60-4.51 (m, 1H), 3.39 (d, J=5.9 Hz, 2H), 2.58 (s, 3H), 1.58 (d, J=7.0 Hz, 3H), 1.18 (d, J=6.0 Hz, 3H), 1.08 (d, J=6.0 Hz, 3H), 0.54 (brs, 4H). LC-MS (M+H)⁺=476.1. RetTime in chiral-HPLC: 3.187 min, Method F.

Example 67

(3-((S)-1-(8-amino-1-methylimidazo[1,5-a]pyrazin-3-yl)ethyl)-5-chloro-6-fluoro-2-isopropoxyphenyl)((2R,6S)-2,6-dimethylmorpholino)methanone (Compound 67)

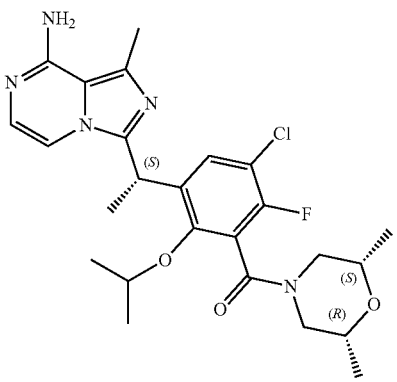

This compound (40 mg, 31%) was prepared from compound 15-13 and (2R,6S)-2,6-dimethylmorpholine in a similar manner to compound 15-14 in Example 15. ¹H NMR (400 MHz, DMSO-d6) δ 7.51-7.41 (m, 0.6H), 7.36-7.28 (m, 0.6H), 7.26 (d, J=5.2 Hz, 0.4H), 7.22 (d, J=5.1 Hz, 0.4H), 6.87 (d, J=5.1 Hz, 0.3H), 6.84-6.80 (m, 0.7H), 6.64 (brs, 2H), 4.82-4.72 (m, 1H), 4.53-4.33 (m, 1.5H), 4.32-4.22 (m, 0.4H), 4.15-4.07 (m, 0.2H), 3.52 (brs, 1.9H), 3.02 (d, J=12.0 Hz, 0.5H), 2.90-2.72 (m, 1H), 2.70-2.64 (m, 0.5H), 2.60-2.56 (m, 3H), 2.49-2.43 (m, 1H), 1.68 (t, J=6.9 Hz, 2.2H), 1.59-1.54 (m, 0.8H), 1.29 (d, J=6.0 Hz, 1H), 1.27-1.21 (m, 4H), 1.18-1.12 (m, 3H), 1.08-1.00 (m, 1H), 0.97-0.85 (m, 3H). LC-MS (M+H)⁺=503.8. RetTime in chiral-HPLC: 2.602 min, Method F.

Example 68

(S)-(3-(1-(8-amino-1-methylimidazo[1,5-a]pyrazin-3-yl)ethyl)-5-chloro-6-fluoro-2-isopropoxyphenyl)(6-oxa-2-azaspiro[3.4]octan-2-yl)methanone (Compound 68)

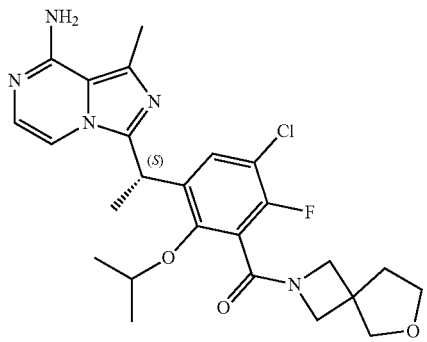

This compound (40 mg, 31%) was prepared from compound 15-13 and 6-oxa-2-azaspiro[3.4]octane oxalate in a similar manner to compound 15-14 in Example 15. $^1$H NMR (400 MHz, DMSO-d6) δ 7.41 (d, J=8.4 Hz, 1H), 7.30-7.26 (m, 1H), 6.83 (brs, 1H), 6.69 (brs, 2H), 4.82-4.74 (m, 1H), 4.35 (brs, 1H), 4.04 (brs, 2H), 3.87-3.61 (m, 6H), 2.57 (s, 3H), 2.22-2.00 (m, 2H), 1.65 (brs, 3H), 1.23 (d, J=10.2 Hz, 6H). LC-MS (M+H)$^+$=501.8. RetTime in chiral-HPLC: 11.092 min, Method A.

Example 69

(3-((S)-1-(8-amino-1-methylimidazo[1,5-a]pyrazin-3-yl)ethyl)-5-chloro-6-fluoro-2-isopropoxyphenyl)((R)-3-methoxypiperidin-1-yl)methanone (Compound 69)

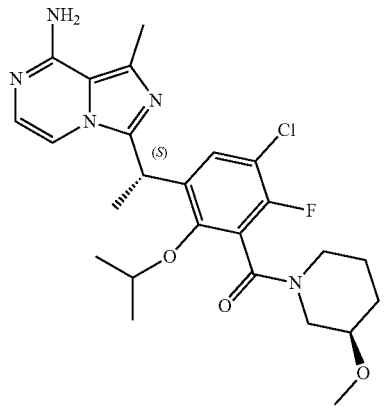

This compound (70 mg, 55%) was prepared from compound 15-13 and (R)-3-methoxypiperidine in a similar manner to compound 15-14 in Example 15. $^1$H NMR (400 MHz, DMSO-d6) δ 7.48-7.27 (m, 2H), 7.07 (brs, 2H), 6.92-6.80 (m, 1H), 4.86-4.72 (m, 1H), 4.58-4.48 (m, 0.5H), 4.45-4.30 (m, 0.5H), 4.30-4.12 (m, 0.5H), 3.82-3.37 (m, 2H), 3.29 (brs, 2H), 3.23-3.10 (m, 1.5H), 3.10-2.88 (m, 1.5H), 2.83 (brs, 0.5H), 2.60-2.56 (m, 3H), 1.89 (brs, 1H), 1.79-1.62 (m, 4H), 1.63-1.53 (m, 1H), 1.32-1.14 (m, 6H), 1.06-1.02 (m, 0.4H), 0.99-0.92 (m, 0.6H). LC-MS (M+H)$^+$=501.8. RetTime in chiral-HPLC: 5.630 min, Method A.

Example 70

(3-((S)-1-(8-amino-1-methylimidazo[1,5-a]pyrazin-3-yl)ethyl)-5-chloro-6-fluoro-2-isopropoxyphenyl)((S)-3-methoxypyrrolidin-1-yl)methanone (Compound 70)

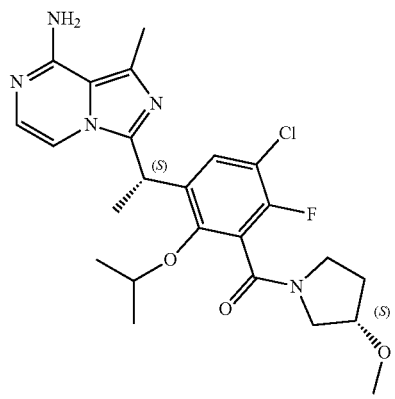

This compound (70 mg, 57%) was prepared from compound 15-13 and (S)-3-methoxypyrrolidine in a similar manner to compound 15-14 in Example 15. $^1$H NMR (400 MHz, DMSO-d6) δ 7.50-7.24 (m, 2H), 7.19-6.74 (m, 3H), 4.85-4.75 (m, 1H), 4.47-4.33 (m, 0.6H), 4.33-4.20 (m, 0.4H), 4.09-3.92 (m, 0.6H), 3.88 (brs, 0.4H), 3.68-3.37 (m, 2H), 3.27-2.91 (m, 5H), 2.65-2.54 (m, 3H), 1.97 (brs, 2H), 1.65 (brs, 2H), 1.54 (brs, 1H), 1.26-1.14 (m, 5H), 0.9-0.84 (m, 1H). LC-MS (M+H)$^+$=501.8. RetTime in chiral-HPLC: 3.679 min, Method F.

Example 71

3-((S)-1-(8-amino-1-methylimidazo[1,5-a]pyrazin-3-yl)ethyl)-5-chloro-6-fluoro-N-((1S,3S)-3-hydroxycyclopentyl)-2-isopropoxybenzamide (Compound 71)

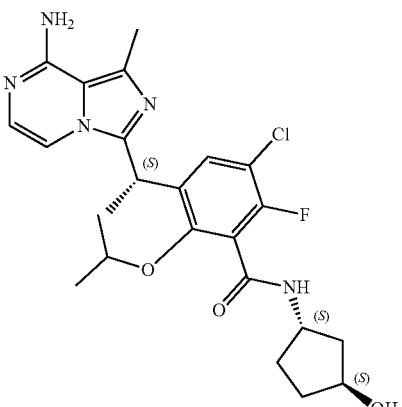

This compound (49 mg, 40%) was prepared from compound 15-13 and (1S,3S)-3-aminocyclopentan-1-ol in a similar manner to compound 15-14 in Example 15. $^1$H NMR (400 MHz, DMSO-d6) δ 8.67 (d, J=7.6 Hz, 1H), 7.45 (d, J=8.6 Hz, 1H), 7.41-7.24 (m, 3H), 6.92 (d, J=5.3 Hz, 1H), 4.81 (q, J=7.0 Hz, 1H), 4.57-4.51 (m, 1H), 4.50-4.40 (m, 1H), 4.40-4.30 (m, 1H), 4.17 (brs, 1H), 2.58 (s, 3H), 2.09-1.97 (m, 1H), 1.91-1.78 (m, 2H), 1.63-1.54 (m, 4H), 1.50-1.34 (m, 2H), 1.18 (d, J=6.0 Hz, 3H), 1.06 (d, J=6.0 Hz, 3H). LC-MS (M+H)$^+$=489.8. RetTime in chiral-HPLC: 6.423 min, Method A.

Example 72

3-((S)-1-(8-amino-1-methylimidazo[1,5-a]pyrazin-3-yl)ethyl)-5-chloro-6-fluoro-N-((2R,3R)-3-hydroxybutan-2-yl)-2-isopropoxybenzamide (Compound 72)

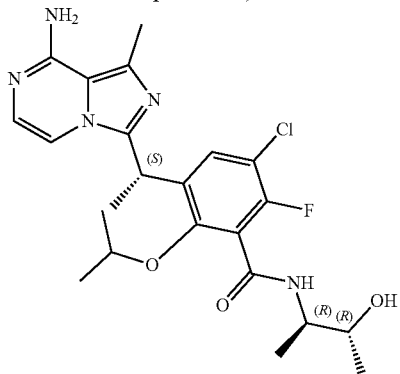

This compound (80 mg, 66%) was prepared from compound 15-13 and (2R,3R)-3-aminobutan-2-ol in a similar manner to compound 15-14 in Example 15. $^1$H NMR (400 MHz, DMSO-d6) δ 8.42 (d, J=8.2 Hz, 1H), 7.40 (d, 8.6 Hz, 1H), 7.31 (d, J=5.1 Hz, 1H), 6.88 (d, J=5.1 Hz, 1H), 6.79 (brs, 2H), 4.79 (q, J=6.7 Hz, 1H), 4.61 (d, J=5.0 Hz, 1H), 4.56-4.46 (m, 1H), 3.97-3.88 (m, 1H), 3.73-3.64 (m, 1H), 2.57 (s, 3H), 1.57 (d, J=7.1 Hz, 3H), 1.17 (d, J=6.0 Hz, 3H), 1.08-1.03 (m, 6H), 1.02 (d, J=6.3 Hz, 3H). LC-MS (M+H)$^+$=477.8. RetTime in chiral-HPLC: 3.655 min, Method C.

Example 73

(S)-3-(1-(8-amino-1-methylimidazo[1,5-a]pyrazin-3-yl)ethyl)-5-chloro-6-fluoro-2-isopropoxy-N-(2-(4-methylpiperazin-1-yl)ethyl)benzamide (Compound 73)

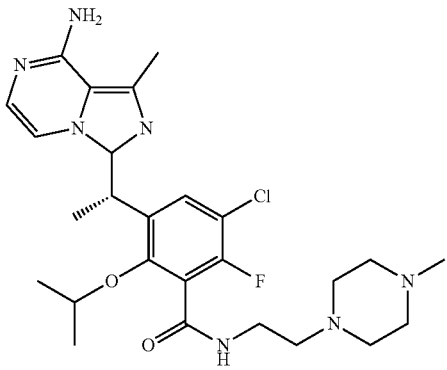 [SMILES: CC1=C2C(N)=NC=CN2C([C@@H](C)c2cc(Cl)c(F)c(C(=O)NCCN3CCN(C)CC3)c2OC(C)C)N1]

This compound (93 mg, 72.1%) was prepared from compound 15-13 and 2-(4-methylpiperazin-1-yl)ethan-1-amine in a similar manner to compound 15-14 in Example 15. 1H NMR (400 MHz, DMSO-d6) δ 8.64-8.61 (t, 1H), 7.39-7.37 (d, J=8.8 Hz, 1H), 7.25-7.24 (d, J=5.2 Hz, 1H), 6.86-6.85 (d, J=4.8 Hz, 1H), 6.43 (brs, 2H), 4.80-4.74 (m, 1H), 4.52-4.46 (m, 1H), 3.41-3.28 (m, 4H), 2.56 (s, 3H), 2.43-2.18 (m, 8H), 2.14 (s, 3H), 1.59-1.57 (d, J=6.8 Hz, 3H), 1.19-1.18 (d, J=5.6 Hz, 3H), 1.10-1.08 (d, J=5.6 Hz, 3H). LC-MS (M+H)$^+$=532.1. HPLC: 214 nm, 96.79%; 254 nm, 100 RetTime in chiral-HPLC: 3.67 min, Method B.

The following compounds were prepared in a similar manner:

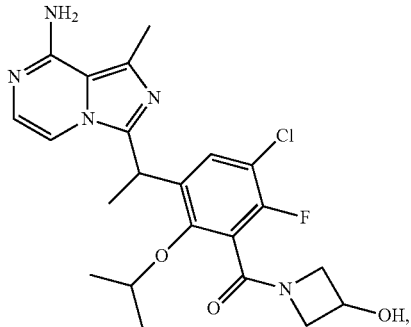

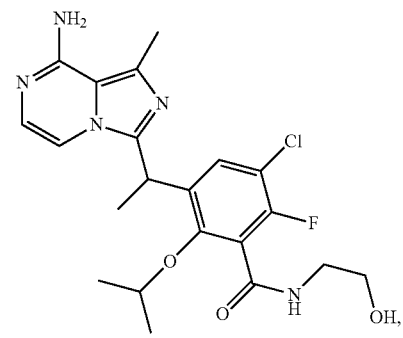

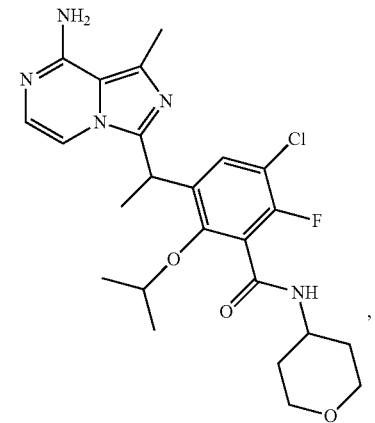

-continued
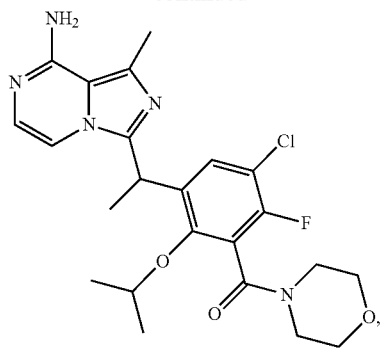
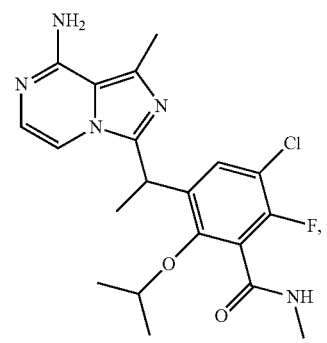
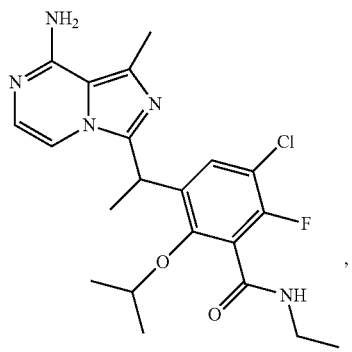
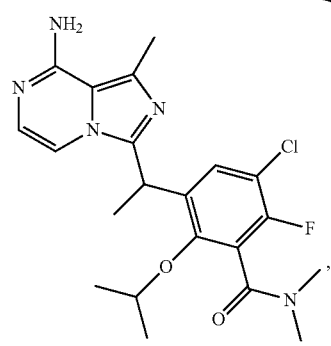
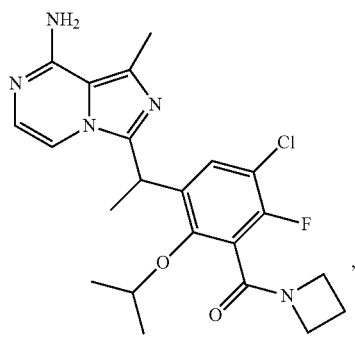
-continued
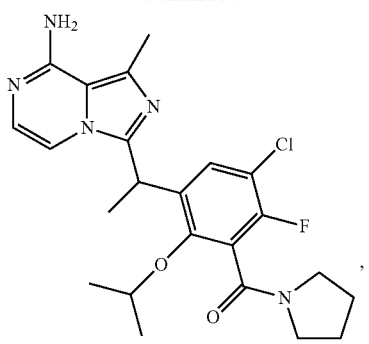
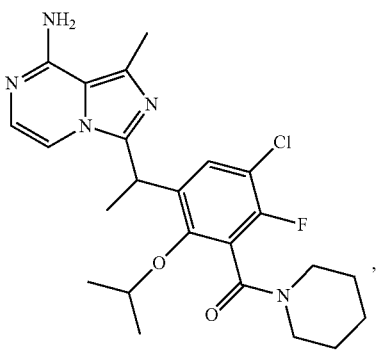
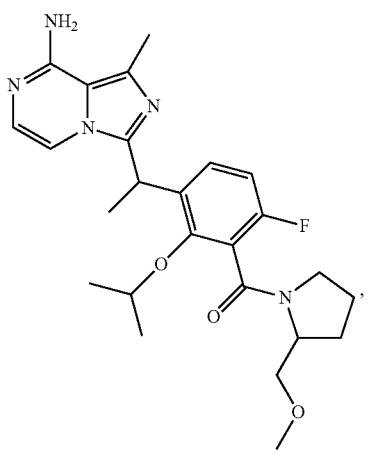
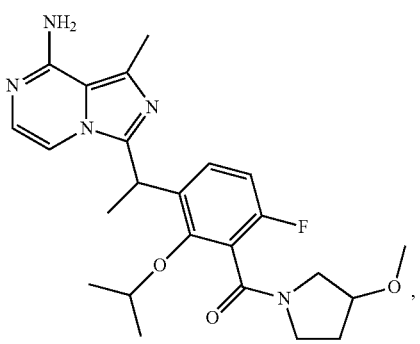

-continued
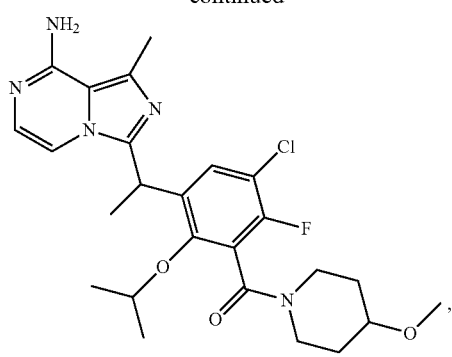
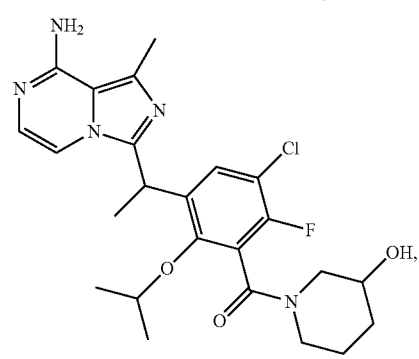
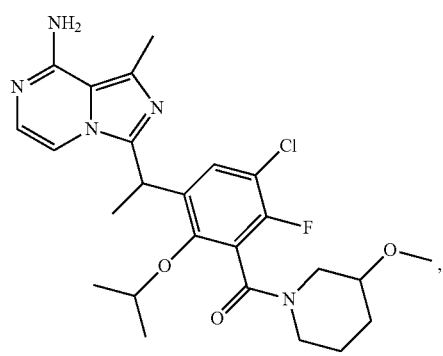
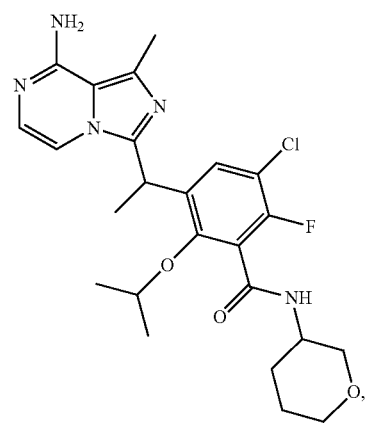
-continued
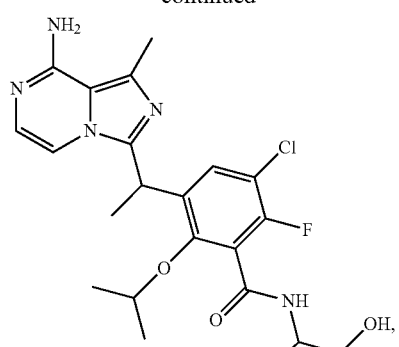
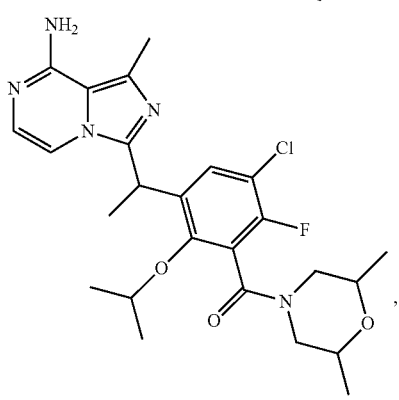
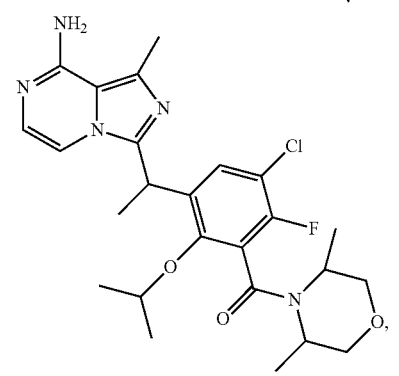
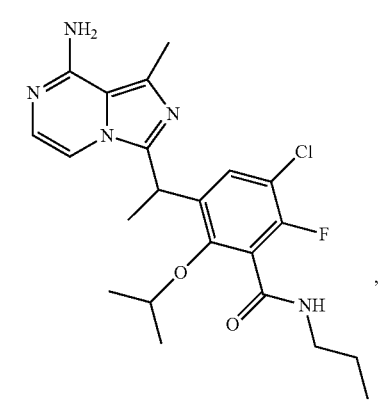

147
-continued
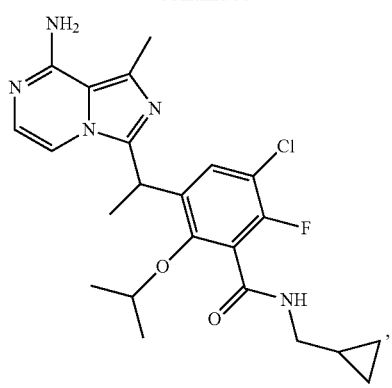
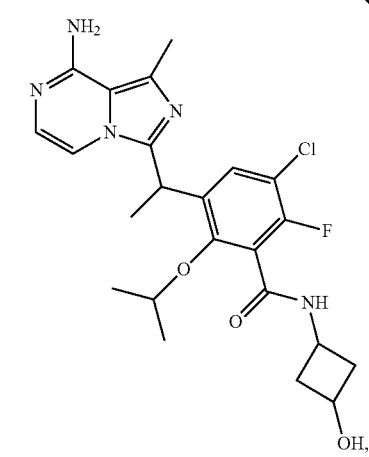
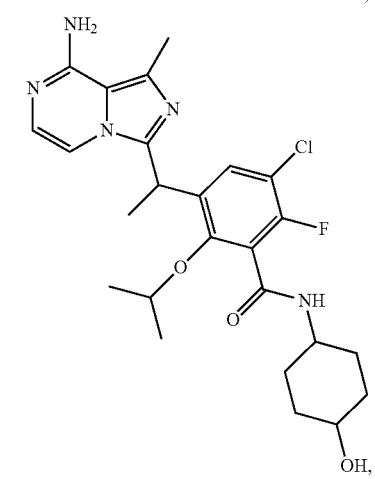
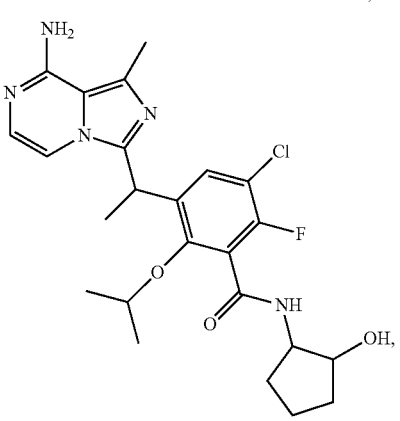
148
-continued
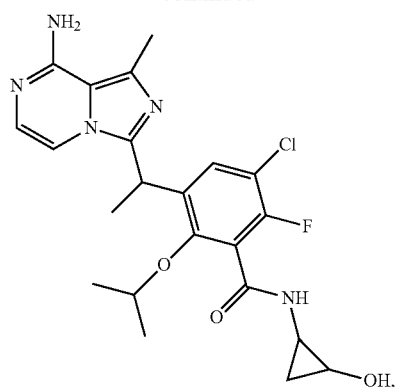
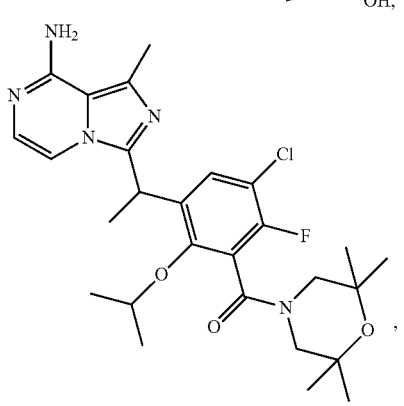
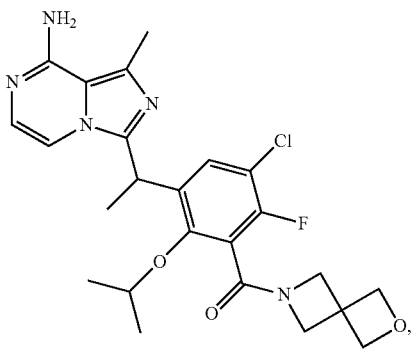
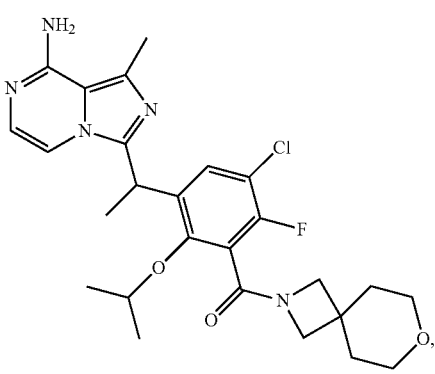

149
-continued
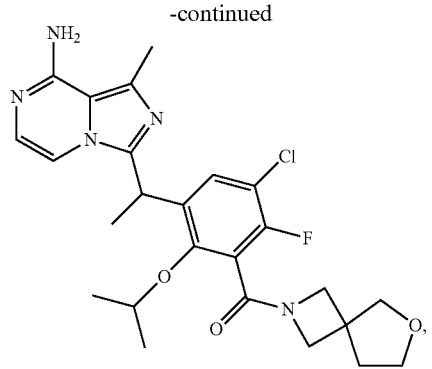
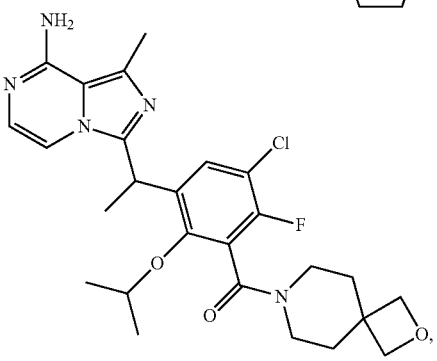
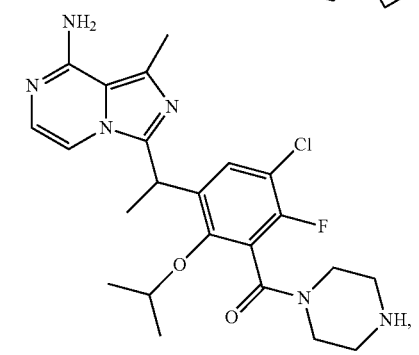
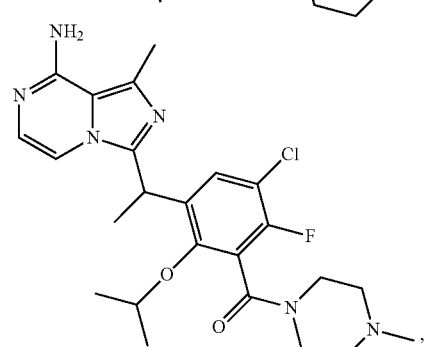
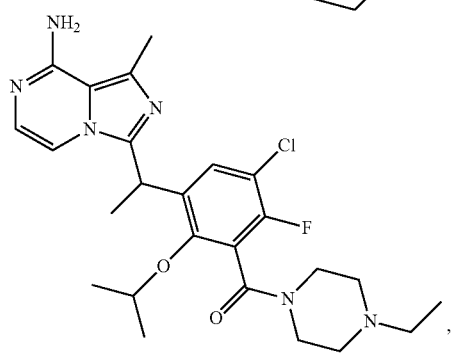
150
-continued
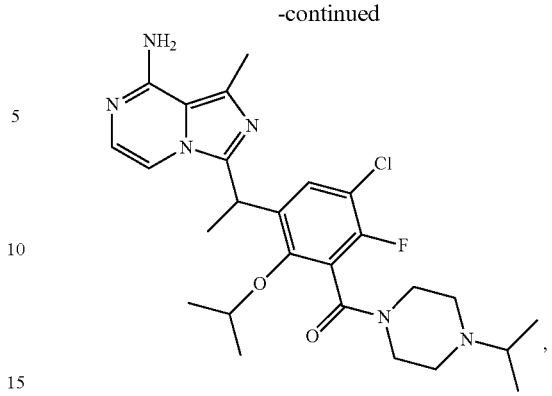
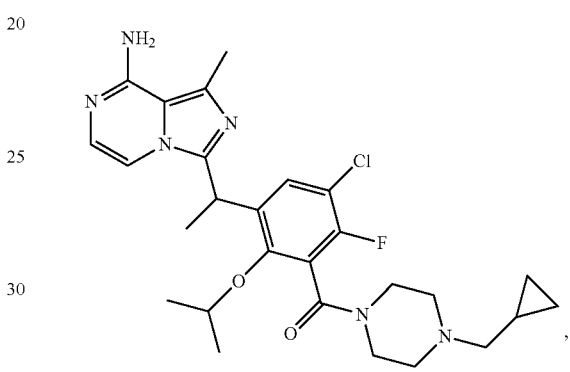
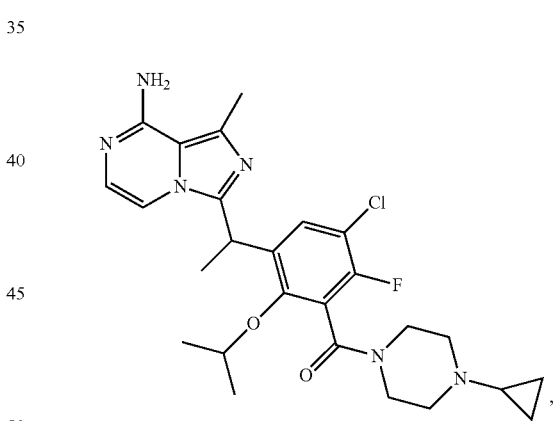
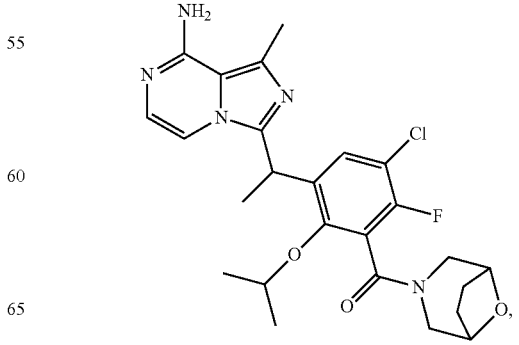

151
-continued
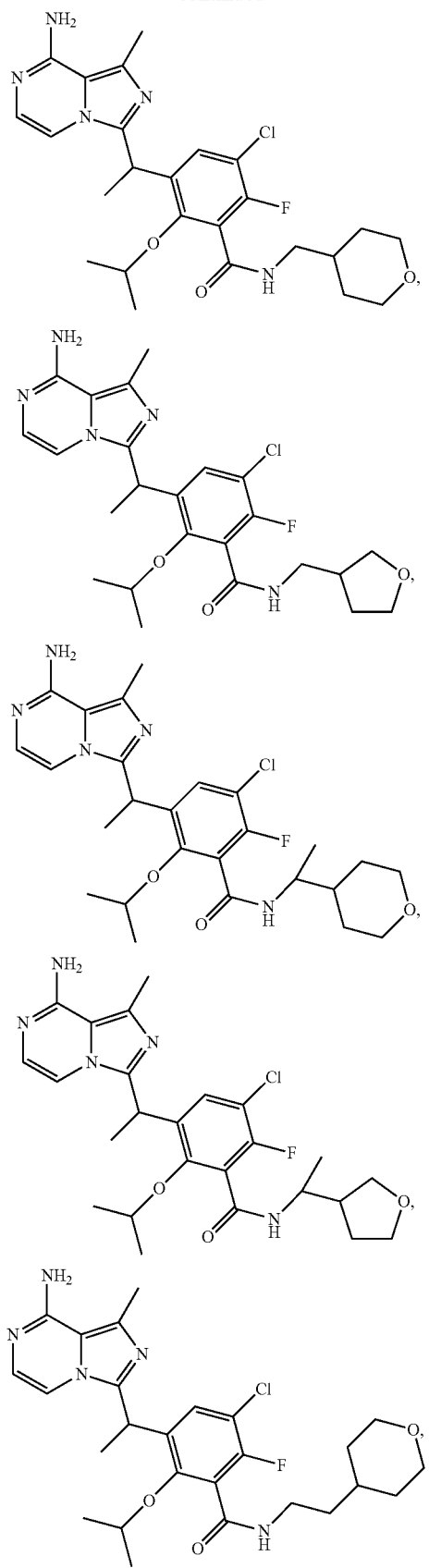
152
-continued
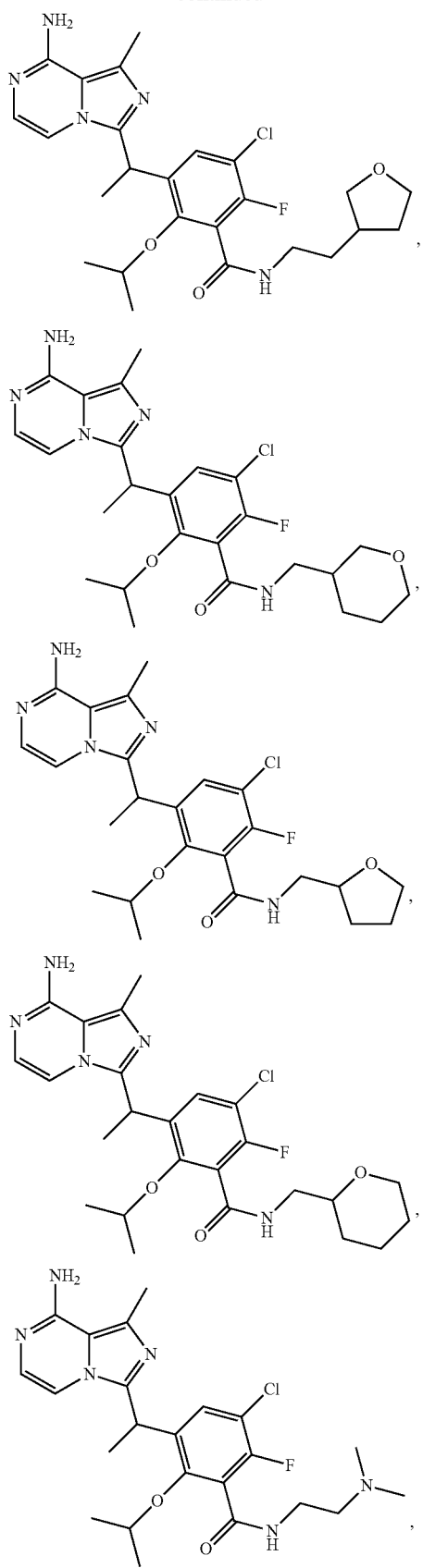

153
-continued
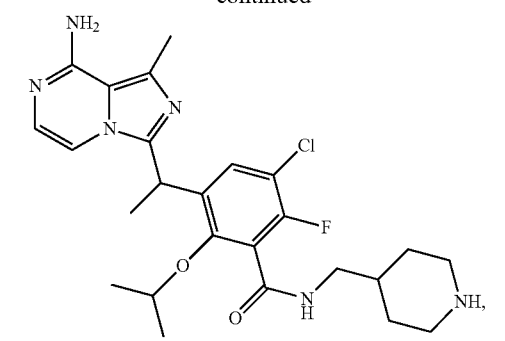
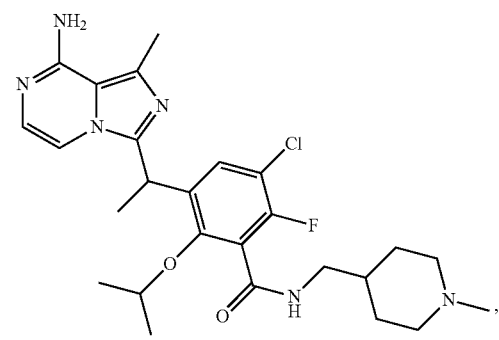
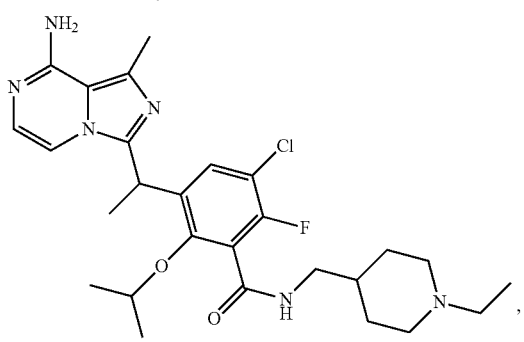
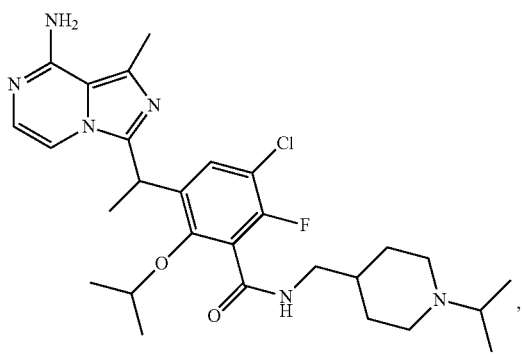
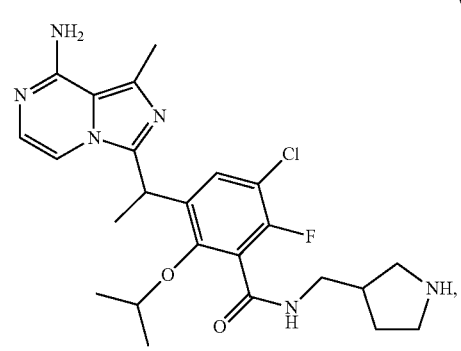
154
-continued
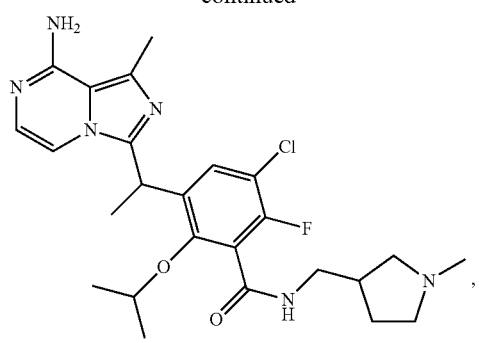
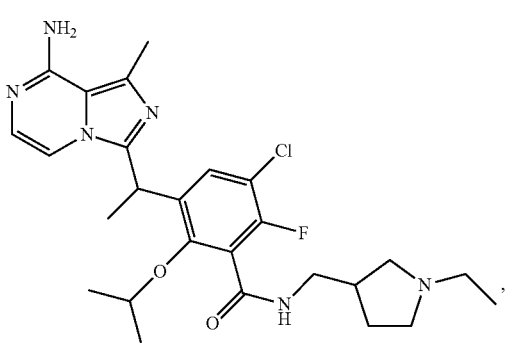
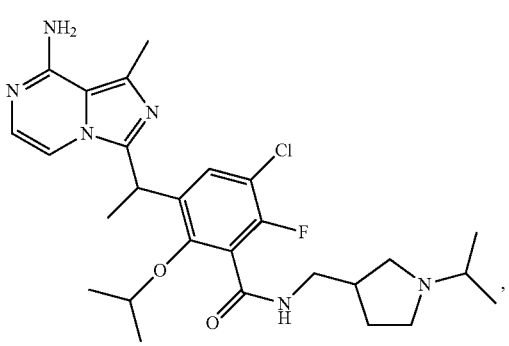
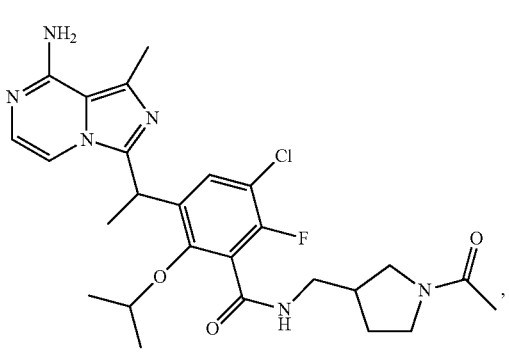

155
-continued
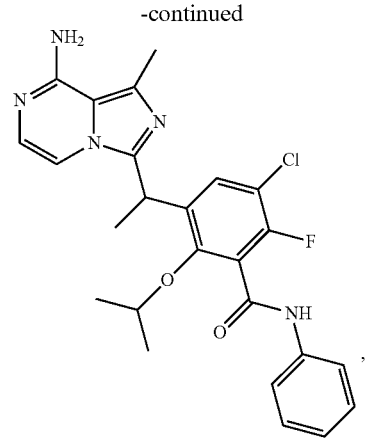
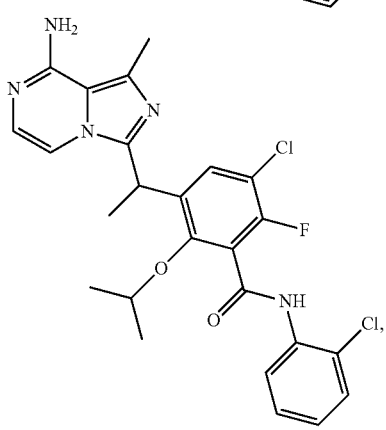
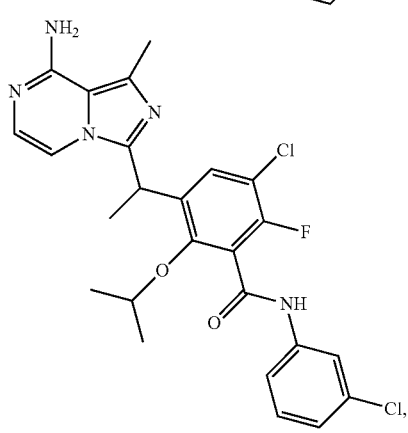
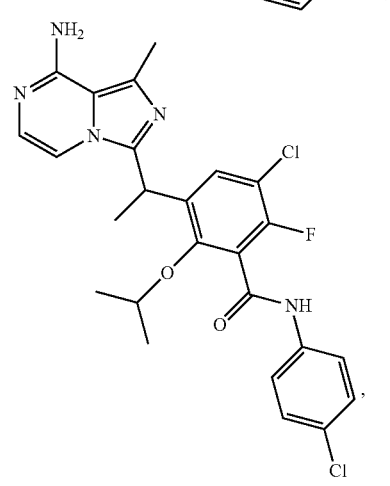
156
-continued
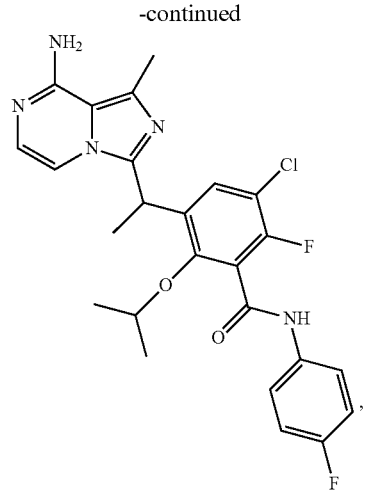
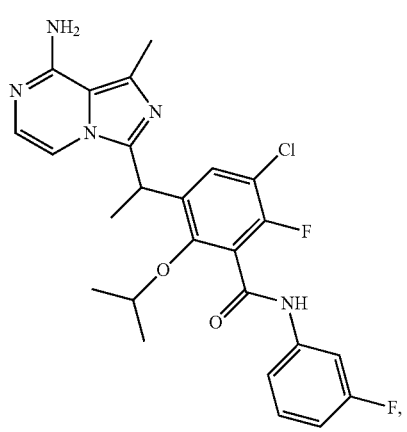
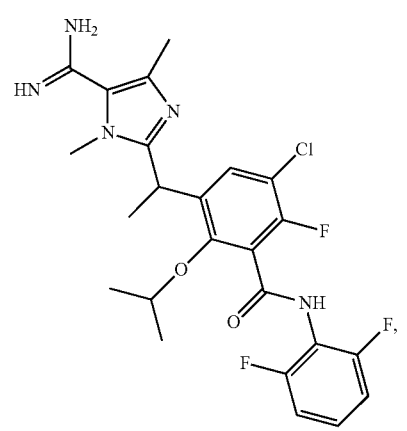

157
-continued
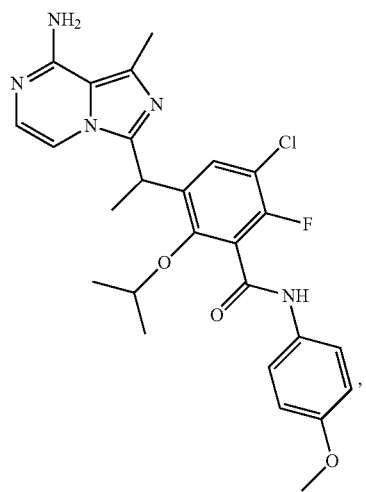
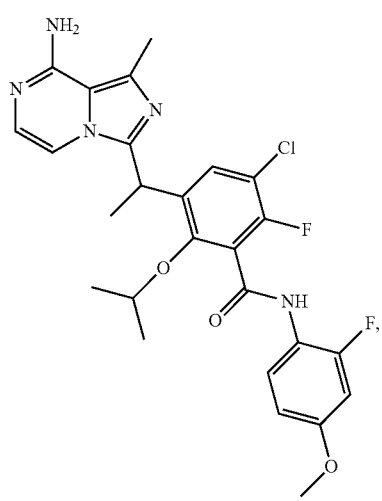
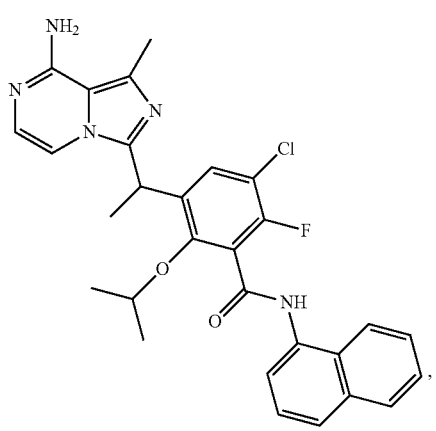
158
-continued
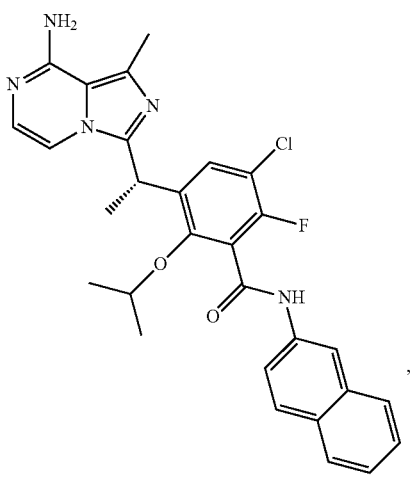
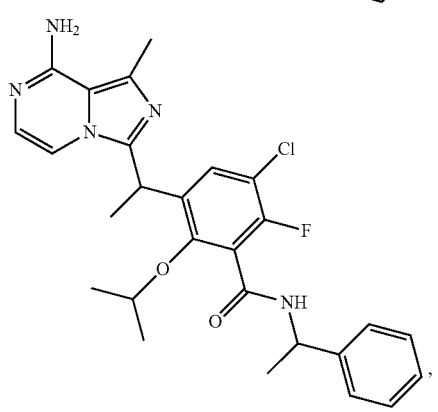
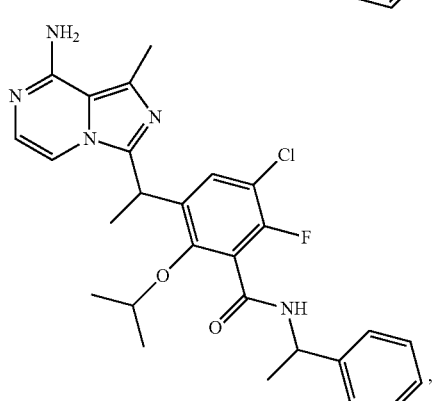
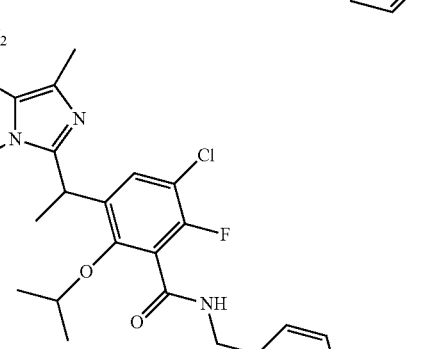

159
-continued
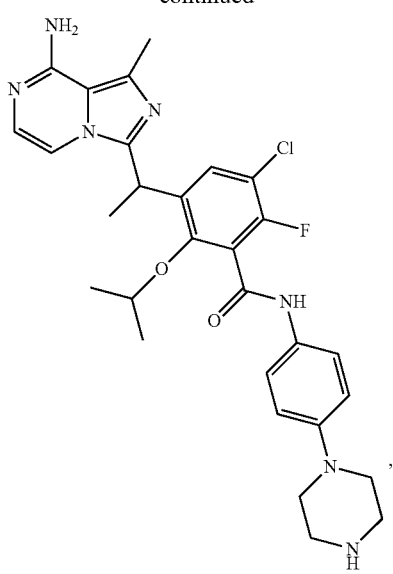
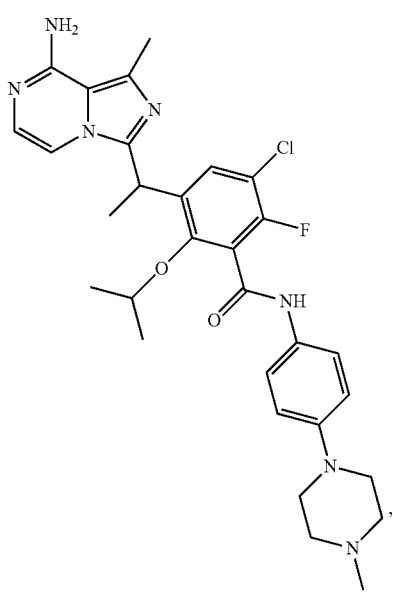
160
-continued
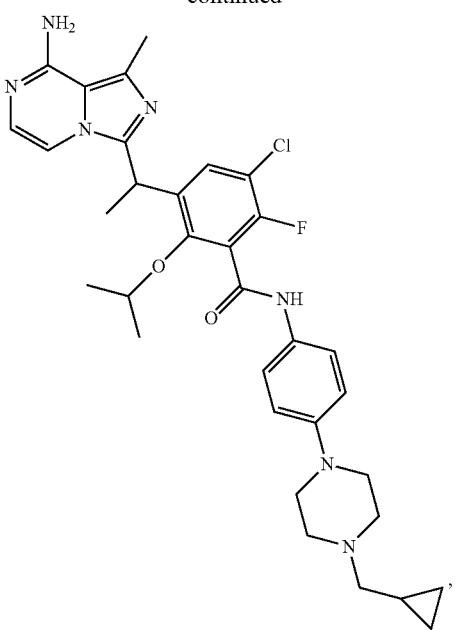
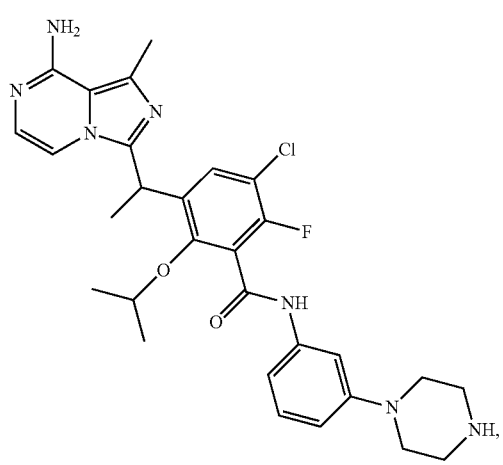
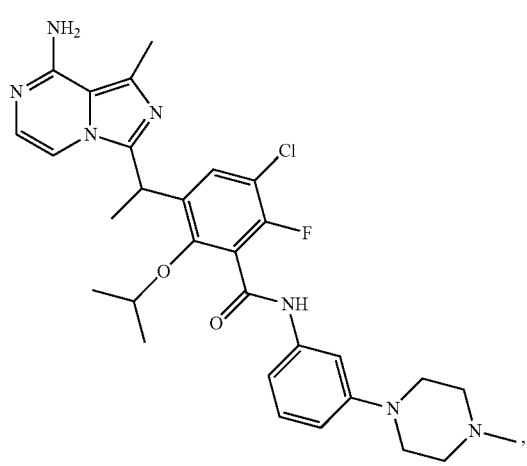

-continued

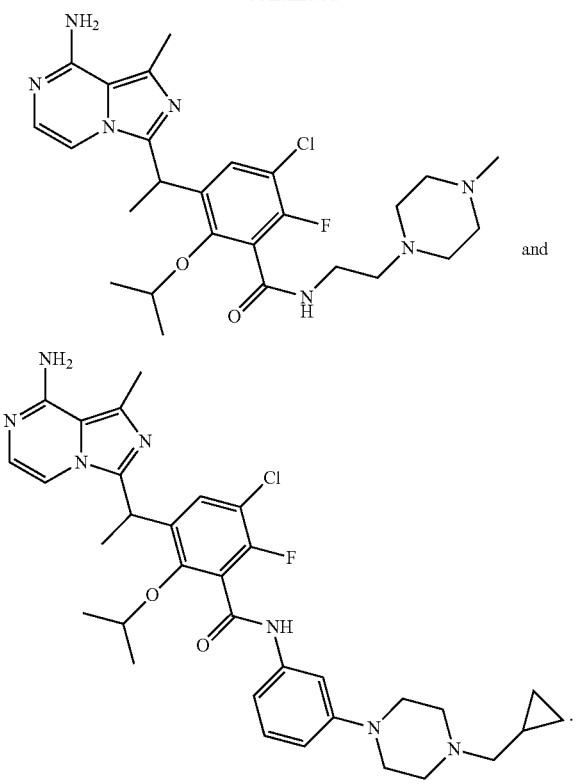

and

Biological Assays

I. PI3Kδ Assay

Compounds disclosed herein were tested for inhibition of PI3Kδ kinase activity using commercial ADP-Glo™ Kinase Assay (Promega Corporation) and following the manufacture's instruction. Briefly, recombinant PI3K (p110δ/p85α) enzyme, lipid kinase substrate and a serial dilution of compounds disclosed herein were incubated for 0.5 hr at room temperature. ATP was added to initiate the kinase reaction. After incubation for 1 hr at room temperature, ADP-Glo™ reagent was added to terminate the kinase reaction and deplete the remaining ATP. After incubation for 1 hr at room temperature, kinase detection reagent was added to simultaneously convert ADP to ATP and allow the newly synthesized ATP to be measured using a luciferase/luciferin reaction. After incubation for 0.5 hr at room temperature, the luminescence generated was measured on a PHERAstar FS plate reader (BMG LABTECH). The residual enzyme activity in presence of increasing concentrations of compounds was calculated based on the luminescence. The $IC_{50}$ for each compound was derived from fitting the data to the four-parameter logistic equation by Graphpad Prism software. $IC_{50}$ of examples is presented in Table 1 as determined by the PI3K delta assay.

II. PI3Kα, β and γ Assays

Compounds disclosed herein were tested for inhibition of recombinant PI3K (p110α/p85α), PI3K (p110β/p85α) and PI3K (p110γ) using the same method as PI3K(p110δ/p85α) except that incubation of 2 hrs was applied to PI3K (p110β/p85α) kinase reaction. Selectivity of examples is presented in Table 1 as determined by PI3K alpha, beta and gamma assays.

TABLE 1

Enzyme Activity $IC_{50}$ or max inhibition (%) at 0.5 μM for the compounds disclosed herein

| Compound | Enzyme activity $IC_{50}$ (nM) or max inhibition (%) at 0.5 μM | | | |
|---|---|---|---|---|
| | PI3Kα | PI3Kβ | PI3Kδ | PI3Kγ |
| 1 | >50000 | >50000 | 9.7 | 9800 |
| 2 | >50000 | >50000 | 14 | 5500 |
| 3 | 49000 | 34000 | 6.3 | 19000 |
| 4 | 25000 | 24000 | 1.9 | 3100 |
| 4A | 13000 | 11000 | 1.0 | 2000 |
| 4B | — | — | >1000 | — |
| 5 | 56000 | 16000 | 3.3 | 10000 |
| 5A | 21000 | 20000 | 1.5 | 6300 |
| 5B | — | — | 93 | — |
| 6 | >50000 | >50000 | 2.9 | 17000 |
| 7 | >50000 | >50000 | 6.0 | 17000 |
| 8 | 49000 | 16000 | 2.3 | 6800 |
| 9 | 43000 | 18000 | 2.9 | 9200 |
| 10 | 34000 | 22000 | 3.0 | 9000 |
| 11 | 31000 | 6200 | 2.0 | 7300 |
| 12 | >50000 | >50000 | 3.7 | 14000 |
| 13A | 20000 | >50000 | 3.0 | 9300 |
| 13B | — | — | >1000 | — |
| 14A | 18000 | 13000 | 1.4 | 7900 |
| 14B | — | — | 320 | — |
| 15 | 36000 | >50000 | 1.8 | 6700 |
| 16 | 20000 | 17000 | 4.0 | 11000 |
| 17 | 77000 | 72000 | 3.8 | 14000 |
| 18 | 19000 | 12000 | 2.4 | 6500 |
| 19 | 33000 | 60000 | 2.0 | 10000 |
| 20 | — | — | 2.1 | — |
| 21 | 33000 | 28000 | 1.4 | 3900 |
| 22 | — | — | 3.7 | — |
| 23 | — | — | 9.9 | — |
| 24 | 36000 | 16000 | 1.6 | 5800 |
| 25 | 24000 | 8700 | 1.9 | 6000 |
| 26 | 24000 | 17000 | 0.86 | 6500 |
| 27 | 32000 | 3000 | 0.93 | 3900 |
| 28 | 24000 | 6800 | 1.2 | 4800 |
| 29 | 11000 | 9900 | 1.1 | 2100 |
| 30 | 17000 | 14000 | 0.97 | 7700 |
| 31 | 25000 | 16000 | 3.1 | 6200 |
| 32 | — | — | 3.2 | — |
| 33 | 9300 | 13000 | 1.3 | 2200 |
| 34 | 36000 | 11000 | 1.4 | 3200 |
| 35 | 46000 | 19000 | 1.3 | 6000 |
| 36 | 9500 | 13000 | 2.0 | 460 |
| 37 | 11000 | 11000 | 0.56 | 2500 |
| 38 | 6100 | 25000 | 1.4 | 3200 |
| 39 | 10000 | 2300 | 0.90 | 28000 |
| 40 | — | — | 6.5 | — |
| 41 | 20000 | 4900 | 0.99 | 5500 |
| 42 | 36000 | 21000 | 1.2 | 4800 |
| 43 | 21000 | >50000 | 2.2 | 3400 |
| 44 | 20000 | 30000 | 0.74 | 5000 |
| 45 | 16000 | 32000 | 1.1 | 2800 |
| 46 | 9700 | 39000 | 0.94 | 2100 |
| 47 | 27000 | 26000 | 2.5 | 5800 |
| 48 | — | — | 9.1 | — |
| 49 | — | — | 3.9 | — |
| 50 | 15000 | 20000 | 1.2 | 6100 |
| 51 | 27000 | 6400 | 0.97 | 4500 |
| 52 | 10000 | 40000 | 1.4 | 2500 |
| 53 | 14000 | 11000 | 0.68 | 2400 |
| 54 | — | — | 11 | — |
| 55 | 13000 | 11000 | 1.8 | 2200 |
| 56 | 28000 | 44000 | 1.9 | 4500 |
| 57 | 18000 | 12000 | 1.1 | 4900 |
| 58 | 14000 | 16000 | 2.2 | 2800 |
| 59A | 8300 | 14000 | 2.1 | 1200 |
| 59B | 14000 | 26000 | 1.5 | 2800 |
| 60 | 11000 | 35000 | 0.95 | 6300 |
| 61 | 21000 | 12000 | 1.4 | 4500 |
| 62 | 17000 | 29000 | 1.4 | 9000 |
| 63 | 38000 | 7400 | 1.1 | 4200 |
| 64 | >50000 | >50000 | 1.6 | 14000 |
| 65 | 50000 | >50000 | 2.9 | 6900 |

TABLE 1-continued

Enzyme Activity IC$_{50}$ or max inhibition (%) at 0.5 µM for the compounds disclosed herein

| Compound | Enzyme activity IC$_{50}$ (nM) or max inhibition (%) at 0.5 µM | | | |
|---|---|---|---|---|
| | PI3Kα | PI3Kβ | PI3Kδ | PI3Kγ |
| 66 | 14000 | 12000 | 2.2 | 3400 |
| 67 | — | — | 8.0 | — |
| 68 | 40000 | 23000 | 1.7 | 4600 |
| 69 | >50000 | >50000 | 2.0 | 5200 |
| 70 | 41000 | >50000 | 1.9 | 6700 |
| 71 | 14000 | 13000 | 1.4 | 3400 |

TABLE 1-continued

Enzyme Activity IC$_{50}$ or max inhibition (%) at 0.5 µM for the compounds disclosed herein

| Compound | Enzyme activity IC$_{50}$ (nM) or max inhibition (%) at 0.5 µM | | | |
|---|---|---|---|---|
| | PI3Kα | PI3Kβ | PI3Kδ | PI3Kγ |
| 72 | — | — | 6.8 | — |
| 73 | 14000 | 14000 | 2.8 | 9500 |

The following assays were also used to determine the pharmacokinetic (PK) data and the blood-brain barrier (BBB) data of some exemplified compounds disclosed herein.

III. Pharmacokinetic Properties of Compounds in Sprague-Dawley Rats After Intravenous (IV) and Oral Administrations (PO)

Dose Formulation Preparation

The injection dosing solution was prepared as follows: 1.0 mg of a test compound was weighed and dissolved in 0.32 mL of dimethyl acetamide (DMA). The solution was then further diluted by 0.36 mL of ethanol and 0.32 mL of propylene glycol. The final concentration of the test compound was 1.0 mg·mL$^{-1}$.

The oral dosing solution was prepared as follows: 5.0 mg of a test compound was weighed and dispersed in 10 mL of 0.5% methyl cellulose (MC). The final concentration of the test compound is 1 mg·mL$^{-1}$.

Animals

Male Sprague-Dawley rats (also summarized in Table 2) were housed in solid bottom polypropylene cages with sterilized bedding and receive sterilized diet and sterilized water. The room was controlled and monitored for humidity (targeted mean range 40% to 70%) and temperature (targeted mean range 18° C. to 26° C.) with 10 to 20 air changes/hour. The light cycle was maintained at 12-h light and 12-h dark. Only animals that appeared to be healthy were selected for this study based on overall health, body weight, or other relevant information. The animals were treated in accordance with a certain treatment schedule as summarized in Table 3.

TABLE 2

Animal information

| Genus | Gender | Species | Source | Age | Weight (g) | Reserved | Selected |
|---|---|---|---|---|---|---|---|
| Rat | Male | Sprague Dawley (SD) | Vital River | 8 weeks | 220-250 | 7 | 6 |

TABLE 3

Animal Treatment Schedule

| Groups | Quantity | Dose Level (mg · kg$^{-1}$) | Conc. (mg · mL$^{-1}$) | Vehicle | Dosing Route | Regimen | Fasted/Fed | Sampling Time |
|---|---|---|---|---|---|---|---|---|
| 1-3 | 3 | 1.0 | 1.0 | 32% DMA, 36% ethanol, 32% propylene glycol | Tail Vein IV | Single | Fasted | Pre-dose, 5, 15, 30 min, 1, 2, 4, 8, 24 h |
| 4-6 | 3 | 5.0 or 10.0 | 1.0 | 0.5% MC | Oral | Single | Fasted | Pre-dose, 15, 30 min, 1, 2, 4, 8, 24 h |

Study Design

All procedures performed on animals were in accordance with established guidelines and reviewed and approved by an independent institutional review board.

The male Sprague-Dawley rats were fasted overnight with free access to drinking water prior to treatment. On day 1, the animals were weighed and actual dose volume for each animal was calculated using the formula below:

$$\text{Dose Volume (mL)} = [\text{Nominal Dose (mg·kg}^{-1})/\text{Dose Concentration (mg·mL}^{-1})] \times \text{Animal Body Weight (kg)} \quad (1)$$

Three rats were given a single IV dose of 1 mg·kg$^{-1}$ via tail vein injection and other three rats were given a single oral dose of 5 or 10 mg·kg$^{-1}$. The dosing solutions were freshly prepared prior to dose administration. The actual body weights and actual volume injected were recorded accordingly. Four hours after dosing, the rats were allowed to intake food.

Blood samples (~150 µL) were collected at different times from the jugular vein catheter into EDTA-K$_2$ coated tubes. Whole blood was processed by centrifugation at 3000 g for 10 min. Plasma samples were collected and kept at −80° C. freezer prior to analysis. The blood sampling time was recorded accordingly.

Sample Test

The dose samples of IV and PO were diluted with MeOH: H$_2$O (4:1, v/v) to achieve the concentration of 2 µg·mL$^{-1}$, respectively. Then, 2.5 µL of the diluted samples were added with 47.5 µL blank plasma, and then were handled as the plasma sample procedure. An aliquot of 10 µL of the mixture was injected into the LC-MS/MS system. The pharmacokinetic (PK) data of the test compounds were generated as shown in Table 4.

TABLE 4

Rat PK data of Compounds 60 and 73

| | IV (1 mpk) | | | | PO (5 mpk for compound 60 and 10 mpk for compound 73) | | | | |
|---|---|---|---|---|---|---|---|---|---|
| Compound | $t_{1/2}$ (h) | Cl (mL · $kg^{-1}$ · $min^{-1}$) | $AUC_{0-inf}$ (h · ng · $mL^{-1}$) | $V_{dSS}$ (L · $kg^{-1}$) | $t_{1/2}$ (h) | $t_{max}$ (h) | $C_{max}$ (ng · $mL^{-1}$) | $AUC_{0-inf}$ (h · ng · $mL^{-1}$) | F % |
| 60 | 0.6 | 76.6 | 218.4 | 3.3 | 2.0 | 0.3 | 132.8 | 159.1 | 14.6 |
| 73 | 8.2 | 86.6 | 193.7 | 59.4 | 5.6 | 1.5 | 220.3 | 918.1 | 34.9 |

IV. Brain Penetration of Compounds in Male C57BL/6 Mice After Oral Administration Dose Formulation Preparation Approximately 4 mg of a test compound was weighed and dispersed in 0.5% methyl cellulose (MC). After that, the whole mixture were vortexed until a solution or suspension was formed. The final concentration of the test compound was 1 mg·$mL^{-1}$. The concentration of test compound in dosing formulations was determined within 85% to 115% of nominal values.

Animals

Male C57BL/6 mice were housed in solid bottom polypropylene cages with sterilized bedding. The room was controlled and monitored for humidity (targeted mean range 40% to 70%) and temperature (targeted mean range 20° to 25° C.) with 10 to 20 air changes/hour. The room was on a 12-hour light/dark cycle except when interruptions were necessitated by study activities. The mice were supplied with sterilized diet and water. All animals were examined upon receipt and were acclimated for at least 3 days. Only animals that appeared to be healthy were selected for the study based on overall health, body weight, or other relevant data as appropriate.

Study Design

All procedures performed on animals were in accordance with established guidelines and reviewed and approved by an independent institutional review board. The animals were treated in accordance with a certain treatment schedule.

The male mice were fasted overnight with free access to drinking water prior to treatment. On day 1, the animals were weighed and actual dose volume for each animal was calculated using the formula below:

Dose Volume (mL) = [Nominal Dose (mg·$kg^{-1}$)/Dose Concentration (mg·$mL^{-1}$)] × Animal Body Weight (kg)   (1)

The mice were administrated with test compound at 10 mg·$kg^{-1}$ via oral gavage, respectively. The dosing formulations were freshly prepared. The actual body weights and actual volume administered were recorded accordingly.

Three mice were sacrificed under carbon dioxide for sample collection at 1, 2 and 4 hours post dose, respectively. Blood samples (~0.2 mL) were collected via cardiac puncture into anticoagulant tubes (coated with EDTA-Ka). The tubes were gently inverted several times to ensure mixing. Whole blood was processed for plasma by centrifugation at 5,500 rpm for 10 min. The brain was collected immediately after euthanasia. The sample collection time was recorded accordingly. After the removal of excess water, the brain was weighed and homogenized with 5× water (w/v) in an ice bath. The samples were kept below −20° C. freezer prior to analysis.

Sample Test

For plasma samples: An aliquot of 10 μL of sample was added with 500 μL ACN which contained IS (Verapamil, 5 ng·$mL^{-1}$ and Glibenclamide, 50 ng·$mL^{-1}$) for protein precipitation, the mixture was vortexed for 1 min, then centrifuged at 13000 rpm for 8 min, then 70 μL of supernatant was added with 70 μL water, then vortexed for 10 min. An aliquot of 10 μL of the mixture was injected into the LC-MS/MS system.

For brain samples: An aliquot of 50 μL of sample was added with 250 μL ACN which contained IS (Verapamil, 5 ng·$mL^{-1}$ and Glibenclamide, 50 ng·$mL^{-1}$) for protein precipitation, the mixture was vortexed for 1 min, then centrifuged at 13000 rpm for 8 min, then 70 μL of supernatant was added with 70 μL water, then vortexed for 10 min. An aliquot of 10 μL of the mixture was injected into the LC-MS/MS system. The blood-brain barrier (BBB) data of the test compounds were generated.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

The invention claimed is:

1. A method for treating a disorder or a disease in a subject, comprising administering to the subject a compound of Formula (I),

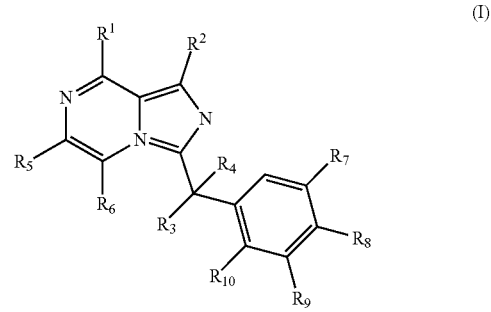

(I)

or a stereoisomer thereof, or a pharmaceutically acceptable salt thereof, wherein:

$R_1$ is —$NR_aR_b$, wherein $R_a$ and $R_b$ are each independently hydrogen or $C_{1-6}$alkyl;

$R_2$ is hydrogen, F, Cl, Br, —$C_{1-6}$alkyl, —$C_{2-6}$alkenyl, —$C_{2-6}$alkynyl, cycloalkyl, heterocyclyl, aryl, heteroaryl, —CN, —NO$_2$, —OR$_{12}$, —SO$_2$R$_{12}$, —COR$_{12}$, —CO$_2$R$_{12}$, —CONR$_{12}$R$_{13}$, —C(=NR$_{12}$)NR$_{13}$R$_{14}$, —NR$_{12}$R$_{13}$, —NR$_{12}$COR$_{13}$, —NR$_{12}$CONR$_{13}$R$_{14}$, —NR$_{12}$CO$_2$R$_{13}$, —NR$_{12}$SONR$_{13}$R$_{14}$, —NR$_{12}$SO$_2$NR$_{13}$R$_{14}$, or —NR$_{12}$SO$_2$R$_{13}$; wherein said —C$_{1-6}$alkyl, —C$_{2-6}$alkenyl, —C$_{2-6}$alkynyl, cycloalkyl, heterocyclyl, aryl or heteroaryl are each independently optionally substituted with at least one substituent R$_{11a}$;

R$_3$ and R$_4$, which may be the same or different, are each independently hydrogen, —C$_{1-6}$alkyl, cycloalkyl, heterocyclyl, aryl, or heteroaryl;

R$_5$ and R$_6$, which may be the same or different, are each independently hydrogen, halogen, —C$_{1-6}$alkyl, —C$_{2-6}$alkenyl, —C$_{2-6}$alkynyl, cycloalkyl, heterocyclyl, aryl, heteroaryl, —CN, —NO$_2$, —OR$_{12}$, —SO$_2$R$_{12}$, —COR$_{12}$, —CO$_2$R$_{12}$, —CONR$_{12}$R$_{13}$, —C(=NR$_{12}$)NR$_{13}$R$_{14}$, —NR$_{12}$R$_{13}$, —NR$_{12}$COR$_{13}$, —NR$_{12}$CONR$_{13}$R$_{14}$, —NR$_{12}$CO$_2$R$_{13}$, —NR$_{12}$SONR$_{13}$R$_{14}$, —NR$_{12}$SO$_2$NR$_{13}$R$_{14}$, or —NR$_{12}$SO$_2$R$_{13}$; wherein said —C$_{1-6}$alkyl, —C$_{2-6}$alkenyl, —C$_{2-6}$alkynyl, cycloalkyl, heterocyclyl, aryl or heteroaryl are each independently optionally substituted with at least one substituent R$_{11b}$;

R$_7$, R$_8$ and R$_{10}$, which may be the same or different, are each independently hydrogen, halogen, —C$_{1-6}$alkyl, —C$_{2-6}$alkenyl, —C$_{2-6}$alkynyl, cycloalkyl, heterocyclyl, aryl, heteroaryl, —CN, —NO$_2$, —OR$_{12}$, —SO$_2$R$_{12}$, —COR$_{12}$, —CO$_2$R$_{12}$, —CONR$_{12}$R$_{13}$, —C(=NR$_{12}$)NR$_{13}$R$_{14}$, —NR$_{12}$R$_{13}$, —NR$_{12}$COR$_{13}$, —NR$_{12}$CONR$_{13}$R$_{14}$, —NR$_{12}$CO$_2$R$_{13}$, —NR$_{12}$SONR$_{13}$R$_{14}$, —NR$_{12}$SO$_2$NR$_{13}$R$_{14}$, or —NR$_{12}$SO$_2$R$_{13}$; wherein said —C$_{1-6}$alkyl, —C$_{2-6}$alkenyl, —C$_{2-6}$alkynyl, cycloalkyl, heterocyclyl, aryl or heteroaryl are each independently optionally substituted with at least one substituent R$_{11c}$;

R$_9$ is —CN, —NO$_2$, —OR$_{12}$, —SO$_2$R$_{12}$, —SO$_2$NR$_{12}$R$_{13}$, —COR$_{12}$, —CO$_2$R$_{12}$, —CONR$_{12}$R$_{13}$, —C(=NR$_{12}$)NR$_{13}$R$_{14}$, —NR$_{12}$COR$_{13}$, —NR$_{12}$CONR$_{13}$R$_{14}$, —NR$_{12}$CO$_2$R$_{13}$, —NR$_{12}$SONR$_{13}$R$_{14}$, —NR$_{12}$SO$_2$NR$_{13}$R$_{14}$, or —NR$_{12}$SO$_2$R$_{13}$;

R$_{11a}$, R$_{11b}$, and R$_{11c}$, which may be the same or different, are each independently hydrogen, halogen, —C$_{1-6}$alkyl, —C$_{2-6}$alkenyl, —C$_{2-6}$alkynyl, haloC$_{1-6}$alkyl, haloC$_{2-6}$alkenyl, haloC$_{2-6}$alkynyl, cycloalkyl, heterocyclyl, aryl, heteroaryl, —CN, —NO$_2$, oxo, —OR$_{12}$, —SO$_2$R$_{12}$, —COR$_{12}$, —CO$_2$R$_{12}$, —CONR$_{12}$R$_{13}$, —C(=NR$_{12}$)NR$_{13}$R$_{14}$, —NR$_{12}$R$_{13}$, —NR$_{12}$COR$_{13}$, —NR$_{12}$CONR$_{13}$R$_{14}$, —NR$_{12}$CO$_2$R$_{13}$, —NR$_{12}$SONR$_{13}$R$_{14}$, —NR$_{12}$SO$_2$NR$_{13}$R$_{14}$, or —NR$_{12}$SO$_2$R$_{13}$; and R$_{12}$, R$_{13}$, and R$_{14}$, which may be the same or different, are each independently hydrogen, —C$_{1-6}$alkyl, —C$_{2-6}$alkenyl, —C$_{2-6}$alkynyl, cycloalkyl, heterocyclyl, aryl, or heteroaryl, wherein said C$_{1-6}$alkyl, —C$_{2-6}$alkenyl, —C$_{2-6}$alkynyl, cycloalkyl, heterocyclyl, aryl, or heteroaryl are each independently optionally substituted with at least one substituent R$_{15}$;

Alternatively, (R$_{12}$ and R$_{13}$), or (R$_{13}$ and R$_{14}$), or (R$_{12}$ and R$_{14}$), together with the atom(s) to which they are attached, form a 3- to 12-membered saturated, partially or fully unsaturated ring comprising 0, 1 or 2 additional heteroatoms independently selected from —NH, —O—, —S—, —SO— or —SO$_2$—, and said ring is optionally substituted with at least one substituent R$_{15}$;

R$_{15}$, at each of its occurrences, is independently hydrogen, halogen, —C$_{1-6}$alkyl, —C$_{2-6}$alkenyl, —C$_{2-6}$alkynyl, cycloalkyl, heterocyclyl, aryl, heteroaryl, —CN, —NO$_2$, oxo, —OR$_{16}$, —SO$_2$R$_{16}$, —COR$_{16}$, —CO$_2$R$_{16}$, —CONR$_{16}$R$_{17}$, —C(=NR$_{16}$)NR$_{17}$R$_{18}$, —NR$_{16}$R$_{17}$, —C$_{1-6}$alkyl-NR$_{16}$R$_{17}$, —NR$_{16}$COR$_{17}$, —NR$_{16}$CONR$_{17}$R$_{18}$, —NR$_{16}$CO$_2$R$_{17}$, —NR$_{16}$SONR$_{17}$R$_{18}$, —NR$_{16}$SO$_2$NR$_{17}$R$_{18}$, or —NR$_{16}$SO$_2$R$_{17}$, wherein said C$_{1-6}$alkyl, —C$_{2-6}$alkenyl, —C$_{2-6}$alkynyl, cycloalkyl, heterocyclyl, aryl, or heteroaryl are each independently optionally substituted with halogen, R$_{19}$, —OR$_{19}$, —COR$_{19}$, —SO$_2$R$_{19}$, or —CO$_2$R$_{19}$;

wherein each of R$_{16}$, R$_{17}$, or R$_{18}$ is independently hydrogen, —C$_{1-6}$alkyl, —C$_{2-6}$alkenyl, —C$_{2-6}$alkynyl, haloC$_{1-6}$alkyl, haloC$_{2-6}$alkenyl, haloC$_{2-6}$alkynyl, cycloalkyl, heterocyclyl, aryl, or heteroaryl; or (R$_{16}$ and R$_{17}$), or (R$_{16}$ and R$_{18}$), or (R$_{17}$ and R$_{18}$), together with the atom(s) to which they are attached, form a 3- to 12-membered saturated, partially or fully unsaturated ring comprising 0, 1 or 2 additional heteroatoms independently selected from —NH, —O—, —S—, —SO— or —SO$_2$—, and said ring is optionally substituted with at least one substituent R$_{19}$, and wherein R$_{19}$ is independently hydrogen, —C$_{1-6}$alkyl, —C$_{2-6}$alkenyl, —C$_{2-6}$alkynyl, haloC$_{1-6}$alkyl, haloC$_{2-6}$alkenyl, haloC$_{2-6}$alkynyl, cycloalkyl, heterocyclyl, aryl, or heteroaryl, wherein said cycloalkyl, heterocyclyl, aryl, or heteroaryl are each optionally substituted with halogen, —C$_{1-6}$alkyl, —C$_{2-6}$alkenyl, —C$_{2-6}$alkynyl, haloC$_{1-6}$alkyl, haloC$_{2-6}$alkenyl, or haloC$_{2-6}$alkynyl; and wherein said —C$_{1-6}$alkyl, —C$_{2-6}$alkenyl, —C$_{2-6}$alkynyl, haloC$_{1-6}$alkyl, haloC$_{2-6}$alkenyl, or haloC$_{2-6}$alkynyl are each optionally substituted with cycloalkyl, heterocyclyl, aryl, or heteroaryl; and wherein the disorder or the disease is a B-cell malignancy, pancreatic cancer, breast cancer, lung cancer, melanoma, systemic lupus erythematosus (SLE), rheumatoid arthritis (RA), or multiple sclerosis (MS).

2. The method of claim 1, wherein the B-cell malignancy is chronic lymphocytic leukemia (CLL), Non-Hodgkin lymphoma (NHL), chronic myeloid leukemia (CML), Mantle cell lymphoma (MCL), small lymphocytic lymphoma (SLL), follicular lymphoma, extranodal marginal zone lymphoma, or diffuse large B cell lymphoma (DLBCL).

3. The method of claim 1, wherein the lung cancer is non-small cell lung cancer.

4. The method of claim 1, wherein:

(a) R$_1$ is —NH$_2$; or (b) R$_2$ is independently hydrogen, halogen, —C$_{1-6}$alkyl, C$_{3-6}$cycloalkyl or C$_{6-10}$aryl, wherein —C$_{1-6}$alkyl, C$_{3-6}$cycloalkyl and C$_{6-10}$aryl are each independently optionally substituted with at least one substituent R$_{11a}$; or (c) R$_3$ and R$_4$ are each independently hydrogen or —C$_{1-6}$alkyl; or (d) R$_5$ and R$_6$, which may be the same or different, are each independently hydrogen, halogen, —C$_{1-6}$alkyl, —C$_{2-6}$alkenyl, —C$_{2-6}$alkynyl, cycloalkyl, heterocyclyl, aryl, or heteroaryl, wherein said —C$_{1-6}$alkyl, —C$_{2-6}$alkenyl, —C$_{2-6}$alkynyl, cycloalkyl, heterocyclyl, aryl or heteroaryl are each independently optionally substituted with at least one substituent R$_{11b}$, wherein R$_{11b}$ is halogen; or (e) R$_7$, R$_8$ and R$_{10}$, which may be the same or different, are each independently hydrogen, halogen, —C$_{1-6}$alkyl, —C$_{2-6}$alkenyl, —C$_{2-6}$alkynyl, cycloalkyl, heterocyclyl, aryl, heteroaryl, or —OR$_{12}$; wherein said —C$_{1-6}$alkyl, —C$_{2-6}$alkenyl, —C$_{2-6}$alkynyl, cycloalkyl, heterocyclyl, aryl or heteroaryl are each independently optionally substituted with at least one substituent $R_{11c}$, wherein $R_{11c}$ is halogen.

5. The method of claim 4, wherein:
   (a) $R_2$ is $C_{1-6}$alkyl; or
   (b) $R_3$ is hydrogen, and $R_4$ is —$C_{1-6}$alkyl; or
   (c) $R_5$ and $R_6$ are both hydrogen; or
   (d) $R_7$ and $R_8$ are each independently hydrogen, halogen or —$C_{1-6}$alkyl; or
   (e) $R_{10}$ is methoxy, ethoxy, propoxy, or isopropoxy.

6. The method of claim 1, wherein $R_9$ is —$CONR_{12}R_{13}$.

7. The method of claim 6, wherein:
   $R_{12}$ is hydrogen;
   $R_{13}$ is $C_{1-6}$alklyl optionally substituted with one substituent $R_{15}$; and
   $R_{15}$ is heterocyclyl optionally substituted with halogen, $R_{19}$, —$OR_{19}$, —$COR_{19}$, —$SO_2R_{19}$, or —$CO_2R_{19}$.

8. The method of claim 7, wherein the heterocyclyl is a 4-, 5-, 6-, 7- or 8-membered saturated monocyclic ring comprising one nitrogen heteroatom or a 5-, 6-, 7- or 8-membered saturated monocyclic ring comprising one nitrogen atom and 1 additional heteroatom selected from —NH, —O—, —S—, —SO— or —SO$_2$—, wherein the heterocyclyl is optionally substituted with halogen, $R_{19}$, —$OR_{19}$, —$COR_{19}$, —$SO_2R_{19}$, or —$CO_2R_{19}$.

9. The method of claim 8, wherein the heterocyclyl is piperidinyl or piperazinyl group optionally substituted with halogen or $C_{1-6}$alkyl.

10. The method of claim 6, wherein:
    $R_{12}$ is hydrogen;
    $R_{13}$ is cycloalkyl optionally substituted with at least one substituent $R_{15}$; and
    $R_{15}$ is —$OR_{16}$, —$CO_2R_{16}$ or —$C_{1-6}$alkyl-$NR_{16}R_{17}$, or —$C_{1-6}$alkyl optionally substituted with —$OR_{19}$, wherein $R_{16}$ and $R_{17}$ together with the atom(s) to which they are attached may optionally form a 5- to 8-membered saturated ring comprising 0, 1 or 2 additional heteroatoms independently selected from —NH, and said ring is optionally substituted with at least one substituent $R_{19}$.

11. The method of claim 10, wherein $R_{13}$ is a $C_3$-$C_8$ cycloalkyl optionally substituted with at least one substituent $R_{15}$.

12. The method of claim 11, wherein $R_{13}$ is a cyclopropyl, cyclobutyl, cyclopentyl, or cyclohexyl, each optionally substituted with at least one substituent $R_{15}$.

13. The method of claim 6, wherein:
    (a) $R_{12}$ is hydrogen, and $R_{13}$ is a 5- to 8-membered heterocyclyl comprising 1 or 2 or 3 heteroatoms selected from O, NH, S, SO, or SO$_2$, optionally substituted with at least one substituent $R_{15}$; or
    (b) $R_{12}$ is hydrogen, and $R_{13}$ is an aryl group selected from phenyl and naphthyl, optionally substituted with at least one substituent $R_{15}$; or
    (c) $R_{12}$ and $R_{13}$ together with the nitrogen atom to which they are attached, form a 3- to 12-membered saturated, partially or fully unsaturated ring comprising 0, 1 or 2 additional heteroatoms independently selected from —NH, —O—, —S—, —SO— or —SO$_2$—, and said ring is optionally substituted with at least one substituent $R_{15}$.

14. The method of claim 6, wherein $R_{13}$ is tetrahydrofurfuryl or tetrahydropyranyl, each optionally substituted with at least one substituent $R_{15}$; and wherein $R_{15}$ is halogen or —$C_{1-6}$alkyl.

15. The method of claim 6, wherein:
    $R_{12}$ is hydrogen;
    $R_{13}$ is an aryl group selected from phenyl and naphthyl, optionally substituted with at least one substituent $R_{15}$; and
    $R_{15}$ is halogen, —$C_{1-6}$ alkyl, —$OR_{16}$, or heterocyclyl optionally substituted with halogen, $R_{19}$, or —$OR_{19}$.

16. The method of claim 6, wherein $R_{12}$ and $R_{13}$ together with the nitrogen atom to which they are attached, form a 4-, or 5- or 6- or 7- or 8-membered saturated monocyclic ring comprising 0 additional heteroatom, and said ring is optionally substituted with at least one substituent $R_{15}$; and wherein $R_{15}$ is halogen, —$OR_{16}$, —$CO_2R_{16}$, or —$C_{1-6}$alkyl optionally substituted with —$OR_{19}$.

17. The method of claim 6, wherein:
    (a) $R_{12}$ and $R_{13}$ together with the nitrogen atom to which they are attached, form a 5-, 6-, 7-or 8-membered saturated monocyclic ring comprising 1 additional heteroatom selected from —NH, —O—, —S—, —SO— or —SO$_2$—, and said ring is optionally substituted with at least one substituent $R_{15}$; or
    (b) $R_{12}$ and $R_{13}$ together with the nitrogen atom to which they are attached, form a 7- to 12-membered saturated bicyclic ring comprising 0 or 1 or 2 additional heteroatoms selected from —N, —O—, —S—, —SO— or —SO$_2$—, and said ring is optionally substituted with at least one substituent $R_{15}$.

18. The method of claim 17, wherein $R_{12}$ and $R_{13}$ together with the nitrogen atom to which they are attached, form a morpholino, morpholinyl or piperazinyl ring, each of which is optionally substituted with at least one substituent $R_{15}$; and wherein $R_{15}$ is hydrogen, halogen, —$C_{1-6}$alkyl, or cycloalkyl, wherein said $C_{1-6}$alkyl, or cycloalkyl are each independently optionally substituted with halogen, $R_{19}$, —$OR_{19}$, —$COR_{19}$, or —$CO_2R_{19}$.

19. The method of claim 17, wherein the bicyclic ring is

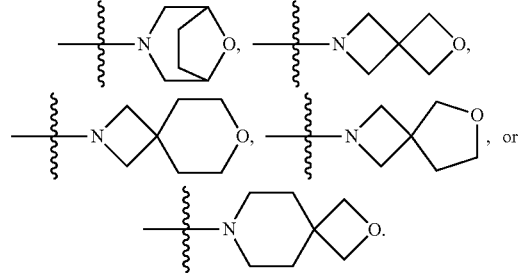

20. The method of claim 6, wherein $R_9$ is

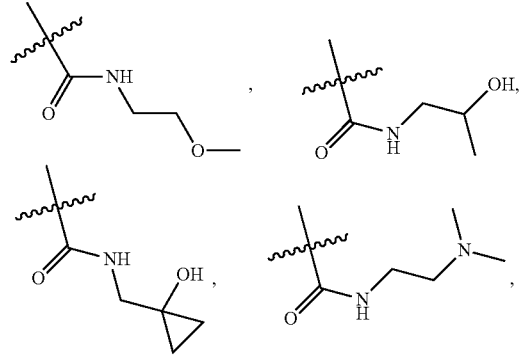

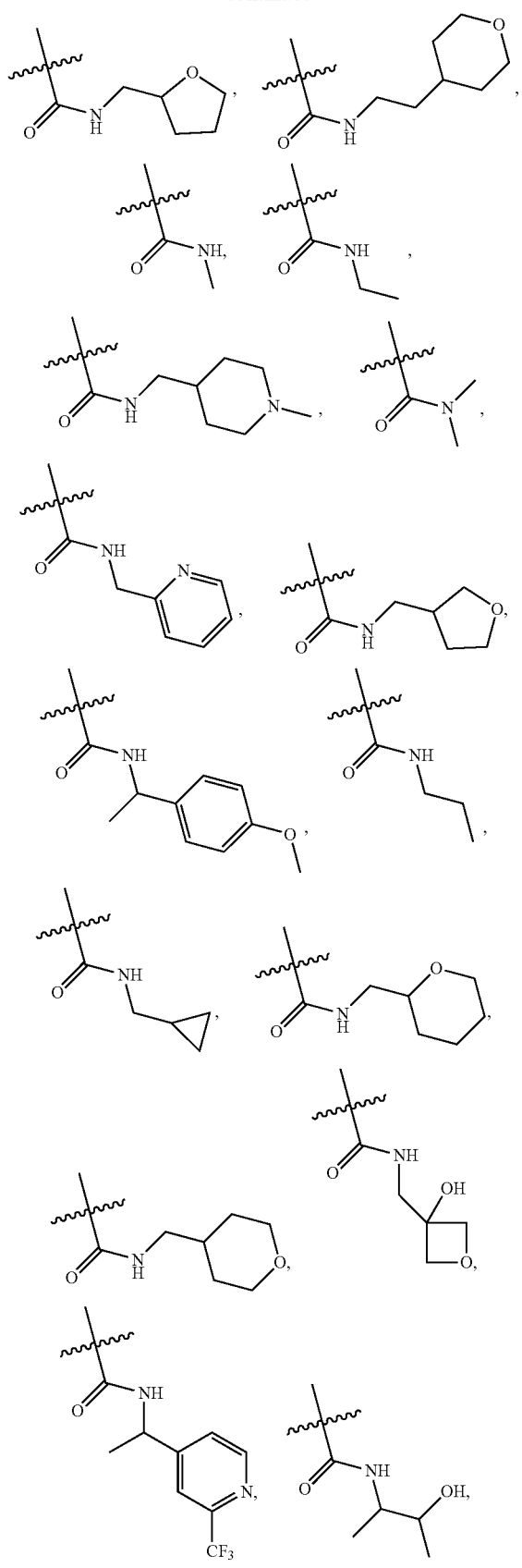
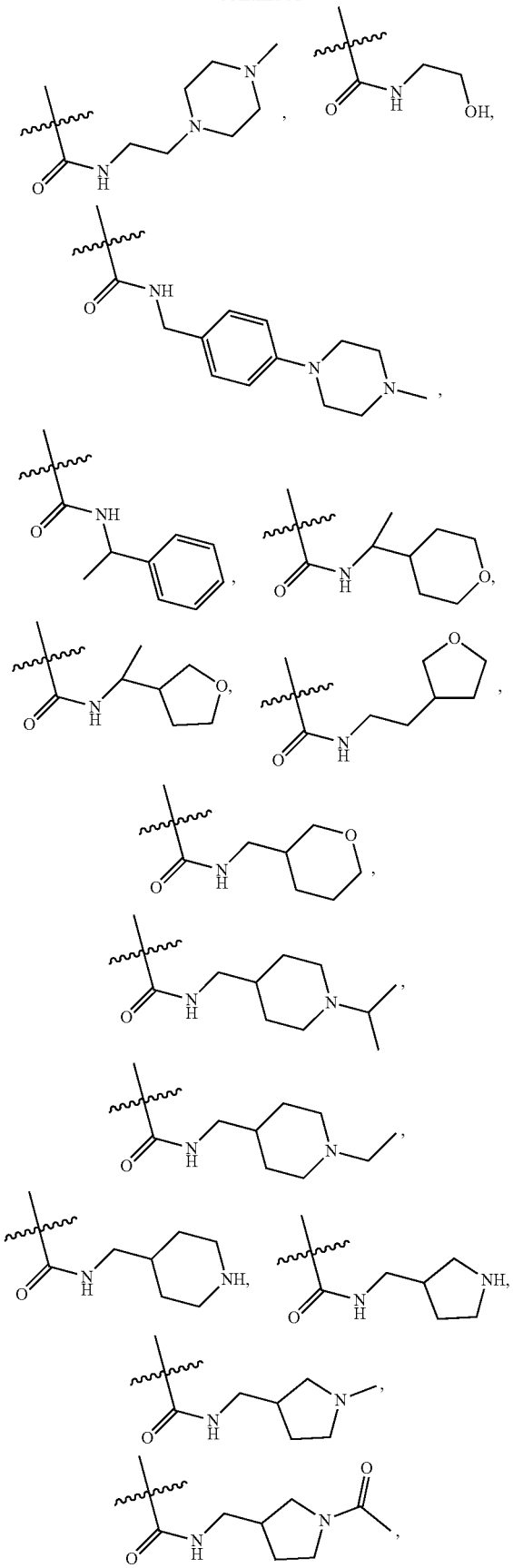

173
-continued
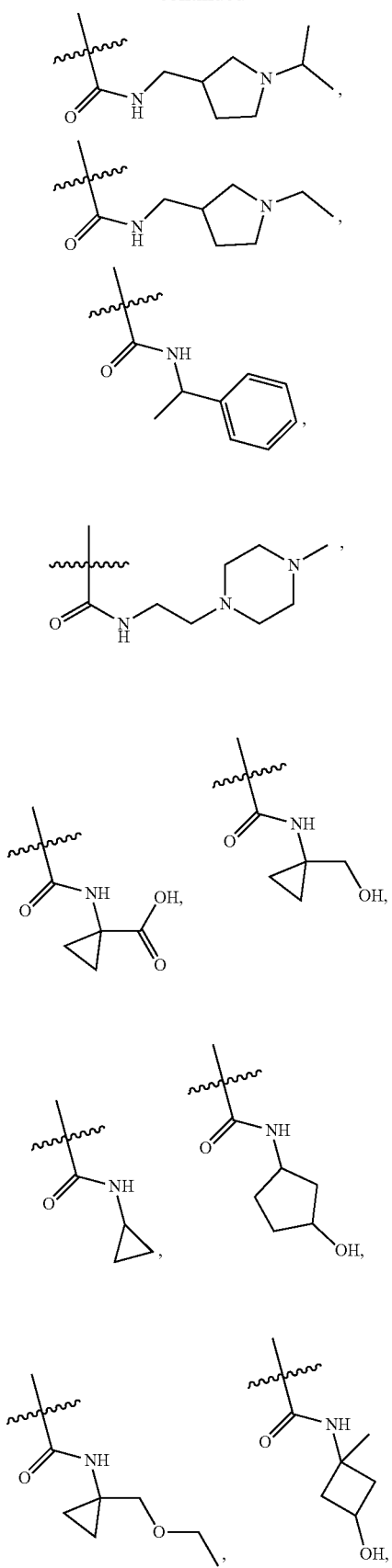
174
-continued
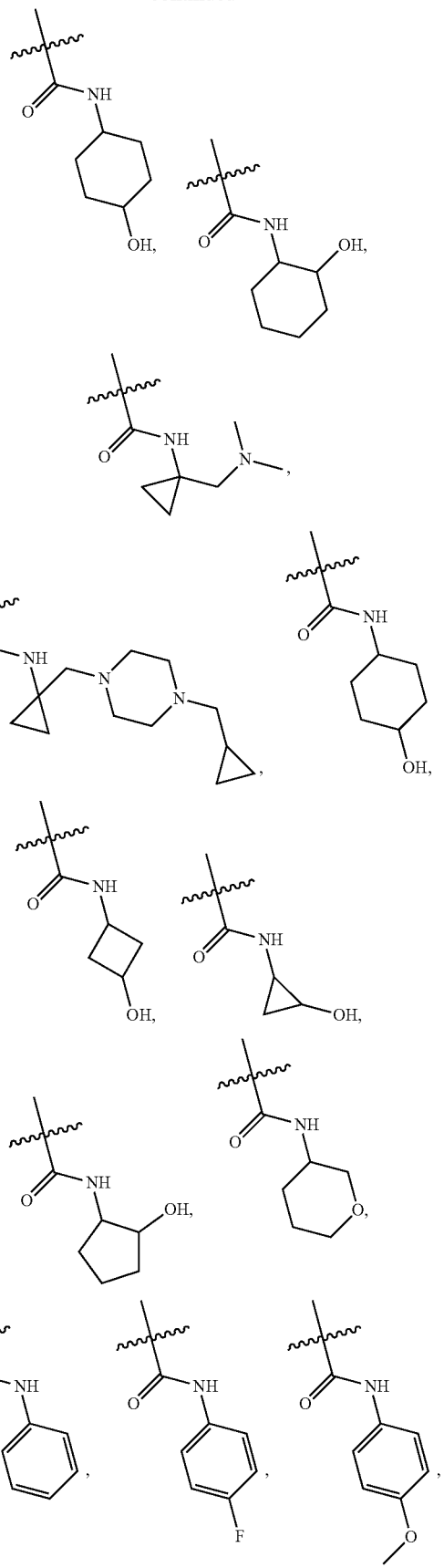

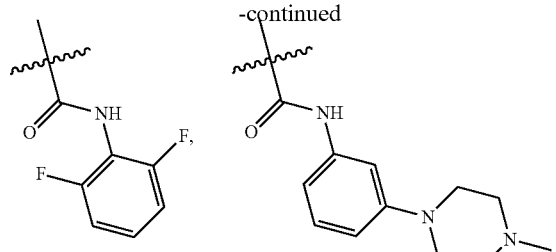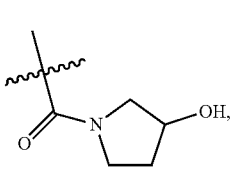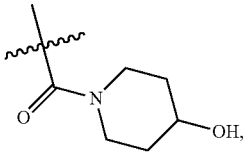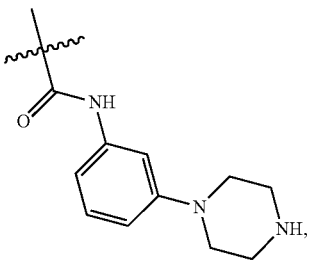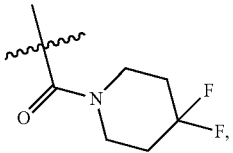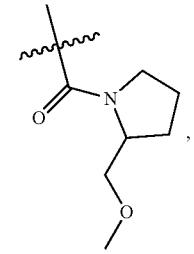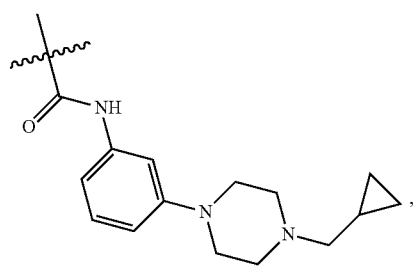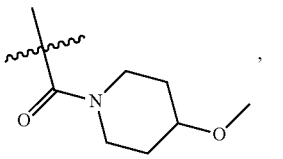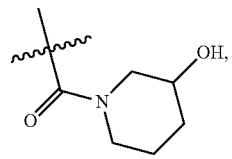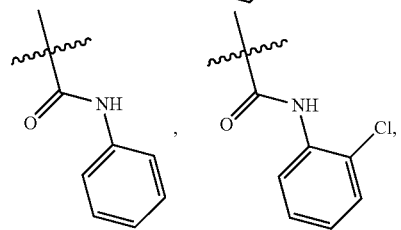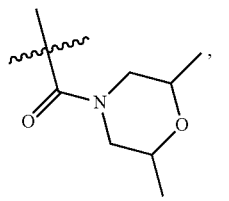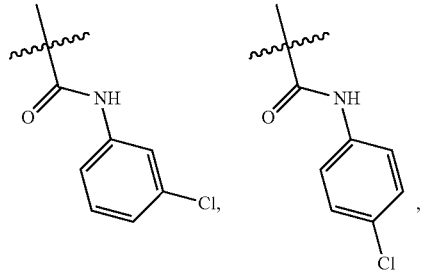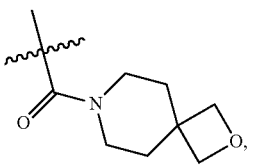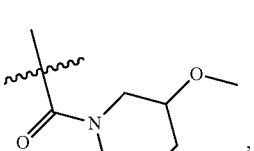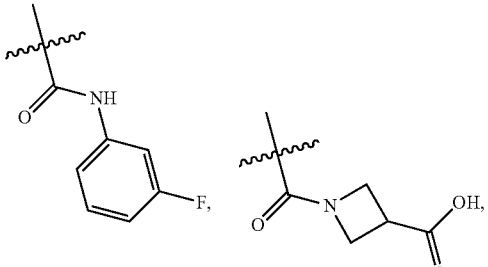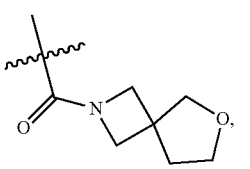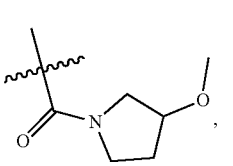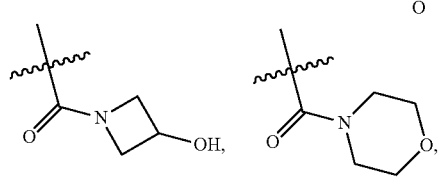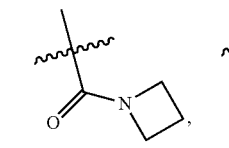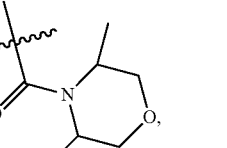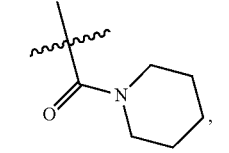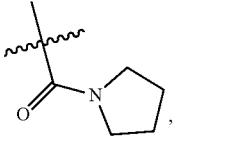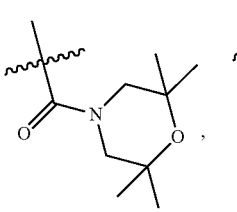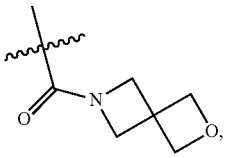

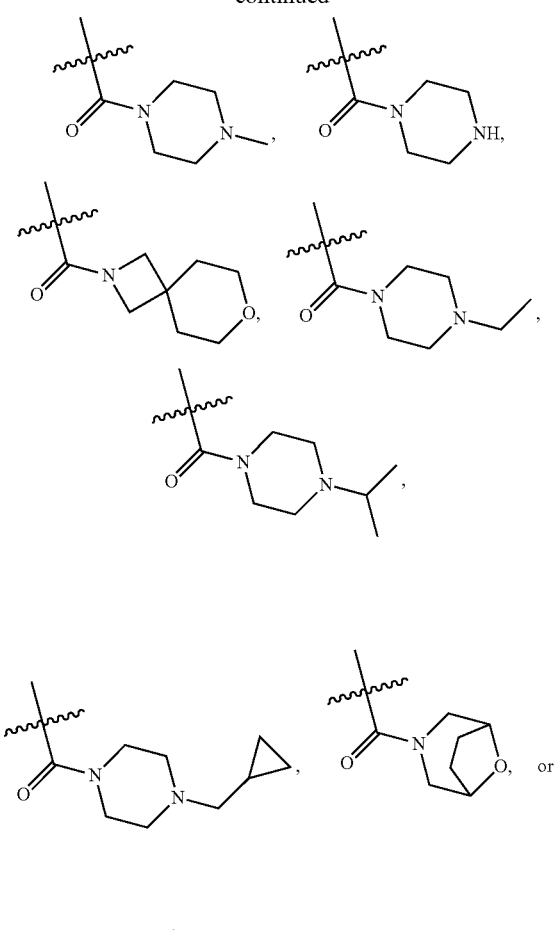
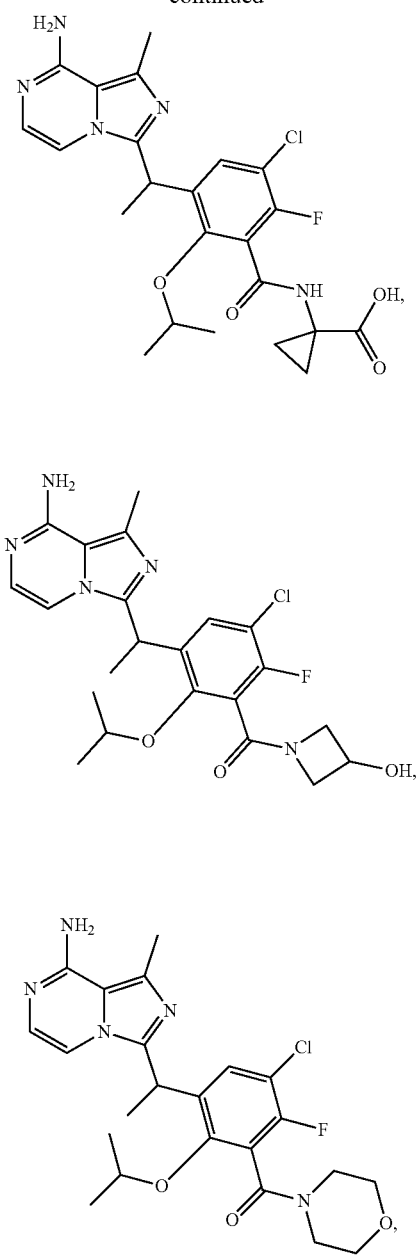
21. The method of claim 1, wherein the carbon atom to which $R_3$ and $R_4$ are attached is in (S)-configuration when $R_3$ and $R_4$ are different.
22. The method of claim 1, wherein the compound is selected from:
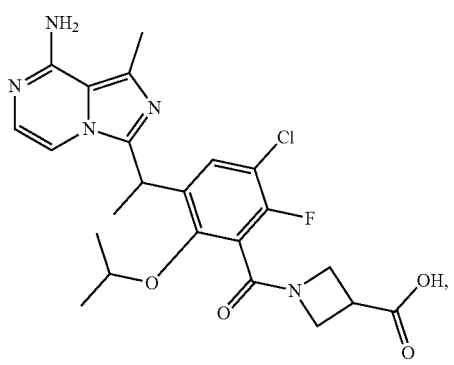
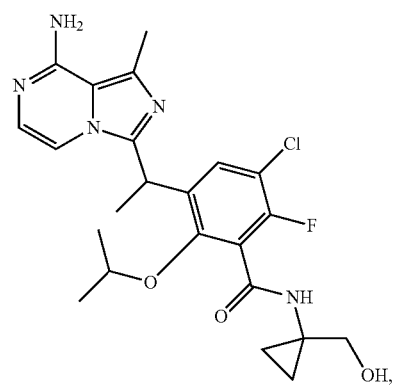

179
-continued
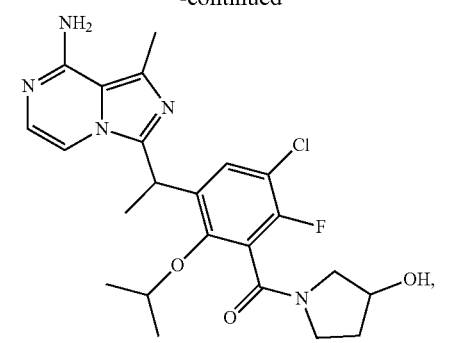
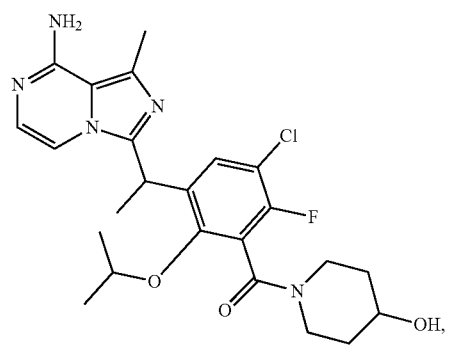
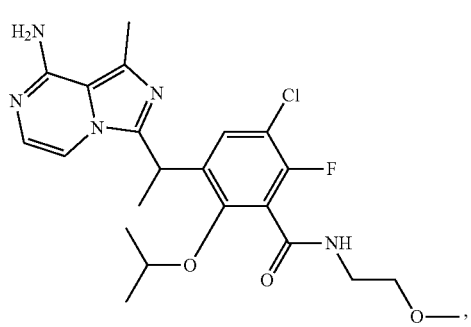
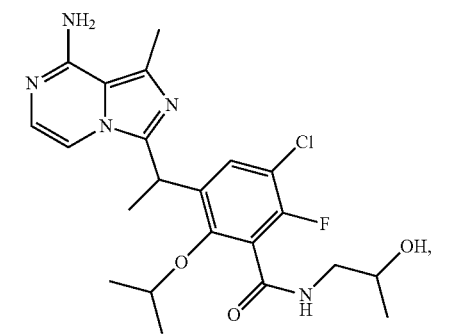
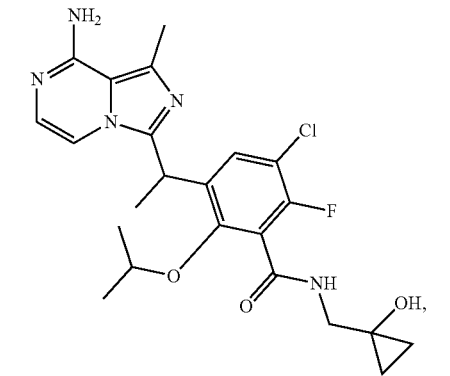
180
-continued
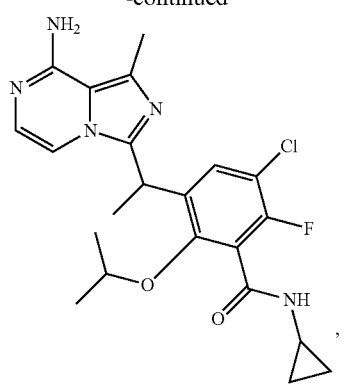
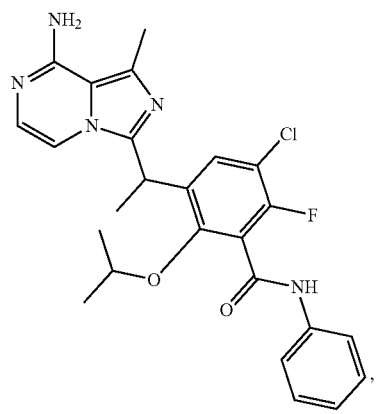
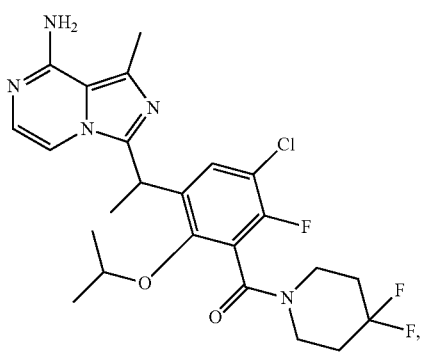
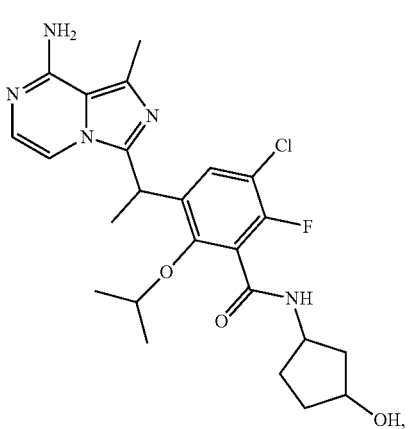

181
-continued
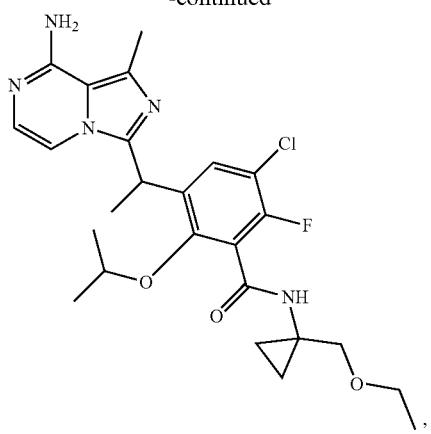
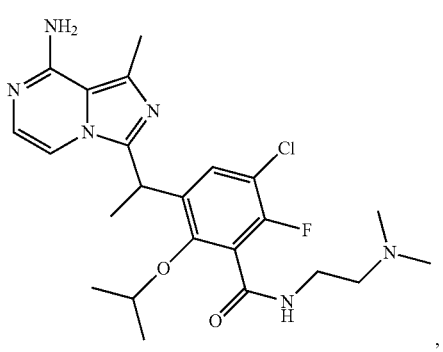
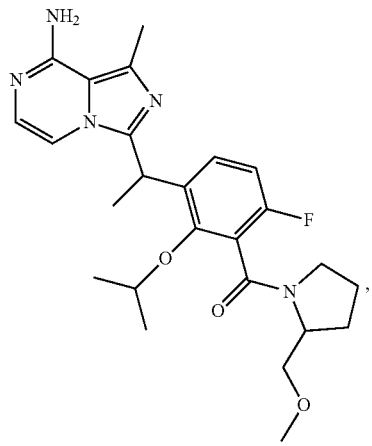
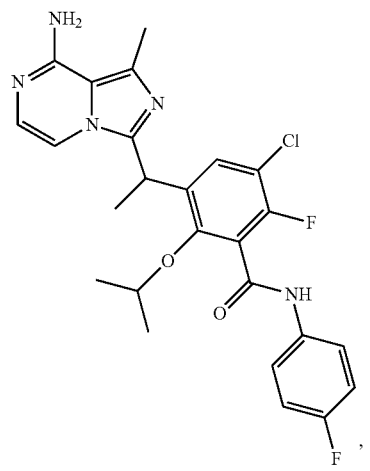
182
-continued
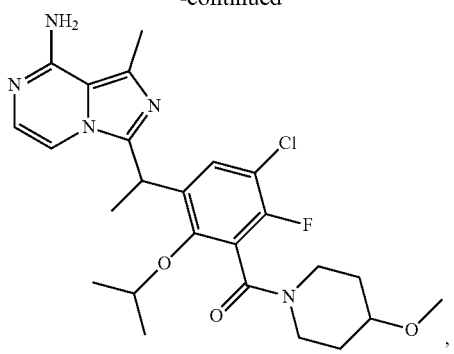
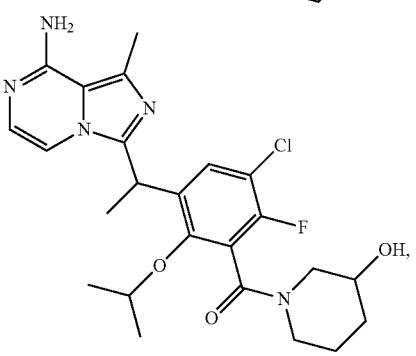
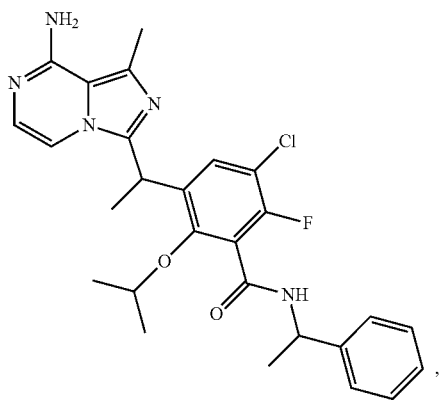
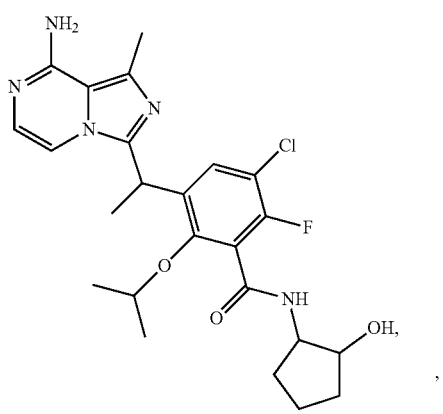

183
-continued
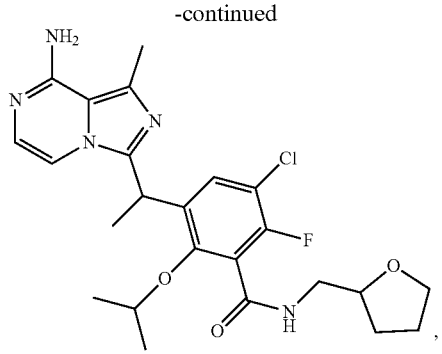
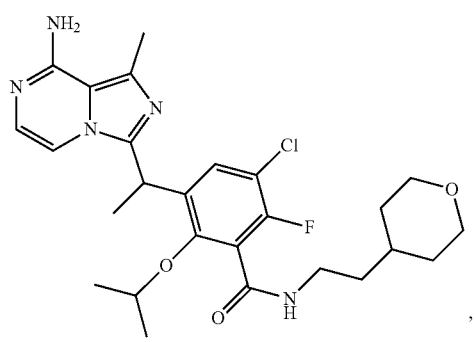
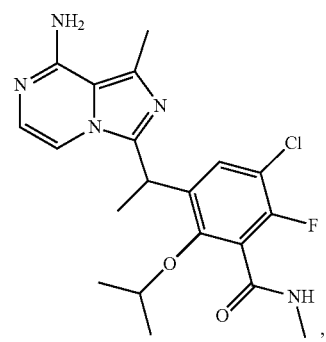
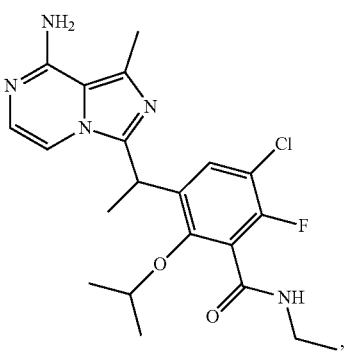
184
-continued
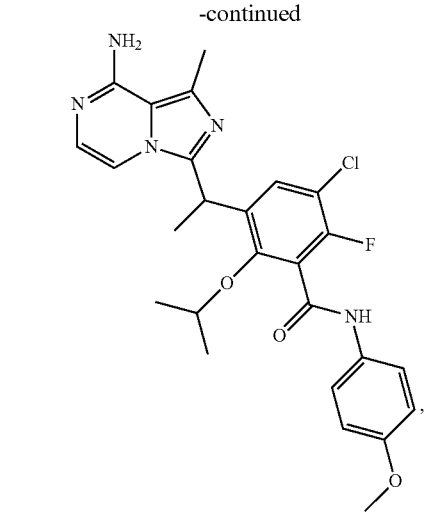
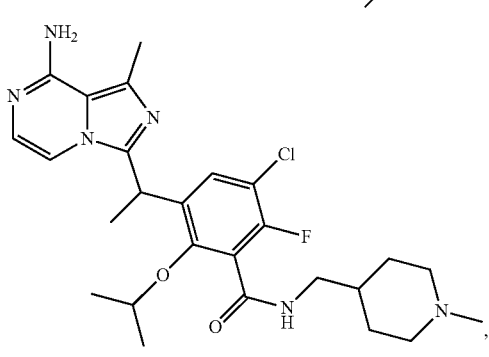
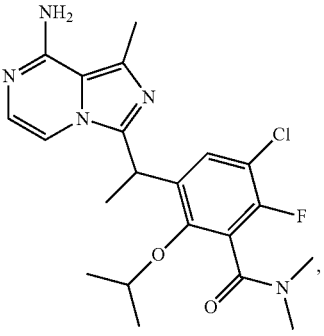
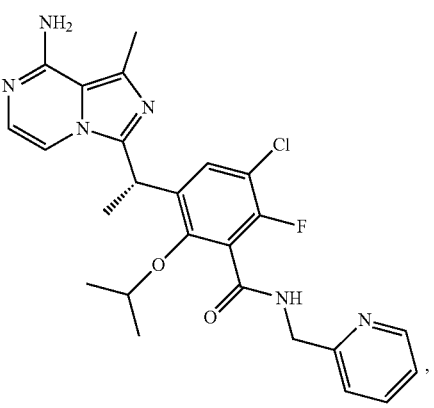

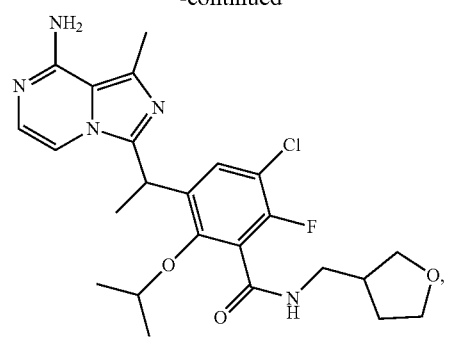
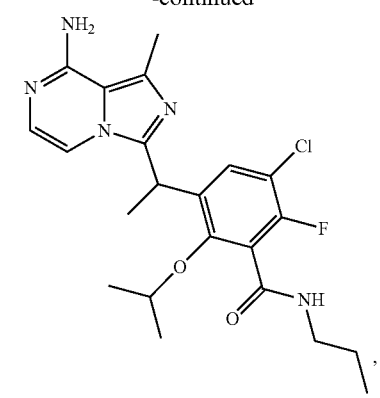
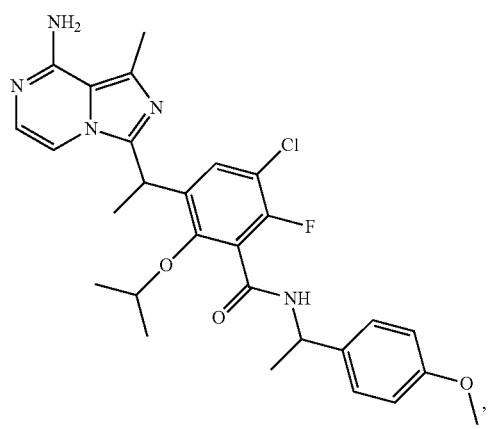
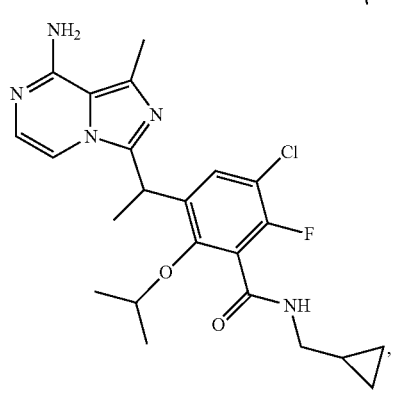
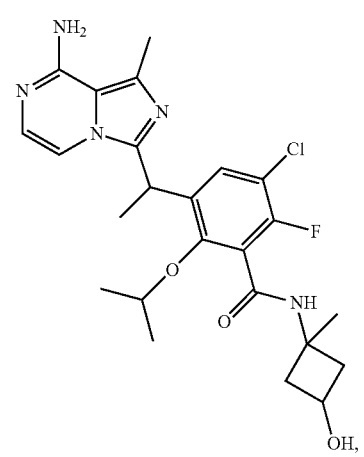
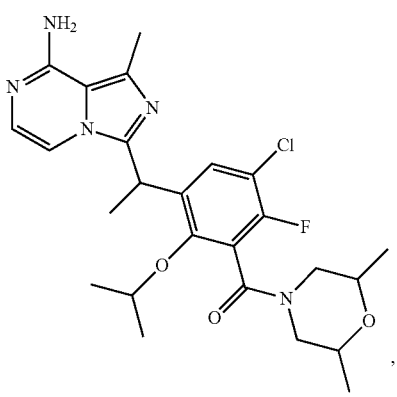
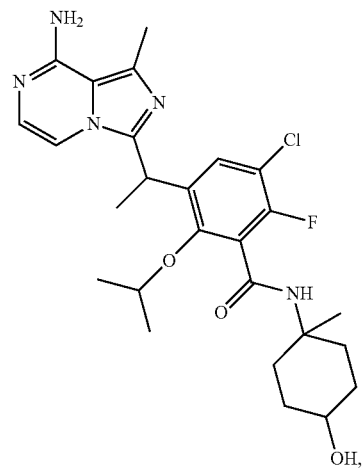
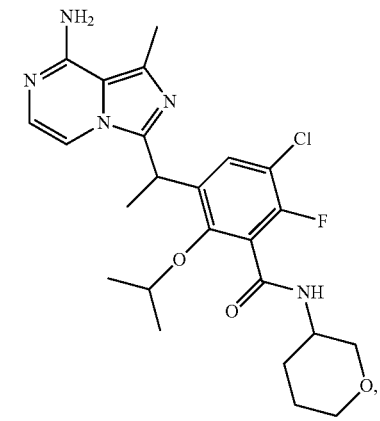

187
-continued
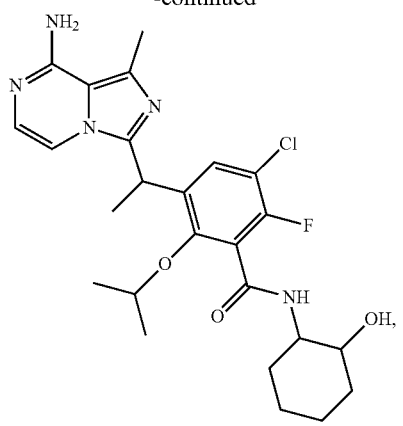
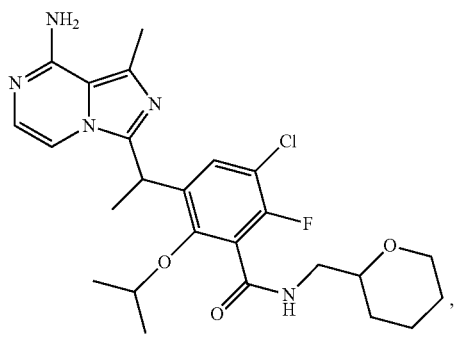
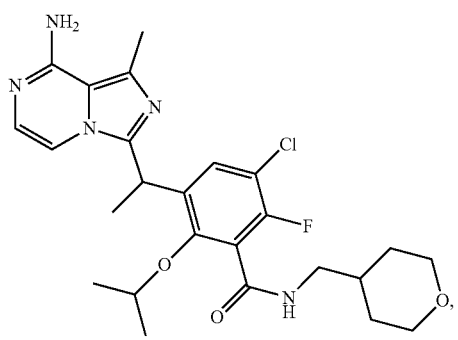
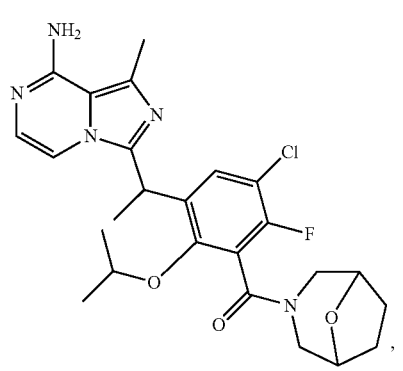
188
-continued
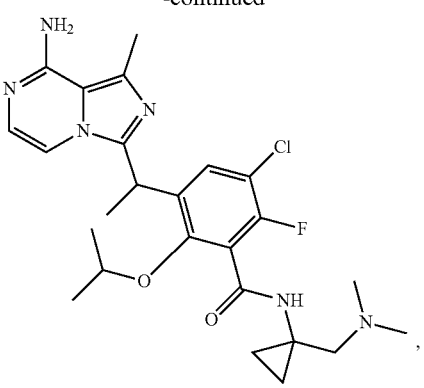
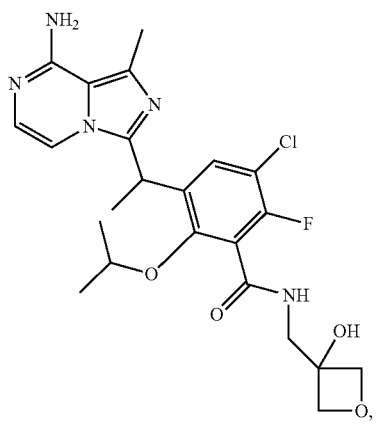
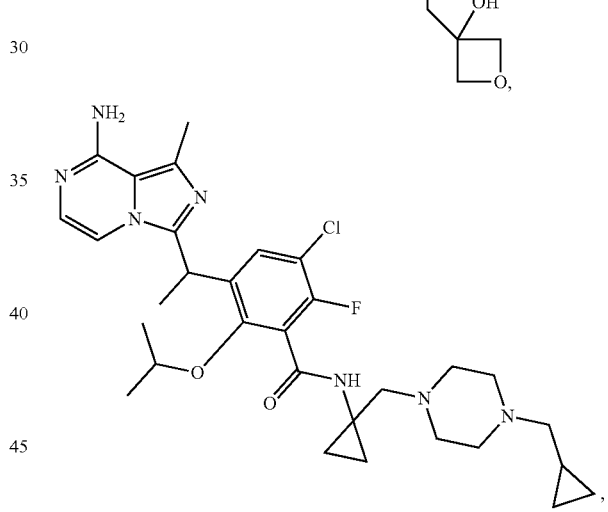
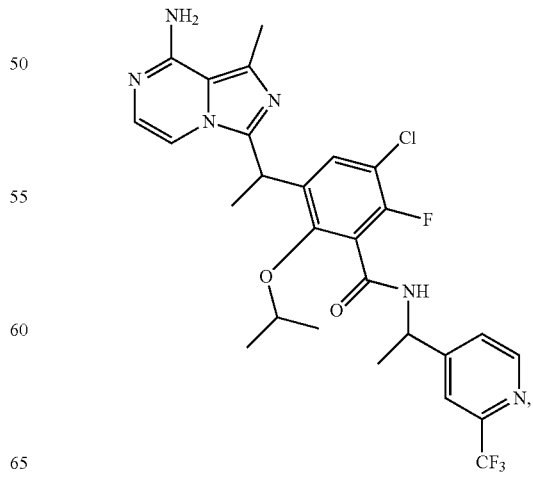

-continued
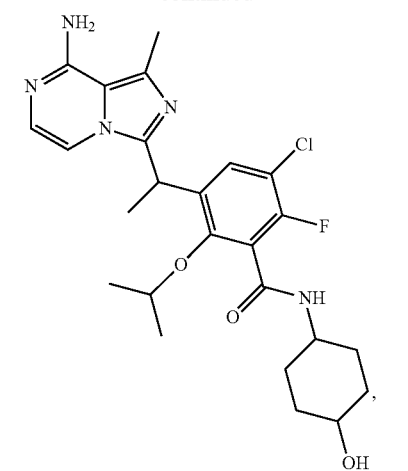
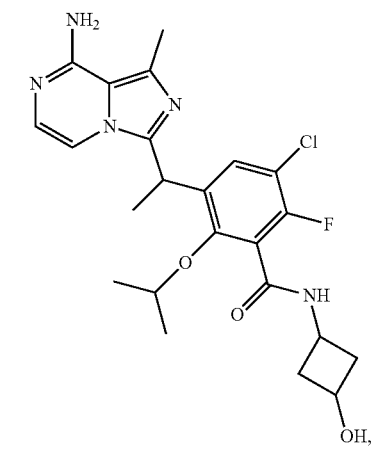
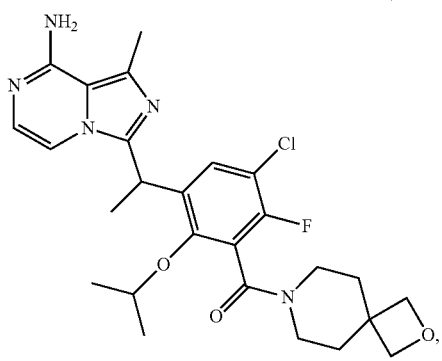
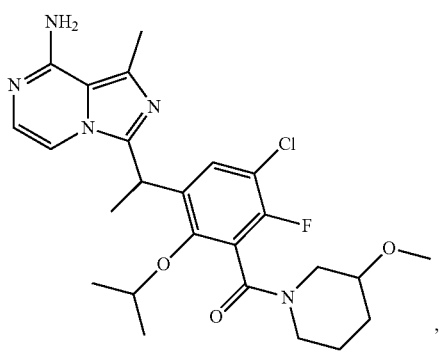
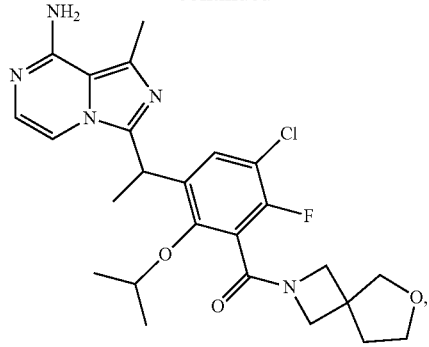
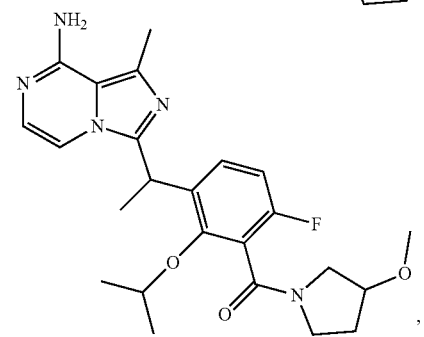
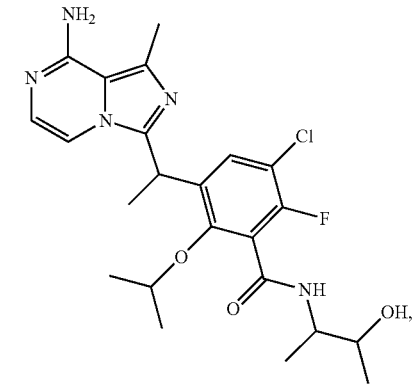
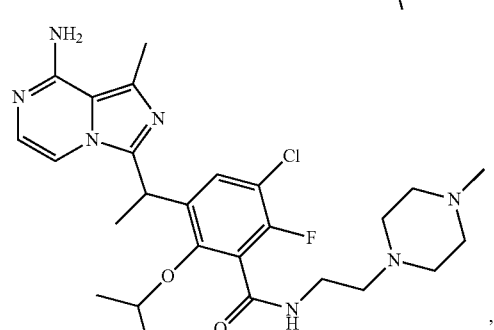
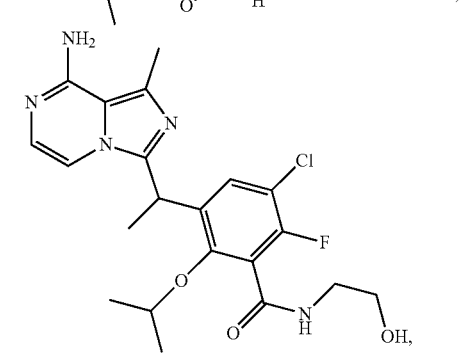

-continued
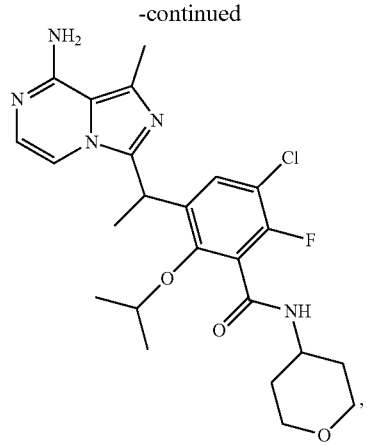
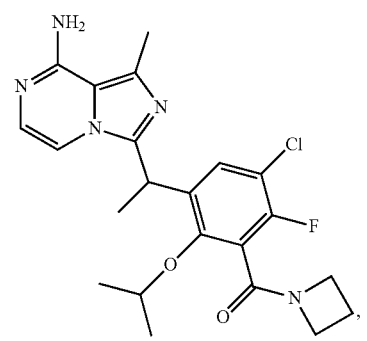
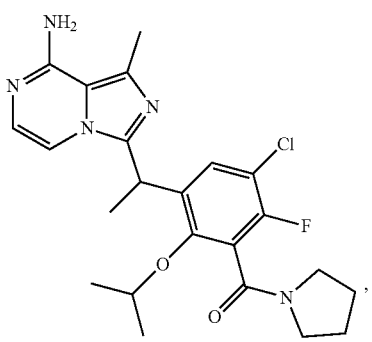
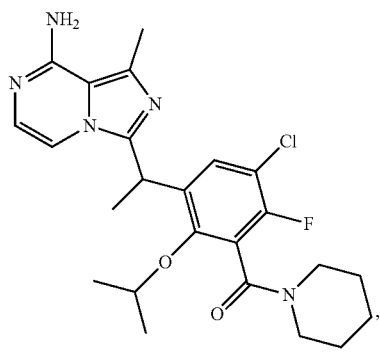
-continued
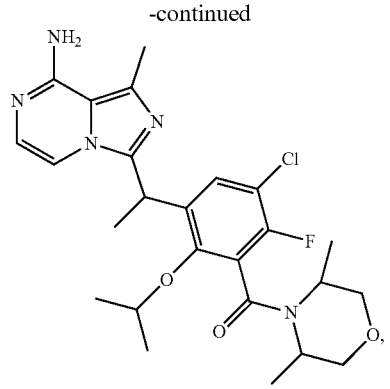
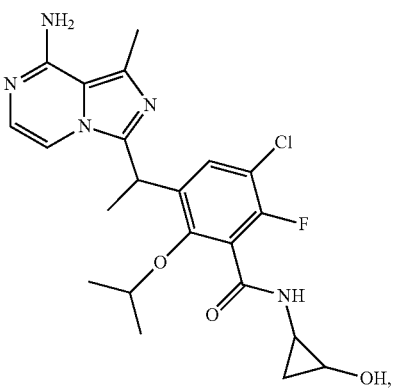
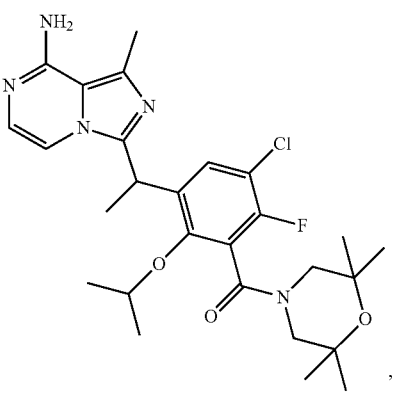
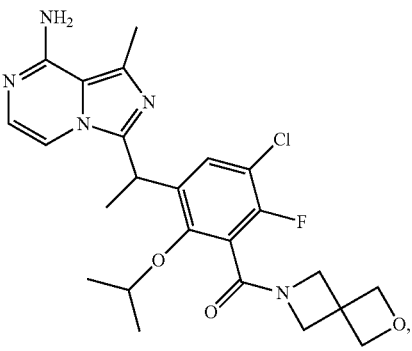

193
-continued
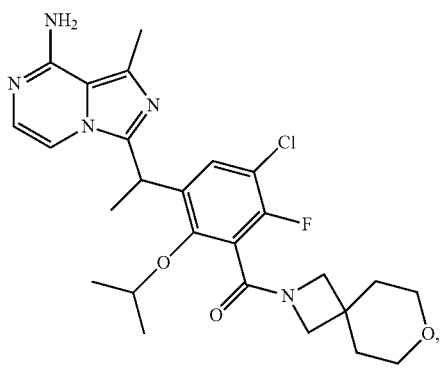
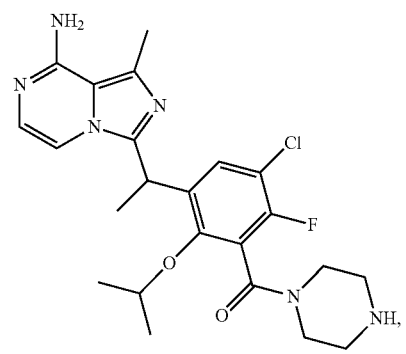
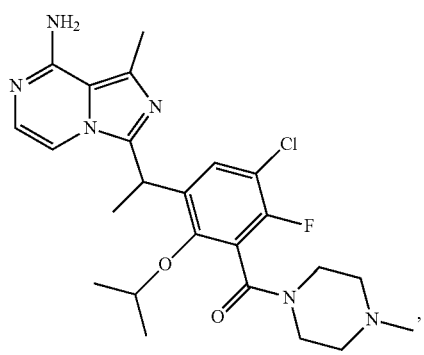
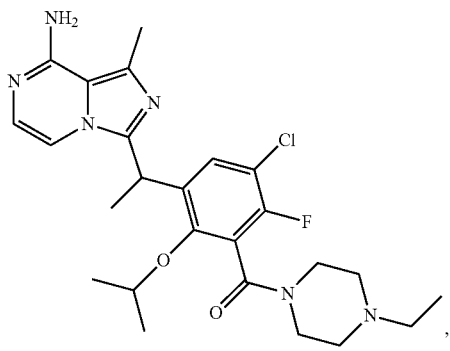
194
-continued
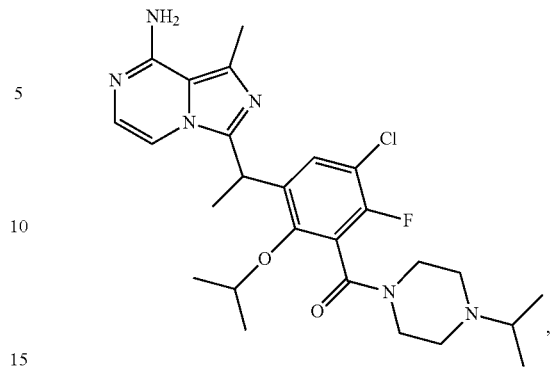
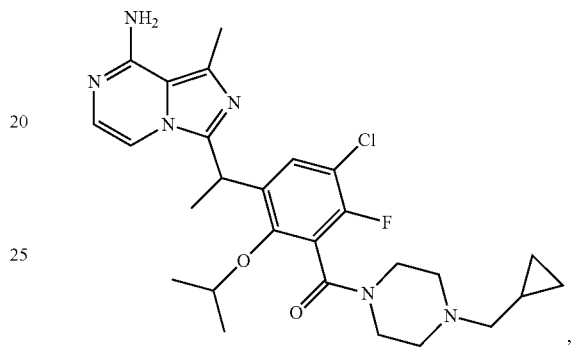
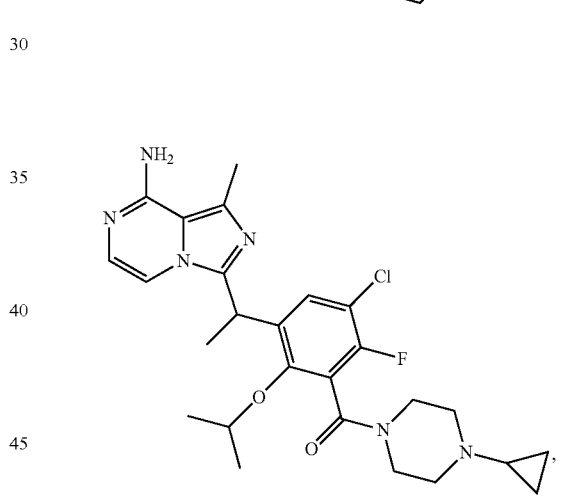
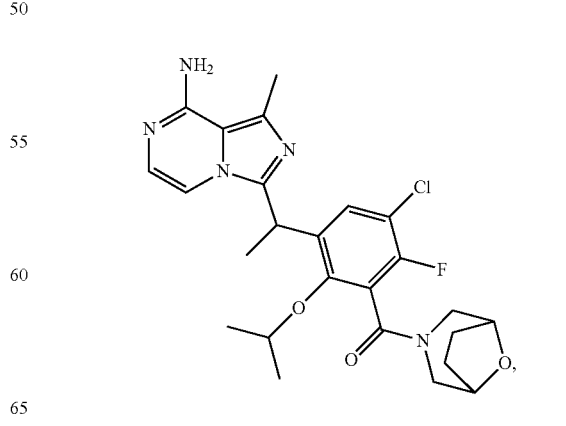

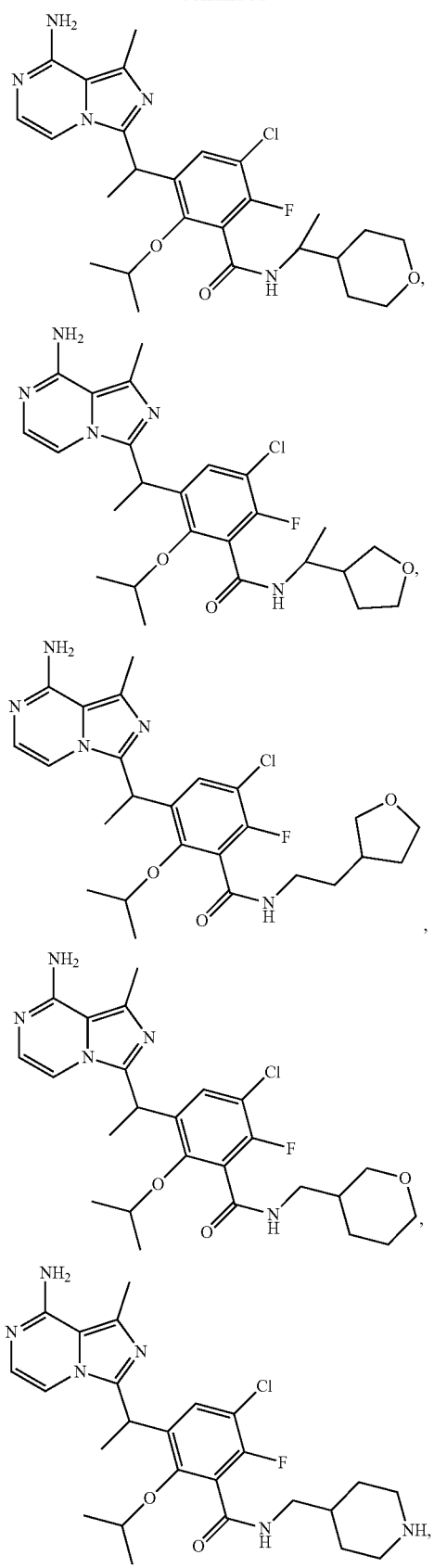
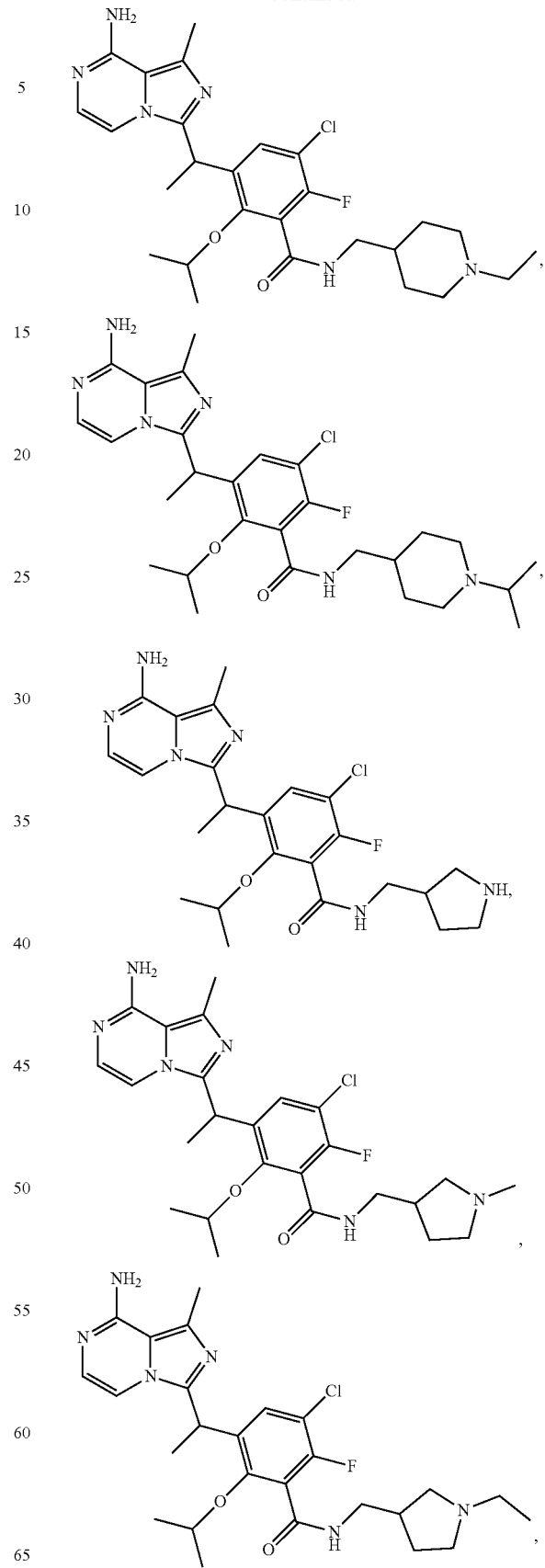

197
-continued
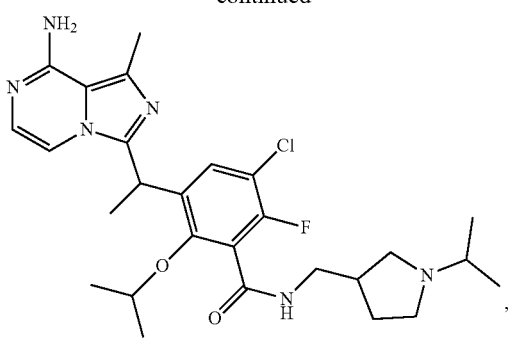
,
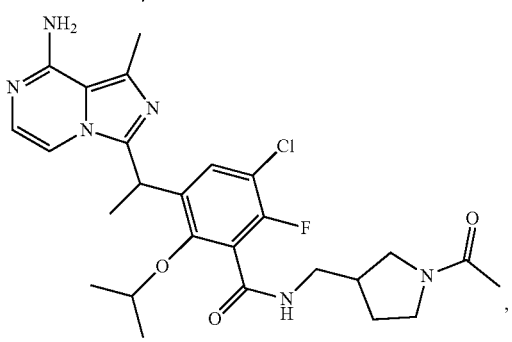
,
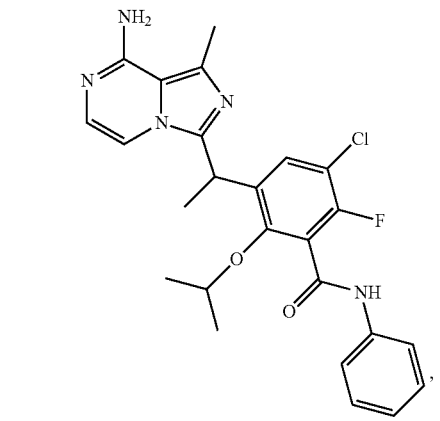
,
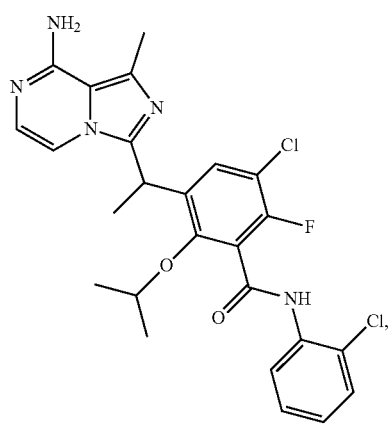
,
198
-continued
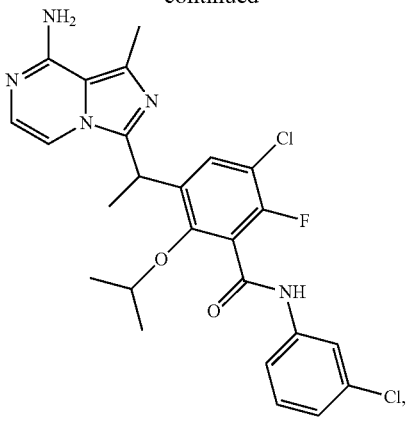
,
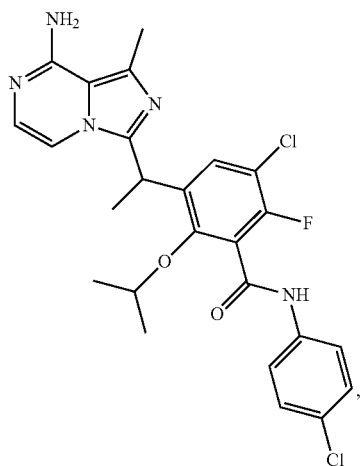
,
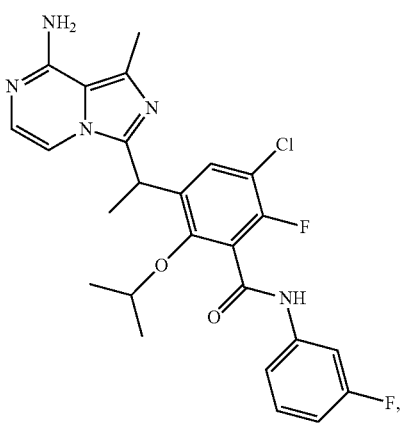
,
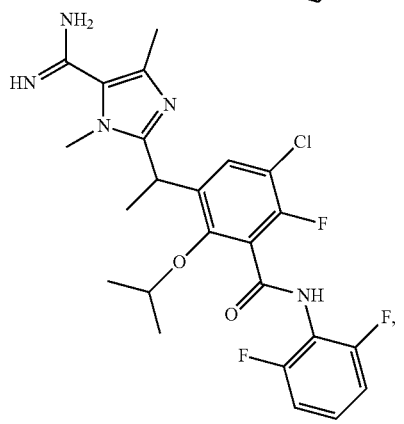
,

199
-continued
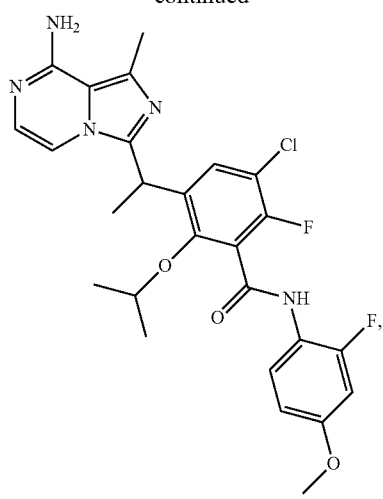
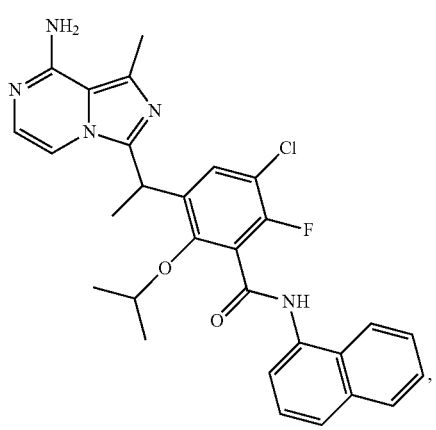
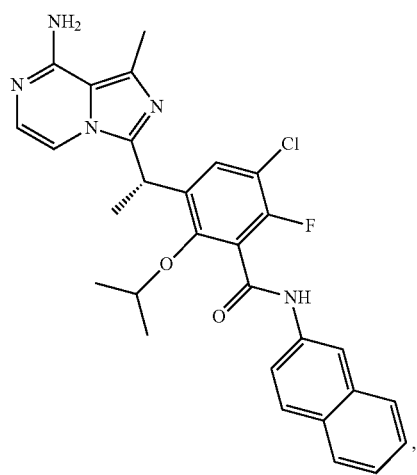
200
-continued
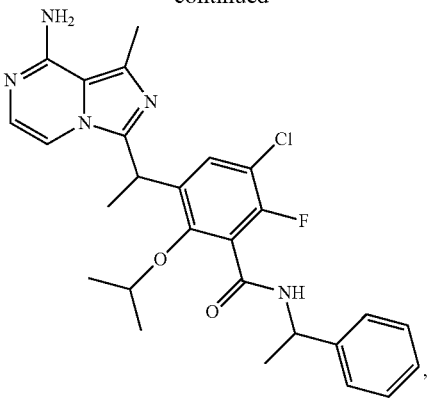
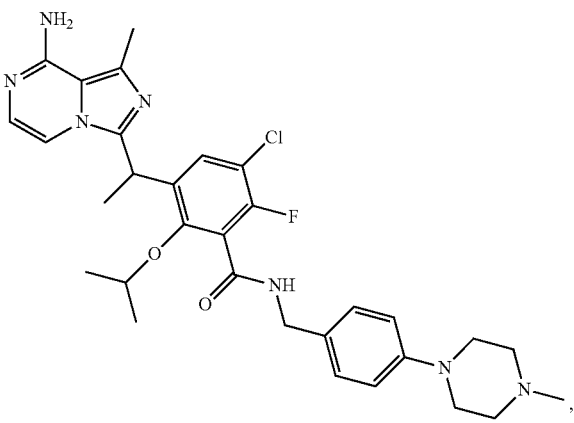
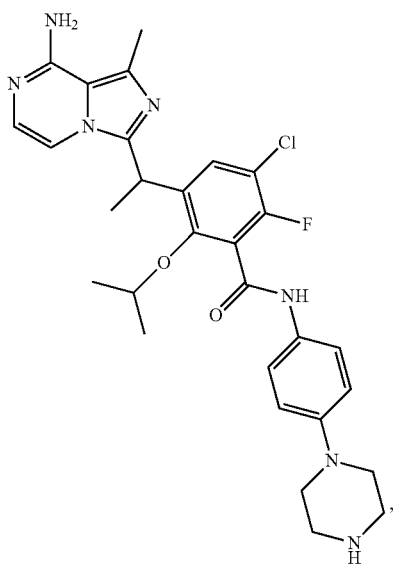

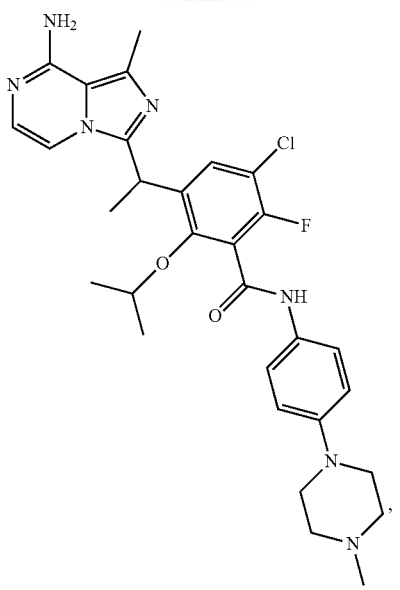
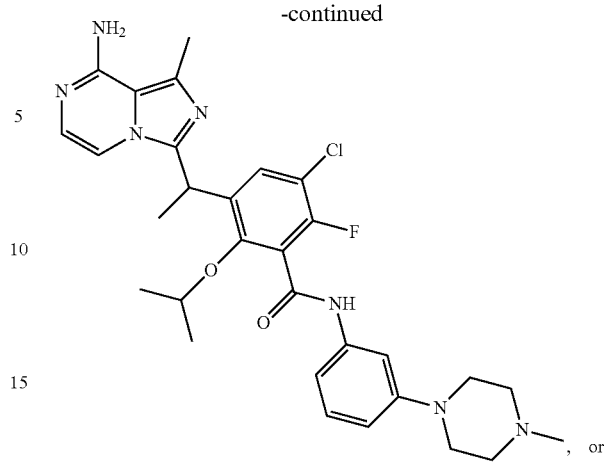
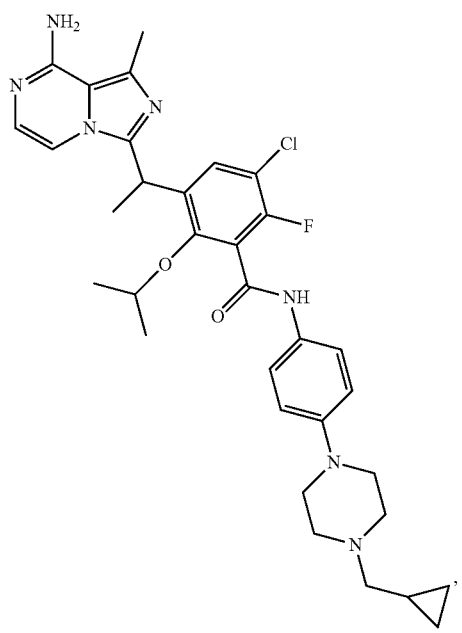
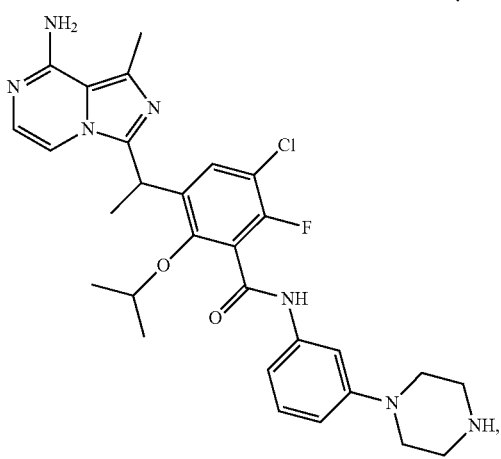
or a stereoisomer thereof, or a pharmaceutically acceptable salt thereof.
23. The method of claim 1, wherein the compound is selected from:
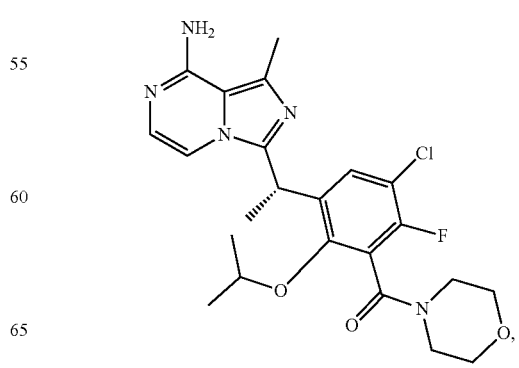

203
-continued
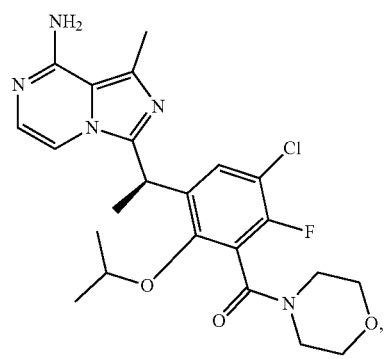
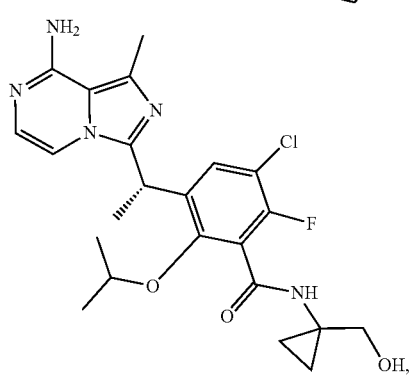
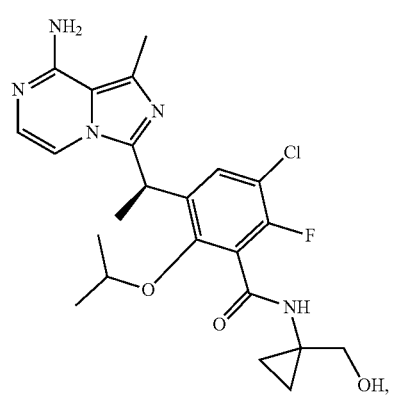
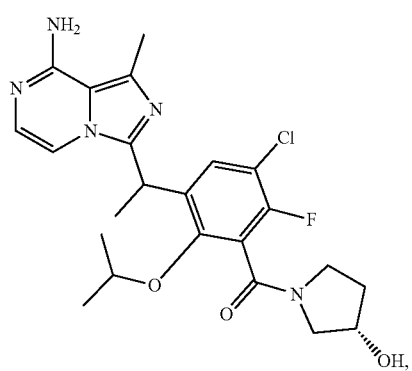
204
-continued
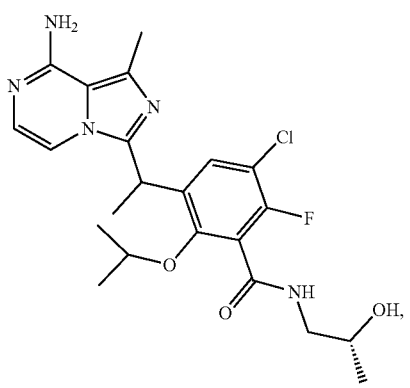
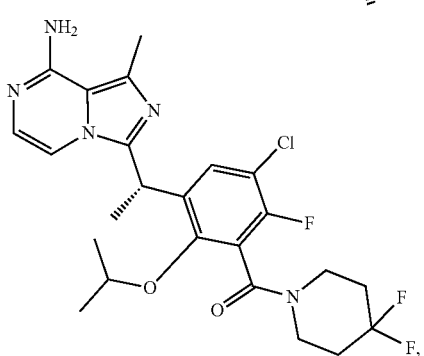
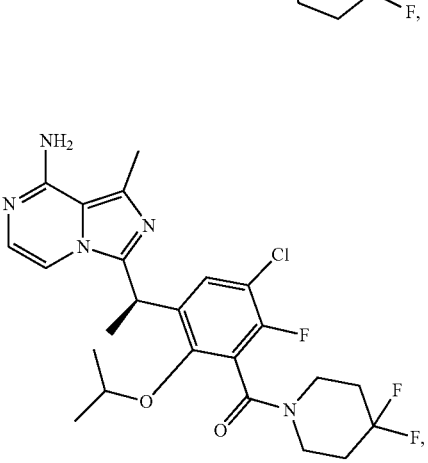
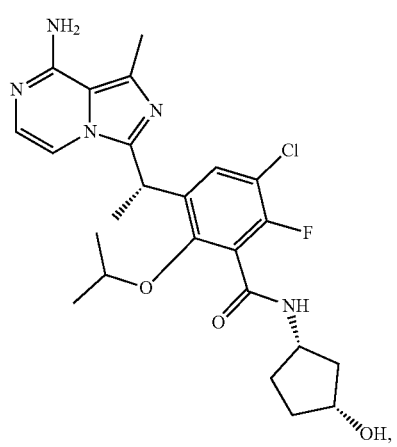

205
-continued
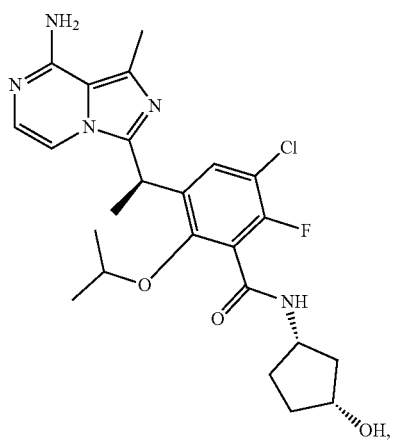
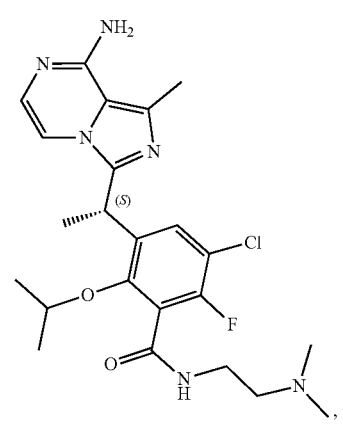
206
-continued
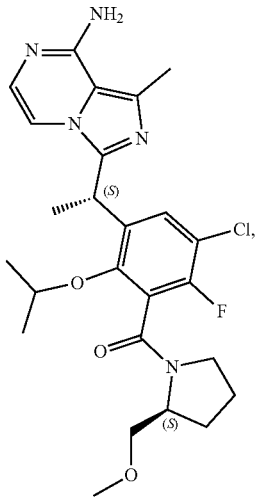
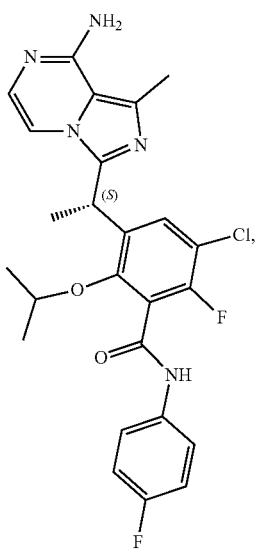
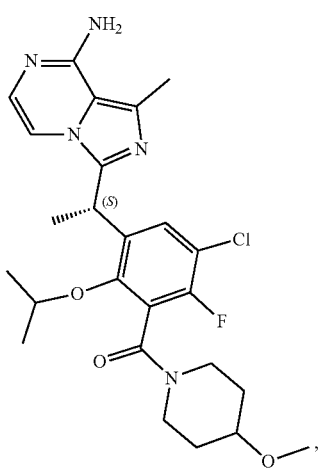

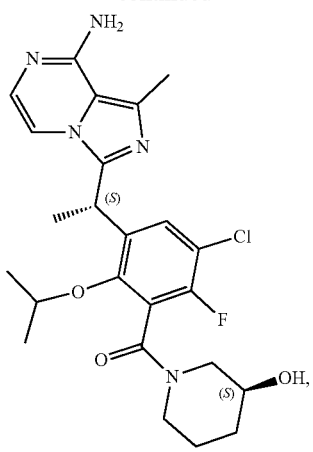
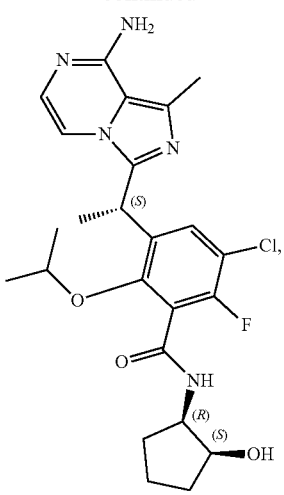
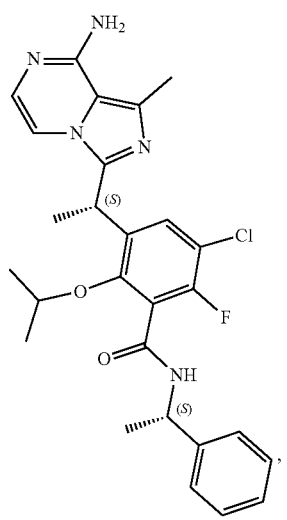
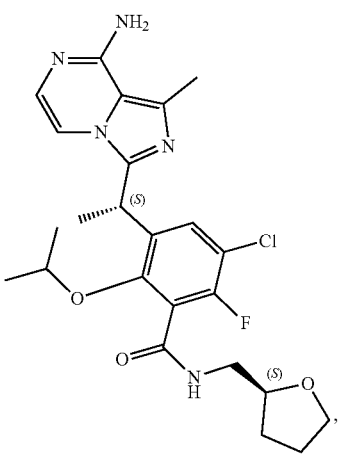
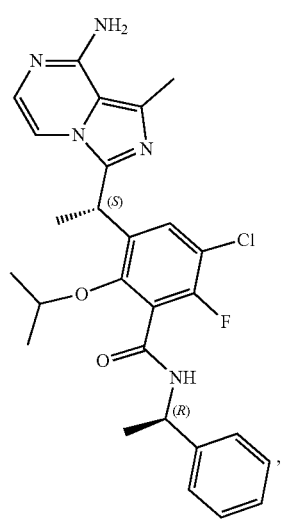
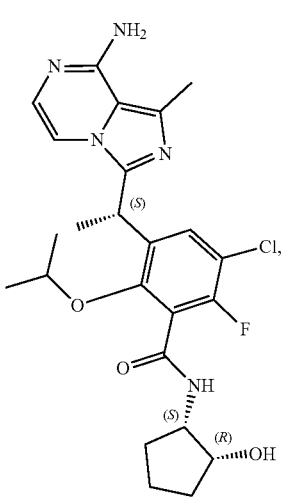

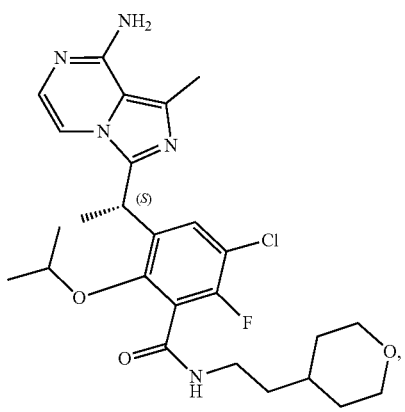
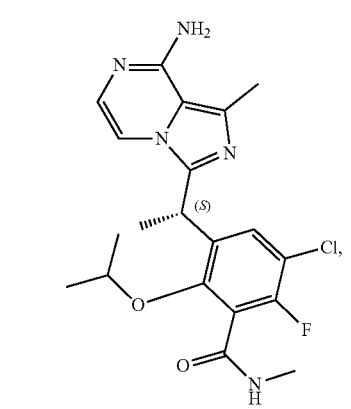
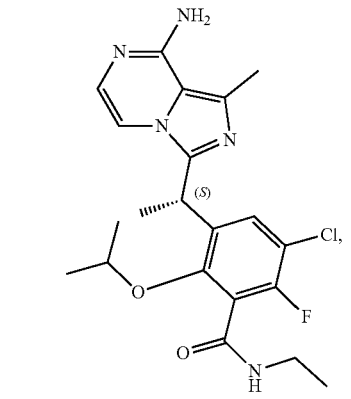
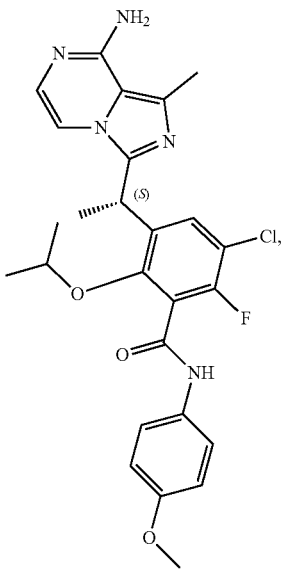
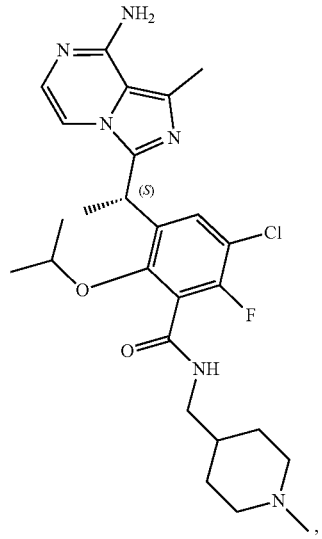
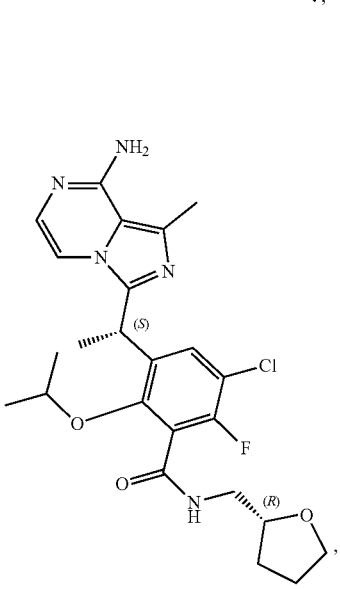

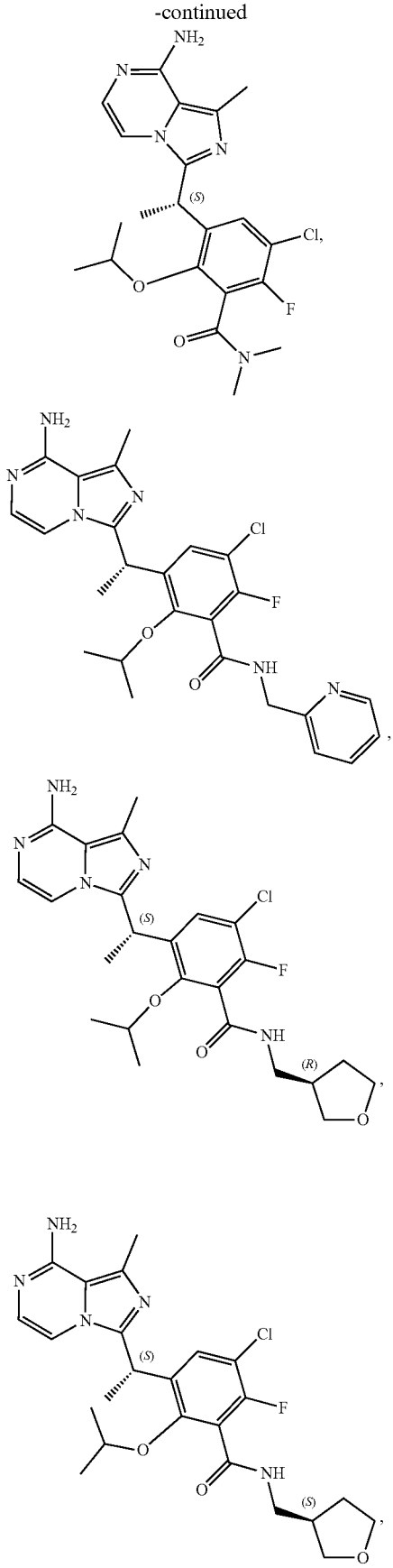
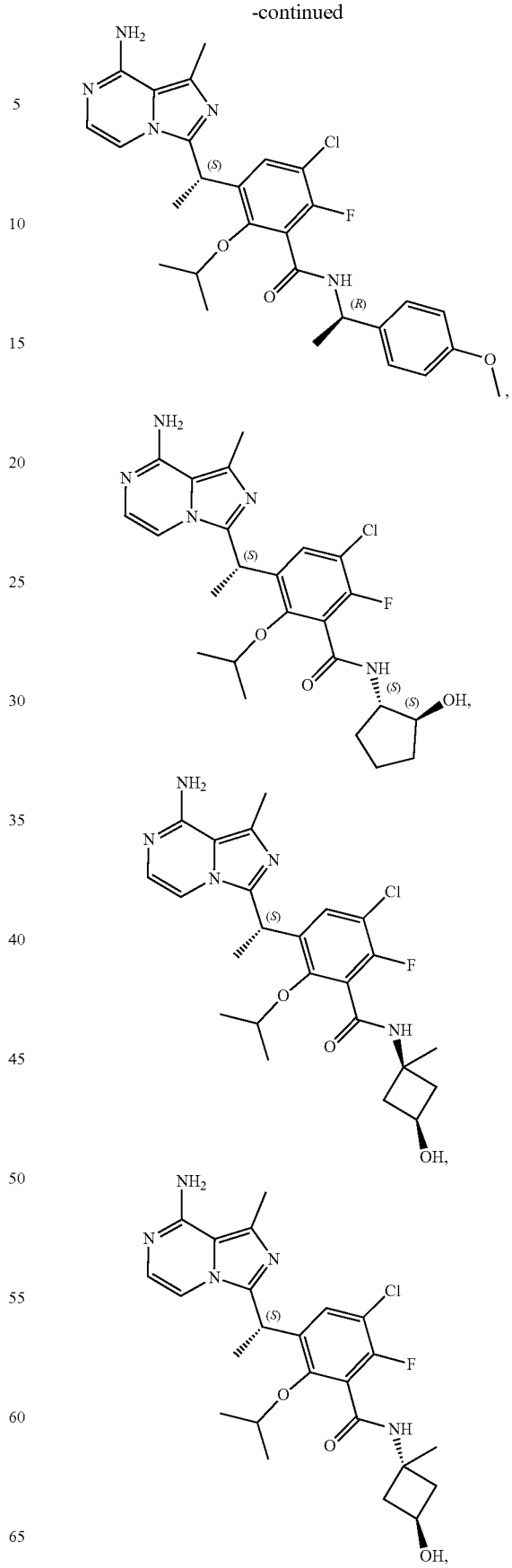

213
-continued
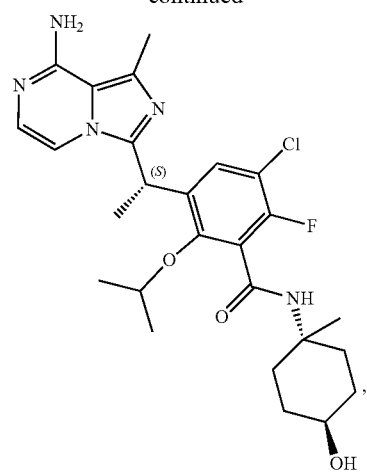
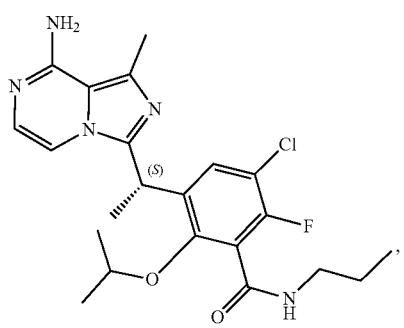
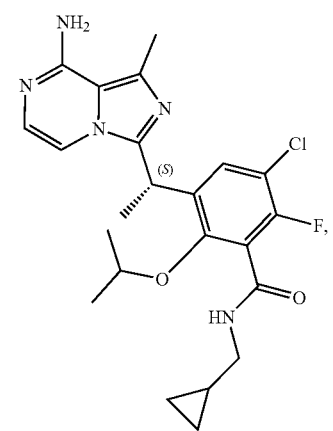
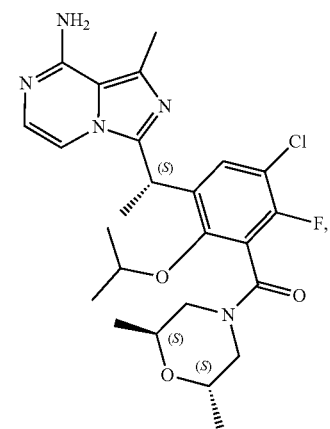
214
-continued
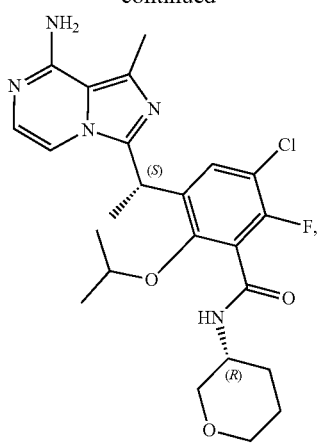
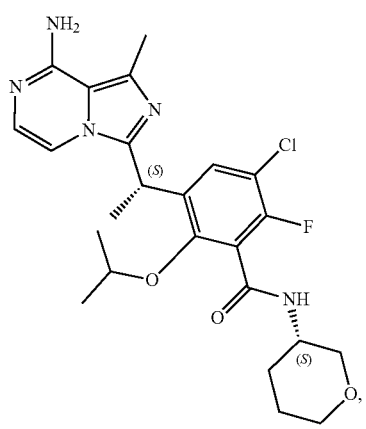
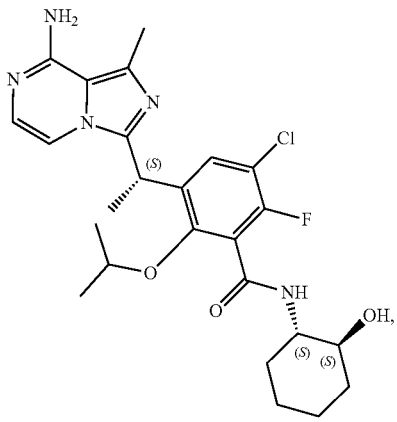
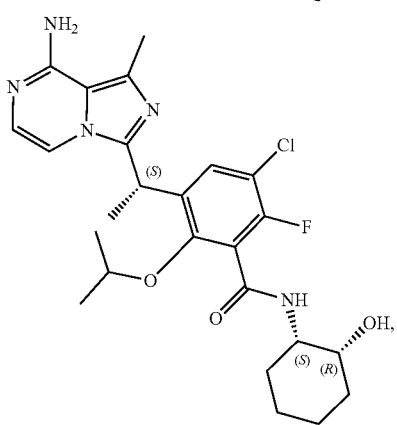

215
-continued
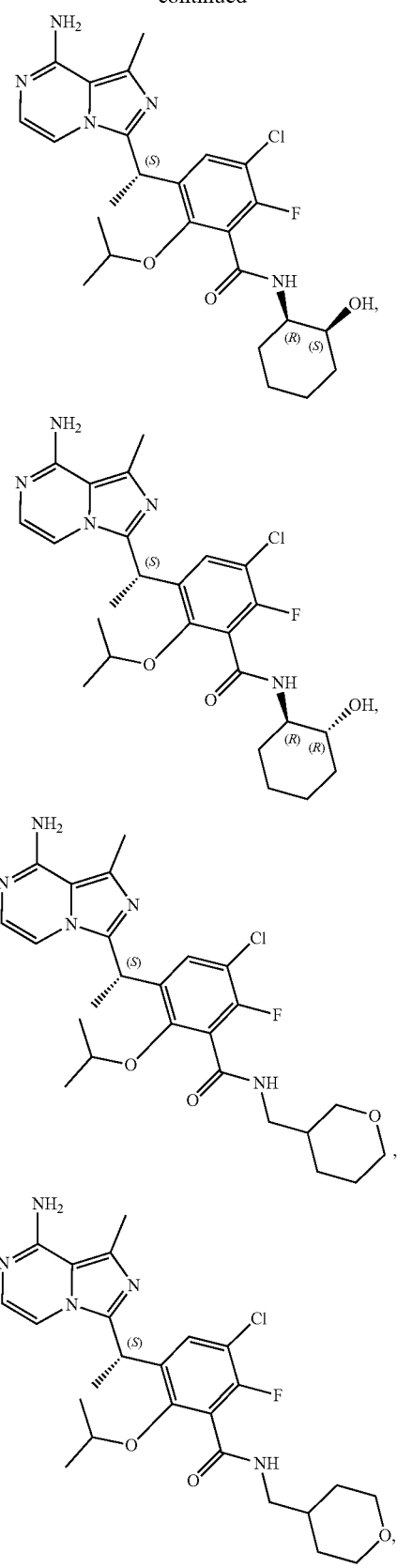
216
-continued
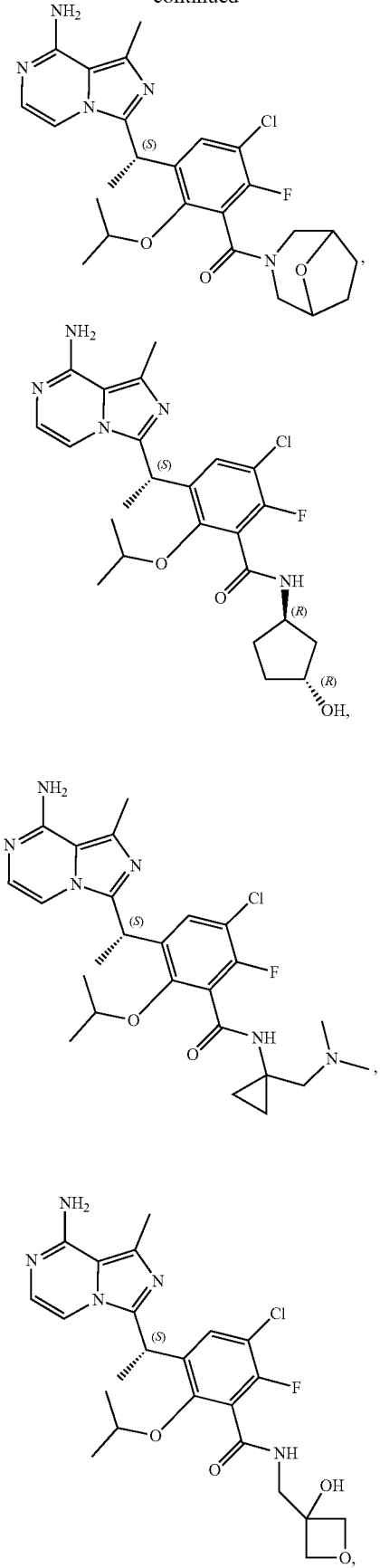

217
-continued
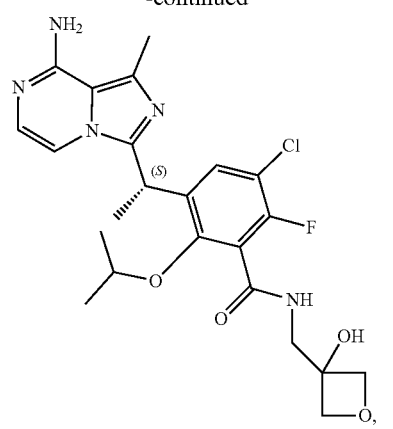
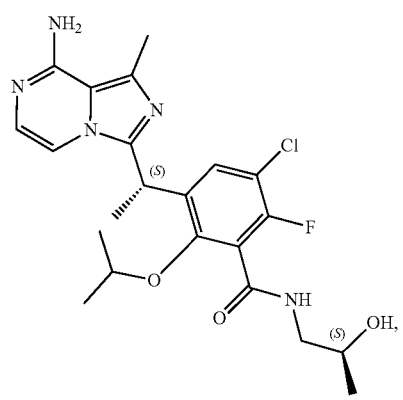
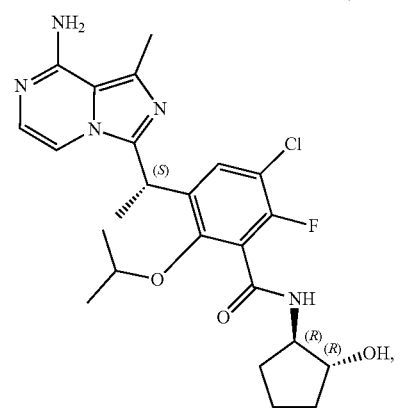
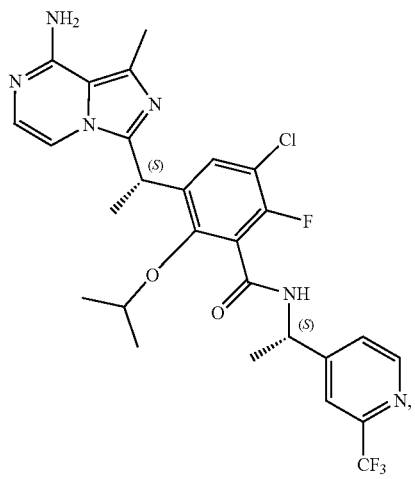
218
-continued
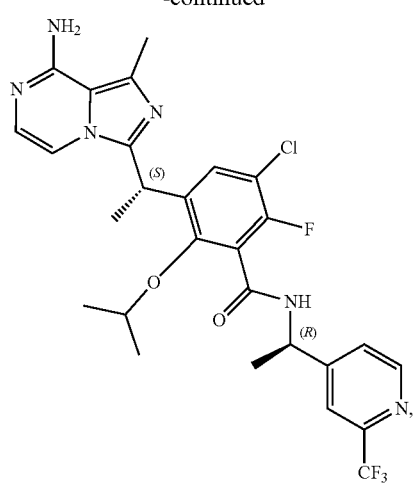
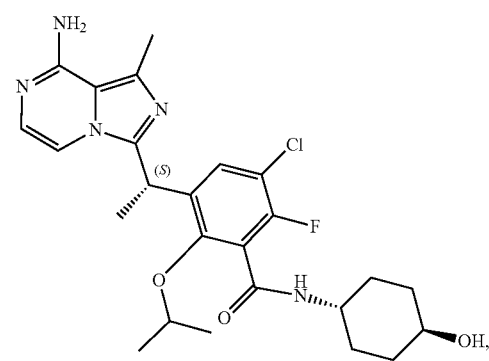
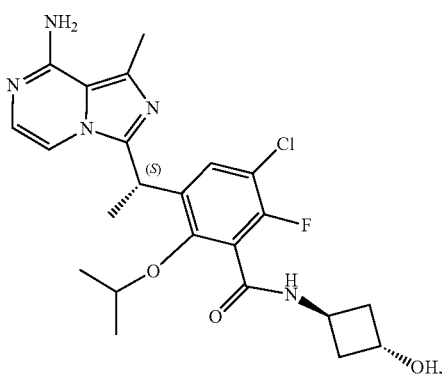
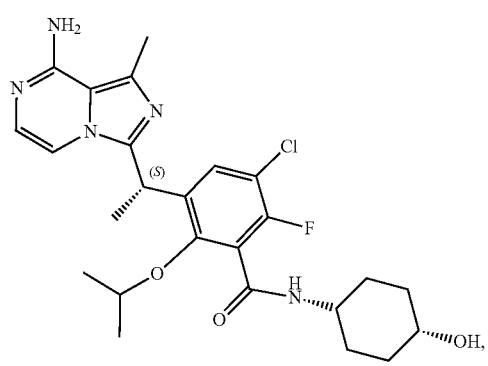

219
-continued
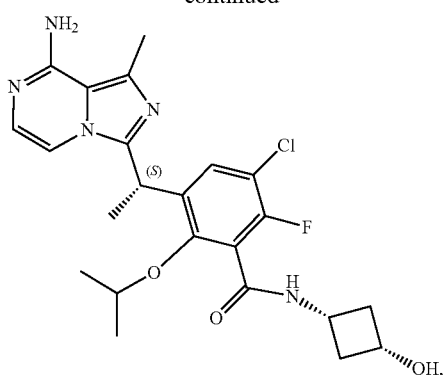
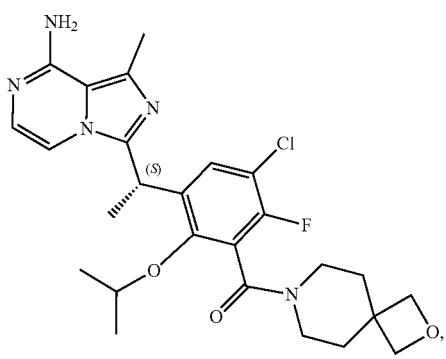
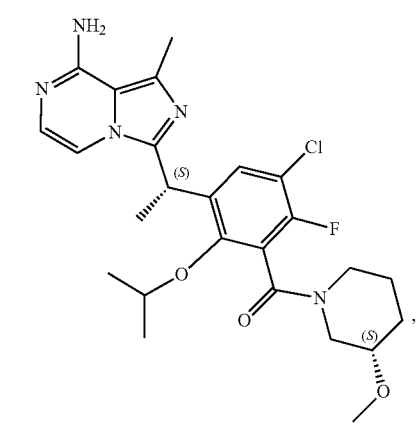
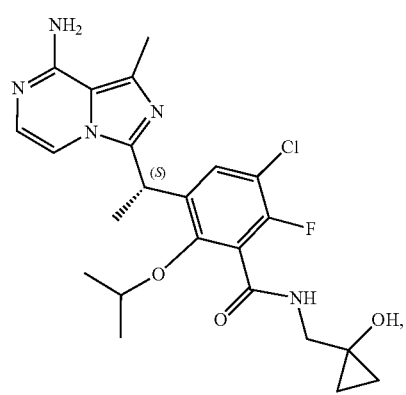
220
-continued
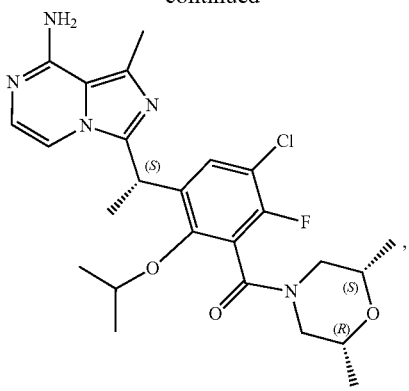
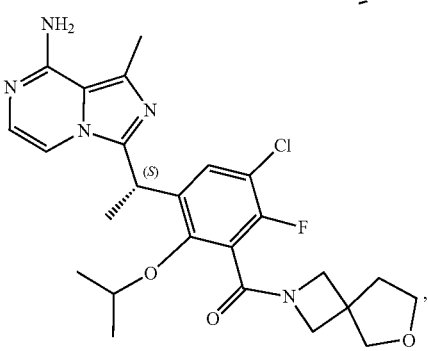
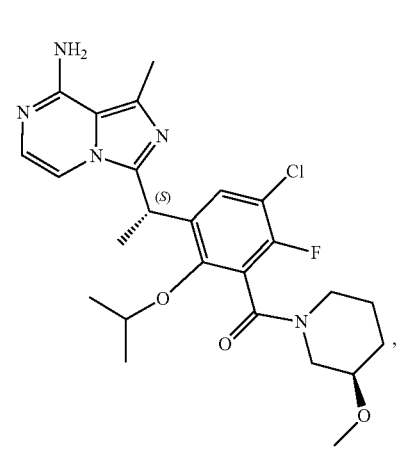
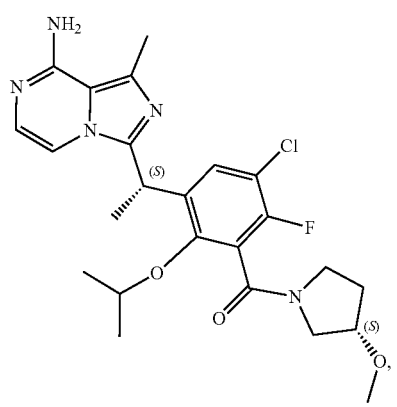

221
-continued
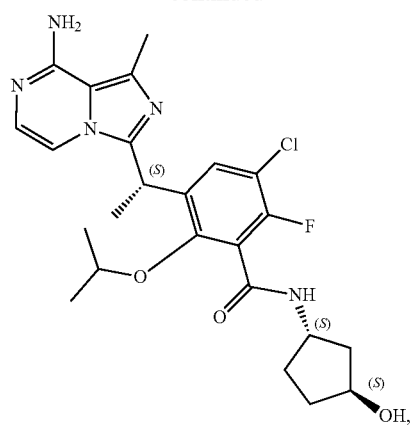
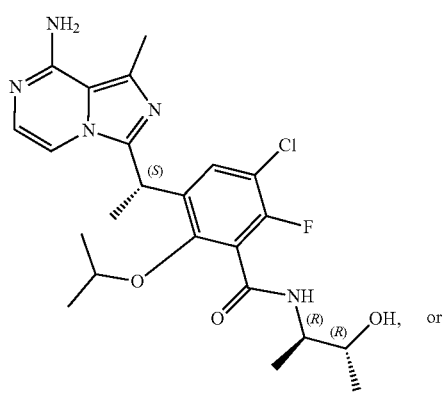
or
222
-continued
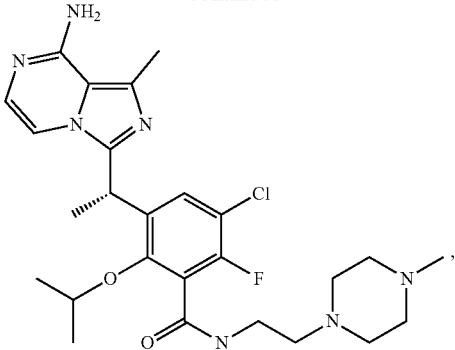
or a stereoisomer thereof, or a pharmaceutically acceptable salt thereof.
* * * * *